(12) United States Patent
Lupardus et al.

(10) Patent No.: US 12,103,954 B2
(45) Date of Patent: Oct. 1, 2024

(54) HETERODIMERIC FC CYTOKINES AND USES THEREOF

(71) Applicant: Synthekine, Inc., Menlo Park, CA (US)

(72) Inventors: Patrick Lupardus, Menlo Park, CA (US); Deepti Rokkam, Sunnyvale, CA (US)

(73) Assignee: Synthekine, Inc., Menlo Park, CA (US)

(*) Notice: Subject to any disclaimer, the term of this patent is extended or adjusted under 35 U.S.C. 154(b) by 0 days.

(21) Appl. No.: 18/582,180

(22) Filed: Feb. 20, 2024

(65) Prior Publication Data

US 2024/0209049 A1 Jun. 27, 2024

Related U.S. Application Data

(63) Continuation of application No. 18/516,047, filed on Nov. 21, 2023, which is a continuation of application No. PCT/US2022/078465, filed on Oct. 20, 2022.

(60) Provisional application No. 63/257,913, filed on Oct. 20, 2021.

(51) Int. Cl.
| C07K 14/54 | (2006.01) |
| A61K 38/00 | (2006.01) |
| A61K 45/06 | (2006.01) |
| A61P 35/00 | (2006.01) |

(52) U.S. Cl.
CPC .......... *C07K 14/5434* (2013.01); *A61K 45/06* (2013.01); *A61P 35/00* (2018.01); *A61K 38/00* (2013.01)

(58) Field of Classification Search
None
See application file for complete search history.

(56) References Cited

U.S. PATENT DOCUMENTS

| 5,731,168 A | 3/1998 | Carter et al. |
| 5,756,085 A | 5/1998 | Sykes et al. |
| 5,891,680 A | 4/1999 | Lieschke et al. |
| 6,682,736 B1 | 1/2004 | Hanson et al. |
| 6,838,260 B2 | 1/2005 | Gillies et al. |
| 6,984,720 B1 | 1/2006 | Korman et al. |
| 7,045,337 B2 | 5/2006 | Schultz et al. |
| 7,141,651 B2 | 11/2006 | Gillies et al. |
| 7,404,956 B2 | 7/2008 | Peters et al. |
| 7,576,193 B2 | 8/2009 | Gillies et al. |
| 7,872,107 B2 | 1/2011 | Webster et al. |
| 7,879,319 B2 | 2/2011 | Gillies et al. |
| 7,915,025 B2 | 5/2011 | Schultz et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,367,805 B2 | 2/2013 | Chamberlain et al. |
| 8,394,925 B2 | 3/2013 | Chamberlain et al. |
| 8,546,543 B2 | 10/2013 | Lazar |
| 8,592,562 B2 | 11/2013 | Kanaan et al. |
| 8,927,518 B1 | 1/2015 | Heller et al. |
| 9,527,926 B2 | 12/2016 | Ho et al. |
| 9,562,109 B2 | 2/2017 | Von Kreudenstin et al. |
| 10,336,818 B2 | 7/2019 | Chamberlain et al. |
| 10,494,437 B2 | 12/2019 | Niwa et al. |
| 10,696,722 B2 | 6/2020 | Kim et al. |
| 10,696,723 B2 | 6/2020 | Winston et al. |
| 11,078,249 B2 | 8/2021 | Kim et al. |
| 11,087,249 B2 | 8/2021 | Leonelli et al. |
| 11,358,999 B2 | 6/2022 | Bernett et al. |
| 11,401,348 B2 | 8/2022 | Lazar et al. |
| 2010/0196315 A1 | 8/2010 | Lacy et al. |
| 2012/0100140 A1 | 4/2012 | Reyes et al. |
| 2020/0032506 A1 | 10/2020 | Mahr et al. |
| 2020/0362005 A1 | 11/2020 | Kim et al. |
| 2021/0355185 A1 | 11/2021 | Bernett et al. |
| 2022/0119533 A1 | 4/2022 | Cheung et al. |
| 2022/0372495 A1 | 11/2022 | Schmidt et al. |
| 2023/0220031 A1 | 7/2023 | Garcia et al. |
| 2024/0132562 A1* | 4/2024 | Lupardus ........... C07K 14/5434 |

FOREIGN PATENT DOCUMENTS

| WO | 92005256 A1 | 4/1992 |
| WO | 2014145907 A1 | 9/2014 |
| WO | 2015124297 A1 | 8/2015 |
| WO | 2016048903 A1 | 4/2016 |
| WO | 2018148445 A1 | 8/2018 |
| WO | 2019149039 A1 | 8/2019 |
| WO | 2019157332 A1 | 8/2019 |
| WO | 2019209965 A2 | 10/2019 |
| WO | 2020/0072821 A3 | 4/2020 |

(Continued)

OTHER PUBLICATIONS

Lee et al. "Development of Highly Efficacious and Safe Targeted Cancer Immunotherapy via IL12-Based TMEKINEtm Platform" J. Immunother. cancer 8:A379 (Year: 2020).*
Anderson, et al. "Construction and biological characterization of an interleukin-12 fusion protein (Flexi-12): delivery to acute myeloid leukemic blasts using adeno-associated virus." Human gene therapy 8, No. 9 (1997): 1125-1135.
Ardolino, et al. "Cytokine therapy reverses NK cell anergy in MHC-deficient tumors." The Journal of clinical investigation 124, No. 11 (2014): 4781-4794.
Aste-Amezaga, et al. "Cooperation of natural killer cell stimulatory factor/interleukin-12 with other stimuli in the induction of cytokines and cytotoxic cell-associated molecules in human T and NK cells." Cellular immunology 156, No. 2 (1994): 480-492.
Atkins, et al. "Phase I evaluation of intravenous recombinant human interleukin 12 in patients with advanced malignancies." Clinical cancer research: an official journal of the American Association for Cancer Research 3, No. 3 (1997): 409-417.

(Continued)

*Primary Examiner* — Sudhakar Katakam
*Assistant Examiner* — Zachary J Miknis
(74) *Attorney, Agent, or Firm* — Kilpatrick Townsend & Stockton LLP

(57) ABSTRACT

The present disclosure provides IL12 and IL23 muteins as partial agonists comprising modified human p40 molecules that associate with human p35 (hP35) and human P19 (hP19) to form modified hIL-12 and IL23 partial agonists wherein the individual components of IL12 and IL23 muteins are linked to engineered Fc domains.

15 Claims, 35 Drawing Sheets

Specification includes a Sequence Listing.

(56) References Cited

FOREIGN PATENT DOCUMENTS

| WO | 2020072821 A2 | 4/2020 |
|---|---|---|
| WO | 2020086758 A1 | 4/2020 |
| WO | 2021016640 A1 | 1/2021 |
| WO | 2021067863 A2 | 4/2021 |
| WO | 2021146436 A2 | 7/2021 |
| WO | 2021146481 A1 | 7/2021 |
| WO | 2021216916 A1 | 10/2021 |

OTHER PUBLICATIONS

Atwell, et al. "Stable heterodimers from remodeling the domain interface of a homodimer using a phage display library." Journal of molecular biology 270, No. 1 (1997): 26-35.
Bastian, et al. "The IL-12 cytokine and receptor family in graft-vs.-host disease." Frontiers in immunology 10 (2019): 988.
Bekaii-Saab, et al. "A phase I trial of paclitaxel and trastuzumab in combination with interleukin-12 in patients with HER2/neu-expressing malignancies." Molecular cancer therapeutics 8, No. 11 (2009): 2983-2991.
Belladonna, et al. "Bioengineering heterodimeric cytokines: turning promiscuous proteins into therapeutic agents." Biotechnology and Genetic Engineering Reviews 29, No. 2 (2013): 149-174.
Benson, et al. "Therapeutic targeting of the IL-12/23 pathways: generation and characterization of ustekinumab." Nature biotechnology 29, No. 7 (2011): 615-624.
Bernett, et al. "564 Potency-reduced and extended half-life IL12 heterodimeric Fc-fusions exhibit strong anti-tumor activity with potentially improved therapeutic index compared to native IL12 agents." (2020).
Bloch, et al. "Structural activation of pro-inflammatory human cytokine IL-23 by cognate IL-23 receptor enables recruitment of the shared receptor IL-12Rβ1." Immunity 48, No. 1 (2018): 45-58.
Boulanger, et al. "Convergent mechanisms for recognition of divergent cytokines by the shared signaling receptor gp130." Molecular cell 12, No. 3 (2003): 577-589.
Boulanger, et al. "Hexameric structure and assembly of the interleukin-6/IL-6 α-receptor/gp130 complex." Science 300, No. 5628 (2003): 2101-2104.
Brunda, et al. "Antitumor and antimetastatic activity of interleukin 12 against murine tumors." The Journal of experimental medicine 178, No. 4 (1993): 1223-1230.
Carter, Paul. "Bispecific human IgG by design." Journal of immunological methods 248, No. 1-2 (2001): 7-15.
Chao, et al. "Isolating and engineering human antibodies using yeast surface display." Nature protocols 1, No. 2 (2006): 755-768.
Chappel, et al. "Identification of the Fc gamma receptor class I binding site in human IgG through the use of recombinant IgG1/IgG2 hybrid and point-mutated antibodies." Proceedings of the National Academy of Sciences 88, No. 20 (1991): 9036-9040.
Choudhary, et al. "Lysine acetylation targets protein complexes and co-regulates major cellular functions." Science 325, No. 5942 (2009): 834-840.
Chua, et al. "Expression cloning of a human IL-12 receptor component. A new member of the cytokine receptor superfamily with strong homology to gp130." Journal of immunology (Baltimore, MD.: 1950) 153, No. 1 (1994): 128-136.
Collison, et al. "The inhibitory cytokine IL-35 contributes to regulatory T-cell function." Nature 450, No. 7169 (2007): 566-569.
Cooper et al., "Mice Lacking Bioactive Il-12 Can Generate Protective, Antigen-specific Cellular Responses to Mycobacterial Infection Only if the Il-12 P40 Subunit is Present." J Immunol 168 (2002): 1322-1327.
Decken, et al. "Interleukin-12 is essential for a protective Th1 response in mice infected with Cryptococcus neoformans." Infection and immunity 66, No. 10 (1998): 4994-5000.
Deiters, et al. "Site-specific PEGylation of proteins containing unnatural amino acids." Bioorganic & Medicinal Chemistry Letters 14, No. 23 (2004): 5743-5745.
Delano, et al. "Convergent solutions to binding at a protein-protein interface." Science 287, No. 5456 (2000): 1279-1283.
Desmyter, et al. "Neutralization of human interleukin 23 by multivalent nanobodies explained by the structure of cytokine-nanobody complex." Frontiers in Immunology 8 (2017): 884.
Dorai, et al. "Role of inter-heavy and light chain disulfide bonds in the effector functions of human immunoglobulin IgG1." Molecular immunology 29, No. 12 (1992): 1487-1491.
Dozier, et al. "Site-specific PEGylation of therapeutic proteins." International journal of molecular sciences 16, No. 10 (2015): 25831-25864.
Economides, et al. "Cytokine traps: multi-component, high-affinity blockers of cytokine action." Nature medicine 9, No. 1 (2003): 47-52.
Fewell, et al. "Treatment of disseminated ovarian cancer using nonviral interleukin-12 gene therapy delivered intraperitoneally." The Journal of Gene Medicine: A cross-disciplinary journal for research on the science of gene transfer and its clinical applications 11, No. 8 (2009): 718-728.
Foss, et al. "In Vitro and In Vivo Bioactivity of Single-Chain Interleukin-12." Scandinavian journal of immunology 50, No. 6 (1999): 596-604.
Gafner, et al. "An engineered antibody-interleukin-12 fusion protein with enhanced tumor vascular targeting properties." International journal of cancer 119, No. 9 (2006): 2205-2212.
Georgy, et al. "Tryptophan (W) at position 37 of murine IL-12/IL-23 p40 is mandatory for binding to IL-12Rβ1 and subsequent signal transduction." Journal of Biological Chemistry 297, No. 5 (2021).
Gillies, et al. "Antibody-IL-12 fusion proteins are effective in SCID mouse models of prostate and colon carcinoma metastases." The Journal of Immunology 160, No. 12 (1998): 6195-6203.
Gillies, wt al. "Bi-functional cytokine fusion proteins for gene therapy and antibody-targeted treatment of cancer." Cancer Immunology, Immunotherapy 51 (2002): 449-460.
Glassman, et al. "Structural basis for IL-12 and IL-23 receptor sharing reveals a gateway for shaping actions on T versus NK cells." Manuscript No. Cell-D-20-00989R5, 85 pages.
Ha, et al. "Immunoglobulin Fc heterodimer platform technology: from design to applications in therapeutic antibodies and proteins." Frontiers in Immunology 7 (2016): 394.
Jiang, et al. "Sustained expression of Fc-fusion cytokine following in vivo electroporation and mouse strain differences in expression levels." Journal of biochemistry 133, No. 4 (2003): 423-427.
Jung, et al. "Heterodimeric Fc-fused IL12 shows potent antitumor activity by generating memory CD8+ T cells." Oncoimmunology 7, No. 7 (2018): e1438800.
Kobayashi, et al. "Identification and purification of natural killer cell stimulatory factor (NKSF), a cytokine with multiple biologic effects on human lymphocytes." The Journal of experimental medicine 170, No. 3 (1989): 827-845.
Kontermann, Roland E. "Half-life extended biotherapeutics." Expert opinion on biological therapy 16, No. 7 (2016): 903-915.
Kopp, et al. "Clinical improvement in psoriasis with specific targeting of interleukin-23." Nature 521, No. 7551 (2015): 222-226.
Koutruba et al., Review of Ustekinumab, an Interleukin-12 and Interleukin-23 Inhibitor Used for the Treatment of Plaque Psoriasis, Therapeutics and Clinical Risk Management, Mar. 8, 2010, 6:123-141.
Lasek, et al. "Interleukin 12: still a promising candidate for tumor immunotherapy?." Cancer Immunology, Immunotherapy 63 (2014): 419-435.
Leong, et al. "Optimized expression and specific activity of IL-12 by directed molecular evolution." Proceedings of the National Academy of Sciences 100, No. 3 (2003): 1163-1168.
Liang, et al. "IL-23 receptor expression on γδ T cells correlates with their enhancing or suppressive effects on autoreactive T cells in experimental autoimmune uveitis." The Journal of Immunology 191, No. 3 (2013): 1118-1125.
Littman, et al. "Th17 and regulatory T cells in mediating and restraining inflammation." Cell 140, No. 6 (2010): 845-858.
Lo, et al. "Effector-attenuating substitutions that maintain antibody stability and reduce toxicity in mice." Journal of Biological Chemistry 292, No. 9 (2017): 3900-3908.

(56) References Cited

OTHER PUBLICATIONS

Low, et al. "Oral and pulmonary delivery of FSH-Fc fusion proteins via neonatal Fc receptor-mediated transcytosis." Human reproduction 20, No. 7 (2005): 1805-1813.
Luo, et al. "Structural basis for the dual recognition of IL-12 and IL-23 by ustekinumab." Journal of molecular biology 402, No. 5 (2010): 797-812.
Lupardus, et al. "The structure of interleukin-23 reveals the molecular basis of p40 subunit sharing with interleukin-12." Journal of molecular biology 382, No. 4 (2008): 931-941.
Mattner, et al. "Genetically resistant mice lacking interleukin-12 are susceptible to infection with Leishmania major and mount a polarized Th2 cell response." European journal of immunology 26, No. 7 (1996): 1553-1559.
Merchant, et al. "An efficient route to human bispecific IgG." Nature biotechnology 16, No. 7 (1998): 677-681.
Murray, Peter J. "The JAK-STAT signaling pathway: input and output integration." The Journal of Immunology 178, No. 5 (2007): 2623-2629.
Nguyen, et al. "Localized interleukin-12 for cancer immunotherapy." Frontiers in immunology 11 (2020): 575597.
Oppmann, et al. "Novel p19 protein engages IL-12p40 to form a cytokine, IL-23, with biological activities similar as well as distinct from IL-12." Immunity 13, No. 5 (2000): 715-725.
Parham, et al. "A receptor for the heterodimeric cytokine IL-23 is composed of IL-12Rβ1 and a novel cytokine receptor subunit, IL-23R." The Journal of Immunology 168, No. 11 (2002): 5699-5708.
Pasche, et al. "The antibody-based delivery of interleukin-12 to the tumor neovasculature eradicates murine models of cancer in combination with paclitaxel." Clinical Cancer Research 18, No. 15 (2012): 4092-4103.
Pegram, et al. "Tumor-targeted T cells modified to secrete IL-12 eradicate systemic tumors without need for prior conditioning." Blood, The Journal of the American Society of Hematology 119, No. 18 (2012): 4133-4141.
Peng, et al. "A single-chain IL-12 IgG3 antibody fusion protein retains antibody specificity and IL-12 bioactivity and demonstrates antitumor activity." The Journal of Immunology 163, No. 1 (1999): 250-258.
Presky, et al. "A functional interleukin 12 receptor complex is composed of two β-type cytokine receptor subunits." Proceedings of the National Academy of Sciences 93, No. 24 (1996): 14002-14007.
Rath, et al. "Fc-fusion proteins and FcRn: structural insights for longer-lasting and more effective therapeutics." Critical reviews in biotechnology 35, No. 2 (2015): 235-254.
Ridgway, et al. "'Knobs-into-holes' engineering of antibody CH3 domains for heavy chain heterodimerization." Protein Engineering, Design and Selection 9, No. 7 (1996): 617-621.
Scallon, et al. "Quantitative in vivo comparisons of the Fcγ receptor-dependent agonist activities of different fucosylation variants of an immunoglobulin G antibody." International immunopharmacology 7, No. 6 (2007): 761-772.
Schlothauer, et al. "Novel human IgG1 and IgG4 Fc-engineered antibodies with completely abolished immune effector functions." Protein Engineering, Design and Selection 29, No. 10 (2016): 457-466.
Schmidt, Stefan R. "Fusion-proteins as biopharmaceuticals-applications and challenges." Curr Opin Drug Discov Devel 12, No. 2 (2009): 284-295.
Schröder, et al. "Non-canonical interleukin 23 receptor complex assembly: p40 protein recruits interleukin 12 receptor β1 via site II and induces p19/interleukin 23 receptor interaction via site III." Journal of Biological Chemistry 290, No. 1 (2015): 359-370.
Schurich, et al. "The third signal cytokine IL-12 rescues the anti-viral function of exhausted HBV-specific CD8 T cells." PLoS pathogens 9, No. 3 (2013): e1003208.
Skiniotis, et al. "Structural organization of a full-length gp130/LIF-R cytokine receptor transmembrane complex." Molecular cell 31, No. 5 (2008): 737-748.
Skrombolas, et al. "Characterization of an IL-12 p40/p35 truncated fusion protein that can inhibit the action of IL-12." Journal of Interferon & Cytokine Research 35, No. 9 (2015): 690-697.
Skrombolas, et al. "Development of an interleukin-12 fusion protein that is activated by cleavage with matrix metalloproteinase 9." Journal of Interferon & Cytokine Research 39, No. 4 (2019): 233-245.
Strohl, William R. "Optimization of Fc-mediated effector functions of monoclonal antibodies." Current opinion in biotechnology 20, No. 6 (2009): 685-691.
Tamura, et al. "Intratumoral delivery of interleukin 12 expression plasmids with in vivo electroporation is effective for colon and renal cancer." Human gene therapy 12, No. 10 (2001): 1265-1276.
Trinchieri, Giorgio. "Interleukin-12 and the regulation of innate resistance and adaptive immunity." Nature Reviews Immunology 3, No. 2 (2003): 133-146.
Tugues, et al. "New insights into IL-12-mediated tumor suppression." Cell Death & Differentiation 22, No. 2 (2015): 237-246.
Valeich, et al. "Taking the Hinge off: An Approach to Effector-Less Monoclonal Antibodies." Antibodies 9, No. 4 (2020): 50.
Vazquez-Lombardi, et al. "Molecular engineering of therapeutic cytokines." Antibodies 2, No. 3 (2013): 426-451.
Vignali, et al. "IL-12 family cytokines: immunological playmakers." Nature immunology 13, No. 8 (2012): 722-728.
Villarino, et al. "Mechanisms of Jak/STAT signaling in immunity and disease." The Journal of Immunology 194, No. 1 (2015): 21-27.
Wang, et al. "A novel IL-23p19/Ebi3 (IL-39) cytokine mediates inflammation in Lupus-like mice." European journal of immunology 46, No. 6 (2016): 1343-1350.
Wang, et al. "Structural biology of shared cytokine receptors." Annual review of immunology 27 (2009): 29-60.
Watford, et al. "Signaling by IL-12 and IL-23 and the immunoregulatory roles of STAT4." Immunological reviews 202, No. 1 (2004): 139-156.
Weiss, et al. "Immunotherapy of cancer by IL-12-based cytokine combinations." Expert opinion on biological therapy 7, No. 11 (2007): 1705-1721.
Wojno, et al. "The immunobiology of the interleukin-12 family: room for discovery." Immunity 50, No. 4 (2019): 851-870.
Xue, et al. "Next-generation cytokines for cancer immunotherapy." Antibody Therapeutics 4, No. 2 (2021): 123-133.
Yoon, et al. "Charged residues dominate a unique interlocking topography in the heterodimeric cytokine interleukin-12." The EMBO journal 19, No. 14 (2000): 3530-3541.
Zhang, et al. "Improving adoptive T cell therapy by targeting and controlling IL-12 expression to the tumor environment." Molecular therapy 19, No. 4 (2011): 751-759.
Zhou, et al. "IL-6 programs TH-17 cell differentiation by promoting sequential engagement of the IL-21 and IL-23 pathways." Nature immunology 8, No. 9 (2007): 967-974.
Altschul, et al., "Basic local alignment search tool." Journal of molecular biology 215, No. 3 (1990): 403-410.
Ahn, et al., "136O: Osimertinib combined with durvalumab in EGFR-mutant non-small cell lung cancer: Results from the Tatton phase Ib trial." Journal of Thoracic Oncology 11, No. 4 (2016): S115.
Atkins, et al., "Phase 1 Evaluation of Intravenous Recombinant Human Interleukin 12 in Patients with Advanced Malignancies," Clinical Cancer Research (1997) 3:409-417.
Anderson, et al., "Construction and Biological Characterization of an Interleukin-12 Fusion Protein (Flexi-12): Delivery to Acute Myeloid Leukemic Blasts Using Adeno-associated Virus," Human Gene Therapy (1997) 8:1125-1135.
Ardolino, et al., "Cytokine Therapy Reverses Nk Cell Anergy in Mhc-deficient Tumors," The Journal of Clinical Investigation (2014) 24(11):4781-4794.
Aste-Amezaga, et al., "Cooperation of Natural Killer Cell Stimulatory Factor/interleukin-12 with Other Stimuli in the Induction of Cytokines and Cytotoxic Cell-associated Molecules in Human T and Nk Cells, "Cell Immunol (1994) 156:480-492.

(56) References Cited

OTHER PUBLICATIONS

Atwell, et al., "Stable Heterodimers from Remodeling the Domain Interface of a Homodimer using a Phage Display Library," J. Mol. Biol. (1997) 270, 26±35.

Bastian, et al., "The IL-12 Cytokine and Receptor Family in Graft-vs.-Host Disease," Frontiers in Immunology (2019) vol. 10 Article 988.

Bekaii-Saab, et al., "A Phase I Trial of Paclitaxel and Trastuzumab in Combination With Interleukin-12 in Patients With Her2/neu-expressing Malignancies," Molecular Cancer Therapeutics (2009) 8(11):2983-2991.

Belladonna et al., "Bioengineering heterodimeric cytokines: turning promiscuous proteins into therapeutic agents," (2013) Biotechnology and Genetic Engineering Reviews, 29:2, 149-174.

Benson, et al. "Therapeutic Targeting of the Il-12/23 Pathways:Generation and Characterization of Ustekinumab," Nature Biotechnology (2011) 29(7):615-624.

Bernett et al., "Potency-Reduced and Extended Half-Life IL12 Heterodimeric Fc-Fusions Exhibit Strong Anti-Tumor Activity With Potentially Improved Therapeutic Index Compared to Native IL12 Agents," J Immunother Cancer 2020;8(Suppl 3):A1-A559,A340.

Bernett, et al., "IL12d potency exhibit strong anti-tumor activity and improved therapeutic index compared to compared to native IL12 agents," 2021 AACR Abstract #1743.

Bloch, et al., "Structural Activation of Pro-inflammatory Human Cytokine IL-23 by Cognate IL-23 Receptor Enables Recruitment of the Shared Receptor IL-12Rβ1," Cell (2018) 48:45-58(1-14).

Boulanger, et al., "Convergent Mechanisms for Recognition of Divergent Cytokines by the Shared Signaling Receptor Gp130," Molecular Cell (2003) 12:577-589.

Boulanger, et al., "Hexameric Structure and Assembly of The Interleukin-6/il-6 Alpha-receptor/gp130 Complex," Science (2003) 300:2101-2104.

Brekke et al., "Structure-Function Relationships of Human IgG," The Immunologist, 2/4, 1994, pp. 125-130.

Brunda, et al., "Antitumor and Antimetastatic Activity of Interleukin 12 Against Murine Tumors," Journal of Experimental Medicine (1993) 178:1223-30.

Caceci, et al., "Fitting curves to data." Byte 9, No. 5 (1984): 340-362.

Carmenate et al., "Human IL-2 Mutein with Higher Antitumor Efficacy Than Wild Type IL-2", Journal of Immunology, vol. 190, No. 12, 2013, pp. 6230-6238.

Cartellieri, et al., "Chimeric antigen receptor-engineered T cells for immunotherapy of cancer." BioMed Research International 2010, No. 1 (2010): 956304.

Carter, et al., "Bispecific Human IgG by Design," Journal of Immunological Methods (2001) 248(1-2):7-15.

Chao, et al., "Isolating and engineering human antibodies using yeast surface display," Nature Protocols (2006) 1(2):755-768.

Chappel, et al., "Identification of the Fc, receptor class I binding site in human IgG through the use of recombinant IgG1/IgG2 hybrid and point-mutated antibodies," PNAS USA (1991) vol. 88,pp. 9036-9040.

Cheadle, et al. "CAR T cells: driving the road from the laboratory to the clinic." Immunological reviews 257, No. 1 (2014): 91-106.

Choudhary, et al., "Lysine Acetylation Targets Protein Complexes and Co-Regulates Major Cellular Functions," Science (2009) 325(5942): 834-840.

Chua, et al., "Expression Cloning of a Human Il-12 Receptor Component. A New Member of The Cytokine Receptor Superfamily with Strong Homology to gp130," The Journal of Immunology (1994) 153(1):128-136.

Collison, et al., "The Inhibitory Cytokine Il-35 Contributes to Regulatory T-cell Function," Nature (2007) 450:566-569.

Cooper, et al., "Mice Lacking Bioactive Il-12 Can Generate Protective, Antigen-specific Cellular Responses to Mycobacterial Infection Only if the Il-12 P40 Subunit is Present," The Journal of Immunology (2002) 168(3):1322-1327.

Curran, et al., "Chimeric antigen receptors for T cell immunotherapy: current understanding and future directions." The journal of gene medicine 14, No. 6 (2012): 405-415.

Decken, et al., "Interleukin-12 is Essential for a Protective Th1 Response in Mice Infected With Cryptococcus Neoformans," Infection and immunity(1998) 66(10):4994-5000.

Deiters, et al., "Site-specific PEGylation of Proteins Containing Unnatural Amino Acids," Bioorganic & Medicinal Chemistry Letters (2004)14(23):5743-5745.

Delano, et al., "Convergent Solutions to Binding at a Protein-protein Interface," Science (2002) 287:1279-1283.

Desmyter, et al., "Neutralization of Human Interleukin 23 by Multivalent Nanobodies Explained by The Structure of Cytokine-nanobody Complex," Frontiers in Immunology (2017) 8:884(1-10).

Devereux, et al. "A comprehensive set of sequence analysis programs for the VAX." (1984): 387-395.

Dorai, et al., "Role of Inter-Heavy and Light Chain Disulfide Bonds in the Effector Functions of Human Immunoglobulin IgG1," Molecular Immunol (1992) vol. 29,No. 12,pp. 1487-1491.

Dozier, et al., "Site-Specific PEGylation of Therapeutic Proteins," International Journal of Molecular Science (2015) 16(10):25831-25864.

Economides, et al., "Cytokine traps: multi-component, high-affinity blockers of cytokine action," Nature Medicine (2003) 9(1), 47-52.

Eyquem, et al., "Targeting a CAR to the TRAC locus with CRISPR/Cas9 enhances tumour rejection." Nature 543, No. 7643 (2017): 113-117.

Fedorov, et al., "PD-1-and CTLA-4-based inhibitory chimeric antigen receptors (iCARs) divert off-target immunotherapy responses." Science translational medicine 5, No. 215 (2013): 215ra172-215ra172.

Fewell, et al., "Treatment of Disseminated Ovarian Cancer Using Nonviral Interleukin-12 Gene Therapy Delivered Intraperitoneally," The Journal of Gene Medicine (2009) 11:718-728.

Foss, et al., "In Vitro and In Vivo Bioactivity of Single-Chain Interleukin-12," Scand. J. Immunol (1999) 50, 596-604.

Fridman et al., "The Use of Cytokines in the Treatment of Solid Tumours", Hematology and Cell Therapy, vol. 39, No. 2, 1997, pp. 105-108.

Gafner, et al., "An engineered antibody-interleukin-12 fusion protein with enhanced tumor vascular targeting properties," Int. J. Cancer: 119, 2205-2212 (2006).

Genestier, et al., "Transforming growth factor β1 inhibits Fas ligand expression and subsequent activation-induced cell death in T cells via downregulation of c-Myc." The Journal of experimental medicine 189, No. 2 (1999): 231-239.

Georgiadis, et al. "Long terminal repeat CRISPR-CAR-coupled "universal" T cells mediate potent anti-leukemic effects." Molecular Therapy 26, No. 5 (2018): 1215-1227.

Georgy, et al., "Tryptophan (W) at position 37 of murine IL-12/IL-23 p40 is mandatory for binding to IL-12Rβ1 and subsequent signal transduction," J. Biol. Chem. (2021) 297(5) 101295.

Gillies, et al., "Antibody-IL-12 Fusion Proteins are Effective in SCID Mouse Models of Prostate and Colon Carcinoma Metastases," The Journal of Immunology, 1998, 160: 6195-6203.

Gillies, et al., "Bi-functional cytokine fusion proteins for gene therapy and antibody-targeted treatment of cancer," Cancer Immunol Immunother (2002) 51: 449-460.

Glassman, et al., "Structural basis for IL-12 and IL-23 receptor sharing reveals a gateway for shaping actions on T versus NK cells," Cell (2021) 184, 983-999.

Glienke, et al. "Advantages and applications of CAR-expressing natural killer cells." Frontiers in pharmacology 6 (2015): 21.

Goldberg, et al. "LAG-3 in cancer immunotherapy." Cancer immunology and immunotherapy (2011): 269-278.

Graham, et al. "Allogeneic CAR-T cells: more than ease of access?." Cells 7, No. 10 (2018): 155.

Gross, et al. "Expression of immunoglobulin-T-cell receptor chimeric molecules as functional receptors with antibody-type specificity." Proceedings of the National Academy of Sciences 86, No. 24 (1989): 10024-10028.

Grosso, et al. "LAG-3 regulates CD8+ T cell accumulation and effector function in murine self-and tumor-tolerance systems." The Journal of clinical investigation 117, No. 11 (2007): 3383-3392.

(56) References Cited

OTHER PUBLICATIONS

Ho, et al., "Immunoglobulin Fc Heterodimer Platform Technology: From Design to Applications in Therapeutic Antibodies and Proteins," Front. Immunol.(2016) vol. 7 | Article 394.
Hogquist, et al. "T cell receptor antagonist peptides induce positive selection." Cell 76, No. 1 (1994): 17-27.
Holscher, et al. "A protective and agonistic function of IL-12p40 in mycobacterial infection." The Journal of Immunology 167, No. 12 (2001): 6957-6966.
Huyton, et al. "An unusual cytokine: Ig-domain interaction revealed in the crystal structure of leukemia inhibitory factor (LIF) in complex with the LIF receptor." Proceedings of the National Academy of Sciences 104, No. 31 (2007): 12737-12742.
Idziorek, et al. "Recombinant human IL-16 inhibits HIV-1 replication and protects against activation-induced cell death (AICD)." Clinical & Experimental Immunology 112, No. 1 (1998): 84-91.
Jensen, et al. "Designing chimeric antigen receptors to effectively and safely target tumors." Current opinion in immunology 33 (2015): 9-15.
Ji et al., "Synergistic Anti-tumor Effect of Glycosylphosphatidylinositol-anchored IL-2 and IL-12", The Journal of Gene Medicine, vol. 6, No. 7, 2004, pp. 777-785.
Jiang et al., "Sustained Expression of Fc-Fusion Cytokine Following In Vivo Electroporation and Mouse Strain Differences in Expression Level," Biochem. (2003)133: 423-427.
Jung et al., "Heterodimeric Fc-fused IL12 shows potent antitumor activity by generating memory CD8 T cells," Oncoimmunology 2018, vol. 7, No. 7, e1438800.
Kabsch, Wolfgang. "xds." Acta Crystallographica Section D: Biological Crystallography 66, No. 2 (2010): 125-132.
Kakarla, et al. "CAR T cells for solid tumors: armed and ready to go?." The Cancer Journal 20, No. 2 (2014): 151-155.
Kobayashi, et al. Identification and Purification of Natural Killer Cell Stimulatory Factor (NKSF), a Cytokine with Multiple Biologic Effects on Human Lymphocytes Journal of Experimental Medicine (1989) 170(3):827-845.
Kontermann "Half-life extended biotherapeutics," Expert Opinion on Biological Therapy(2016) 16(7): 903-915.
Kopp, et al., "Clinical Improvement in Psoriasis With Specific Targeting of Interleukin-23," Nature (2015) 521:222-226(1-15).
Koutruba, et al. "Review of Ustekinumab, an Interleukin-12 and Interleukin-23 Inhibitor Used for the Treatment of Plaque Psoriasis," Therapeutics and Clinical Risk Management (2010) 6:123-141.
Kundu, et al. "Selective neutralization of IL-12 p40 monomer induces death in prostate cancer cells via IL-12-IFN-β." Proceedings of the National Academy of Sciences 114, No. 43 (2017): 11482-11487.
Lasek, et al., "Interleukin 12: Still a Promising Candidate for Tumor Immunotherapy?" Cancer Immunol Immunother (2014) 63:419-35.
Leahy, et al. "Structure of a fibronectin type III domain from tenascin phased by MAD analysis of the selenomethionyl protein." Science 258, No. 5084 (1992): 987-991.
Leong et al., "Optimized expression and specific activity of IL-12 by directed molecular evolution," PNAS Feb. 4, 2003 vol. 100 No. 3 1163-1168.
Liang, et al., "IL-23 Receptor Expression on γδT Cells Correlates with Their Enhancing or Suppressive Effects on Autoreactive T Cells in Experimental Autoimmune Uveitis," The Journal of Immunology (2013) 191(3):1118-1125.
Lieschke et al., "Biactive murine and human interleukin-12 fusion proteins which retain antitumor activity in vivo," Nature Biotechnology (1997) 16:35.
Littman, et al., "Th17 and Regulatory T Cells in Mediating and Restraining Inflammation," Cell (2010) 140:845-858.
Li-Weber, et al. "Vitamin E inhibits CD95 ligand expression and protects T cells from activation-induced cell death." The Journal of clinical investigation 110, No. 5 (2002): 681-690.
Lo, et al., "Effector-attenuating Substitutions That Maintain Antibody Stability and Reduce Toxicity in Mic," J Biological Chermistry vol. 292 • No. 9 • Mar. 3, 2017.
Low, et al., "Oral and pulmonary delivery of FSH-Fc fusion proteins via neonatal Fc receptor-mediated transcytosis," Human Reproduction (2005) 20(7):1805-1813.
Luo et al., Structural Basis for the Dual Recognition of Il-12 and Il-23 by Ustekinumab Journal of Molecular Biology (2010) 402:797-812.
Lupardus, et al. The Structure of Interleukin-23 Reveals the Molecular Basis of P40 Subunit Sharing With Interleukin-12, Journal of Molecular Biology (2008) 382(4):931-941.
Matrosovich, et al. "Solid-phase assays of receptor-binding specificity." Influenza Virus: Methods and Protocols (2012): 71-94.
Mattner, et al., "Genetically Resistant Mice Lacking Interleukin-12 are Susceptible to Infection With Leishmania Major and Mount a Polarized Th2 Cell Response," European Journal of Immunology (1996) 26:1553-1559.
Merchant et al., "An efficient route to human bispecific IgG," Nature Biotechnology vol. 16:677 ULY 1998.
Morin, et al. "Collaboration gets the most out of software." elife 2 (2013): e01456.
Moore et al., "A robust heterodimeric Fc platform engineered for efficient development of bispecific antibodies of multiple formats," Methods 154 (2019) 38-50.
Morrison, et al. "Structural determinants of human IgG function." The Immunologist 2, No. 4 (1994): 119-124.
Munson, et al. "Ligand: a versatile computerized approach for characterization of ligand-binding systems." Analytical biochemistry 107, No. 1 (1980): 220-239.
Murray, "The JAK-STAT Signaling Pathway: Input and Output Integration," Journal of Immunology (2007) 178(5):2623-2629.
Nguyen et al., "Localized Interleukin-12 for Cancer Immunotherapy," Frontiers in Immunology (2020) Article#575597.
Oh, et al. "Secretion of recombinant interleukin-22 by engineered Lactobacillus reuteri reduces fatty liver disease in a mouse model of diet-induced obesity." MSphere 5, No. 3 (2020): 10-1128.
Oppmann, et al. "Novel P19 Protein Engages Il-12p40 to Form a Cytokine, Il-23, With Biological Activities Similar as Well as Distinct From Il-12," Cell (2000) 13:715-725.
Pardoll, Drew M. "The blockade of immune checkpoints in cancer immunotherapy." Nature reviews cancer 12, No. 4 (2012): 252-264.
Parham, et al., "A Receptor for the Heterodimeric Cytokine Il-23 is Composed of Il-12rbeta1 and a Novel Cytokine Receptor Subunit, Il-23r," The Journal of Immunology (2002) 168(11):5699-5708.
Pasche, et al., "The Antibody-based Delivery of Interleukin-12 to the Tumor Neovasculature Eradicates Murine Models of Cancer in Combination With Paclitaxel," Cancer Therapy: Preclinical (2012) 18(15):4092-4103.
Application No. PCT/US2021/027838, International Search Report and Written Opinion, mailed Oct. 31, 2021, 12 pages.
Application No. PCT/US2022/078439, International Search Report and Written Opinion, mailed Jul. 10, 2023, 12 pages.
Application No. PCT/US2022/078465, International Preliminary Report on Patentability, Mailed on May 2, 2024, 10 pages.
Application No. PCT/US2022/078465, International Search Report and Written Opinion, Mailed on Jul. 11, 2023, 14 pages.
Application No. PCT/US2022/078465, "Invitation to Pay Additional Fees and, Where Applicable, Protest Fee", Apr. 3, 2023, 3 pages.
Application No. PCT/US2023/077331, International Search Report and the Written Opinion, Mailed on Feb. 26, 2024, 15 pages.
Pegram, et al., "Tumor-targeted T Cells Modified to Secrete Il-12 Eradicate Systemic Tumors Without Need for Prior Conditioning," Blood (2012)119(18):4133-4141.
Pegram, et al. "CD28z cars and armored cars." The Cancer Journal 20, No. 2 (2014): 127-133.
Peng et al., "A Single-Chain IL-12 IgG3 Antibody Fusion Protein Retains Antibody Specificity and IL-12 Bioactivity and Demonstrates Antitumor Activity," The Journal of Immunology, 1999, 163: 250-258.
Pflanz, et al. "IL-27, a heterodimeric cytokine composed of EBI3 and p28 protein, induces proliferation of naive CD4+ T cells." Immunity 16, No. 6 (2002): 779-790.

(56) References Cited

OTHER PUBLICATIONS

Presky, et al., "A Functional Interleukin 12 Receptor Complex is Composed of Two Beta-type Cytokine Receptor Subunits," Proceedings of the National Academy of Sciences (1996) 93(24):14002-14007.
Rath et al., "Fc-fusion proteins and FcRn: structural insights for longer-lasting and more effective therapeutics," Crit Rev Biotechnol, Early Online: 1-20.
Riddell, et al. "Adoptive therapy with chimeric antigen receptor-modified T cells of defined subset composition." The Cancer Journal 20, No. 2 (2014): 141-144.
Ridgway, et al., 'Knobs-into-holes' Engineering of Antibody Ch3 Domains for Heavy Chain Heterodimerization, Protein Engineering, Design and Selection (1996) 9(7):617-621.
Riethmueller, et al. "Proteolytic origin of the soluble human IL-6R in vivo and a decisive role of N-glycosylation." PLoS biology 15, No. 1 (2017): e2000080.
Rossjohn, et al. "T cell antigen receptor recognition of antigen-presenting molecules." Annual review of immunology 33, No. 1 (2015): 169-200.
Sadelain, et al. "The basic principles of chimeric antigen receptor design." Cancer discovery 3, No. 4 (2013): 388-398.
Sambrook, et al. Molecular cloning: a laboratory manual. vol. 1, No. Ed. 4. 2012, 34 pages.
Sasikumar, et al. "Oral immune checkpoint antagonists targeting PD-L1/VISTA or PD-L1/Tim3 for cancer therapy." In AACR annual meeting. 2016.
Scallon et al., "Quantitative in vivo comparisons of the Fcγ receptor-dependent agonist activities of different fucosylation variants of an immunoglobulin G antibody," International Immunopharmacology (2007) 7:761-772.
Schlothauer et al., "Novel human IgG1 and IgG4 Fc-engineered antibodies with completely abolished immune effector functions," Protein Engineering, Design & Selection, 2016, vol. 29 No. 10, pp. 457-466.
Schmidt, "Fusion proteins as biopharmaceuticals—Applications and challenges," Current Opinion in Drug Discovery & Development 2009 12(2): 1367-6733.
Schroder, et al. Non-canonical Interleukin 23 Receptor Complex Assembly: P40 Protein Recruits Interleukin 12 Receptor B1 via Site Ii and Induces P19/interleukin 23 Receptor Interaction via Site III Journal of Biological Chemistry (2015) 290(1):359-370.
Schulich, et al., "The Third Signal Cytokine Il-12 Rescues the Anti-viral Function of Exhausted Hbv-specific Cd8 T Cells," PLOS Pathogens, e1003208 9(3):1-12.
Shi, et al., Cyclos[orin A Inhibits Activation-Induced Cell Death in T-Cell Hybridomas andThymocytes, Nature, vol. 339, Jun. 22, 1989, 625-626.
Skiniotis, et al., "Structural Organization of a Full-length Gp130/lif-r Cytokine Receptor Transmembrane Complex," Molecular Cell (2008) 31:737-748.
Skrombolas, et al., "Characterization of an IL-12 p40/p35 Truncated Fusion Protein That Can Inhibit the Action of IL-12," Journal of Interferon & Cytokine Research vol. 35, No. 9, 2015.
Steidler, et al. "Biological containment of genetically modified Lactococcus lactis for intestinal delivery of human interleukin 10." Nature biotechnology 21, No. 7 (2003): 785-789.
Strohl, "Optimization of Fc-mediated effector functions of monoclonal antibodies," Current Opinion in Biotechnology 2009, 20:685-691.
Szabo, et al. "Regulation of the interleukin (IL)-12R 2 subunit expression in developing T helper 1 (Th1) and Th2 cells." The Journal of experimental medicine 185, No. 5 (1997): 817-824.
Takeshita, et al. "Cloning of the γ chain of the human IL-2 receptor." Science 257, No. 5068 (1992): 379-382.
Tamura, et al., "Intratumoral Delivery of Interleukin 12 Expression Plasmids With in Vivo Electroporation is Effective for Colon and Renal Cancer," Human Gene Therapy (2001) 12:1265-1276.
Thul, et al. "A subcellular map of the human proteome." Science 356, No. 6340 (2017): eaal3321.
Trinchieri, "Interleukin-12 and the Regulation of Innate Resistance and Adaptive Immunity," Nature Reviews Immunology (2003) 3(2):133-146.
Tseng, et al. "Anti-CD47 antibody-mediated phagocytosis of cancer by macrophages primes an effective antitumor T-cell response." Proceedings of the National Academy of Sciences 110, No. 27 (2013): 11103-11108.
Tugues et al., "New insights into IL-12-mediated tumor suppression," Cell Death and Differentiation (2015) 22, 237-246.
Valeich et al., "Taking the Hinge off: An Approach to Effector-Less Monoclonal Antibodies," Antibodies {2020), 9: 50.
Vance, et al. "Listening to each other: Infectious disease and cancer immunology." Science immunology 2, No. 7 (2017): eaai9339.
Vazquez-Lombardi et al., "Molecular Engineering of Therapeutic Cytokines," Antibodies (2013) 2: 426-451.
Vignali, et al., "Il-12 Family Cytokines: Immunological Playmakers," Nature Immunology (2012) 13(8):722-728.
Villarino, et al., "Mechanisms of Jak/stat Signaling in Immunity and Disease," The Journal of Immunology (2015) 194(1):21-27.
Von Heijne, Gunnar, ed. Sequence analysis in molecular biology: treasure trove or trivial pursuit. Elsevier, 2012.; TIBS 13, Oct. 1988, 1 page.
Vonrhein, et al. "Automated structure solution with autoSHARP." Macromolecular Crystallography Protocols: vol. 2: Structure Determination (2007): 215-230.
Wang et al., "IgG Fc engineering to modulate antibody effector functions," Protein Cell 2018, 9(1):63-73.
Wang, et al., "A Novel IL-23p19/Ebi3 (IL-39) Cytokine Mediates Inflammation in Lupus-like Mice," European Journal of Immunology (2016) 46:1343-1350.
Wang, et al., "Structural Biology of Shared Cytokine Receptors," Annual Review of Immunology (2009)27:29-60.
Wang, et al. "Selection of pd1/pd-l1 x-aptamers." Biochimie 145 (2018): 125-130.
Watford, et al., "Signaling by IL-12 and IL-23 and the Immunoregulatory Roles of STAT4," Immunological Reviews (2004) 202:139-156.
Weiss et al., "Immunotherapy of Cancer by IL-12-based Cytokine Combinations," Expert Opin Biol Ther. Nov. 2007 ; 7(11): 1705-1721.
Wojno, et al., "The Immunobiology of the Interleukin-12 Family: Room for Discovery," Immunity (2019) 50(4):851-870.
Woo, et al. "Immune inhibitory molecules LAG-3 and PD-1 synergistically regulate T-cell function to promote tumoral immune escape." Cancer research 72, No. 4 (2012): 917-927.
Wu, et al. "Immunotherapies: the blockade of inhibitory signals." International journal of biological sciences 8, No. 10 (2012): 1420.
Xue, et al. "Next-generation cytokines for cancer immunotherapy," Antibody Therapeutics, 2021, vol. 4, No. 2 123-133.
Yen, et al. "IL-23 is essential for T cell-mediated colitis and promotes inflammation via IL-17 and IL-6." The Journal of clinical investigation 116, No. 5 (2006): 1310-1316.
Yeste, et al. "IL-21 induces IL-22 production in CD4+ T cells." Nature communications 5, No. 1 (2014): 1-13.
Yodoi, et al. "TCGF (IL 2)-receptor inducing factor (s). I. Regulation of IL 2 receptor on a natural killer-like cell line (YT cells)." Journal of immunology (Baltimore, MD.: 1950) 134, No. 3 (1985): 1623-1630.
Yoon, et alNPL. "Charged residues dominate a unique interlocking topography in the heterodimeric cytokine interleukin-12." The EMBO journal (2000).
Yoshimoto, et al. "IL-12 up-regulates IL-18 receptor expression on T cells, Th1 cells, and B cells: synergism with IL-18 for IFN-γ production." The Journal of Immunology 161, No. 7 (1998): 3400-3407.
Zhou, et al., IL-6 programs T (H)-17 cell differentiation by promoting sequential engagement of the IL-21 and IL-23 pathways., 2007, 8. DOI: https://doi. org/10.1038/ni1488. PMID: https://www. ncbi. nlm. nih. gov/pubmed/17581537 (6): 967-974.
Zhou, Fang. "Molecular mechanisms of IFN-γ to up-regulate MHC class I antigen processing and presentation." International reviews of immunology 28, No. 3-4 (2009): 239-260.

(56) References Cited

OTHER PUBLICATIONS

Zhu, et al. "Differentiation of effector CD4 T cell populations." Annual review of immunology 28, No. 1 (2009): 445-489.
Zitvogel, et al. "Cancer immunotherapy of established tumors with IL-12. Effective delivery by genetically engineered fibroblasts." Journal of immunology (Baltimore, MD.: 1950) 155, No. 3 (1995): 1393-1403.

* cited by examiner

```
P29460 IL12B_HUMAN    1   MCHQQLVISWFSLVFLASPLVAIWELKKDVYVVELDWYPDAPGEMVVLTCDTPEEDGITW   60
Q3ZAX5 Q3ZAX5_MOUSE   1   MCPQKLTISWFAIVLLVSPLMAMWELEKDVYVVVEVDWTPDAPGETVNLTCDTPEEDDITW  60
                          **  : :**** :* :*   :*:*** ****:*  *****  ****:********* ***

P29460 IL12B_HUMAN    61  TLDQSSEVLGSGKTLTIQVKEFGDAGQYTCHKGGEVLSHSLLLLHKKEDGIWSTDILKDQ  120
Q3ZAX5 Q3ZAX5_MOUSE  61  TSDQRHGVIGSGKTLTITVKEFLDAGQYTCHKGGETLSHSHLLLHKKENGIWSTEILKNF  120
                          * **   *:******** **** ************ ****:*** ****:*****:***:

P29460 IL12B_HUMAN   121  KEPKNKTFLRCEAKNYSGRFTCWWLTTISTDLTFSVKSSRGSSDPQGVTCGAATLSAERV  180
Q3ZAX5 Q3ZAX5_MOUSE 121  ----KNKTFLKCEAPNYSGRFTCSWLVQRNMDLKFNIKSSSDPDSRAVTCGMASLSAEKV  177
                              ****** *** ******* **:  . **:.:*** **..  .****  *****:*

P29460 IL12B_HUMAN   181  RGDNKEYE-YSVECQEDSACPAAEESLPIEVMVDAVHKLKYENYTSSFFIRDIIKPDPPK  239
Q3ZAX5 Q3ZAX5_MOUSE 178  TLDQRDYEKYSVSCQEDVTCPTAEETLPIELALEARQQNKYENYSTSFFIRDIIKPDPPK  237
                          : :.:*** ***.**** :**:*** ****:.::*.::***** :*************

P29460 IL12B_HUMAN   240  NLQLKPLKNSRQVEVSWEYPDTWSTPHSYFSLTFCVQVQGKSKREKK------DRVFT  291
Q3ZAX5 Q3ZAX5_MOUSE 238  NLQMKPLKNS-QVEVSWEYPDSWSTPHSYFSLKFFVRIQRKKEKMKETEEGCNQKGAFLV 296
                          ***:****** **********:*********.* ** :*.***:*        :  *

P29460 IL12B_HUMAN   292  DKTSATVICRKKNASISVRAQDRYYSSSWSEWASVPCS---        328
Q3ZAX5 Q3ZAX5_MOUSE 297  EKTSTEVQC-KGGNVCVQAQDRYYNSSCSKWACVPCRVRS         335
                          :***: * * *   .*. .*****.** *.** ***

FIG. 7
```

```
P29459 IL12A_HUMAN    1   MCHQQLVISWFSLVFLASPLVAIWELKKDVYVVELDWYPDAPGEMVVLTCDTPEEDGITW   60
P43431 IL12A_MOUSE    1   MCQSRYLLFLATLALLNHLSLARVIPVSGP----ARCLSQSRNLKTTTDDMVKTAREKLK   56
                          **:.: *:**.:.****.*:.:**:..**:        :**..:*:. .**:**:**.*

P29459 IL12A_HUMAN    61  FYPCTSEEIDHEDITKDKTSTVEACLPLELTKNESCLNSRETSFITNGSCLASRKTSFMM   120
P43431 IL12A_MOUSE    57  HYSCTAEDIDHEDITRDQTSTLKTCLPLELHKNESCLPLELHKNESCLATRETSSTTRGSCLPPQKTSLMM   116
                          .*.**.:********:*:***::.******.*****   .:***** :*:**.:*:**

P29459 IL12A_HUMAN    121 ALCLSSIYEDLKMYQVEFKTMNAKLLMDPKRQIFLDQNMLAVIDELMQALNFNSETVPQK   180
P43431 IL12A_MOUSE    117 TLCLGSIYEDLKMYQTEFQAINAALQNHNHQQIIDKGMLVAIDELMQSLNHNGETLRQK   176
                          :***.*********.**:::**.*   :*:::**: :.:**.*********:**.*.**

P29459 IL12A_HUMAN    181 SSLEEPDFYKTKIKLCILLHAFRIRAVTIDRVMSYLNAS   219
P43431 IL12A_MOUSE    177 PPVGEADPYRVKNKLCILLHAFSTRVVTINRVMGYLSSA   215
                          .. *  * *:.*:*:******. *.***:****.**.:*
```

FIG. 8

HETERODIMERIC FC CYTOKINES AND USES THEREOF

CROSS-REFERENCE TO RELATED PATENT APPLICATIONS

The present application is a continuation of U.S. application Ser. No. 18/516,047, filed Nov. 21, 2023, which is a continuation application of International Patent Application No. PCT/US2022/078465, filed Oct. 20, 2022, which claims benefit of priority to U.S. Provisional Patent Application No. 63/257,913, filed Oct. 20, 2021, the disclosures of which are hereby incorporated by reference in their entirety for all purposes.

REFERENCE TO AN ELECTRONIC SEQUENCE LISTING

The contents of the electronic sequence listing (106249-1400893-007120US_Sequence.xml; size: 312,158 bytes; and date of creation: Nov. 21, 2023) is herein incorporated by reference in its entirety.

BACKGROUND OF THE INVENTION

Receptors for cytokines are typically multimers of cell surface expressed proteins that stimulate signaling via the interaction of their intracellular domains. Cytokines act as specific ligands for the extracellular domains of cytokine receptor subunits and facilitate the multimerization of such receptor subunits so as to bring the intracellular domains of such cytokine receptor subunits into proximity such that intracellular signaling may occur. Certain cytokine receptor subunits are shared among different cytokines and the nature of the cytokine determines which receptor subunits are multimerized to form the cytokine receptor complex and the intracellular signaling pattern that results. Cytokines thus act to bridge individual receptor subunits into a receptor complex that results in intracellular signaling.

The intracellular domains of cytokine receptor subunits possess JAK binding domains which are typically located in the box1/box2 region of the intracellular domain of the cytokine receptor subunit near the interior surface of the cell membrane. Intracellular JAK kinases associate with these JAK binding domains. When the intracellular domains of receptor subunits are brought into proximity, typically by the binding of the cognate ligand for the receptor to the extracellular domains of the receptor subunits, the JAKs phosphorylate each other. Four Janus kinases have been identified in mammalian cells: JAK1, JAK2, JAK3 and TYK2. Ihle, et al. (1995) Nature 377 (6550): 591-4, 1995: O'Shea and Plenge (2012) Immunity 36 (4): 542-50. The phosphorylation of the JAK induces a conformational change in the JAK providing the ability to further phosphorylate other intracellular proteins which initiates a cascade that results in activation of multiple intracellular factors which transduce the intracellular signal associated with the receptor. The resulting intracellular responses, such as gene transcription, are frequently collectively referred to as downstream signaling.

In many instances, the proteins which are phosphorylated by the JAKs are members of the signal transducer and activator of transcription (STAT) protein family. Seven members of the mammalian STAT family have been identified to date: STAT1, STAT2, STAT3, STAT4, STAT5a STAT5b, and STAT6. Delgoffe, et al., (2011) Curr Opin Immunol. 23 (5): 632-8: Levy and Darnell (2002) Nat Rev Mol Cell Biol. 3 (9): 651-62 and Murray, (2007) J Immunol. 178 (5): 2623-9. The selective interplay of activated JAK and STAT proteins, collectively referred to as the JAK/STAT pathway, provide for a wide variety of intracellular responses observed in response to cytokine binding.

Human IL-12 (hIL-12) is a heterodimeric cytokine comprised of the human p35 (also referred to as hIL-12A, Uniprot Ref. 29459) and human p40 (also referred to as hIL-12B, Uniprot Ref. 29460) subunits. The hIL-12 heterodimer is also referred to as p70. hIL-12 is produced by dendritic cells, macrophages and neutrophils. hIL-12 is typically identified as a T cell stimulating factor which can stimulate the proliferation and activation of T cells. hIL12 stimulates the production of IFNγ and TNFα and modulates the cytotoxic activity of NK and CD8+ cytotoxic T cells. hIL12 was first identified and referred to as cytotoxic lymphocyte maturation factor. Stern, et al (1990) Proc Natl Acad Sci USA 87:6808-6812 and Gately, et al. U.S. Pat. No. 6,683,046 issued Jan. 27, 2004. hIL-12 is also involved in immune cell differentiation in particular the differentiation of naïve T cells into Th1 (CD4+) cells. hIL-12 is also reported to provide anti-angiogenic activity. Since its discovery more than 30 years ago, hIL-12 has been proposed and evaluated for use in the treatment of a variety of neoplastic diseases, viral and bacterial infections. See, e.g. Lasek, et al (2014) Cancer Immunol Immunother (2014) 63:419-435.

hIL-12 binds to the hIL-12 receptor, a heterodimeric complex of hIL12 receptor subunit beta-1 (IL-12Rβ1, also referred to in the scientific literature as IL-12RB1 or CD212, Uniprot Ref. P42701) and hIL-12 receptor subunit beta-2 (hIL-12Rβ2 also referred to in the scientific literature as hIL-12Rβ2, Uniprot Ref. Q99665). hIL12Rβ1 and hIL12Rβ2 are members of the class I cytokine receptor family and have homology to gp130. The expression of hIL12Rβ1 and hIL12Rβ2 are upregulated in response to hIL-12 with the majority of hIL12Rβ2 being found on activated T cells.

hIL12Rβ1 is a constitutively expressed type I transmembrane protein that belongs to the hemopoietin receptor superfamily. hIL12Rβ1 binds with low affinity to hIL-12. hIL12Rβ1 is required for binding to the hIL-12p40 subunit and it is associated with the Janus kinase (Jak) family member Tyk-2. The binding IL12p40 and IL12p35 subunits of IL12 to IL12Rβ1 and IL12Rβ2, respectively, results in the dimerization of IL-12Rβ1 and IL-12Rβ2. In response to the dimerization of IL-12Rβ1 and IL-12Rβ2, Jak-2 and Tyk-2 are transphosphorylated, further activating Jak2 and Tyk2 kinase activity which results in phosphorylation of the IL12Rβ1 and IL12Rβ 2 intracellular domains. The phosphorylated intracellular signaling domain of IL12Rβ2 provides a binding site for STAT4. STAT4 binds to phosphorylated IL-12Rβ2 and is subsequently phosphorylated. Phosphorylated STAT4 induces dimerization with another phosphorylated STAT4 molecule. The phosphorylated STAT4 homodimers translocate to the nucleus resulting in, among other activities, the promotion of IFN-γ gene transcription. IFN-γ induces the activity and proliferation of macrophages, NK cells, and T cells, which also secrete IL-12.

In addition to forming one of the components of the hIL-12 receptor, hIL-12Rβ1 is also a component of the hIL-23 receptor. The hIL-23 receptor is a heterodimer of hIL-23R (Uniprot Ref. Q5VWK5) and hIL-12Rβ1. hIL-23 binds hIL-23R with an affinity of 44 nanomolar (nM) but binds to hIL-12Rβ1 with a significantly lower affinity of 2 micromolar (μM). There is no apparent direct binding of hIL-23R to hIL12Rβ1, the completion of the hIL-23h:IL-23R:hIL-12Rβ1 complex mediated by the initial formation of the hIL-23:hIL-23R complex which in turn binds to IL12Rβ1. IL23 is a heterodimeric cytokine comprised of the p40) and p19 subunits. Although the IL12 and IL23 receptors share the IL12Rβ1 receptor subunit, the IL12 and IL23 receptors induce distinct downstream signaling patterns. While IL12 has been implicated as useful in the treatment of a variety of neoplastic diseases, IL23 inhibitors (such as ustekinumab, guselkumab, tildrakizumab, and risankizumab) are primarily indicated for the treatment of autoimmune disorders such as psoriatic arthritis and moderate to severe plaque psoriasis.

In addition to forming a subunit of IL12 and IL23, p40 has significant bioactivity. P40 is reported to exist as both a monomer and a disulfide linked homodimer (p80) which has a chemoattractant role for macrophages mediated by IL12Rβ1 alone and may act as an IL-12 and IL-23 antagonist by competing for their receptors. Holscher, C. (2004) Med Microbiology and Immunology 193 (1) 1-17.

IL12 has many properties which suggested its use in the treatment of cancers including the stimulation of IFNγ production by NK cells, enhancement of the cytolytic properties of NK cells and cytotoxic T cells, and inhibition of angiogenesis. IL12 exhibited significant antitumor activity in animal models which led to its evaluation in Phase I and Phase II clinical trials in the treatment of a variety of cancers in the late 1990s. Lasek, et al., supra. While beneficial effects were observed, the significant adverse events observed resulted in termination of the clinical trials. In the ensuing time, a variety of approaches have been evaluated for the use of hIL12 molecules and gene therapy vectors encoding hIL12 but the toxicity associated with these agents has, so far, limited their development to Phase I and Phase II clinical trials and there are no commercially available therapeutic agents comprising IL12.

Because different cell types respond to the binding of ligands to their cognate receptors with different sensitivities, modulation of the affinity of the heterodimeric hIL-12 ligand (or its individual components) for the hIL-12 receptor (or its individual components) relative to wild-type hIL-12 (i.e., comprising wild-type p35 and p40) can stimulate desired activities on target cells while reducing undesired activities on non-target cells. In some embodiments, an hIL-12 partial agonists of the present disclosure comprises a modified p40 subunit polypeptide that provides intracellular signaling characteristic of wt hIL12 on desired cell types, while providing significantly less intracellular signaling on undesired cell types. This is achieved, for example, by contacting the cell with IL12 partial agonists comprising a heterodimeric hIL12Fc mutein with a modified binding affinity for hIL-12Rβ1, or causing different $E_{max}$ for hIL-12Rβ1 as compared to the binding affinity of wild-type or parental hIL-12p40 polypeptide for hIL-12Rβ1.

Glassman, et al. (2021) Cell 184 (4): 983-999 describe the crystal structure of the IL12 and IL23 receptors and describe residues of p40 that interact with the IL12Rβ1 receptor. In particular, Glassman, et al. describe IL12 partial agonists comprising a modified p40 subunit that preserved CD8+ T cell IFNγ induction and tumor cell killing but exhibit reduced activation and cytokine production from NK cells. The stimulation of NK cells is associated with significant systemic side effects such as capillary leak syndrome. IL12 partial agonists that selectively activate CD8+ T cells without significant upregulation of NK cells retain the beneficial antitumor effects of IL12 while mitigating systemic toxicity associated with the activation of NK cells. The IL12 partial agonists produced potent antitumor immunity with reduced toxicity relative to IL-12 in preclinical mouse tumor models.

To maximize the antitumor effect of IL12, it is desirable to provide a sustained systemic level of the cytokine. The in vivo half-life of recombinant human IL12 (rhIL12), while longer than other cytokines such as IL2, remains comparatively short. The half-life of wild-type rhIL-12 following intravenous bolus injection of a single 500 ng/kg dose of rhIL12, the maximum tolerated dose in the study, was observed to be between 5.3 hours and 10.3 hours, Atkins, et al (1997) Clinical Cancer Research 3:409-417. However, the toxicity associated with wt hIL12 treatment has been an impediment to the development of extended delivery forms of IL12. As previously noted, sustained and targeted delivery of IL12 has been evaluated but has not yet provided a successful IL12 therapeutic agent.

Fc fusion conjugates have been shown to increase the systemic half-life of biopharmaceuticals, and thus the biopharmaceutical product can require less frequent administration. Engineered Fc domains have been extensively investigated in the context of therapeutic antibodies, particularly bi-specific antibodies, with numerous Fc engineered antibodies being developed and commercialized. See, e.g. Czajkowsky, et al. (2012) EMBO Mol Med 4:1015-1028. Fc binds to the neonatal Fc receptor (FcRn) on endothelial cells that line the blood vessels, and, upon binding, the Fc fusion molecule is protected from degradation and re-released into the circulation, keeping the molecule in circulation longer. These properties of the Fc domain are believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. A variety of modifications to the Fc domain(s), referred to as Fc engineering, have been developed that provide for particular beneficial features to the Fc domain as modulation of effector function (Wang, et al. (2018) Protein Cell 9 (1): 63-73) For example, Zalevsky, et al. describe the amino acid substitutions M428L and N434S (EU numbering), frequently referred to as "LS" modification, to extend half-life. Zalevsky, et al. (2010) Nature Biotechnology 28:157-159.

Fc conjugates of IL12 have been described in the literature. For example, Gillies, et al. described a IL12 Fc conjugate with each of the wild-type p35 and wild-type P40 subunits expressed as a fusion protein with an Fc subunit. Gillies, et al. (1998) J. Immunol. 160:6195-6203 and Gillies, et al. U.S. Pat. No. 6,838,260 issued Jan. 4, 2005. Similarly, Kim et al, (PCT/KR2017/008676 published Feb. 15, 2018 as WO/2018/030806; U.S. Pat. No. 11,078,249 issued Aug. 3, 2021: U.S. Pat. No. 10,696,722 issued Jun. 30, 2020) describe IL12 Fc conjugate where the p35 and P40 subunits were expressed as a fusion proteins with Fc domains wherein the Fc domains are modified to promote heterodimerization. Cheung, et al. (PCT International Patent Application no PCT/US2019/057721 published Apr. 30, 2020 as WO/2020/086758) and Bigelow, et al (PCT International Patent Application PCT/US2021/028701 published Oct. 28, 2021 qw WO/2021/216916) describe and IL12 Fc conjugates. Bernett, et al. (PCT International Patent Application PCT/US19/54570 published Apr. 9, 2020 as WO/2020/072821, United States Patent Publication US 2020/0216509 published Jul. 9, 2020: U.S. Pat. No. 11,358,999 issued Jun. 14, 2022) describe IL2 Fc conjugates comprising wild-type and modified p35 and P40 subunits. See also, Epstein, et al. Chinese Patent Application Serial No CN201410597561.4A published May 4, 2016

The present disclosure provides IL12 and IL23 muteins as partial agonists comprising modified human p40 molecules that associate with human p35 (hP35) and human P19 (hP19) to form modified hIL-12 and IL23 partial agonists wherein the individual components of IL12 and IL23 muteins are linked to engineered Fc domains. The IL12 and IL23 agonists of the present disclosure retain many beneficial properties of the wild-type parent molecules from which they are derived while mitigating associated toxicities associated with wild type IL12 and IL23.

SUMMARY OF THE DISCLOSURE

The present disclosure is directed to methods and compositions that modulate the multiple effects of hIL-12 binding so that desired therapeutic signaling occurs, particularly in a desired cellular or tissue subtype, while minimizing undesired activity and/or intracellular signaling in other cellular or tissue subtypes. In some embodiments, the present disclosure provides heterodimeric hIL12Fc muteins having an extended duration of action in vivo in a mammalian subject.

In some embodiments the present disclosure provides heterodimeric hIL12Fc muteins comprising a heterodimeric protein comprising first and second fusion proteins, the first fusion protein comprising a human p35 polypeptide having 90% or greater, alternatively 91% or greater, alternatively 92% or greater, alternatively 93% or greater, alternatively 94% or greater alternatively 95% or greater, alternatively 96% or greater, alternatively 97% or greater, alternatively 98% or greater, alternatively 99% or greater, alternatively 100% sequence identity to the SEQ ID NO: 2 (wild type mature hP35), a first upper hinge region of a human immunoglobulin molecule, and a first Fc domain of a human immunoglobulin molecule ("hP35Fc") and the second fusion protein comprising a human p40 mutein ("hP40M") polypeptide having 90% or greater, alternatively 91% or greater, alternatively 92% or greater, alternatively 93% or greater, alternatively 94% or greater alternatively 95% or greater, alternatively 96% or greater, alternatively 97% or greater, alternatively 98% or greater, alternatively 99% or greater, sequence identity to the SEQ ID NO: 4 (wild type mature hP40), the human p40 mutein comprising one or more amino acid substitutions at one or more positions selected from the group consisting of W37, P39, D40, A41, K80, E81, F82, K106, E108, D115, H216, K217, L218, and K219 (numbered in accordance with SEQ ID NO: 3), a second upper hinge region of a human immunoglobulin molecule, and a second Fc domain of a human immunoglobulin molecule ("hP40MFc") wherein the first and second Fc domains are modified to promote heterodimerization.

In some embodiments the present disclosure provides heterodimeric hIL12Fc muteins comprising a human p40 mutein ("hP40M") polypeptide comprising one or more amino acid substitutions at one or more positions selected from the group consisting of W37, P39, D40, A41, K80, E81, F82, K106, E108, D115, H216, K217, L218, K219 and K282 (numbered in accordance with SEQ ID NO: 3). In some embodiments the present disclosure provides heterodimeric hIL12Fc muteins comprising a human p40) mutein ("hP40M") polypeptide comprising one or more amino acid substitutions at one or more positions selected from the group consisting of E81, F82, K106, and K217 (numbered in accordance with SEQ ID NO: 3). In some embodiments the present disclosure provides heterodimeric hIL12Fc muteins comprising a human p40 mutein ("hP40M") polypeptide comprising one or more amino acid substitutions at one or more positions selected from the group consisting of E81, F82, K106, and K217 (numbered in accordance with SEQ ID NO: 3). In some embodiments the present disclosure provides heterodimeric hIL12Fc muteins comprising a human p40) mutein ("hP40M") polypeptide that comprises a set of amino acid substitutions (numbered in accordance with SEQ ID NO: 3) selected from the group consisting of: E81A/F82A; E81A/F82A/K106A; and E81A/F82A/K106A/K217A.

In some embodiments the present disclosure provides heterodimeric hIL12Fc muteins comprising a human p40) mutein ("hP40M") polypeptide comprising one or more amino acid substitutions at one or more positions selected from the group consisting of E81, F82, K106, and K217 further comprising an amino acid substitution at position K282 (numbered in accordance with SEQ ID NO: 3). In some embodiments the present disclosure provides heterodimeric hIL12Fc muteins comprising a human p40) mutein ("hP40M") polypeptide that comprises a set of amino acid substitutions (numbered in accordance with SEQ ID NO: 3) selected from the group consisting of: E81A/F82A/K282A; E81A/F82A/K282G; E81A/F82A/K282N; E81A/F82A/K282Q; E81A/F82A/K106A; E81A/F82A/K106A/K282A; E81A/F82A/K106A/K282G; E81A/F82A/K106A/K282N; E81A/F82A/K106A/K282Q; E81A/F82A/K106A/K217A/K282A; E81A/F82A/K106A/K217A/K282Q; E81A/F82A/K106A/K217A/K282N; and E81A/F82A/K106A/K217A/K282G In some embodiments the present disclosure provides heterodimeric hIL12Fc muteins comprising a human p40) mutein ("hP40M") polypeptide wherein the hP40 mutein is selected from the group consisting of SEQ ID NOS: 4, 6, 8, 10, 155, 156, 157, 158, 159, 160, 161, and 162.

In some embodiments the modifications to the Fc domains of the heterodimeric hIL12Fc mutein to promote heterodimerization. In some embodiments the modifications to the Fc domains of the heterodimeric hIL12Fc mutein to promote heterodimerization are complementary "knob-into-hole" mutations. In some embodiments, the modifications of the Fc domains to promote heterodimerization of the hP35Fc and hP40MFc domains comprises the amino acid substitution T366W ("knob") in the first domain and the amino acid substitutions T366S/L368A/Y407V ("hole") in the second domain.

In some embodiments the present disclosure provides a heterodimeric hIL12Fc mutein wherein the hP35Fc and hP40MFc polypeptides of the heterodimeric hIL12Fc mutein are covalently linked via one disulfide bond, optionally two disulfide bonds, optionally three disulfide bonds, or optionally four disulfide bonds. In some embodiments, the hP35Fc and hP40MFc are covalently linked via a disulfide bond between the sulfhydryl group of amino acid C96 of the hP35 domain of the hP35Fc and the sulfhydryl group of amino acid C199 of the hP40M domain of the hP40MFc. In some embodiments, the hP35Fc and hP40MFc are covalently linked via a disulfide bond between the sulfhydryl group of amino acid C226 of the lower hinge domain of the hP35Fc and the sulfhydryl group of amino acid C226 of the lower hinge domain of the hP40MFc. In some embodiments, the hP35Fc and hP40MFc are covalently linked via a disulfide bond between the sulfhydryl group of amino acid C229 of the lower hinge domain of the hP35Fc and the sulfhydryl group of amino acid C229 of the lower hinge domain of the hP40MFc. In some embodiments, a first Fc domain comprises the amino acid substitution S354C, and the second Fc domain comprises the amino acid substitution Y349C. In some embodiments, the heterodimeric hIL12Fc mutein comprises a first Fc domain comprising the amino acid substitution S354C and the second Fc domain comprising the amino acid substitution Y349C and wherein the hP35Fc and hP40MFc domains are linked via a disulfide bond between the S354C of the first Fc domain and Y349C of the second Fc domain. In some embodiments, the hP35Fc and hP40MFc of the heterodimeric hIL12Fc mutein are covalently linked via one or more, optionally two or more optionally three or more disulfide bonds, optionally four or more disulfide bonds between the side chains of the following cysteine residue pairs: (a) C96 of the hP35 and C199 of the hP40M; (b) between C226 of the first Fc monomer and the C226 of the second Fc monomer, (c) between C229 of the first Fc monomer and the C229 of the second Fc monomer; and (d) between S354C of the first Fc domain comprising a S354C amino acid substitution and Y349C of the second Fc domain comprising a Y349C amino acid substitution.

In some embodiments the present disclosure provides a heterodimeric hIL12Fc mutein wherein either or both of the hP35Fc and hP40MFc subunits of the heterodimeric hIL12Fc mutein comprise one or more amino acid substitutions to reduce effector function. In some embodiments, the hP35Fc and/or hP40MFc polypeptides comprise a set of amino acid substitutions selected from the group consisting of: (a) L234A/L235A/P329A ("LALAPA"); L234A/L235A/P329G ("LALAPG"); L234A/L235E/G237A/A330S/P331S ("AEASS"); and L234F/L235E/P331S ("FES").

In some embodiments the present disclosure provides a heterodimeric hIL12Fc mutein wherein either or both of the hP35Fc and hP40MFc subunits of the heterodimeric hIL12Fc mutein comprises an amino acid substitution at position C220 (EU numbering) of the upper hinge domain to eliminate the sulfhydryl side chain. In some embodiments, the substitution at position C220 is C220S (EU numbering) substitution.

In some embodiments the present disclosure provides a heterodimeric hIL12Fc mutein wherein either or both of the hP35Fc and hP40MFc subunits of the heterodimeric hIL12Fc mutein comprises amino acid substitutions in the Fc domain at positions M428 and/or N434 (EU numbering). In some embodiments the amino acid substitutions at positions M428 and/or N434 are M428L and/or N434S.

In some embodiments the present disclosure provides a heterodimeric hIL12Fc mutein wherein either or both of the hP35Fc and hP40MFc subunits of the heterodimeric hIL12Fc mutein comprises amino acid deletions in the Fc domain at positions G446 and/or K447 (EU numbering).

In some embodiments the present disclosure provides a heterodimeric hIL12Fc mutein wherein either or both of the hP35Fc and hP40MFc subunits of the heterodimeric hIL12Fc mutein are PEGylated. In some embodiments, either or both of the hP35Fc and hP40MFc subunits are PEGylated via the sulfhydryl side chain of amino acid C220 of the upper hinge.

In some embodiments the present disclosure provides a heterodimeric hIL12Fc mutein wherein the heterodimeric hIL12Fc mutein: (i) induces hIL-12 signaling in CD8+ T cells; and (ii) has decreased (for example, at least about a 10%, 20%, 30%, 40%, 50%, 60%, or 70% decreased) hIL-12 signaling in NK cells compared to a wildtype hIL-12 comprising a p40 polypeptide lacking the one or more amino acid substitutions.

In some embodiments the present disclosure provides a heterodimeric hIL12Fc mutein wherein the heterodimeric hIL12Fc mutein activates interferon gamma (IFNγ) in CD8+ T cells and has decreased IFNγ signaling in CD8+ T cells, for example, at least about a 10%, 20%, 30%, 40%, 50%, 60%, or 70% decrease, compared to the wildtype IL12 comprising a p40 subunit lacking such amino acid substitutions.

In some embodiments the present disclosure provides a heterodimeric hIL12Fc mutein wherein the heterodimeric hIL12Fc mutein has a reduced binding affinity, for example, at least about a 10%, 20%, 30%, 40%, 50%, 60%, or 70% reduction, for hIL-12Rβ1 compared to the binding affinity of a wildtype IL12.

In some embodiments the present disclosure provides a heterodimeric hIL12Fc mutein wherein the heterodimeric hIL12Fc mutein has decreased STAT-4 mediated signaling, for example, at least about a 10%, 20%, 30%, 40%, 50%, 60%, or 70% decrease, compared to wildtype hIL12 in a when evaluated in a mammalian cell-based assay.

In some embodiments the present disclosure provides heterodimeric hIL23Fc muteins comprising a first fusion protein comprising a human p19 polypeptide having 90% or greater, alternatively 91% or greater, alternatively 92% or greater, alternatively 93% or greater, alternatively 94% or greater alternatively 95% or greater, alternatively 96% or greater, alternatively 97% or greater, alternatively 98% or greater, alternatively 99% or greater, alternatively 100% sequence identity to SEQ ID NO:178, a first upper hinge region of a human immunoglobulin molecule, and a first Fc domain of a human immunoglobulin molecule ("hP19Fc") and a second fusion protein comprising a human p40 mutein polypeptide having 90% or greater, alternatively 91% or greater, alternatively 92% or greater, alternatively 93% or greater, alternatively 94% or greater alternatively 95% or greater, alternatively 96% or greater, alternatively 97% or greater, alternatively 98% or greater, alternatively 99% or greater, sequence identity to the SEQ ID NO: 4 (wild type mature hP40) comprising one or more amino acid substitutions at one or more positions selected from the group consisting of W37, P39, D40, A41, Q64, K80, E81, F82, A85, K106, E108, D115, H216, K217, L218, and K219 (numbered in accordance with SEQ ID NO: 3), a second upper hinge region of a human immunoglobulin molecule, and a second Fc domain of a human immunoglobulin molecule ("hP40MFc") wherein the first and second Fc domains are modified to promote heterodimerization.

In some embodiments the modifications to the Fc domains of the heterodimeric hIL23Fc mutein to promote heterodimerization are complementary "knob-into-hole" mutations. In some embodiments, the modifications of the Fc domains to promote heterodimerization of the hP19Fc and hP40MFc domains comprises the amino acid substitution T366W ("knob") in the first domain and the amino acid substitutions T366S/L368A/Y407V ("hole") in the second domain.

In some embodiments the present disclosure provides a heterodimeric hIL23Fc mutein wherein the hP19Fc and hP40MFc polypeptides of the hIL23 are covalently linked via one disulfide bond, optionally two disulfide bonds, optionally three disulfide bonds, or optionally four disulfide bonds. In some embodiments, the hP19Fc and hP40MFc are covalently linked via a disulfide bond between the sulfhydryl group of amino acid C76 of the hP19 domain (numbered in accordance with the pro-hP19 sequence comprising the signal peptide, Uniprot Reference No. Q9NPF7) of the hP19Fc and the sulfhydryl group of amino acid C199 of the hP40M domain of the hP40MFc. In some embodiments, the hP19Fc and hP40MFc are covalently linked via a disulfide bond between the sulfhydryl group of amino acid C226 of the hP19Fc and the sulfhydryl group of amino acid C226 of the hP40MFc. In some embodiments, the hP35Fc and hP40MFc are covalently linked via a disulfide bond between the sulfhydryl group of amino acid C229 of the hP19 Fc and the sulfhydryl group of amino acid C229 of the hP40M domain. In some embodiments, a first Fc domain comprises the amino acid substitution S354C and the second Fc domain comprises the amino acid substitution Y349C. In some embodiments, the heterodimeric hIL23Fc mutein comprises a first Fc domain comprising the amino acid substitution S354C and the second Fc domain comprising the amino acid substitution Y349C and wherein the hP19Fc and hP40MFc domains are linked via a disulfide bond between the S354C of the first Fc domain and Y349C of the second Fc domain. In some embodiments, the hP19Fc and hP40MFc of the heterodimeric hIL23Fc mutein are covalently linked via one or more, optionally two or more optionally three or more disulfide bonds, optionally four or more disulfide bonds between the side chains of the following groups of cystine pairs: (a) C76 of the hP19 and C199 of the hP40M; (b) between C226 of the first Fc monomer and the C226 of the second Fc monomer, (c) between C229 of the first Fc monomer and the C229 of the second Fc monomer; and (d) between S354C of the first Fc domain comprising a S354C amino acid substitution and Y349C of the second Fc domain comprising a Y349C amino acid substitution.

In some embodiments the present disclosure provides a heterodimeric hIL23Fc mutein wherein either or both of the hP19Fc and hP40MFc subunits of the heterodimeric hIL23Fc mutein comprise one or more amino acid substitutions to reduce effector function. In some embodiments, the hP19Fc and/or hP40MFc polypeptides comprise a set of amino acid substitutions selected from the group consisting of: (a) L234A/L235A/P329A ("LALAPA"); L234A/L235A/P329G ("LALAPG"); L234A/L235E/G237A/A330S/P331S ("AEASS"); and L234F/L235E/P331S ("FES").

In some embodiments the present disclosure provides a heterodimeric hIL23Fc mutein wherein either or both of the hP19Fc and hP40MFc subunits of the heterodimeric hIL23Fc mutein comprises an amino acid substitution at position C220 (EU numbering) of the upper hinge domain to eliminate the sulfhydryl side chain. In some embodiments, the substitution at position C220 is C220S (EU numbering) substitution.

In some embodiments the present disclosure provides a heterodimeric hIL23Fc mutein wherein either or both of the hP19Fc and hP40MFc subunits of the heterodimeric hIL23Fc mutein comprises amino acid substitutions in the Fc domain at positions M428 and/or N434 (EU numbering). In some embodiments the amino acid substitutions at positions M428 and/or N434 are M428L and/or N434S.

In some embodiments the present disclosure provides a heterodimeric hIL23Fc mutein wherein either or both of the hP19Fc and hP40MFc subunits of the heterodimeric hIL23Fc mutein are PEGylated. In some embodiments, either or both of the hP35Fc and hP40MFc subunits are PEGylated via the sulfhydryl side chain of amino acid C220 of the upper hinge.

In some embodiments the present disclosure provides a heterodimeric hIL23Fc mutein wherein the hP19Fc and hP40MFc polypeptides are covalently linked via one disulfide bond, optionally two disulfide bonds, optionally three disulfide bonds, or optionally four disulfide bonds.

In some embodiments, the present disclosure provides a nucleic acid sequence encoding a polypeptide of the formula #1:

$$\text{hP40M-L1}_a\text{-UH1-Fc1} \quad [1]$$

wherein: hP40M is an human P40 mutein comprising one or more amino acid substitutions at positions selected from the group consisting of positions W37, P39, D40, A41, K80, E81, F82, K106, E108, D115, H216, K217, L218, and K219 numbered in accordance with wild-type pre-human P40 (SEQ ID NO:3); L1 is a GSA linker and a is selected from 0 (absent) or 1 (present); UH1 is an upper hinge domain of human immunoglobulin independently selected from the group consisting of the IgG1, IgG2, IgG3 and IgG4 upper hinge, optionally comprising the amino acid substitution C220S (EU numbering); Fc1 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization.

In some embodiments, the present disclosure provides a nucleic acid sequence of the formula #2:

$$\text{hP35-L2}_b\text{-UH2-Fc2} \quad [2]$$

wherein: hP35 is a polypeptide having at least 90%, alternatively at least 91%, alternatively at least 92%, alternatively at least 93%, alternatively at least 94%, alternatively at least 95%, alternatively at least 96%, alternatively at least 97%, alternatively at least 98%, or alternatively at least 99%, or 100% sequence identity to SEQ ID NO:2; L2 is a GSA linker and b is selected from 0 (absent) or 1 (present); UH2 is an upper hinge domain of human immunoglobulin independently selected from the group consisting of the IgG1, IgG2, IgG3 and IgG4 upper hinge, optionally comprising the amino acid substitution C220S (EU numbering); and Fc2 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization.

In some embodiments, the present disclosure provides an expression cassette encoding a heterodimeric hIL12Fc mutein comprising a nucleic acid sequence encoding an hP35Fc polypeptide and a hP40MFc polypeptide operably linked to one or more heterologous nucleic acid sequences, wherein the nucleic acid sequences encoding the hP35Fc polypeptide and hP40MFc polypeptide are: (a) under the control a single promoter and (b) are linked via an intervening sequence that facilitates co-expression. In some embodiments wherein the nucleic acid sequences encoding the hP35Fc polypeptide and hP40MFc polypeptide are linked via an intervening sequence that facilitates co-expression, the nucleic acid sequence encoding the p35Fc polypeptide is 5' relative to the nucleic acid sequence encoding the hP40MFc polypeptide. In some embodiments wherein the nucleic acid sequences encoding the hP35Fc polypeptide and hP40MFc polypeptide are linked via an intervening sequence that facilitates co-expression, the nucleic acid sequence encoding the p40MFc polypeptide is 5' relative to the nucleic acid sequence encoding the hP35Fc polypeptide. In some embodiments, the intervening sequence to facilitate co-expression is an IRES element or a T2A sequence.

In some embodiments, the present disclosure provides an expression cassette encoding a heterodimeric hIL23Fc mutein comprising a nucleic acid sequence encoding hP19Fc polypeptide and a hP40MFc polypeptide operably linked to one or more heterologous nucleic acid sequences, wherein the nucleic acid sequences encoding the hP19Fc polypeptide and hP40MFc polypeptide are: (a) under the control a single promoter and (b) are linked via an intervening sequence that facilitates co-expression. In some embodiments wherein the nucleic acid sequences encoding the hP19Fc polypeptide and hP40MFc polypeptide are linked via an intervening sequence that facilitates co-expression, the nucleic acid sequence encoding the p19Fc polypeptide is 5' relative to the nucleic acid sequence encoding the hP40MFc polypeptide. In some embodiments wherein the nucleic acid sequences encoding the hP19Fc polypeptide and hP40MFc polypeptide are linked via an intervening sequence that facilitates co-expression, the nucleic acid sequence encoding the p40MFc polypeptide is 5' relative to the nucleic acid sequence encoding the hP19Fc polypeptide. In some embodiments, the intervening sequence to facilitate co-expression is an IRES element or a T2A sequence.

In some embodiments, the present disclosure provides an expression cassette encoding a heterodimeric hIL23Fc mutein comprising a nucleic acid sequence encoding hP19Fc polypeptide and a hP40MFc polypeptide operably linked to one or more heterologous nucleic acid sequences, wherein the nucleic acid sequences encoding the hP19Fc polypeptide and hP40MFc polypeptide are: (a) under the control a single promoter and (b) are linked via an intervening sequence that facilitates co-expression in a mammalian cell.

The present disclosure further provides a recombinant vector encoding a heterodimeric hIL12Fc mutein, the vector comprising a first expression cassette encoding an hP35Fc polypeptide and the same or a second vector comprising a second expression cassette comprising a nucleic acid sequence encoding a hP40MFc polypeptide. In some embodiments, the vector is viral vector. In some embodiments, the vector is non-viral vector.

The present disclosure further provides a recombinant vector encoding a heterodimeric hIL23Fc mutein, the vector comprising a first expression cassette encoding an hP19Fc polypeptide and the same or a second vector comprising a second expression cassette comprising a nucleic acid sequence encoding a hP40MFc polypeptide. In some embodiments, the vector is viral vector. In some embodiments, the vector is non-viral vector.

Further provided is a recombinantly modified cell comprising a nucleic acid molecule or vector of the disclosure. In some embodiments, the cell is a prokaryotic cell, such as a bacterial cell. In some embodiments, the cell is a eukaryotic cell, such as a mammalian cell. Also provided is a cell culture comprising at least one recombinantly modified cell of the disclosure, and a culture medium.

In some embodiments, the recombinantly modified cell is transformed with a recombinant vector encoding a heterodimeric hIL12Fc mutein, the vector comprising a first expression cassette encoding an hP35Fc polypeptide and a second expression cassette comprising a nucleic acid sequence encoding a hP40MFc polypeptide. In some embodiments, the recombinantly modified cell is transformed with a recombinant vector encoding a heterodimeric hIL23Fc mutein, the vector comprising a first expression cassette encoding an hP19Fc polypeptide and a second expression cassette comprising a nucleic acid sequence encoding a hP40MFc polypeptide.

In some embodiments, the recombinantly modified cell is transformed with a first vector comprising a nucleic acid sequence encoding a hP35Fc polypeptide operably linked to one or more expression control sequences and a second vector comprising an expression cassette comprising a nucleic acid sequence encoding a hP40MFc polypeptide operably linked to one or more expression control sequences. In some embodiments, the recombinantly modified cell is transformed with a first vector comprising a nucleic acid sequence encoding a hP19Fc polypeptide operably linked to one or more expression control sequences and a second vector comprising an expression cassette comprising a nucleic acid sequence encoding a hP40MFc polypeptide operably linked to one or more expression control sequences. In some embodiments, the cell is a prokaryotic cell, such as a bacterial cell. In some embodiments, the cell is a eukaryotic cell, such as a mammalian cell. Also provided is a cell culture comprising at least one recombinantly modified cell of the disclosure, and a culture medium.

The present disclosure further provides methods for the recombinant production, isolation, purification and characterization of a heterodimeric hIL12Fc mutein or heterodimeric hIL23Fc mutein. Thus, provided herein is a method for producing a heterodimeric hIL12Fc mutein or heterodimeric hIL23Fc mutein of the disclosure. In some embodiments, the method comprises a) providing one or more recombinantly modified cells comprising a nucleic acid molecule or vector comprising a nucleic acid sequence encoding a heterodimeric hIL12Fc mutein or heterodimeric hIL23Fc muteins as disclosed herein; and b) culturing the one or more cells in a culture medium such that the cells produce the heterodimeric hIL12Fc mutein encoded by the nucleic acid sequence. In some embodiments, the method further comprises the step of (c) isolating and/or purifying the modified hIL-12p40) polypeptide. Also provided is a heterodimeric hIL12Fc mutein produced by the above method.

The present disclosure further provides a pharmaceutical composition comprising a heterodimeric hIL12Fc mutein or heterodimeric hIL23Fc mutein of the present disclosure. In some embodiments, the pharmaceutical composition comprises a heterodimeric hIL12Fc mutein or heterodimeric hIL23Fc mutein of the present disclosure and a pharmaceutically acceptable carrier. In some embodiments, the pharmaceutical composition comprises a nucleic acid molecule or vector of the disclosure. In some embodiments, the pharmaceutical composition comprises a recombinantly modified cell of the disclosure. In some embodiments, the recombinantly modified cell is a mammalian cell.

The present disclosure further provides method of treating a mammal suffering from a neoplastic disease the method comprising the step of contacting the mammal with a pharmaceutical formulation of a heterodimeric hIL23Fc mutein as disclosed herein. The present disclosure further provides method of treating a mammal suffering from a neoplastic disease the method comprising the step of contacting the mammal with a pharmaceutical formulation of a heterodimeric hIL23Fc mutein wherein the heterodimeric hIL23Fc mutein is a heterodimeric hIL23Fc mutein of Table 8.

In some embodiments, in the method of treating neoplastic disease with a pharmaceutical formulation of a heterodimeric hIL23Fc mutein the dose of the heterodimeric hIL12Fc mutein provided to the mammal is from 10 ug/kg to 500 ug/kg, alternatively from 10 ug/kg to 250 ug/kg, alternatively from 10 ug/kg to 80 ug/kg, alternatively from 10 ug/kg to 40 ug/kg, alternatively from 10 ug/kg to 30 ug/kg, alternatively from 10 ug/kg to 20 ug/kg, or alternatively about 15 ug/kg.

The present disclosure further provides method of treating a mammal suffering from a neoplastic disease the method comprising the step of contacting the mammal with a pharmaceutical formulation of a heterodimeric hIL23Fc mutein as disclosed herein in combination with one or more supplementary therapeutic agents. In some embodiments the one or more supplementary therapeutic agents supplementary therapeutic agent is selected from the group consisting of checkpoint inhibitors, cytokines, or a therapeutic antibodies. In some embodiments of the method of the present disclosure the one or more supplementary therapeutic agents supplementary therapeutic agent is a checkpoint inhibitor is selected from the group consisting of an anti-PD1 antibody, an anti-PDL1 antibody, an anti-CTLA4 antibody and an anti-LAG3 antibody. In some embodiments of the method of the present disclosure the one or more supplementary therapeutic agents supplementary therapeutic agent is a polypeptide having at least 90%, alternatively at least 95%, alternatively at least 97%, alternatively at least 98%, alternatively at least 99%, or alternatively 100% sequence identity with human interleukin-2.

In some embodiments of the method of the present disclosure the one or more supplementary therapeutic agents supplementary therapeutic agent is a human IL2 mutein comprising one or more amino acid substitutions or deletions at positions 1, 2, 3, 4, 5, 6, 18, 22, 125, and 126 numbered in accordance with mature wild type human IL2. In some embodiments of the methods of the present disclosure, the one or more supplementary therapeutic agents supplementary therapeutic agent is a biased IL2 mutein having reduced affinity for the CD132 subunit of the IL2 receptor as described in are Emmerich, et al., PCT International Application Number PCT/US2021/013456 published Jul. 22, 2021 as WO2021/146436A2; Emmerich, et al PCT/US2021/013514 published Jul. 22, 2021 as WO2021/146481A1 and Garcia, et al PCT/US2018/062122 published May 31, 2019 as WO2019/104092A1, the entire teachings of which are hereby incorporated by reference.

In some embodiments of the methods of the present disclosure, the one or more supplementary therapeutic agents supplementary therapeutic agent is a biased human IL2 mutein comprising amino acid substitutions at positions 18, 22 and 126 numbered in accordance with mature wild type human IL2. In some embodiments of the methods of the present disclosure, the one or more supplementary therapeutic agents supplementary therapeutic agent is a biased human IL2 mutein comprising amino acid substitutions 18R, Q22E and Q126K. In some embodiments of the methods of the present disclosure, the one or more supplementary therapeutic agents is a biased IL2 mutein comprising amino acid substitutions t positions 18, 22 and 126 numbered in accordance with mature wild type human IL2 that is PEGylated.

In some embodiments, present disclosure provides a method of treating a neoplastic disease with heterodimeric hIL23Fc mutein, alone or in combination with one or more supplementary agents, wherein the neoplastic disease characterized by a tumor with T cell infiltration. In some embodiments, present disclosure provides a method of treating a neoplastic disease with heterodimeric hIL23Fc mutein, alone or in combination with one or more supplementary agents, wherein the neoplastic disease is selected from the group consisting of melanoma, renal cell carcinoma (RCC), ovarian cancer, cervical cancer, non-small cell lung cancer (NSCLC), head and neck cancer, pancreatic cancer, and microsatellite instability (MSI) high cancers.

In another aspect, the disclosure provides a method for modulating hIL12-mediated signaling in a subject, the method comprising administering to the subject an effective amount of a pharmaceutical composition comprising a heterodimeric hIL12Fc mutein described herein. In some embodiments, the hIL12-mediated signaling comprises STAT4-mediated signaling. In some embodiments, the STAT4-mediated signaling is determined by an assay selected from the group consisting of a gene expression assay, a phospho-flow signaling assay, and an enzyme-linked immunosorbent assay (ELISA). In some embodiments, the STAT4-mediated signaling in the subject is reduced by about 20%, alternatively by about 30%, alternatively by about 40%, alternatively by about 50%, alternatively by about 60%, alternatively by about 70%, alternatively by about 80%, alternatively by about 90%, alternatively by about 100% compared to a reference level. In some embodiments, the administered composition results in a reduced capacity to induce expression of IFN-γ relative to the wild type hIL12.

The heterodimeric hIL12Fc muteins or heterodimeric hIL23Fc muteins of the present disclosure are useful in the treatment and/or prevention of disease in mammalian subjects. Thus, in another aspect, the disclosure provides a method for treating a health condition in a subject in need thereof, the method comprising administering to the subject a therapeutically effective amount of composition comprising: a heterodimeric hIL12Fc mutein or heterodimeric hIL23Fc mutein; a nucleic acid molecule(s) or vector(s) comprising a nucleic acid sequence(s) encoding a heterodimeric hIL12Fc mutein or heterodimeric hIL23Fc mutein; a recombinantly modified cell comprising a nucleic acid molecule(s) or vector(s) described herein; or a pharmaceutical composition comprising one or more of the foregoing as described herein.

In another aspect, the disclosure provides a method of treating a neoplastic, infectious or autoimmune disease in a subject in need thereof, the method comprising administering to the subject a therapeutically effective amount of a modified a heterodimeric hIL12Fc mutein or heterodimeric hIL23Fc mutein, a nucleic acid molecule(s) or vector(s) comprising a nucleic acid sequence(s) encoding a heterodimeric hIL12Fc mutein or heterodimeric hIL23Fc mutein; a recombinantly modified cell comprising a nucleic acid molecule or vector described herein or a pharmaceutical composition described herein. In some embodiments, the present disclosure provides for the treatment or prevention of an autoimmune disease in a mammalian subject by the administration of a therapeutically effective amount of a heterodimeric hIL23Fc mutein of the present disclosure. In some embodiments, the present disclosure provides for the treatment or prevention of neoplastic disease in a mammalian subject by the administration of a therapeutically effective amount of a heterodimeric hIL12Fc mutein of the present disclosure.

In some embodiments, the present disclosure provides for the treatment or prevention of neoplastic disease in a mammalian subject by the administration of a therapeutically effective amount of a heterodimeric hIL12Fc mutein of the present disclosure in combination with one or more supplementary therapeutic agents.

Also provided is a kit for modulating hIL-12-mediated or hIL-23 signaling in a subject, or treating a health condition in a subject in need thereof. In some embodiments, the kit comprises a heterodimeric hIL12Fc mutein or heterodimeric hIL23Fc mutein described herein. In some embodiments, the kit comprises a nucleic acid molecule or vector comprising a nucleic acid sequence encoding a heterodimeric hIL12Fc mutein or heterodimeric hIL23Fc mutein described herein, a nucleic acid molecule or vector comprising a nucleic acid sequence encoding a heterodimeric hIL12Fc mutein and/or heterodimeric hIL23Fc mutein described herein, or a nucleic acid molecule. In some embodiments the kit comprises a recombinantly modified cell comprising a nucleic acid molecule or vector described herein, or a pharmaceutical composition described herein.

BRIEF DESCRIPTION OF THE FIGURES

FIGS. 1A, 1B and 1C illustrate the effect of wild type hIL12 in comparison to hIL12 muteins comprising amino acid substitutions E81A/F82A indicated as "2xAla", E81A/F82A/K106A indicated as "3xAla" and substitution W37A, on CD8, CD4 and NK cells, respectively. FIGS. 1D, 1E and 1F provide the results of IFNγ induction of KiH heterodimeric hIL12Fc muteins comprising hIL12 in comparison to KiH heterodimeric hIL12Fc muteins comprising amino acid substitutions E81A/F82A indicated as "2xAla Fc", E81A/F82A/K106A indicated as "3xAla Fc" and substitution W37A (W37A Fc), on CD8, CD4 and NK cells, respectively.

FIG. 7 provides an amino acid sequence alignment of the wild type human and murine p40 (IL12Ra) proteins (SEQ ID NOS: 109 and 3, respectively) with the signal peptide sequence highlighted.

FIG. 8 provides an amino acid sequence alignment of the wild type human and murine and human p35 (IL12Rb) proteins (SEQ ID NOS: 107 and 1, respectively).

FIG. 9A provides the concentration in picograms per milliliter (pg/mL) of murine interferon gamma in serum of treatment groups A-E of Table 12 at 0 hours (pretreatment) and 4 hours, 1 day and 7 days following treatment with the test agent. FIG. 9B relates to the murine interferon gamma levels in serum of treatment groups F, G, and H of Table 12 at 0 hours (pretreatment) and 4 hours, 1 day and 7 days following treatment with the test agent.

DETAILED DESCRIPTION OF THE INVENTION

Figure 1A:
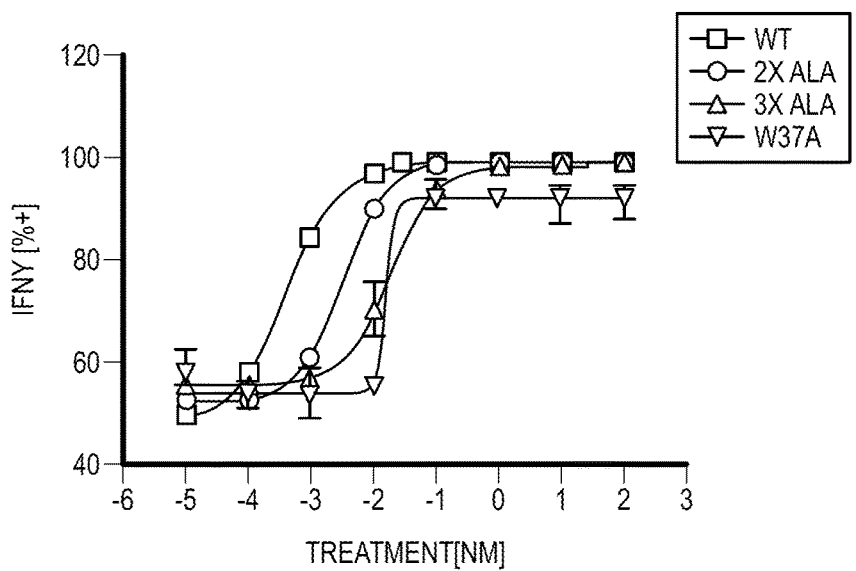
FIGS. 1A-1F provide the results of an evaluation of interferon gamma induction (vertical axis) with respect to increasing concentrations of the test agent (horizontal axis) in CD8, CD4 and NK cells.
Figure 1B:
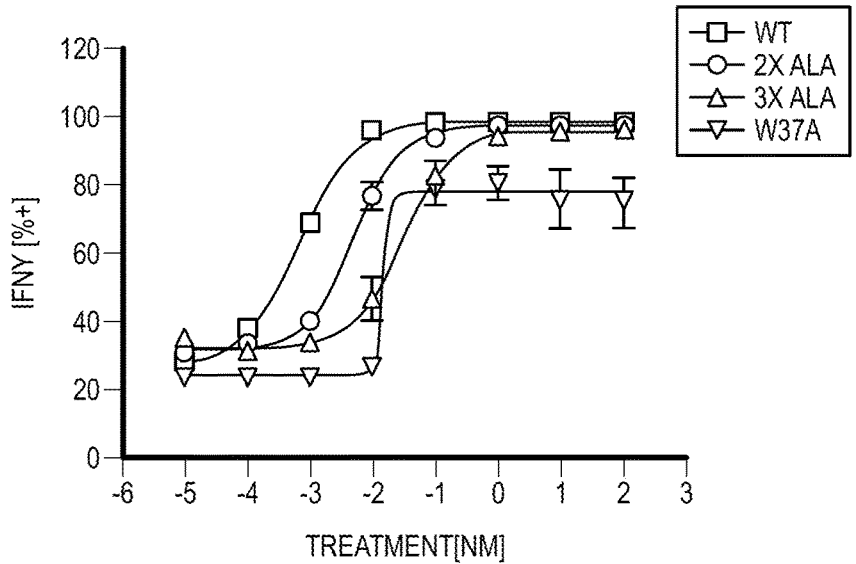
Figure 1C:
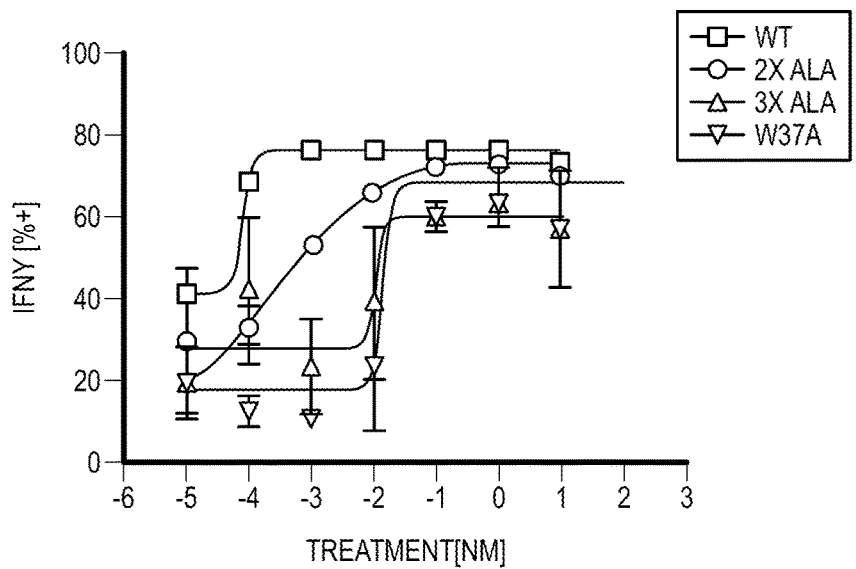
Figure 1D:
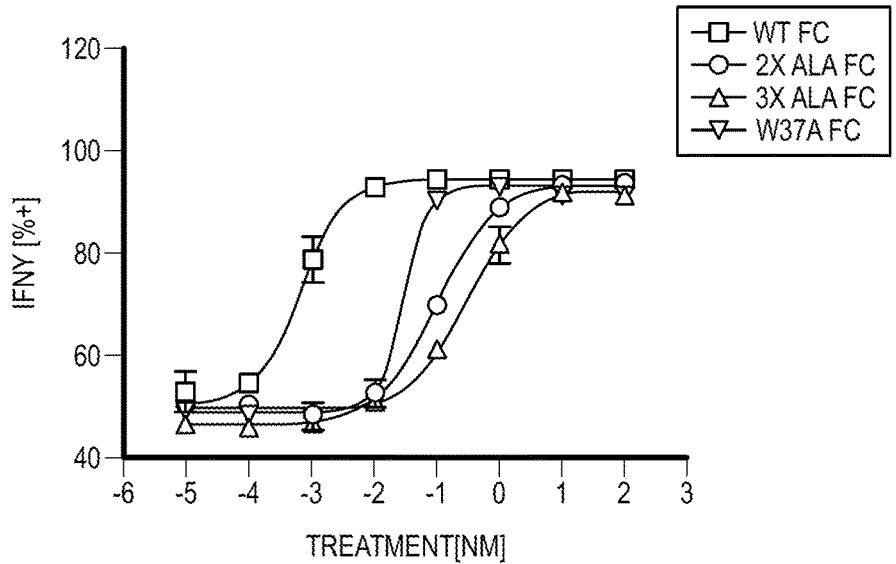
Figure 1E:
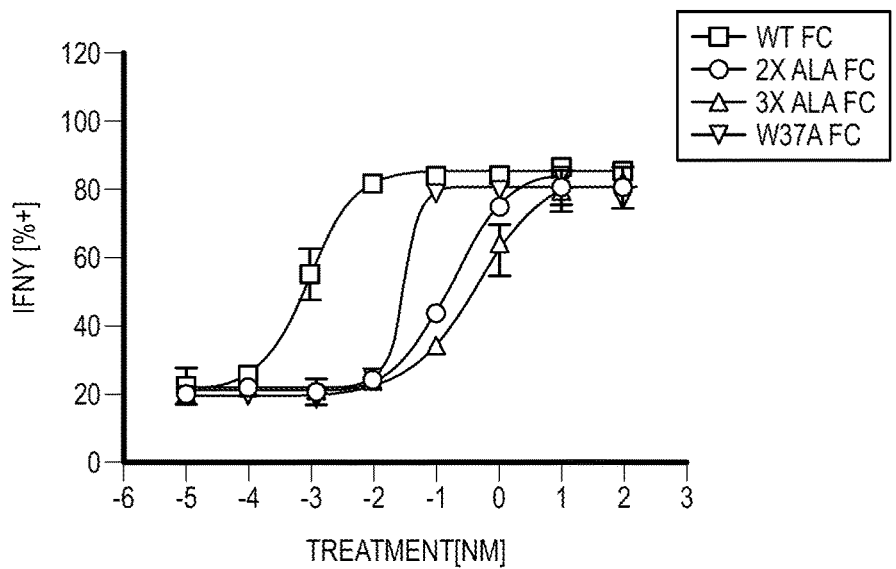
Figure 1F:
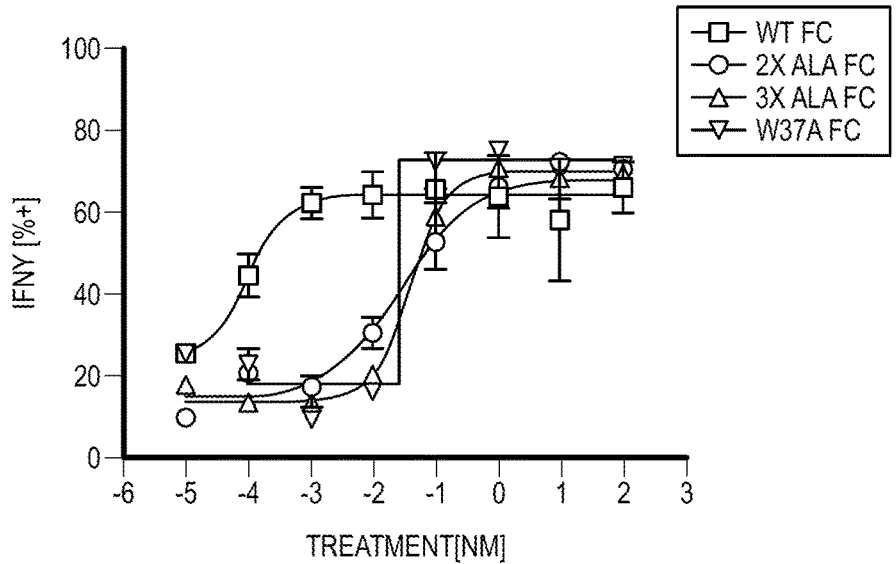
Figure 2A:
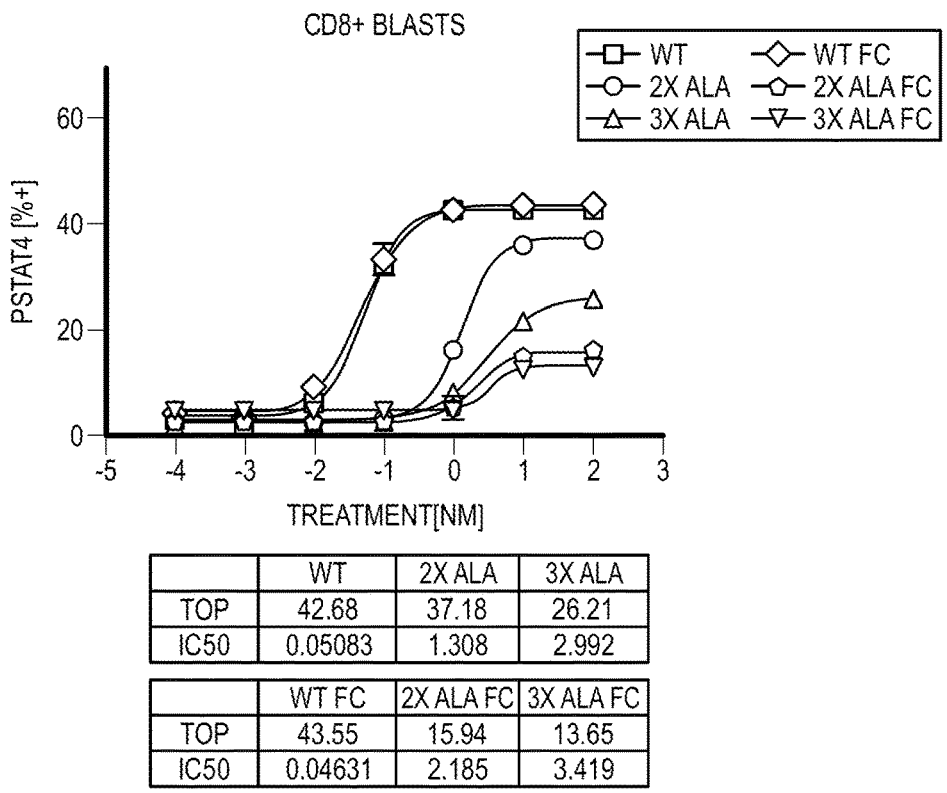
FIGS. 2A-2D provide the results of an evaluation of interferon-γ and STAT4 induction (vertical axis) with respect to increasing concentrations of test agents indicated on CD8+ T cells (FIG. 2A), CD4+ T cells (FIG. 2B), and NK cells from two different human donors (FIGS. 2C and 2D)
Figure 2B:
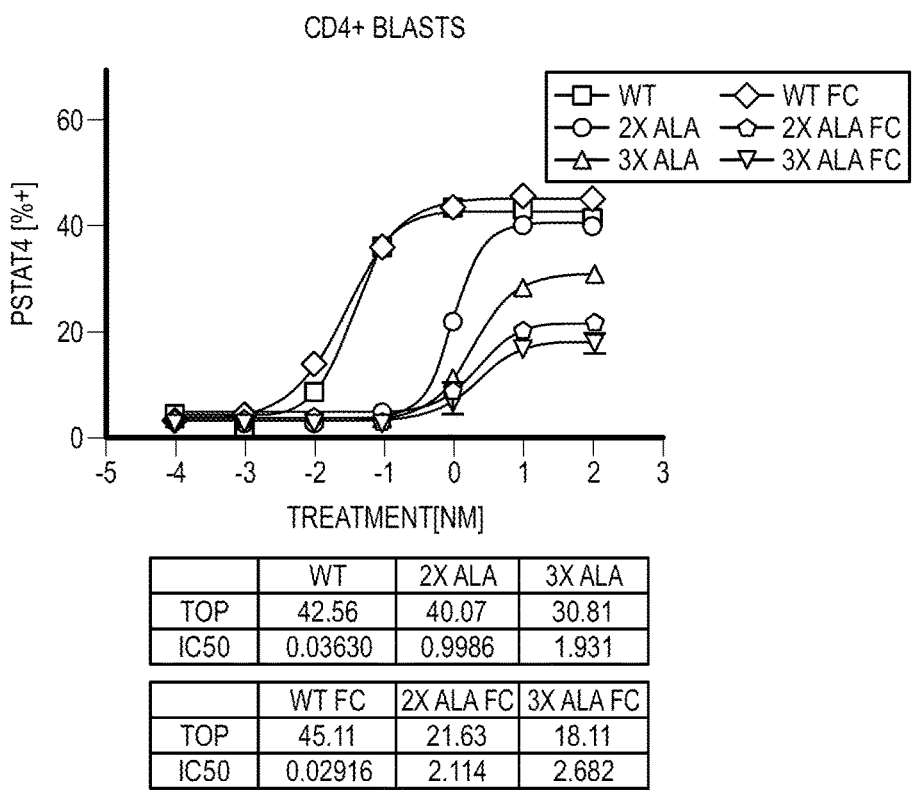
Figure 2C:
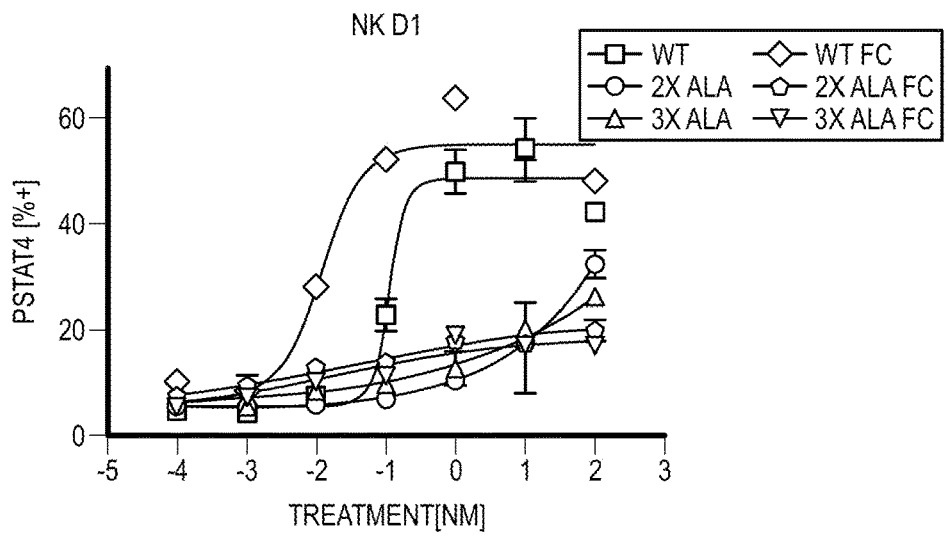
Figure 2D:
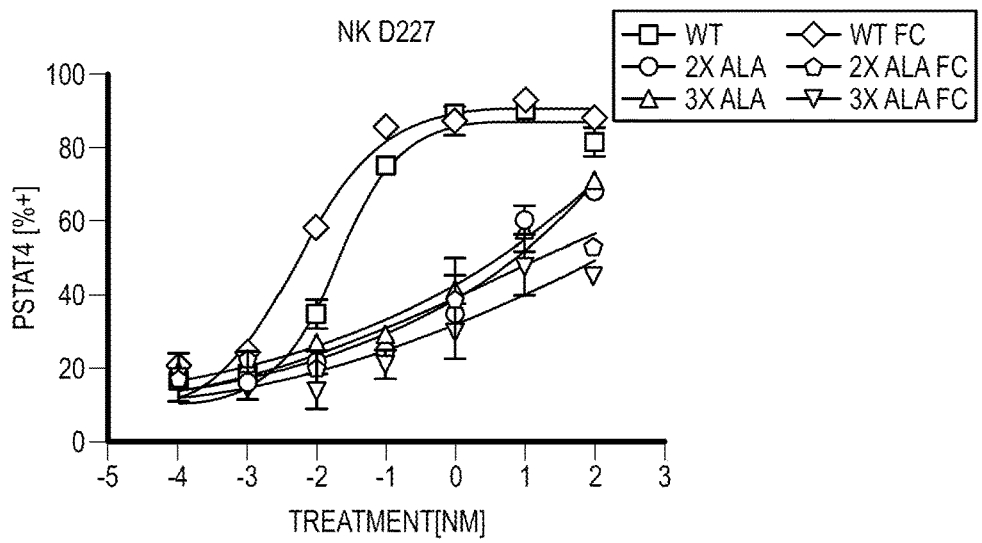
Figure 3A:
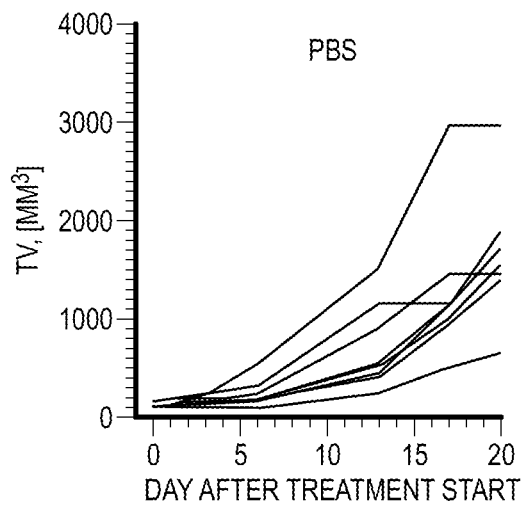
FIGS. 3A-3I provide spider plots of the of the tumor volume over time of mice treated with various murine IL12 agents and murine IL12Fc muteins in an MC38 tumor model study as described more fully below. Tumor volume is provided on the Y axis and time is on the X axis.
Figure 3B:
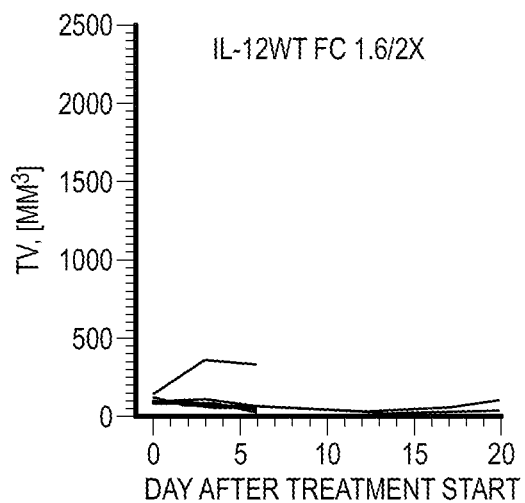
Figure 3C:
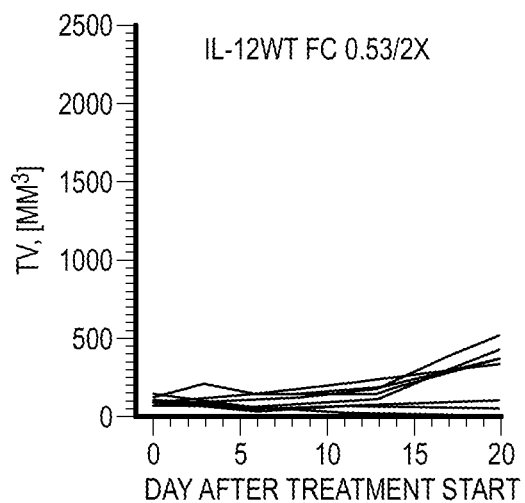
Figure 3D:
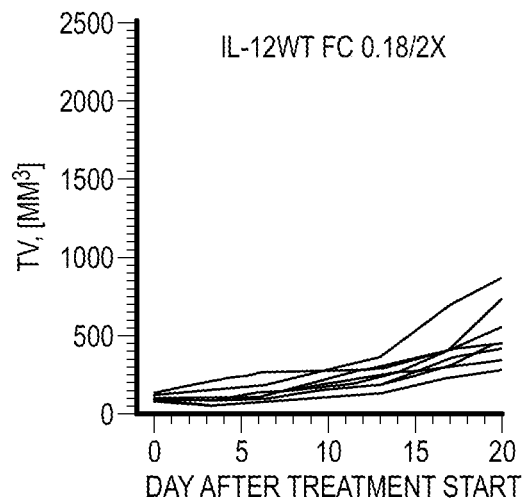
Figure 3E:
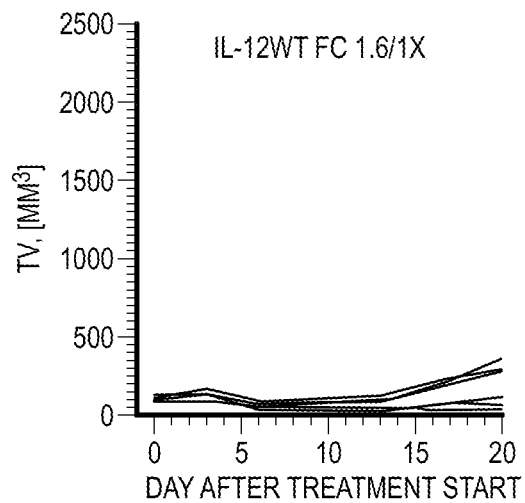
Figure 3F:
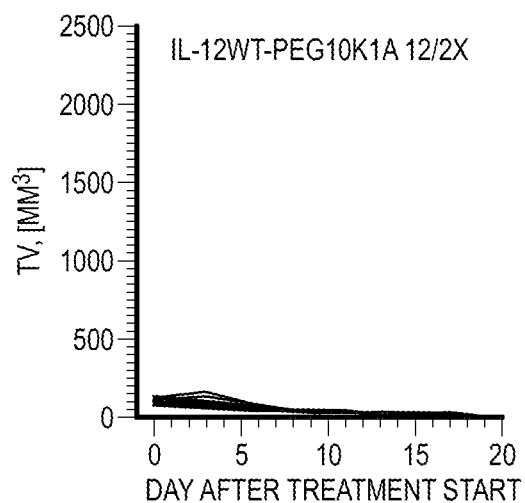
Figure 3G:
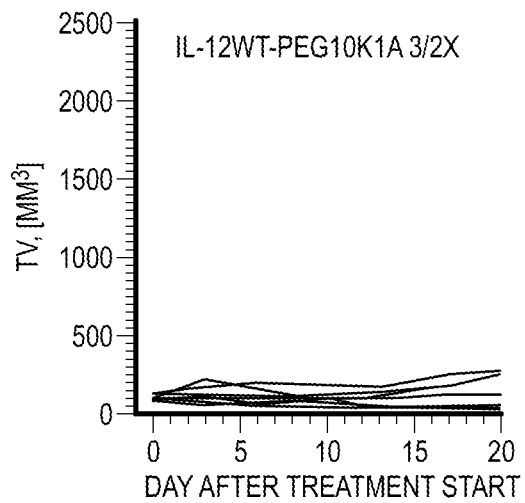
Figure 3H:
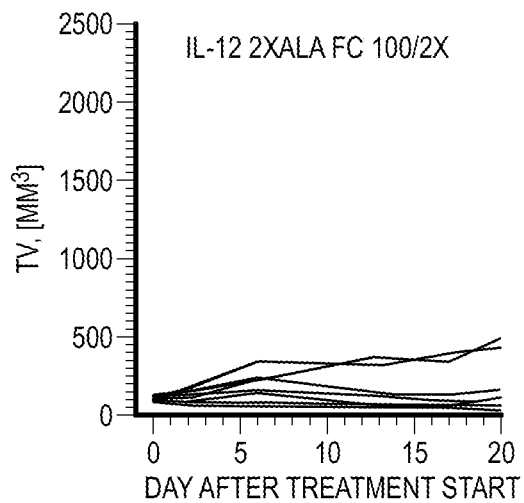
Figure 3I:
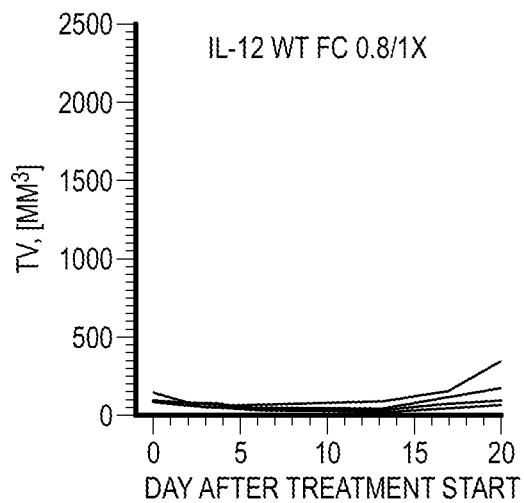
Figure 4A:
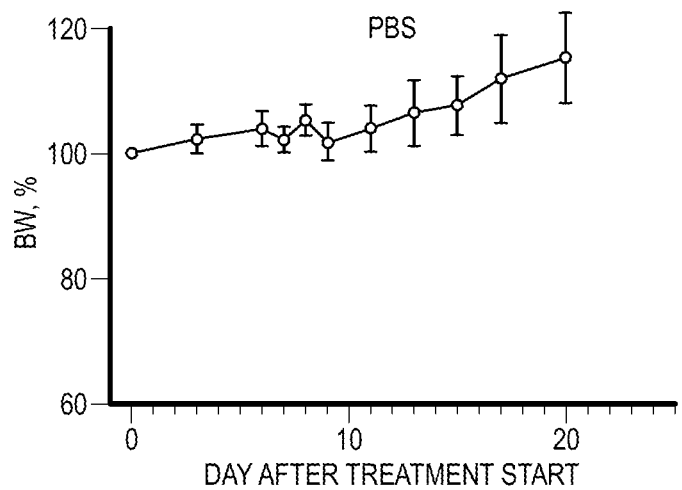
FIGS. 4A-4I provide bodyweights (Y axis) of mice treated over time (X axis) of mice treated with various murine IL12 agents and murine IL12Fc muteins in an MC38 tumor model study as described more fully below.
Figure 4B:
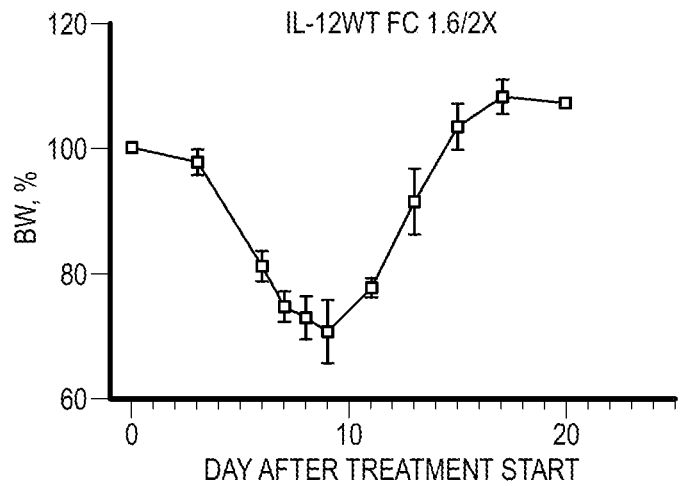
Figure 4C:
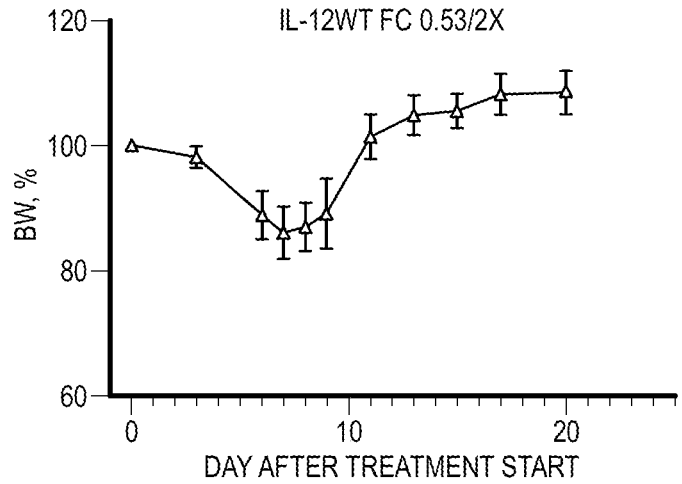
Figure 4D:
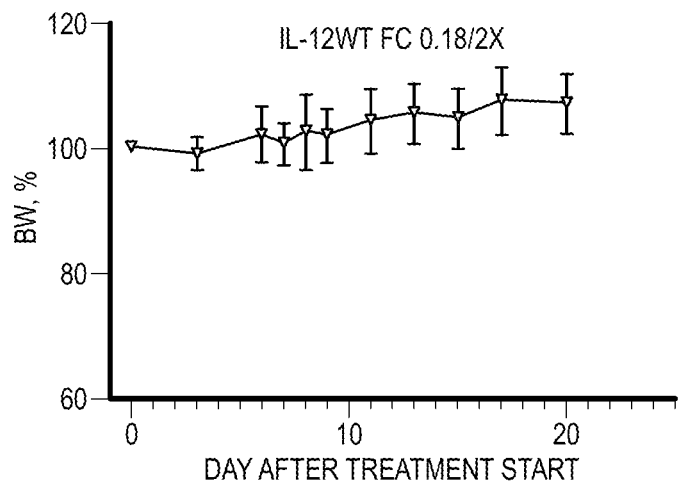
Figure 4E:
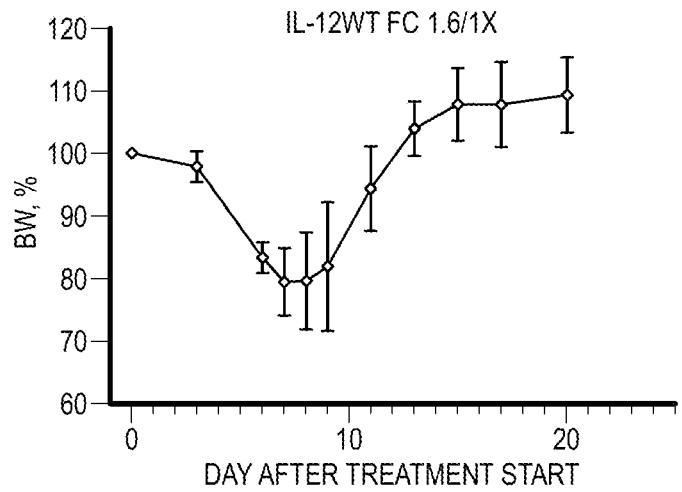
Figure 4F:
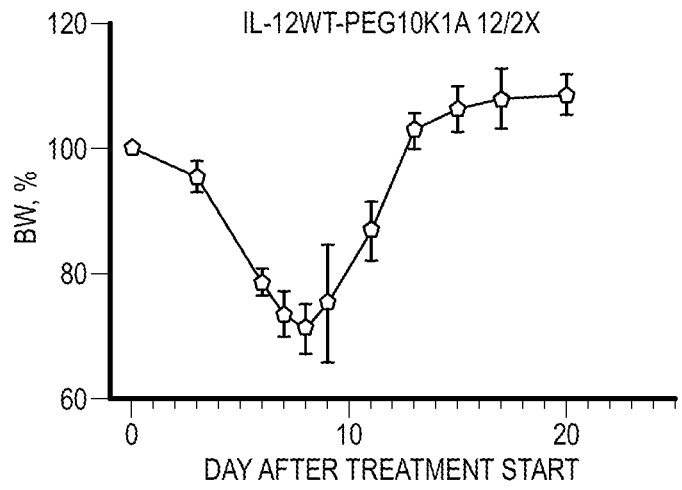
Figure 4G:
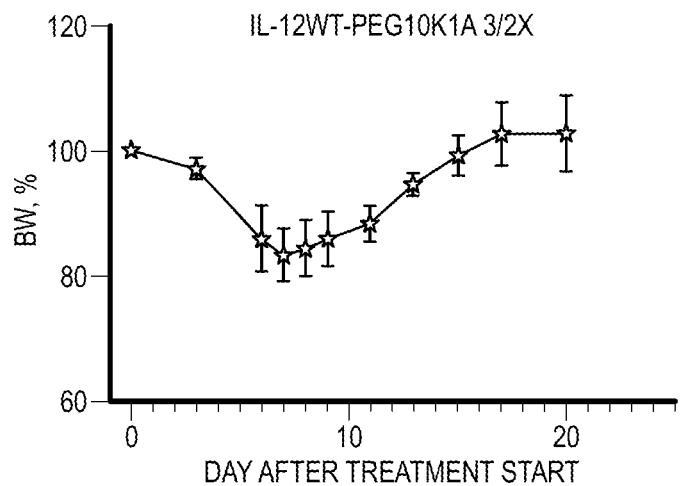
Figure 4H:
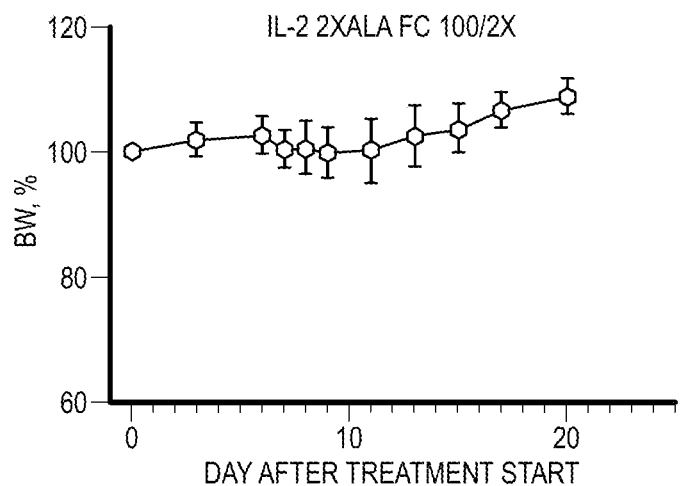
Figure 4I:
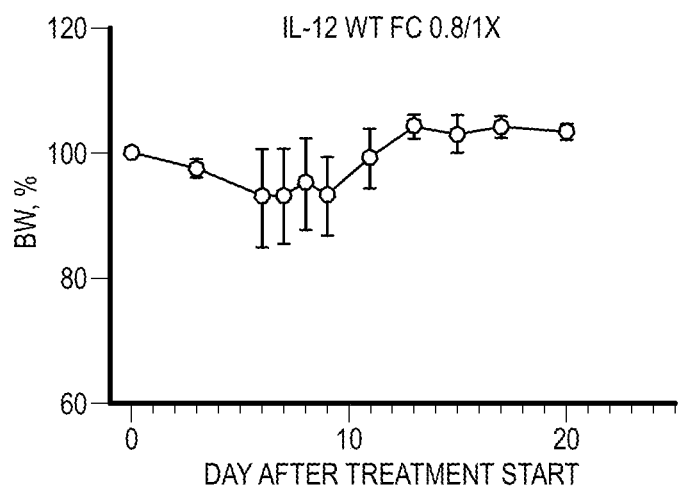

To facilitate the understanding of present disclosure, certain terms and phrases are defined below as well as throughout the specification. The definitions provided herein are non-limiting and should be read in view of the knowledge of one of skill in the art.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications, patents, published patent applications, GenBank accession numbers and UniProt reference numbers mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Publications cited herein and the material for which they are cited are hereby specifically incorporated by reference in their entireties. Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); AA or aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=once weekly; QM=once monthly; HPLC=high performance liquid chromatography; BW=body weight; U=unit; ns=not statistically significant; PBS=phosphate-buffered saline; PCR=polymerase chain reaction; HSA=human serum albumin; MSA=mouse serum albumin; DMEM=Dulbeco's Modification of Eagle's Medium; EDTA=ethylenediaminetetraacetic acid.

It will be appreciated that throughout this disclosure reference is made to amino acids according to the single letter or three letter codes. For the reader's convenience, the single and three letter amino acid codes are provided in Table 1.

TABLE 1

Naturally Occurring Amino Acids and Abbreviations

| Amino Acid | Single Letter Abbreviation | Three Letter Abbreviation |
|---|---|---|
| Glycine | G | Gly |
| Proline | P | Pro |
| Alanine | A | Ala |
| Valine | V | Val |
| Leucine | L | Leu |
| Isoleucine | I | Ile |
| Methionine | M | Met |
| Cysteine | C | Cys |
| Phenylalanine | F | Phe |
| Tyrosine | Y | Tyr |
| Tryptophan | W | Trp |
| Histidine | H | His |
| Lysine | K | Lys |
| Arginine | R | Arg |
| Glutamine | Q | Gln |
| Asparagine | N | Asn |
| Glutamic Acid | E | Glu |
| Aspartic Acid | D | Asp |
| Serine | S | Ser |
| Threonine | T | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Nomenclature of Amino Acid Substitutions and Deletions

The present disclosure provides variant polypeptides comprising amino acid substitutions relative to the wild-type or parent polypeptide. The following nomenclature is used herein to refer to substitutions, deletions or insertions. Residues may be designated herein by the one-letter or three-letter amino acid code of the naturally occurring amino acid found in the wild-type molecule.

P19 Residue Numbering: In the present disclosure, the numbering of amino acid residues of human P19 is made in reference to the number of the "pro" form of hP19 as provided in SEQ ID NO: 177.

P35 Residue Numbering: In the present disclosure, the numbering of amino acid residues of human P35 is made in reference to the number of the "pro" form of hP35 as provided in SEQ ID NO: 1.

P40 Residue Numbering: In the present disclosure, the numbering of amino acid residues of human P40 is made in reference to the number of the "pro" form of hP40 as provided in (SEQ ID NO: 3). In reference to the hP40 muteins, substitutions are designated herein by the one letter amino acid code followed by the pro-hp40 (SEQ ID NO: 3) amino acid position followed by the one letter amino acid code which is substituted. For example, an hP40 mutein having the modification "E81A" refers to a substitution of the glutamic acid (E) residue at position 81 of the (SEQ ID NO: 3) with an alanine (A) residue at this position. A deletion of an amino acid reside is referred to as "des" or the symbol "Δ" followed by the amino acid residue and its position.

Immunoglobulin, Upper Hinge and Fc Residue Numbering: There are a variety of numbering conventions that are employed with respect to the numbering of amino acid residues of immunoglobulins including Kabat numbering, Chothia numbering, EU numbering and IMGT numbering conventions. In the context of the present disclosure, the numbering of amino acid residues of immunoglobulin molecules including domains thereof including the upper hinge and Fc domain (comprising the lower hinge, CH2 and CH3 domains) is made in accordance with EU Numbering conventions. Translation of EU numbering conventions used herein to Kabat numbering, Chothia numbering, or IMGT numbering conventions is readily understood by those of skill in the art. Dondelinger, et al. (2018) *Understanding the Significance and Implications of Antibody Numbering and Antigen-Binding Surface Residue Definition* Frontiers in Immunology Volume 9 Article #: 2278.

Additionally, in certain instances herein. an "M" suffix may be added to a polypeptide number (e.g. DR1535M) to identify such sequence as a "mature" molecule lacking a signal sequence so as to distinguish the polypeptide from the precursor molecule containing the signal peptide which precursor form may be identified with a "P" suffix such as DR1535P.

Definitions

Unless otherwise indicated, the following terms are intended to have the meaning set forth below. Other terms are defined elsewhere throughout the specification.

The term "about" refers to a value that is plus or minus 10% of a numerical value described herein, such as plus or minus 1%, 2%, 3%, 4%, 5%, 6%, 7%, 8%, 9%, or 10% of numerical value described herein. The term "about" also applies to all numerical ranges described herein. All values described herein are understood to be modified by the term "about" whether or not the term "about" is explicitly recited in reference to a given value.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand. The term activate is also used in reference to a cell that expresses a receptor wherein one more biological activities of the cell are modulated (e.g. upregulation or downregulation of STAT4 signaling) in response to binding of a ligand for such receptor.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, and the ability to modulate immunological activity such as inflammatory response. "Activity" is typically expressed as a level of a biological activity per unit of agent tested such as [catalytic activity]/[mg protein], [immunological activity]/[mg protein], international units (IU) of activity. [STAT3 phosphorylation]/[mg protein], [STAT4 phosphorylation]/[mg protein][proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g., a modified hIL-12p40 polypeptide, hIL-12 mutein comprising a heterodimeric hIL12Fc mutein or hIL-23 mutein comprising a modified hIL-12p40 polypeptide; an engineered cell expressing a modified hIL-12p40 polypeptide, hIL-12 mutein comprising a modified hIL-12p40 polypeptide, or a hIL-23 mutein comprising a modified hIL-12p40 polypeptide; or a pharmaceutical formulation comprising one or more of the foregoing), alone or in combination with one or more supplementary agents. Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant (KD), a ratio of the dissociation rate constant between the molecule and its target (Koff) and the association rate constant between the molecule and its target (Kon).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in modulation of cell proliferation or pathways or the cell cycle. In some embodiments, an agonist is a modified form of a cognate ligand that binds to its cognate receptor and alters the state of the cognate receptor in a biological response that mimics the biological effect of the interaction of the naturally occurring cognate ligand with its cognate receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result in the signal cascade typically initiated by the receptor and may modify the actions of an agonist at that receptor. Inverse agonists are agents that produce a pharmacological response that is opposite in direction to that of an agonist.

Antagonist: As used herein, the term "antagonist" or "inhibitor" refers to a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell. In some instances, an antagonist may be a mutein of the naturally occurring ligad such that binding to receptor is maintained but there is no downstream signaling.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups are considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Corresponding To: As used herein, the terms "correspondence" or "corresponding to" in the context of an amino acid or nucleic acid sequence refers to the equivalent position of a reference sequence that is aligned with one or more other sequences to maximize the percentage of sequence identity. For example, an "amino acid position corresponding to amino acid position [X]" of a specified hIL-12p40 polypeptide refers to equivalent positions, based on alignment, in other hIL-12p40 polypeptides, including structural homologues and variants. The corresponding position can be based on a reference, wild-type or parental sequence, for example the wild-type mature hp40 amino acid sequence of SEQ ID NO:4.

Derived From: As used herein, the term "derived from" is used in the context of an amino acid sequence or nucleic acid to indicate that the polypeptide or nucleic acid has a sequence that is based on that of a reference polypeptide or nucleic acid and is not meant to be limiting as to the source or method by which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results in the maximal (100%) response of a measurable parameter in response to such agent. Similarly, the term $EC_{50}$ (which is commonly used in the field of pharmacodynamics) refers to the concentration of an agent sufficient to result in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and EC50 is the drug concentration to give the half-maximal effect.

Enriched: As used herein in the term "enriched" refers to a sample comprising a species of interest (e.g. a molecule or cell) wherein the sample is non-naturally manipulated so that a species of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein which is external to the plasma membrane of the cell on which it is expressed. A cell surface protein comprising and ECD may be a transmembrane protein, a cell surface or membrane associated protein that comprising a domain associated with the cell membrane but which lacks an intracellular domain.

Identity: The term "identity." as used herein in reference to polypeptide or DNA sequences, refers to the subunit sequence identity between two molecules. When a subunit position in both of the molecules is occupied by the same amino acid or nucleotide then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) J. Mol. Biol. 215:403-410 and Altschul, et al. (1977) Nucleic Acids Res. 25:3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0)). For amino acid sequences, a scoring matrix is used to calculate the cumulative score. Extension of the word hits in each direction are halted when: (a) the cumulative alignment score falls off by the quantity X from its maximum achieved value: the cumulative score goes to zero or below; due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS (USA) 89:10915-10919).

In An Amount Sufficient Amount to Effect a Response: As used herein the phrase "in an amount sufficient to cause a response" is used in reference to the amount of an agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise. In some embodiments, a subject in need of treatment has been diagnosed with a disease or condition, for example, cancer, an autoimmune disorder or an infection.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise. In some embodiments, prevention refers to reducing, forestalling or delaying the onset of a particular disease, or reducing forestalling or delaying a recurrence of a particular disease, for example, after treatment for that disease. A recurrence does not necessarily have to be after curing or remission of a disease. It is sufficient to have one or more clinical symptoms reappear after a period devoid of those symptoms, for example, a period after treatment for cancer, an autoimmune disease or an infection.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. A cell surface protein comprising an ICD may be a transmembrane protein, a cell surface or membrane associated protein that comprising a domain associated with the cell membrane but which lacks an extracellular domain. The ICD may include the entire cytoplasmic portion of a transmembrane protein or membrane associated protein, or intracellular protein. A cell surface protein may be a transmembrane protein, a cell surface or membrane associated protein that comprising a domain associated with the cell membrane but which lacks an intracellular domain.

Isolated: As used herein the term "isolated" is used in reference to a polypeptide of interest that, if naturally occurring, is in an environment different from that in which it naturally occurs. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Ligand: As used herein, the term "ligand" refers to a molecule that specifically binds a receptor and causes a change in the receptor to effect a change in the activity of the receptor or a response in cell that expresses that receptor. In one embodiment, the term "ligand" refers to a molecule or complex thereof that can act as an agonist or antagonist of a receptor. The complex of a ligand and receptor is termed a "ligand-receptor complex" (for example, and hIL-12-hIL-12 receptor complex). In some examples, the term "cognate ligand" and "cognate receptor" are used to denote a naturally occurring ligand and the receptor to which such ligand exhibits selective binding in a naturally occurring biological systems. For example, hIL-12 is the cognate ligand for the hIL-12 receptor. In another example, hIL-23 is the cognate ligand for the hIL-23 receptor.

Modified: As used herein, the term "modified" refers to a molecule, such as a polypeptide, whose structure has been changed relative to an unmodified parental molecule. A modified polypeptide typically retains one or more activities or functions of the unmodified parental molecule. For example, a modified IL-12 p40 polypeptide can activate hIL-12 signaling in a cell expressing the hIL-12 receptor as part of a heterodimer (i.e., a p35/p40 complex), but can have improved properties relative to the unmodified polypeptide. The term modified includes amino acid substitutions that are not present in a parental or wild-type hIL-12, and includes variants and mutants of an hIL-12 p40 polypeptide.

Modulate: As used herein, the terms "modulate", "modulation" and the like refer to the ability of an agent, for example, a test agent, to cause a response, either positive or negative or directly or indirectly, in a system, including a biological system, or biochemical pathway. The term modulator includes both agonists (including partial agonists, full agonists and superagonists) and antagonists.

Mutein: As used herein, the term "mutein" is used to refer to modified versions of wild type polypeptides comprising modifications to the primary structure (i.e. amino acid sequence) of such polypeptide. The term mutein may refer to the polypeptide itself, a composition comprising the polypeptide, or a nucleic acid sequence that encodes it. A mutein may be at least about 99% identical to the parent polypeptide, alternatively at least about 98% identical, alternatively at least about 97% identical, alternatively at least about 96% identical, alternatively at least about 95% identical, alternatively at least about 94% identical, alternatively at least about 93% identical, alternatively at least about 92% identical, alternatively at least about 91% identical, or alternatively at least about 90% identical. In some instances as used herein, the compositions comprise a hP40 mutein wherein the hP40 comprises an amino acid sequence least about 99% identical to the wt hP40 (SEQ ID NO:4), alternatively at least about 98% identical, alternatively at least about 97% identical, alternatively at least about 96% identical, alternatively at least about 95% identical, alternatively at least about 94% identical, alternatively at least about 93% identical, alternatively at least about 92% identical, alternatively at least about 91% identical, or alternatively at least about 90% identical. As used herein the term "mutein" refers to a variant of a naturally occurring hIL-12 (i.e., a p35/p40 complex) or hIL-23 (i.e., a p19/p40 complex), i.e., a heterodimer that retains one or more biological activities of the parent, naturally occurring heterodimeric hIL-12 or hIL-23 from which it was derived comprising a hP40 mutein.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein (e.g., Emax) is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutant or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide). The term parent polypeptide can also be used interchangeably with "reference polypeptide."

Partial Agonist: As used herein, the term "partial agonist" refers to a molecule (e.g., a ligand) that specifically binds to and activates a given receptor but possesses only partial activation of the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide." "peptide." and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof. A course of action to prevent a disease, disorder or condition in a subject is typically applied in the context of a subject who is predisposed to developing a disease, disorder, or condition due to genetic, experiential, or environmental factors of developing a particular disease, disorder or condition. In certain instances, the terms "prevent", "preventing", "prevention" are also used to refer to the slowing of the progression of a disease, disorder, or condition from an existing state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain referred to as a transmembrane domain (TM). The binding of a ligand to the receptor results in a conformational change in the receptor resulting in a measurable biological effect. In some instances, where the receptor is a membrane spanning polypeptide comprising an ECD, TM and ICD, the binding of a ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response." for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "downregulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of activation of T cells in response to the administration of a test agent may be determined by flow cytometric methods. In some methods, a response can be measured by determining the level of STAT (e.g., STAT3, STAT4) phosphorylation, or IFNγ production, in accordance with methods well known in the art.

Significantly Reduced Binding: As used herein, the term "exhibits significantly reduced binding" is used with respect to a variant of a first molecule (e.g., a ligand) which exhibits a significant reduction in the affinity for a second molecule (e.g., receptor) relative to the parent form of the first molecule. With respect to variant ligands, for example, a variant hIL-12p40) polypeptide or a hIL-12 mutein described herein, a variant ligand "exhibits significantly reduced binding" if the mutein binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived.

Specifically Binds: As used herein the term "specifically binds" refers to the degree of affinity for which a first molecule exhibits with respect to a second molecule. In the context of binding pairs (e.g., ligand/receptor) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. Specific binding may be assessed using techniques known in the art including but not limited to competition ELISA assays, radioactive ligand binding assays (e.g., saturation binding. Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8K. Biacore 8K+, Biacore S200, Biacore T200 (Cytiva, 100 Results Way, Marlborough MA 01752).

Subject: The terms "recipient". "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition comprising the protein.

Suffering From: As used herein, the term "suffering from" refers to a determination made by a physician with respect to a subject based on the available objective or subjective information accepted in the field for the identification of a disease, disorder or condition including but not limited to X-ray, CT-scans, conventional laboratory diagnostic tests (e.g., blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8+ T cells, cytotoxic CD8+ T cells, naïve CD4+ T cells, helper T cells, e.g., TH1, TH2, TH9, TH11, TH22, TFH: regulatory T cells, e.g., TRI. Tregs, inducible Tregs: memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL12 receptor referred to interchangeably as IL12R cell, IL12R+ cell, IL12R T cell, or IL12R+ T cell.

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide. As used herein in the context of nucleic acids, the "5'-terminus" (or "five-prime terminus") and "3'-terminus" (or "carboxyl terminus") refer to the extreme ends of the nucleic acid sequence, respectively, while the terms "5" and "3" refer to relative positions in the nucleic acid sequence of the polypeptide toward the 5'-terminus and the 3'-terminus, respectively, and can include the residues at the 5'-terminus and 3'-terminus, respectively.

Therapeutically Effective Amount: As used herein to the phrase "therapeutically effective amount" refers to the quantity of an agent when administered to a subject, either alone or as part of a pharmaceutical composition or treatment regimen, in a single dose or as part of a series of doses, provides a positive effect on any quantitative or qualitative symptom, aspect, or characteristic of a disease, disorder or condition. A therapeutically effective amount can be ascertained by measuring relevant physiological effects, and it may be adjusted in connection with a dosing regimen and in response to diagnostic analysis of the subject's condition. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography. X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. In one embodiment, a therapeutically effective amount is an amount of an agent when used alone or in combination with another agent provides an provides a positive effect on any quantitative or qualitative symptom, aspect, or characteristic of a disease, disorder or condition and does not result in non-reversible serious adverse events in the course of administration of the agent to the mammalian subject.

Treat: The terms "treat", "treating", treatment" and the like refer to a course of action (such as contacting the subject with pharmaceutical composition comprising a hIL-12 mutein alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder, or condition) or ameliorates one or more symptoms associated with the presence of the disease in the subject.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

It will be understood that individual embodiments, which are separately described herein for clarity and brevity, can be combined without limitation. Thus, the present disclosure includes one or more, or all, combinations of the embodiments described herein as if each and every combination was individually and explicitly disclosed. This also applies to any and all sub-combinations of the embodiments disclosed herein, such that the present disclosure includes one or more, or all, sub-combinations of the embodiments described herein as if each and every sub-combination was individually and explicitly disclosed.

Wild Type hIL12:

Wild type human IL12 (wt hIL12) is a covalently disulfide linked heterodimeric protein comprising two wild type subunits, hP40 and hP35. The naturally occurring form of hIL12 comprises an interchain disulfide linkage between residue C96 of p35 (numbered in accordance with SEQ ID NO:1) and residue C199 of p40 (numbered in accordance with SEQ ID NO: 3).

Wild Type Human P35:

The wild type human P35 monomer (wt hP35) is expressed as a 219 amino acid pro-protein (SEQ ID NO:1) comprising a 22 amino acid signal sequence which is post-translationally removed to render a 197 amino acid mature protein (SEQ ID NO:2). Wild type hP35 (wt hP35) contains two intrachain disulfide linkages, the first between residues C64 and C196 and the second between residues C85 and C123 (numbered in accordance with SEQ ID NO:1). The canonical amino acid sequence of the human pro-P35 protein (UniProt Reference No. P29459) with the signal sequence (underlined) is:

(SEQ ID NO: 1)
MCPARSLLLVATLVLLDHLSLARNLPVATPDPGMFPCLHHSQNLLRA

VSNMLQKARQTLEFYPCTSEEIDHEDITKDKTSTVEACLPLELTKNESC

LNSRETSFITNGSCLASRKTSFMMALCLSSIYEDLKMYQVEFKTMNAK

LLMDPKRQIFLDQNMLAVIDELMQALNFNSETVPQKSSLEEPDFYKTK

IKLCILLHAFRIRAVTIDRVMSYLNAS.

The mature form of the wild-type human P35 (wt hP35) less the 22 amino acid signal sequence is expressed as a 197 amino acid mature protein having the amino acid sequence:

(SEQ ID NO: 2)
RNLPVATPDPGMFPCLHHSQNLLRAVSNMLQKARQTLEFYPCTSEEID

HEDITKDKTSTVEACLPLELTKNESCLNSRETSFITNGSCLASRKTSFM

MALCLSSIYEDLKMYQVEFKTMNAKLLMDPKRQIFLDQNMLAVIDEL

MQALNFNSETVPQKSSLEEPDFYKTKIKLCILLHAFRIRAVTIDRVMSY

LNAS.

Wild Type Human P40:
Wild type human P40 (wt hP40) is expressed as a 328 amino acid pro-protein (SEQ ID NO: 3) comprising a 22 amino acid signal sequence which is post-translationally removed to render a 306 amino acid mature protein (SEQ ID NO: 4). Wild type hP40 (wt hP40) contains four intrachain disulfides between residues C50 and C90, C131 and C142, C170 and C193, and C300 and C327 (numbered in accordance with SEQ ID NO:3). The canonical amino acid sequence of the hP40 pro-protein (UniProt Reference No. P29460) with the signal sequence (underlined) is:

(SEQ ID NO: 3)
MCHQQLVISWFSLVFLASPLVAIWELKKDVYVVELDWYPDAPGEMV

VLTCDTPEEDGITWTLDQSSEVLGSGKTLTIQVKEFGDAGQYTCHKGG

EVLSHSLLLLHKKEDGIWSTDILKDQKEPKNKTFLRCEAKNYSGRFTC

WWLTTISTDLTFSVKSSRGSSDPQGVTCGAATLSAERVRGDNKEYEYS

VECQEDSACPAAEESLPIEVMVDAVHKLKYENYTSSFFIRDIIKPDPPK

NLQLKPLKNSRQVEVSWEYPDTWSTPHSYFSLTFCVQVQGKSKREKK

DRVFTDKTSATVICRKNASISVRAQDRYYSSSWSEWASVPCS

The mature form of the wild-type human P40 (wt hP40) less the 22 amino acid signal sequence is expressed as a 306 amino acid mature protein (SEQ ID NO:4)

(SEQ ID NO: 4)
IWELKKDVYVVELDWYPDAPGEMVVLTCDTPEEDGITWTLDQSSEVL

GSGKTLTIQVKEFGDAGQYTCHKGGEVLSHSLLLLHKKEDGIWSTDIL

KDQKEPKNKTFLRCEAKNYSGRFTCWWLTTISTDLTFSVKSSRGSSDP

QGVTCGAATLSAERVRGDNKEYEYSVECQEDSACPAAEESLPIEVMV

DAVHKLKYENYTSSFFIRDIIKPDPPKNLQLKPLKNSRQVEVSWEYPDT

WSTPHSYFSLTFCVQVQGKSKREKKDRVFTDKTSATVICRKNASISVR

AQDRYYSSSWSEWASVPCS

IL12 Receptor:
The IL12 receptor comprises the IL12Rβ1 and IL12Rβ2 subunits. IL12 receptor activation results from the binding of IL12 cytokine ligand to both IL12Rβ1 and IL12Rβ2. The binding of the IL12 cytokine ligand to the IL12 receptor complex activates the Janus tyrosine kinases, Tyk2 and Jak2, associated with IL12Rβ1 and IL12Rβ2, respectively, to phosphorylate the cytoplasmic tails of the receptors. This results in the recruitment of signal transducer and activator of transcription 4 (STAT4). Homodimerization of STAT4 results in its release from the receptor and translocation of the phosphorylated STAT4 homodimer into the nucleus, where it binds to STAT4-binding elements of the IFN-γ gene to produce IFN-γ.

Heterodimeric hIL12Fc Muteins:
In some embodiments, the present disclosure provides heterodimeric hIL12Fc muteins comprising p40 muteins which have improved pharmacological or therapeutic properties, and methods of using such compositions.

The present disclosure provides a heterodimeric hIL12Fc mutein, the heterodimeric hIL12Fc mutein comprising a first polypeptide of the formula #1:

$$hP40M\text{-}L1_a\text{-}UH1\text{-}Fc1 \quad [1]$$

and a second polypeptide of the formula #2:

$$hP35\text{-}L2_b\text{-}UH2\text{-}Fc2 \quad [2]$$

wherein:
hP35 is a polypeptide having at least 90%, alternatively at least 91%, alternatively at least 92%, alternatively at least 93%, alternatively at least 94%, alternatively at least 95%, alternatively at least 96%, alternatively at least 97%, alternatively at least 98%, alternatively at least 99% or alternatively 100% sequence identity to SEQ ID NO:2;

hP40M is an human P40 mutein comprising one or more amino acid substitutions at positions selected from the group consisting of positions W37, P39, D40, A41, K80, E81, F82, K106, E108, D115, H216, K217, L218, and K219 numbered in accordance with wild-type pre-human P40 (SEQ ID NO:3), and optionally otherwise identical to SEQ ID NO:4, or is at least 90%, alternatively at least 91%, alternatively at least 92%, alternatively at least 93%, alternatively at least 94%, alternatively at least 95%, alternatively at least 96%, alternatively at least 97%, alternatively at least 98%, or alternatively at least 99% sequence identity to SEQ ID NO:4;

L1 and L2 are GSA linkers and a and b are independently selected from 0 (absent) or 1 (present);

UH1 and UH2 are each an upper hinge domain of human immunoglobulin independently selected from the group consisting of the IgG1, IgG2, IgG3 and IgG4 upper hinge, optionally comprising the amino acid substitution C220S (EU numbering);

Fc1 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization with Fc2, and Fc2 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization with Fc1, and wherein the polypeptide of formula 1 and the polypeptide of formula 2 are linked by at least one interchain disulfide bond.

In some embodiments, the polypeptide of formula 1 is selected from the group consisting of SEQ ID NOS: 80, 83, 85, 86, 88, 90 92, 121, 129, 132, 135, 138, 141, 144, 147, 150, and 153 or any P40M-Fc sequence in the informal sequence listing.

In some embodiments, the polypeptide of formula 2 comprises any one of SEQ ID NOS: 81, 82, 84, 87, 89, 91, 93, and 124 or any hp35-Fc sequence in the informal sequence listing.

In some embodiments, L1 and L2 are independently selected from the group consisting SEQ ID NOS: 27-79. In some embodiments, L1 and L2 are independently selected from the group consisting SEQ ID NOS: 36, 37 and 65.

In some embodiments, UH1 and UH2 are selected from the group consisting of SEQ ID NO: 11 and SEQ ID NO:12.

In some embodiments the present disclosure provides a heterodimeric hIL12Fc mutein comprising a first polypeptide selected from the group consisting of SEQ ID NOS: 80, 83, 85, 86, 88, 90, 92, 121, 129, 132, 135, 138, 141, 144, 147, 150, and 153 and a second polypeptide selected from the group consisting of SEQ ID NOS: 81, 82, 84, 87, 89, 91, 93, and 124.

In some embodiments the present disclosure provides a heterodimeric hIL12Fc mutein comprising a polypeptide of SEQ ID NO: 80 and a polypeptide of SEQ ID NO: 81.

In some embodiments the present disclosure provides a heterodimeric hIL12Fc mutein comprising a polypeptide of SEQ ID NO: 121 and a polypeptide of SEQ ID NO: 124.

In some embodiments the present disclosure provides a heterodimeric hIL12Fc mutein comprising a polypeptide of SEQ ID NO: 83 and a polypeptide of SEQ ID NO: 82.

In some embodiments the present disclosure provides a heterodimeric hIL12Fc mutein comprising a polypeptide of SEQ ID NO: 141 and a polypeptide of SEQ ID NO: 124

In some embodiments the present disclosure provides a heterodimeric hIL12Fc mutein comprising a polypeptide of SEQ ID NO: 144 and a polypeptide of SEQ ID NO: 124

In some embodiments the present disclosure provides a heterodimeric hIL12Fc mutein comprising a polypeptide of SEQ ID NO: 129 and a polypeptide of SEQ ID NO: 124.

In some embodiments the present disclosure provides a heterodimeric hIL12Fc mutein comprising a polypeptide of SEQ ID NO: 147 and a polypeptide of SEQ ID NO: 82.

In some embodiments the present disclosure provides a heterodimeric hIL12Fc mutein comprising a polypeptide of SEQ ID NO: 150 and a polypeptide of SEQ ID NO: 82.

In some embodiments the present disclosure provides a heterodimeric hIL12Fc mutein comprising a polypeptide of SEQ ID NO: 153 and a polypeptide of SEQ ID NO: 82.

In some embodiments the present disclosure provides a heterodimeric hIL12Fc mutein comprising a polypeptide of SEQ ID NO: 135 and a polypeptide of SEQ ID NO: 124.

In some embodiments the present disclosure provides a heterodimeric hIL12Fc mutein comprising a polypeptide of SEQ ID NO: 138 and a polypeptide of SEQ ID NO: 124.

In some embodiments the present disclosure provides a recombinant mammalian host cell comprising a first nucleic acid sequence encoding a polypeptide of SEQ ID NO: 80 and a second nucleic acid sequence encoding polypeptide of SEQ ID NO: 81.

In some embodiments the present disclosure provides a recombinant mammalian host cell comprising a first nucleic acid sequence encoding a polypeptide of SEQ ID NO: 121 and a second nucleic acid sequence encoding polypeptide of SEQ ID NO: 124.

In some embodiments the present disclosure provides a recombinant mammalian host cell comprising a first nucleic acid sequence encoding a polypeptide of SEQ ID NO: 83 and a second nucleic acid sequence encoding polypeptide of SEQ ID NO: 82.

In some embodiments the present disclosure provides a recombinant mammalian host cell comprising a first nucleic acid sequence encoding a polypeptide of SEQ ID NO: 141 and a polypeptide of SEQ ID NO: 124

In some embodiments the present disclosure provides a recombinant mammalian host cell comprising a first nucleic acid sequence encoding a polypeptide of SEQ ID NO:144 and a second nucleic acid sequence encoding polypeptide of SEQ ID NO: 124

In some embodiments the present disclosure provides a recombinant mammalian host cell comprising a first nucleic acid sequence encoding a polypeptide of SEQ ID NO: and a second nucleic acid sequence encoding polypeptide of SEQ ID NO: 124.

In some embodiments the present disclosure provides a recombinant mammalian host cell comprising a first nucleic acid sequence encoding a polypeptide of SEQ ID NO: 147 and a second nucleic acid sequence encoding polypeptide of SEQ ID NO: 82.

In some embodiments the present disclosure provides a recombinant mammalian host cell comprising a first nucleic acid sequence encoding a polypeptide of SEQ ID NO: 150 and a second nucleic acid sequence encoding polypeptide of SEQ ID NO: 82.

In some embodiments the present disclosure provides a recombinant mammalian host cell comprising a first nucleic acid sequence encoding a polypeptide of SEQ ID NO: 153 and a second nucleic acid sequence encoding polypeptide of SEQ ID NO: 82.

In some embodiments the present disclosure provides a recombinant mammalian host cell comprising a first nucleic acid sequence encoding a polypeptide of SEQ ID NO: 135 and a second nucleic acid sequence encoding polypeptide of SEQ ID NO: 124.

In some embodiments the present disclosure provides a recombinant mammalian host cell comprising a first nucleic acid sequence encoding a polypeptide of SEQ ID NO: 138 and a second nucleic acid sequence encoding polypeptide of SEQ ID NO: 124.

Human P40 Muteins

The heterodimeric hIL12Fc muteins of the present disclosure comprise a modified human P40 polypeptide or "hP40 mutein" (also abbreviated "hp40M" or "hP40M") comprising one or more amino acid substitutions, modifications and/or deletions at the interface with the extracellular domain of IL12Rβ1 which result in a reduction of the binding affinity of hp40M to IL12Rβ1 relative to the mature form of wt hP40 (SEQ ID NO:4). In some embodiments, the binding affinity of the hP40 mutein for the extracellular domain of hIL12Rβ1 is reduced by about 10%, alternatively by about 20%, alternatively by about 30%, alternatively by about 40%, alternatively by about 50%, alternatively by about 60%, alternatively by about 60%, alternatively by about 70%, alternatively by about 80%, alternatively by about 900%, alternatively to about 100% compared to binding affinity of a reference polypeptide (wt hP40) as determined by surface plasmon resonance (SPR) spectroscopy. In some embodiments, the hP40M is a modified wild type human hp40 polypeptide having at least 70% sequence identity to SEQ ID NO:4 (e.g., at least 70%, 75%, 80%, 85%, 90%, 91%, 92%, 93%, 94%, 95%, 96%, 97%, 98%, or 99% sequence identity to SEQ ID NO:4). In some embodiments, the hP40M comprises one or more amino acid substitutions at residues selected from the group consisting of W37, P39, D40, A41, K80, E81, F82, K106, E108, D115, H216, K217, L218, and K219 numbered in accordance with SEQ ID NO:3. In some embodiments, the hP40M comprises one or more amino acid substitutions at residues selected from the group consisting of E81, F82, K106, and K217 numbered in accordance with SEQ ID NO:3. In some embodiments the one or more amino acid substitutions at positions W37, P39, D40, A41, K80, E81, F82, K106, E108, D115, H216, K217, L218, and K219 are selected from the group consisting of P39A, D40A, E81A, F82A, K106A, D109A, K217A, K219A. In some embodiments, the hP40 mutein comprises two or more amino acid substitutions at residues selected from the group consisting of W37, P39, D40, A41, K80, E81, F82, K106, E108, D115, H216, K217, L218, and K219 numbered in accordance with SEQ ID NO:3. In some embodiments, the hP40M comprises two or more amino acid substitutions at residues selected from the group consisting of E81, F82, K106, and K217 numbered in accordance with SEQ ID NO:3. In some embodiments, the hP40 mutein comprises three or more amino acid substitutions at residues selected from the group consisting of W37, P39, D40, A41, K80, E81, F82, K106, E108, D115, H216, K217, L218, and K219 numbered in accordance with SEQ ID NO:3. In some embodiments wherein the hP40M comprises two or more amino acid substitutions at W37, P39, D40, A41, K80, E81, F82, K106, E108, D115, H216, K217, L218, and K219, the two or more substitutions comprise a set of amino acid substitutions selected from the group consisting of the sets of amino acid substitutions: E81A/F82A, E81K/F82A, E81L/F82A, E81H/F82A and E81S/F82A. In some embodiments, the hP40) mutein comprises three or more amino acid substitutions at residues selected from the group consisting of E81, F82, K106, and K217 numbered in accordance with SEQ ID NO:3. In some embodiments, the hP40M comprises three or more amino acid substitutions at residues selected from the group consisting of W37, P39, D40, A41, K80, E81, F82, K106, E108, D115, H216, K217, L218, and K219 numbered in accordance with SEQ ID NO:3. In some embodiments wherein the hP40 mutein comprises three or more amino acid substitutions at W37, P39, D40, A41, K80, E81, F82, K106, E108, D115, H216, K217, L218, and K219, the three or more substitutions comprise a set of amino acid substitutions selected from the group consisting of the sets of amino acid substitutions: W37A/E81A/F82A; E81A/F82A/K106A; E81A/F82A/K106A/K219A, E81A/F82A/K106N, E81A/ F82A/K106Q, E81A/F82A/K106T, and E81A/F82A/ K106R. In some embodiments, the hP40 mutein comprises four or more amino acid substitutions at residues selected from the group consisting of W37, P39, D40, A41, K80, E81, F82, K106, E108, D115, H216, K217, L218, and K219 numbered in accordance with SEQ ID NO:3. In some embodiments wherein the hP40 mutein comprises four or more amino acid substitutions at W37, P39, D40, A41, K80, E81, F82, K106, E108, D115, H216, K217, L218, and K219, the four or more substitutions comprise a set of amino acid substitutions selected from the group consisting of the sets of amino acid substitutions: E81A/F82A/K106A/K217A, 81A/F82A/K106A/E108A/D115A and P39A/D40A/E81A/ F82A.

In some embodiments, the hP40M comprises the set of amino acid substitutions E81A/F82A and is referred to herein as "2xAla" (SEQ ID NO:6). In some embodiments, the hP40M comprises the set of amino acid substitutions E81A/F82A/K106A and is referred to herein as "3xAla" (SEQ ID NO:8). In some embodiments, the hP40M comprises the set of amino acid substitutions E81A/F82A/K106A/K217A and is referred to herein as "4xAla" (SEQ ID NO: 10).

In some embodiments, the binding affinity of heterodimeric hIL12Fc muteins of the present disclosure comprising one or more, optionally two or more, optionally three or more, or optionally 4 or more amino acid substitutions at residues selected from the group consisting of W37, P39, D40, A41, K80, E81, F82, K106, E108, D115, H216, K217, L218, and K219 (numbered in accordance with SEQ ID NO:3) for the extracellular domain (ECD) of IL12Rβ1 is reduced by at least 5%, optionally by at least 10%, optionally by at least 20%, optionally by at least 30%, optionally by at least 40%, optionally by at least 50%, optionally by at least 60%, optionally by at least 70%, relative to the binding affinity of wild type hP40 (SEQ ID NO:4) for the extracellular domain (ECD) of IL12Rβ1 as determined by surface plasmon resonance.

Properties of the Heterodimeric hIL12Fc Muteins

In some embodiments, the heterodimeric hIL12Fc muteins described herein provide cell-type biased signaling of the downstream signal transduction mediated through the IL12 receptor compared to a reference polypeptide (e.g., wild type hIL12). In some embodiments, the reduced binding affinity the hP40 mutein of the heterodimeric hIL12Fc mutein to IL12Rβ1 results in a reduction in STAT4-mediated signaling compared to a reference polypeptide (wt hIL12). In some embodiments, heterodimeric hIL12Fc muteins of the present disclosure are partial agonists. In some embodiments, the heterodimeric hIL12Fc muteins described herein are partial agonists of STAT3-mediated signaling ("STAT3 signaling") and/or STAT4 mediated signaling ("STAT4 signaling"). In some embodiments, the heterodimeric hIL12Fc muteins have reduced STAT3-mediated signaling compared to a reference polypeptide (wt hIL12). In some embodiments, the STAT3 signaling and/or STAT4 signaling is determined by an assay selected from the group consisting of by a gene expression assay, a phospho-flow signaling assay, and an enzyme-linked immunosorbent assay (ELISA).

The heterodimeric hIL12Fc muteins comprising the hP40 muteins described herein provide selective activation of certain cell types which provides beneficial properties, such as anti-inflammatory properties, and/or have reduced undesirable properties, such as pro-inflammatory side effects compared to wt hIL12. In some embodiments, the heterodimeric hIL12Fc muteins comprising the hP40 muteins described herein provide cell-type biased signaling of the downstream signal transduction mediated through the IL12 receptor compared to a reference polypeptide (e.g., wild type hIL12). For example, the heterodimeric hIL12Fc muteins of the present disclosure retain the property of wild-type hIL12 to stimulate or activate IL12 signaling in CD8+ T cells but exhibit a reduction of IFNγ and/or STAT4-mediated signaling in natural killer (NK) cells. In some embodiments, the cell-type biased signaling of the heterodimeric hIL12Fc muteins comprising the hP40 muteins described herein of the present disclosure includes the ability to provide substantial IL12 signaling (e.g., at least 30%, alternatively at least 40%, alternatively at least 50%, alternatively at least 60%, alternatively at least 70%, alternatively at least 80%, alternatively at least 90%) of the activity of wt hIL12 in CD8+ T cells. In some embodiments, the heterodimeric hIL12Fc muteins described herein exhibit increased STAT4 signaling in CD8+ T cells by 10%, 20%, 30%, 40%, 50%, 60%, 70%, 80%, 90%, 100%, 200%, 300%, 400% or greater and decrease STAT4 signaling in NK cells, for example, at least about a 10%, 20%, 30%, 40%, 50%, 60%, or 70% decrease, as compared to a reference polypeptide (wt hIL12). In some embodiments, the heterodimeric hIL12Fc muteins described herein activate interferon gamma (IFNγ) in CD8+ cells by 10%, 20%, 30%, 40%, 50%, 60%, 70%, 80%, 90%, 100%, 200%, 300%, 400% and decreased IFNγ signaling in NKT cells by at least 10%, 20%, 30%, 40%, 50%, 60%, or 70% compared to a reference polypeptide (wt hIL12). Thus, the heterodimeric hIL12Fc muteins comprising the hP40 muteins described herein exhibit reduced activation of NK cells while retaining the ability to stimulate CD8+ T cells.

GSA Linkers:

In the polypeptides of formulae [1] and [2], Fc domain fusions incorporating a p40) mutein and/or p35 may optionally contain a GSA linker molecule between the p40) mutein and the upper hinge. As used herein the term "GSA linker" refers to a polypeptide having 4, 5, 6, 7, 8, 9, 10, 11, 12, 13, 14, 15, 16, 17, 18, 19 or 20 amino acids comprised of amino acids selected from the group consisting of glycine, serine and alanine. In some embodiments, the polypeptide linker is a glycine-serine polymer of the structure $(GGGGS_m)_n$, $(GGGS_m)_n$, $(GGGA_m)_n$ and $(GGGGA_m)_n$, and combinations thereof, where m, n, and o are each independently selected from 1, 2, 3 or 4. In the construction of such polymers, it may be desirable to avoid repeated "GSG" sequences which potentially may provide introduction of a non-naturally occurring glycosylation site. Exemplary glycine-serine linkers include but are not limited to the monomers: GGGS (referred to as "G4S"), GGGGA (referred to as "G4A"), GGGS (referred to as "G3S") and GGGA (referred to as "G3A"), or homopolymers (e.g. "GGGGSGGGS" also referred to as (G4S) 2) or heteropolymers thereof. Exemplary GSA linkers are provided in Table 2 below:

TABLE 2

Exemplary GSA Linkers

| Name/Ref | Amino Acid Sequence | SEQ ID NO: |
|---|---|---|
| (G3A)2 | GGGAGGGA | 27 |
| (G3A)4 | GGGAGGGAGGGA | 28 |
| (G3AG2)2 | GGGAGGGGGAGG | 29 |
| (G3S)3 | GGGSGGGSGGGS | 30 |
| (G3SG2)2 | GGGSGGGGSGG | 31 |
| (G4A)2 | GGGGAGGGGA | 32 |
| (G4a)3 | GGGGAGGGGAGGGGA | 33 |
| (G4AG)2 | GGGGAGGGGAG | 34 |
| (G4AG2)2 | GGGGAGGGGGAGG | 35 |
| (G4S)2 | GGGGSGGGGS | 36 |
| (G4S)3 | GGGGSGGGGSGGGGS | 37 |
| (G4SG)2 | GGGGSGGGGSG | 38 |
| (G4SG2)2 | GGGGSGGGGGSGG | 39 |
| (G5AG)2 | GGGGGAGGGGGAG | 40 |
| (G5SG)2 | GGGGGSGGGGGSG | 41 |
| G2AG | GGAG | 42 |
| G3A | GGGA | 43 |
| G3A-G3S | GGGAGGGS | 44 |
| G3A-G3S-G3A | GGGAGGGSGGGA | 45 |
| G3A-G4S | GGGAGGGGS | 46 |
| G3A-G4SA | GGGAGGGGA | 47 |
| G3AG2 | GGGAGG | 48 |
| G3AG2 G4AG | GGGAGGGGGAG | 49 |
| G3S | GGGS | 50 |
| G3S-G3A-GGGS | GGGSGGGAGGGS | 51 |
| G3SG2-G4SG | GGGSGGGGGSG | 52 |
| G4A | GGGGA | 53 |
| G4A-G4S-G4A | GGGGGGGSGGGGA | 54 |
| G4A-G4S-G4S | GGGGAGGGGSGGGGS | 55 |
| G4A-G4AG | GGGGGGGAG | 56 |
| G4A-G4S | GGGGAGGGGS | 57 |
| G4A-G4SG | GGGGAGGGGSG | 58 |
| G4AG | GGGGAG | 59 |
| G4AG G4SG2 | GGGGAGGGGSG | 60 |
| G4AG-G4AG | GGGGGGGGAG | 61 |
| G4AG-G4SG | GGGGAGGGGSG | 62 |
| G4AG2 | GGGGAGG | 63 |
| G4AG2 G3SG2 | GGGGAGGGGSGG | 64 |
| G4S | GGGGS | 65 |
| G4S-G4A-G4A | GGGGSGGGGAGGGGA | 66 |
| G4S-G4A-G4S | GGGGSGGGGAGGGGS | 67 |
| G4S-G4S-G4A | GGGGSGGGGSGGGGA | 68 |
| G4S-G4A | GGGGSGGGGA | 69 |
| G4S-G4AG | GGGGSGGGGAG | 70 |
| G4S-G4SG | GGGGSGGGGSG | 71 |
| G4SG G3AG2 | GGGGSGGGGAGG | 72 |
| G4SG-G4AG | GGGGSGGGGAG | 73 |
| G4SG-G4SG | GGGGSGGGGSG | 74 |
| G4SG2 G5SG | GGGGSGGGGGSG | 75 |
| G5AG | GGGGGAG | 76 |
| G5SG G4AG2 | GGGGGSGGGGAGG | 77 |

TABLE 2-continued

Exemplary GSA Linkers

| Name/Ref | Amino Acid Sequence | SEQ ID NO: |
|---|---|---|
| GAG2 | GAGG | 78 |
| GSG2 | GAGG | 79 |

Upper Hinge:

The heterodimeric hIL12Fc muteins of the present disclosure are heterodimers comprising polypeptides of the formulae [1] and [2], which each incorporate an upper hinge region of a human immunoglobulin molecule. The term "upper hinge" or "UH" refers to an amino acid sequence corresponding to amino acid residues 216-220 (EU numbering) of a human immunoglobulin molecule. In some embodiments, the upper hinge region is a naturally occurring upper hinge region of a human immunoglobulin selected from the LH regions of human IgG1, human IgG2, human IgG3 and human IgG4 upper hinge domains. In some embodiments, the upper hinge region is the upper hinge region of a human IgG1 immunoglobulin. In some embodiments, the upper hinge region is the upper hinge region of a human IgG1 immunoglobulin comprising the pentameric amino acid sequence: EPKSC (SEQ ID NO: 11).

In some embodiments, the upper hinge region contains an unpaired cysteine residue at position 220 (EU numbering) that typically, in a complete immunoglobulin molecule, binds to a cysteine on a light chain. When only the Fc domain is used comprising the hinge domain, the unpaired cysteine in the hinge domain creates the potential of the formation of improper disulfide bonds. Consequently, in some embodiments the cysteine at position 220 (C220, numbered in accordance with EU numbering) is substituted with an amino acid that does not promote disulfide bonding. In some embodiments, the Fc domain comprises a C220S mutation having the amino acid sequence EPKSS (SEQ ID NO:12).

Fc1 and Fc2:

The heterodimeric hIL12Fc muteins of the present disclosure are heterodimers comprising polypeptides of the formulae [1] and [2], which each incorporate an Fc region (Fc1 and Fc2) of a human immunoglobulin molecule modified to promote heterodimerization.

As used herein the term "Fc" and "Fc monomer" are used interchangeably herein to designate the monomeric polypeptide subunit of an Fc dimer. An Fc comprises an amino acid sequence (from amino to carboxy terminal) comprising a lower hinge domain and the CH2 and CH3 domains of a human immunoglobulin molecule. In some embodiments, the Fc monomer is a polypeptide comprising the lower hinge domain and the CH2 and CH3 domains of a human immunoglobulin molecule domains of human IgG1, human IgG2, human IgG3 and human IgG4 hinge domains. The CH2 domain of hIgG1 corresponds to amino acid residues 231-340 (EU numbering) and is provided as SEQ ID NO: 14. The CH3 domain of hIgG1 corresponds to amino acid residues 341-447 (EU numbering) and is provided as SEQ ID NO: 15.

The polypeptides of the formulae [1] and [2] each incorporate a lower hinge region of a human immunoglobulin. As used herein, the term "lower hinge" or "LH" refers to an amino acid sequence corresponding to amino acid residues 221-229 (EU numbering) of a human immunoglobulin molecule. In some embodiments, the lower hinge region is a naturally occurring lower hinge region of a human immunoglobulin selected from the LH regions of IgG1, IgG2, IgG3 and IgG4 lower hinge domains. In some embodiments, the lower hinge region is the lower hinge region of a human IgG1 immunoglobulin. In some embodiments, the lower hinge region is the lower hinge region of a human IgG1 immunoglobulin comprising the decametric amino acid sequence: DKTHTCPPCP (SEQ ID NO:13).

In some embodiments, Fc1 and Fc2 are derived from a polypeptide corresponding to amino acids 221-447 (EU numbering) of the human IgG1 immunoglobulin having the amino acid sequence (EU numbering indicated, SEQ ID NO: 16):

```
                                          (SEQ ID NO: 16)
         230        240        250        260
    DKTHTCPPCP APELLGGPSV FLFPPKPKDT LMISRTPEVT 270        280.       290.       300
    CVVVDVSHED PEVKFNWYVD GVEVHNAKTK PREEQYNSTY 310        320        330        340
    RVVSVLTVLH QDWLNGKEYK CKVSNKALPA PIEKTISKAK 350        360        370        380
    GQPREPQVYT LPPSRDELTK NQVSLTCLVK GFYPSDIAVE 390        400        410        420
    WESNGQPENN YKTTPPVLDS DGSFFLYSKL TVDKSRWQQG 430        440        447
    NVFSCSVMHE ALHNHYTQKS LSLSPGK
```

As indicated in above sequence, the C-terminal residue of the wild-type form of the IgG1 Fc domain is a lysine, referred to as K447 in accordance with EU numbering. The K447 is inconsistently removed by the producer cell during recombinant product. As a result, the population of recombinant Fc monomers may be heterogenous in that some fraction of the recombinantly produced Fc monomers will contain K447 and others will not. Such inconsistent proteolytic processing by producer cells may therefore result in a heterogenous population of hIL12Fc. Typically, particularly in the context of human pharmaceutical agents, such heterogeneity of the active pharmaceutical ingredient is to be avoided. Consequently, in addition to modifications to the Fc monomer sequence promote heterodimerization, the present disclosure provides Fc monomers that further comprising a deletion of the C-terminal K447 or a deletion of G446 and K447 and nucleic acid sequences encoding Fc monomers comprising a: (a) a deletion of the lysine residue at position 447 (K447, EU numbering, abbreviated as ΔK447 or des-K447), or (b) deletion of both the glycine at position 456 (G446 EU numbering, abbreviated as des-G446) and K447 (this double deletion of G446 and K447 being referred to herein as des-G446/des-K447 or ΔG446/ΔK447).

Modification of Hp40 K282 to Avoid Proteolytic Cleavage

In some embodiments, the heterodimeric IL12Fc muteins of the present disclosure comprise an amino acid substitution of the lysine (K) residue at position 260 (K260) of the mature form of the human p40 polypeptide (SEQ ID NO: 4 corresponding to position 282 of the human p40 precursor polypeptide SEQ ID NO: 3). As described in Webster, et al (U.S. Pat. No. 7,872,107 issued Jan. 18, 2011), a substitution at position 260 of the mature human p40 polypeptide renders the human p40 polypeptide resistant to proteolytic cleavage. In some embodiments, the human p40 polypeptide of the heterodimeric IL12Fc muteins of the present disclosure comprise a substitution of the lysine at position K282 (numbered in accordance with SEQ ID NO:3) polypeptide with a non-basic amino acid. In some embodiments the non-basic amino acid is selected from the group consisting of alanine, glycine, asparagine or glutamine. In some embodiments, the p40 polypeptide of the heterodimeric IL12Fc muteins of the present disclosure comprise a mutation at position K282 (numbered in accordance with SEQ ID NO:3) selected from the group consisting of K282G, K282A, K282N, K282Q (numbered in accordance with SEQ ID NO:3).

In some embodiments, the heterodimeric IL12Fc muteins of the present disclosure comprise the human p40 polypeptide comprising a set of amino acid substitutions selected from the group consisting of E81A/F82A/K106A/K282G, E81A/F82A/K106A/K282A, E81A/F82A/K106A/K282N, and E81A/F82A/K106A/K282Q (numbered in accordance with SEQ ID NO:3). In some embodiments, the heterodimeric IL12Fc muteins of the present disclosure comprise the human p40 polypeptide comprising a set of amino acid substitutions selected from the group consisting of E81A/F82A/K282G, E81A/F82A/K282A, E81A/F82A/K282N, and E81A/F82A/K282Q (numbered in accordance with SEQ ID NO:3).

In one embodiment, the present disclosure provides a heterodimeric IL12Fc mutein comprising a human p40 mutein having the amino acid sequence:

(SEQ ID NO: 155)
IWELKKDVYVVELDWYPDAPGEMVVLTCDTPEEDGITWTLDQSSEVL

GSGKTLTIQVKAAGDAGQYTCHKGGEVLSHSLLLLHAKEDGIWSTDI

LKDQKEPKNKTFLRCEAKNYSGRFTCWWLTTISTDLTFSVKSSRGSS

DPQGVTCGAATLSAERVRGDNKEYEYSVECQEDSACPAAEESLPIEV

MVDAVHKLKYENYTSSFFIRDIIKPDPPKNLQLKPLKNSRQVEVSWE

YPDTWSTPHSYFSLTFCVQVQGKSGREKKDRVFTDKTSATVICRKNA

SISVRAQDRYYSSSWSEWASVPCS.

In one embodiment, the present disclosure provides a heterodimeric IL12Fc mutein comprising a human p40 mutein having the amino acid sequence:

(SEQ ID NO: 156)
IWELKKDVYVVELDWYPDAPGEMVVLTCDTPEEDGITWTLDQSSEVL

GSGKTLTIQVKAAGDAGQYTCHKGGEVLSHSLLLLHAKEDGIWSTDI

LKDQKEPKNKTFLRCEAKNYSGRFTCWWLTTISTDLTFSVKSSRGSS

DPQGVTCGAATLSAERVRADNKEYEYSVECQEDSACPAAEESLPIEV

MVDAVHKLKYENYTSSFFIRDIIKPDPPKNLQLKPLKNSRQVEVSWE

YPDTWSTPHSYFSLTFCVQVQGKSGREKKDRVFTDKTSATVICRKNA

SISVRAQDRYYSSSWSEWASVPCS.

In one embodiment, the present disclosure provides a heterodimeric IL12Fc mutein comprising a human p40 mutein having the amino acid sequence:

(SEQ ID NO: 157)
IWELKKDVYVVELDWYPDAPGEMVVLTCDTPEEDGITWTLDQSSEVL

GSGKTLTIQVKAAGDAGQYTCHKGGEVLSHSLLLLHAKEDGIWSTDI

LKDQKEPKNKTFLRCEAKNYSGRFTCWWLTTISTDLTFSVKSSRGSS

DPQGVTCGAATLSAERVRNDNKEYEYSVECQEDSACPAAEESLPIEV

MVDAVHKLKYENYTSSFFIRDIIKPDPPKNLQLKPLKNSRQVEVSWE

YPDTWSTPHSYFSLTFCVQVQGKSGREKKDRVFTDKTSATVICRKNA

SISVRAQDRYYSSSWSEWASVPCS.

In one embodiment, the present disclosure provides a heterodimeric IL12Fc mutein comprising a human p40 mutein having the amino acid sequence:

(SEQ ID NO: 158)
IWELKKDVYVVELDWYPDAPGEMVVLTCDTPEEDGITWTLDQSSEVLGS

GKTLTIQVKAAGDAGQYTCHKGGEVLSHSLLLLHAKEDGIWSTDILKDQ

KEPKNKTFLRCEAKNYSGRFTCWWLTTISTDLTFSVKSSRGSSDPQGVT

CGAATLSAERVRQDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSGREKKDRVFTDKTSATVICRKNASISVRAQDRYYS

SSWSEWASVPCS.

In one embodiment, the present disclosure provides a heterodimeric IL12Fc mutein comprising a human p40 mutein having the amino acid sequence:

(SEQ ID NO: 159)
IWELKKDVYVVELDWYPDAPGEMVVLTCDTPEEDGITWTLDQSSEVLGS

GKTLTIQVKAAGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSGREKKDRVFTDKTSATVICRKNASISVRAQDRYYS

SSWSEWASVPCS.

In one embodiment, the present disclosure provides a heterodimeric IL12Fc mutein comprising a human p40 mutein having the amino acid sequence:

(SEQ ID NO: 160)
IWELKKDVYVVELDWYPDAPGEMVVLTCDTPEEDGITWTLDQSSEVLGS

GKTLTIQVKAAGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRADNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSGREKKDRVFTDKTSATVICRKNASISVRAQDRYYS

SSWSEWASVPCS,

In one embodiment, the present disclosure provides a heterodimeric IL12Fc mutein comprising a human p40 mutein having the amino acid sequence:

(SEQ ID NO: 161)
IWELKKDVYVVELDWYPDAPGEMVVLTCDTPEEDGITWTLDQSSEVLGS

GKTLTIQVKAAGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRNDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSGREKKDRVFTDKTSATVICRKNASISVRAQDRYYS

SSWSEWASVPCS.

In one embodiment, the present disclosure provides a heterodimeric IL12Fc mutein comprising a human p40 mutein having the amino acid sequence:

(SEQ ID NO: 162)
IWELKKDVYVVELDWYPDAPGEMVVLTCDTPEEDGITWTLDQSSEVLGS

GKTLTIQVKAAGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRQDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSGREKKDRVFTDKTSATVICRKNASISVRAQDRYYS

SSWSEWASVPCS

Modifications of Fc Subunits to Promote Heterodimerization

As provided in formulae [1] and [2] above, the Fc1 and Fc2 monomers of the dimeric Fc contain amino acid substitutions that promote heterodimerization between Fc1 and Fc2. A variety of techniques are established for the promotion of heterodimerization of Fc domains. See, e.g. Kim, et al., U.S. Pat. No. 11,087,249, issued Aug. 3, 2021. In some embodiments, the modifications to promoter heterodimerization of the Fc1 and Fc2 monomers are the HF-TA mutations and the HA-TF mutations as described in Moore, et al (2011) mAbs 3 (6): 546-557. The HF-TA method employs the S364H/T394F substitutions on one Fc monomer and the Y349T/F405A substitutions on the complementary Fc monomer. The (HA-TF) method employs the S364H/F405A substitutions on one Fc monomer and the Y349T/T394F substitutions on the complementary Fc monomer. Alternatively, the Fc1 and Fc2 monomers are modified to promote heterodimerization by the ZW1 heterodimerization method which employs the T350V/L351Y/F405A/Y407V substitutions on one Fc monomer and the T350V/T366L/K392L/T394W substitutions on the complementary Fc monomer. Von Kreudenstein, et al (2013) mAbs, 5 (5): 646-654. Alternatively, the Fc1 and Fc2 monomers are modified to promote heterodimerization by the EW-RVT heterodimerization method which employs the K360E/K409W substitutions on one Fc monomer and the Q347R/D399V/F405T substitutions on the complementary Fc monomer. Choi, et al (2015) Molecular Immunology 65 (2): 377-83.

In one embodiment, Fc1 and Fc2 are modified to promote heterodimerization by the employment of the "knob-into-hole" (abbreviated KiH) modification as exemplified herein. The KiH modification comprises one or more amino acid substitutions in a first Fc monomer (e.g. Fc1) that create a bulky "knob" domain on a first Fc and one or more amino acid substitutions on a second Fc monomer (e.g. Fc2) that create a complementary pocket or "hole" to receive the "knob" of the first Fc monomer.

A variety of amino acid substitutions have been established for the creation of complementary knob and hole Fc monomers. See, e.g. Ridgway, et al (1996) Protein Engineering 9 (7): 617-921; Atwell, et al (1997) J. Mol. Biol. 270:26-35; Carter, et al. U.S. Pat. No. 5,807,706 issued Sep. 15, 1998; Carter, et al U.S. Pat. No. 7,695,936 issued Apr. 13, 2010; Zhao et al. "A new approach to produce IgG4-like bispecific antibodies," Scientific Reports 11:18630 (2021); Cao et al. "Characterization and Monitoring of a Novel Light-heavy-light Chain Mispair in a Therapeutic Bispecific Antibody," and Liu et al. "Fc Engineering for Developing Therapeutic Bispecific Antibodies and Novel Scaffolds". Frontiers in Immunology. 8:38. doi: 10.3389/fimmu.2017.00038 (2017).

In some embodiments, the Fc domain comprises two Fc monomers wherein the CH3 domain of a first Fc monomer wherein the threonine at (EU numbering) position 366 is modified with a bulky residue (e.g. a T366W) create a "knob" and the substitution, and a second Fc monomer comprising one or more substitutions in complementary residues of the CH3 domain of the second Fc monomer to create a pocket or "hole" to receive the bulky residue, for example by amino acid substitutions such as T366S, L368A, and/or Y407V.

In one embodiment, the Fc1 monomer of formula 1 is a "knob" modified Fc monomer comprising the amino acid substitution T366W and the Fc2 monomer of formula 2 is a "hole" modified Fc comprising the set of amino acid substitutions T366S/L368A/Y407V.

Alternatively, the Fc1 monomer of formula 1 is a "hole" modified Fc monomer comprising the set of amino acid substitutions T366S/L368A/Y407V and the Fc2 monomer of formula 2 is a "knob" modified Fc monomer comprising the amino acid substitution T366W.

An example of an engineered Fc heterodimeric pair comprising complementary KiH modifications is provided in Table 3 below:

TABLE 3

Amino Acid Substitution Sets of Complementary IgG1 KiH Heterodimeric Pairs

| Fc Dimer No. | Fc Monomer | Amino Acid Substitution Set (EU Numbering) |
|---|---|---|
| 1 | Knob | T366W |
| | Hole | T366S/L368A/Y407V |

As noted, the heterodimeric hIL12Fc muteins of the present disclosure are provided as a complementary heterodimeric pair of polypeptides of the formulae [1] and [2] wherein the first and second polypeptide are linked by at least one disulfide bond. In some embodiments, the incorporation of a disulfide bond between the polypeptides of formulae [1] and [2] may be achieved by cysteine substitutions at particular points within the Fc1 and Fc2 domains. In one embodiment, the Fc1 domain of the polypeptide of formula [1] is derived from the Fc domain of hIgG1 comprising an amino acid substitution S354C (EU numbering) and the Fc2 domain of the polypeptide of formula [2] is derived from the Fc domain of hIgG1 comprising an amino acid substitution Y349C (EU numbering) to provide a disulfide bond between the S354C of Fc1 and Y349C of Fc2. Alternatively, the Fc1 domain of the polypeptide of formula [1] is derived from the Fc domain of hIgG1 comprising an amino acid substitution Y349C (EU numbering) and the Fc2 domain of the polypeptide of formula [2] is derived from the Fc domain of hIgG1 comprising an amino acid substitution S354C (EU numbering) to provide a disulfide bond between the S354C of Fc1 and Y349C of Fc2.

In some embodiments, the hP35Fc and hP40MFc of the heterodimeric hIL12Fc mutein are covalently linked via one or more, optionally two or more optionally three or more disulfide bonds, optionally four or more disulfide bonds between the side chains of the following groups of cystine pairs: (a) C96 of the hP35 and C199 of the hP40M; (b) between C226 of the first Fc monomer and the C226 of the second Fc monomer, (c) between C229 of the first Fc monomer and the C229 of the second Fc monomer; and (d) between S354C of the first Fc domain comprising a S354C amino acid substitution and Y349C of the second Fc domain comprising a Y349C amino acid substitution.

Further examples of complementary KiH engineered heterodimeric Fc pairs that may be used in the practice of the present disclosure are provided in Table 4 below.

TABLE 4

Knob-into-Hole Fc Dimer Pairs

| Fc Dimer Pair. | Monomer Type | Monomer SEQ ID | UH Sequence* | UH SEQ ID | Fc Amino Acid Substitutions (EU Numbering) | Fc Seq ID |
|---|---|---|---|---|---|---|
| 2 | Knob | 19 | wt | 11 | T366W | 17 |
|  | Hole | 20 | wt | 11 | T366S/L368A/Y407V | 18 |
| 3 | Knob | 21 | C220S | 12 | T366W | 17 |
|  | Hole | 22 | C220S | 12 | T366S/L368A/Y407V | 18 |
| 4 | Knob | 23 | wt | 11 | T366W | 17 |
|  | Hole | 24 | wt | 11 | T366S/L368A/Y407V | 18 |
| 5 | Knob | 25 | C220S | 12 | S354C/T366W | 17 |
|  | Hole | 26 | C220S | 12 | Y349C/T366S/L368A/Y407V | 18 |

*wt = wt hIgG1; C220S refers to wt hIgG1 with a C to S mutation at position 220 (EU numbering)

Modifications to Reduce Effector Functions

In some embodiments the amino acid sequence of the Fc1 and/or Fc2 monomers modified to promote heterodimerization may be further modified to reduce effector function. In some embodiments, the Fc domain may be modified to substantially reduce binding to Fc receptors (FcγR and FcR) which reduces or abolishes antibody directed cytotoxicity (ADCC) effector function. Modification of Fc domains to reduce effector function are well known in the art. See, e.g., Wang, et al. (2018) *IgG Fc engineering to modulate antibody effector functions*, Protein Cell 9 (1): 63-73. For example, mutation of the lysine residue at position 235 (EU numbering) from leucine (L) to glutamic acid (E) is known to reduce effector function by reducing FcgR and C1q binding. Alegre, et al. (1992) J. Immunology 148:3461-3468. Additionally, substitution of the two leucine (L) residues at positions 234 and 235 (EU numbering) in the IgG1 hinge region with alanine (A), i.e., L234A and L235A, results in decreased complement dependent cytotoxicity (CDC) and antibody dependent cellular cytotoxicity (ADCC). Hezereh et al., (2001) J. Virol 75 (24): 12161-68. Furthermore, mutation of the proline at position 329 (EU numbering) to alanine (P329A) or glycine, (P329G) mitigates effector function and may be combined with the L234A and L235A substitutions. In some embodiments, the Fc domains (Fc1 and Fc2) of the compositions of the present invention may comprises the amino acid substitutions L234A/L235A/P329A (EU numbering) referred to as the "LALAPA" substitutions or L234A/L235A/P329G (EU numbering) referred to as the "LALAPG" substitutions. In some embodiments, the Fc domains (Fc1 and Fc2) of the compositions of the present disclosure may comprises the amino acid substitutions E233P/L234V/L235A/ΔG237 (referred to in the scientific literature as the PVAdelG mutation).

In some embodiments, the Fc domains (Fc1 and Fc2) of the compositions of the present disclosure are from hIgG4. In such instances where the Fc domains of the heterodimeric IL12 and IL23 muteins are derived from hIgG4, attenuation of effector function may be achieve by introduction of the S228P and/or the L235E mutations (EU numbering).

Examples of paired KiH Fc dimeric constructs that may be incorporated into the hIL12 and heterodimeric hIL23Fc muteins of the present disclosure are provided in Table 5 below:

TABLE 5

Amino Acid Substitution Sets of Complementary IgG1 KiH UH/Fc Heterodimeric Pairs Comprising Mutations to Reduce Effector Function

| Fc Dimer No. | UH Fc Monomer | Amino Acid Substitution Set (EU Numbering) |
|---|---|---|
| 6 | Knob | L234A/L235A/P329A/T366W/ΔK447 |
|  | Hole | L234A/L235A/P329A/T366S/L368A/Y407V/ΔK447 |
| 7 | Knob | C220S/L234A/L235A/P329A/T366W/ΔK447 |
|  | Hole | C220S/L234A/L235A/P329A/T366S/L368A/Y407V/ΔK447 |
| 8 | Knob | L234A/L235A/P329A/S354C/T366W/ΔK447 |
|  | Hole | L234A/L235A/P329A/Y349C/T366S/L368A/Y407V/ΔK447 |
| 9 | Knob | C220S/L234A/L235A/P329A/S354C/T366W/ΔK447 |
|  | Hole | C220S/L234A/L235A/P329A/Y349C/T366S/L368A/Y407V/ΔK447 |
| 10 | Knob | L234A/L235A/P329G/T366W/ΔK447 |
|  | Hole | L234A/L235A/P329G/T366S/L368A/Y407V/ΔK447 |
| 11 | Knob | C220S/L234A/L235G/P329A/T366W/ΔK447 |
|  | Hole | C220S/L234A/L235G/P329A/T366S/L368A/Y407V/ΔK447 |
| 12 | Knob | L234A/L235A/P329G/S354C/T366W/ΔK447 |
|  | Hole | L234A/L235A/P329G/Y349C/T366S/L368A/Y407V/ΔK447 |
| 13 | Knob | C220S/L234A/L235A/P329G/S354C/T366W/ΔK447 |
|  | Hole | C220S/L234A/L235A/P329G/Y349C/T366S/L368A/Y407V/ΔK447 |
| 14 | Knob | L234A/L235E/G237A/A330S/P331S/T366W/ΔK447 |
|  | Hole | L234A/L235E/G237A/A330S/P331S/T366S/L368A/Y407V/ΔK447 |
| 15 | Knob | C220S L234A/L235E/G237A/A330S/P331S/T366W/ΔK447 |
|  | Hole | C220S/L234A/L235E/G237A/A330S/P331S/T366S/L368A/Y407V/ΔK447 |
| 16 | Knob | L234A/L235E/G237A/A330S/P331S/S354C/T366W/ΔK447 |
|  | Hole | L234A/L235E/G237A/A330S/P331S/Y349C/T366S/L368A/Y407V/ΔK447 |

TABLE 5-continued

Amino Acid Substitution Sets of Complementary IgG1 KiH UH/Fc Heterodimeric Pairs Comprising Mutations to Reduce Effector Function

| Fc Dimer No. | UH Fc Monomer | Amino Acid Substitution Set (EU Numbering) |
|---|---|---|
| 17 | Knob | C220S/L234A/L235E/G237A/A330S/P331S/S354C/T366W/ΔK447 |
|  | Hole | C220S/L234A/L235E/G237A/A330S/P331S/Y349C/T366S/L368A/Y407V/ΔK447 |
| 18 | Knob | L234F/L235E/P331S/T366W/ΔK447 |
|  | Hole | L234F/L235E/P331S/T366S/L368A/Y407V/ΔK447 |
| 19 | Knob | C220S/L234F/L235E/P331S/T366W/ΔK447 |
|  | Hole | C220S/L234F/L235E/P331S//L368A/Y407V/ΔK447 |
| 20 | Knob | L234F/L235E/P331S/S354C/T366W/ΔK447 |
|  | Hole | L234F/L235E/P331S/Y349C/T366S/L368A/Y407V/ΔK447 |
| 21 | Knob | C220S/S/L234F/L235E/P331S/354C/T366W/ΔK447 |
|  | Hole | C220S/L234F/L235E/P331S/Y349C/T366S/L368A/Y407V/ΔK447 |

Fc Sequence Modifications to Extend Duration of Action:

In some embodiments the amino acid sequence of the Fc1 and/or Fc2 monomers modified to promote heterodimerization may be further modified to incorporate amino acid substitutions which extend the duration of action of the molecule and prevent clearance. In some embodiments, such modifications to the Fc monomer include the amino acid substitutions M428L and N434S (EU numbering) referred to as the "LS" modification. The LS modification may optionally be combined with amino acid substitutions to reduce effector function and provide for disulfide bonds between Fc1 and Fc2. Table 6 below provides exemplary Fc1 and Fc1 heterodimeric pairs possessing complementary sequence modifications to promote heterodimerization that may be employed in the design of the Fc1 and Fc2 polypeptides of the formulae [1] and [2].

The following Table 6 provides exemplary Fc heterodimeric pairs which may be used in the preparation of Fc1 and Fc2 polypeptides of the heterodimeric hIL12Fc muteins of the present disclosure:

TABLE 6

Amino Acid Substitution Sets of Complementary IgG1 KiH UH/Fc Heterodimeric Pairs Comprising Mutations to Reduce Effector Function and LS Halflife Extensions

| Fc Dimer No. | UH/Fc Monomer | Amino Acid Substitution Set (EU Numbering) |
|---|---|---|
| 22 | Knob | L234A/L235A/P329A/T366W/M428L/N434S/ΔK447 |
|  | Hole | L234A/L235A/P329A/T366S/L368A/Y407V/M428L/N434S/ΔK447 |
| 23 | Knob | C220S/L234A/L235A/P329A/T366W/M428L/N434S/ΔK447 |
|  | Hole | C220S/L234A/L235A/P329A/T366S/L368A/Y407V/M428L/N434S/ΔK447 |
| 24 | Knob | L234A/L235A/P329A/S354C/T366W/M428L/N434S/ΔK447 |
|  | Hole | L234A/L235A/P329A/Y349C/T366S/L368A/Y407V/M428L/N434S/ΔK447 |
| 25 | Knob | C220S/L234A/L235A/P329A/S354C/T366W/M428L/N434S/ΔK447 |
|  | Hole | C220S/L234A/L235A/P329A/Y349C/T366S/L368A/Y407V/M428L/N434S/ΔK447 |
| 26 | Knob | L234A/L235A/P329G/T366W/M428L/N434S/ΔK447 |
|  | Hole | L234A/L235A/P329G/T366S/L368A/Y407V/M428L/N434S/ΔK447 |
| 27 | Knob | C220S/L234A/L235G/P329A/T366W/M428L/N434S/ΔK447 |
|  | Hole | C220S/L234A/L235G/P329A/T366S/L368A/Y407V/M428L/N434S/ΔK447 |
| 28 | Knob | L234A/L235A/P329G/S354C/T366W/M428L/N434S/ΔK447 |
|  | Hole | L234A/L235A/P329G/Y349C/T366S/L368A/Y407V/M428L/N434S/ΔK447 |
| 29 | Knob | C220S/L234A/L235A/P329G/S354C/T366W/M428L/N434S/ΔK447 |
|  | Hole | C220S/L234A/L235A/P329G/Y349C/T366S/L368A/Y407V/M428L/N434S/ΔK447 |
| 30 | Knob | L234A/L235E/G237A/A330S/P331S/T366W/M428L/N434S/ΔK447 |
|  | Hole | L234A/L235E/G237A/A330S/P331S/T366S/L368A/Y407V/M428L/N434S/ΔK447 |
| 31 | Knob | C220S L234A/L235E/G237A/A330S/P331S/T366W/M428L/N434S/ΔK447 |
|  | Hole | C220S/L234A/L235E/G237A/A330S/P331S/T366S/L368A/Y407V/M428L/N434S/ΔK447 |
| 32 | Knob | L234A/L235E/G237A/A330S/P331S/S354C/T366W/M428L/N434S/ΔK447 |
|  | Hole | L234A/L235E/G237A/A330S/P331S/Y349C/T366S/L368A/Y407V/M428L/N434S/ΔK447 |
| 33 | Knob | C220S/L234A/L235E/G237A/A330S/P331S/S354C/T366W/M428L/N434S/ΔK447 |
|  | Hole | C220S/L234A/L235E/G237A/A330S/P331S/Y349C/T366S/L368A/Y407V/ M428L/N434S/ΔK447 |
| 34 | Knob | L234F/L235E/P331S/T366W/M428L/N434S/ΔK447 |
|  | Hole | L234F/L235E/P331S/T366S/L368A/Y407V/M428L/N434S/ΔK447 |
| 35 | Knob | C220S/L234F/L235E/P331S/T366W/M428L/N434S/ΔK447 |
|  | Hole | C220S/L234F/L235E/P331S//L368A/Y407V/M428L/N434S/ΔK447 |
| 36 | Knob | L234F/L235E/P331S/S354C/T366W/M428L/N434S/ΔK447 |
|  | Hole | Y L234F/L235E/P331S/349C/T366S/L368A/Y407V/M428L/N434S/ΔK447 |
| 37 | Knob | C220S/S/L234F/L235E/P331S/354C/T366W/M428L/N434S/ΔK447 |
|  | Hole | C220S/L234F/L235E/P331S/Y349C/T366S/L368A/Y407V/M428L/N434S/ΔK447 |

In some embodiments, the Fc domains (Fc1 and Fc2) of the compositions of the present disclosure are from hIgG4. In such instances where the Fc domains of the heterodimeric IL12 and IL23 muteins are derived from hIgG4, heterodimerization of the Fc1 and Fc2 domains by the introduction of the mutations K370E, K409W and E357N, D399V, F405T (EU numbering) in the complementary Fc sequences that comprise the heterodimeric Fc domain.

Fc Modifications to Eliminate Glycosylation Sites

In some embodiments the amino acid sequence of the Fc1 and/or Fc2 monomers modified to promote heterodimerization may be further modified to eliminate N-linked or O-linked glycosylation sites. Aglycosylated variants of Fc domains, particularly of the IgG1 subclass are known to be poor mediators of effector function. Jefferies et al. 1998, Immol. Rev., vol. 163, 50-76). It has been shown that glycosylation at position 297 (EU numbering) contributes to effector function. Edelman, et al (1969) PNAS (USA) 63:78-85. In some embodiments, the Fc domains of the compositions of the present disclosure comprise one or modifications to eliminate N- or O linked glycosylation sites. Examples of modifications at N297 to eliminate glycosylation sites in the Fc domain include the amino acid substitutions N297Q and N297G.

PEGylation

In some embodiments, the polypeptides of formulae [1] and/or [2] of the heterodimeric hIL12Fc muteins of the present disclosure may be conjugated to one or more polyethylene glycol molecules or "PEGylated." Although the method or site of PEG attachment to the binding molecule may vary, in certain embodiments the PEGylation does not alter, or only minimally alters, the activity of the binding molecule.

The present disclosure provides PEGylated heterodimeric hIL12Fc muteins. In some embodiments, hP35Fc polypeptide of the heterodimeric hIL12Fc mutein PEGylated. In some embodiments, hP40MFc polypeptide of the heterodimeric hIL12Fc mutein PEGylated. In some embodiments, both the hP35Fc and the hP40MFc of the heterodimeric hIL12Fc mutein are PEGylated.

The present disclosure provides PEGylated heterodimeric hIL23Fc muteins. In some embodiments, hP19Fc polypeptide of the heterodimeric hIL23Fc mutein PEGylated. In some embodiments, hP40MFc polypeptide of the heterodimeric hIL23Fc mutein PEGylated. In some embodiments, both the hP19Fc and the hP40MFc of the heterodimeric hIL23Fc mutein are PEGylated.

In some embodiments, conjugation of the PEG moiety may be accomplished via a sulfhydryl (—SH) group of a cysteine residue. In some embodiments, the PEGylation of the d heterodimeric hIL12Fc muteins is provided at one or both of the naturally occurring cysteine residues at position 220 (C220, EU Numbering) of the upper hinge region of the hP35Fc and/or the hP40MFc heterodimeric hIL12Fc muteins. In some embodiments, the PEGylation heterodimeric hIL23Fc muteins is provided at one or both of the naturally occurring cysteine residues at position 220 (C220, EU Numbering) of the upper hinge region of the hP19Fc and/or the hP40MFc heterodimeric hIL23Fc muteins. In preparing PEGylated heterodimeric hIL12Fc muteins or PEGylated heterodimeric hIL23Fc muteins where conjugation of the PEG molecule is provided at position C220, the above referenced C220S modification of the upper hinge region is not employed.

PEGs suitable for conjugation to a polypeptide sequence are generally soluble in water at room temperature, and have the general formula

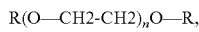

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

PEGylation of the heterodimeric hIL12Fc muteins and heterodimeric hIL23Fc muteins of the present disclosure may be facilitated by the incorporation of one or more non-natural amino acids having side chains to facilitate selective PEG conjugation. Specific PEGylation sites can be chosen such that PEGylation of the binding molecule does not affect its binding to the target receptors.

In certain embodiments, the increase in half-life is greater than any decrease in biological activity. PEGs suitable for conjugation to a polypeptide sequence are generally soluble in water at room temperature, and have the general formula R(O—CH2-CH2)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa, or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula R(O—CH2-CH2)$_n$O—R, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimidyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with the side chain of lysine residues to form a carbamate linkage but are also known to react with histidine and tyrosine residues. Use of a PEG-aldehyde linker targets a single site on the N-terminus of a polypeptide through reductive amination.

Pegylation frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General PEGylation strategies known in the art can be applied herein.

The PEG can be bound to a binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF), a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 KDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

In some embodiments, a linker can used to join the PEG molecule to the heterodimeric hIL12Fc mutein or heterodimeric hIL23Fc mutein. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers are described in Section IV. Further, a multimer (e.g., 1, 2, 3, 4, 5, 6, 7, 8, 9, 10, 10-20, 20-30, or 30-50) of these linker sequences may be linked together to provide flexible linkers that may be used to conjugate two molecules. In some embodiments, the linker is a GSA linker as described above. Alternative to a polypeptide linker, the linker can be a chemical linker, e.g., a PEG-aldehyde linker. In some embodiments, the binding molecule is acetylated at the N-terminus by enzymatic reaction with N-terminal acetyltransferase and, for example, acetyl CoA. Alternatively, or in addition to N-terminal acetylation, the binding molecule can be acetylated at one or more lysine residues, e.g., by enzymatic reaction with a lysine acetyltransferase. See, for example Choudhary et al. (2009) Science 325 (5942): 834 840.

In some embodiments, the present disclosure provides PEGylated heterodimeric hIL12Fc muteins and heterodimeric hIL23Fc muteins, wherein the PEG is conjugated to the heterodimeric hIL12Fc or hIL23Fc mutein is a linear or branched PEG molecule having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms. In some embodiments, the PEG is conjugated to the N-terminus of the hP35Fc and/or hP40MFc polypeptide.

Exemplary Heterodimeric hIL12Fc Muteins:

The following table provides a summary of particular compositions of the present disclosure comprising KiH heterodimerization, are provided in Table 7 below

TABLE 7

Exemplary KiH p35 Hole and hP40M Knob Constructs

| Knob or Hole | Name | SEQ ID NO | hIL12 Subunit | Linker | UH (EU Numbering) | Fc Domain Mutations (EU Numbering) |
|---|---|---|---|---|---|---|
| HOLE | DR1535 | 81 | Wt hP35 | (G4S) 3 | C220S | Y349C/T366S/L368A/Y407V/ΔK447 |
| HOLE | DR1536 | 82 | Wt hP35 | (G4S) 2 | C220S | Y349C/T366S/L368A/Y407V/ΔK447 |
| HOLE | DR1572 | 84 | Wt hP35 | (G4S) 2 | wt | Y349C/T366S/L368A/Y407V/ΔK447 |

TABLE 7-continued

Exemplary KiH p35 Hole and hP40M Knob Constructs

| Knob or Hole | Name | SEQ ID NO | hIL12 Subunit | Linker | UH (EU Numbering) | Fc Domain Mutations (EU Numbering) |
|---|---|---|---|---|---|---|
| HOLE | DR1589 | 87 | Wt hP35 | (G4S) 3 | C220S | Y349C/T366S/L368A/Y407V/ΔK447 |
| HOLE | DR1591 | 89 | Wt hP35 | none | C220S | Y349C/T366S/L368A/Y407V/ΔK447 |
| HOLE | DR1596 | 91 | Wt hP35 | (G4S) 4 | C220S | Y349C/T366S/L368A/Y407V/ΔK447 |
| HOLE | DR1598 | 93 | Wt hP35 | (G4S) 2 | C220S | Y349C/T366S/L368A/Y407V/ΔK447 |
| KNOB | DR1442 | 80 | hp40 3xAla | None | C220S | S354C/T366W/ΔK447 |
| KNOB | DR1537 | 83 | hp40 3xAla | (G4S) 2 | C220S | S354C/T366W/ΔK447 |
| KNOB | DR1573 | 85 | hp40 3xAla | (G4S) 2 | wt | S354C/T366W/ΔK447 |
| KNOB | DR1588 | 86 | hP40 3xAla | none | C220S | S354C/T366W/ΔK447 |
| KNOB | DR1590 | 88 | hp40 3xAla | none | C220S | S354C/T366W/ΔK447 |
| KNOB | DR1595 | 90 | hp40 3xAla | (G4S) 2 | C220S | S354C/T366W/ΔK447 |
| KNOB | DR1597 | 92 | hp40 3xAla | (G4S) 2 | C220S | S354C/T366W/ΔK447 |

In some embodiments, the present disclosure provides heterodimeric hIL12Fc muteins, the heterodimeric hIL12Fc mutein comprising a first polypeptide of the formula #1:

$$\text{hP40M-L1}_a\text{-UH1-Fc1} \quad [1]$$

and a second polypeptide of the formula #2:

$$\text{hP35-L2}_b\text{-UH2-Fc2} \quad [2]$$

wherein the polypeptide of formula 1 is selected from the group consisting of SEQ ID NOS: 80, 83, 85, 86, 88, 90, 92, 121, 129, 141, 144, 147, 150 and 153, and the second polypeptide of formula #2 is selected from the group consisting of SEQ ID NOS: 81, 82, 84, 87, 89, 91, 93, and 124.

In some embodiments, the hIL12Fc muteins of the present disclosure are the heterodimeric hIL12Fc muteins provided in Table 8 below.

TABLE 8

Exemplary Heterodimeric hIL 12 Fc Muteins

| Heterodimeric hIL12 Fc mutein number | hP40M Fc Name | SEQ ID NO: | hP35 Fc Name | SEQ ID NO: |
|---|---|---|---|---|
| 1 (STK021) | DR1442M | 80 | DR1535M | 81 |
| 2 (STK-022) | DR1947M | 121 | DR1948M | 124 |
| 3 (STK-023) | DR1537M | 83 | DR1536M | 82 |
| 4 | DR2086M | 141 | DR1948M | 124 |
| 5 | DR2087M | 144 | DR1948M | 124 |
| 6 (STK-026) | DR2088M | 129 | DR1948M | 124 |
| 7 | DR2090M | 147 | DR1536 M | 82 |
| 8 | DR2091M | 150 | DR1536M | 82 |
| 9 (STK-027) | DR2092M | 153 | DR1536M | 82 |
| 10 (STK-028) | DR2455M | 135 | DR1948M | 124 |
| 11 (STK-029) | DR2456M | 138 | DR1948M | 124 |

1. STK-021 (DR1442M/DR1535M)

In one embodiment, the present disclosure provides a heterodimeric hIL12Fc mutein, the heterodimeric hIL12Fc mutein comprising a first polypeptide of the formula #1:

$$\text{hP40M-L1}_a\text{-UH1-Fc1} \quad [1]$$

and a second polypeptide of the formula #2:

$$\text{hP35-L2}_b\text{-UH2-Fc2} \quad [2]$$

wherein a=1 and b=1, and
the polypeptide of formula #1 comprises the amino acid sequence:

```
                                                    (SEQ ID NO: 80)
IWELKKDVYVVELDWYPDAPGEMVVLTCDTPEEDGITWTLDQSSEVLGSGKTLTIQVKAAGDA

GQYTCHKGGEVLSHSLLLLHAKEDGIWSTDILKDQKEPKNKTFLRCEAKNYSGRFTCWWLTTI

STDLTFSVKSSRGSSDPQGVTCGAATLSAERVRGDNKEYEYSVECQEDSACPAAEESLPIEVM

VDAVHKLKYENYTSSFFIRDIIKPDPPKNLQLKPLKNSRQVEVSWEYPDTWSTPHSYFSLTFC

VQVQGKSKREKKDRVFTDKTSATVICRKNASISVRAQDRYYSSSWSEWASVPCSEPKSSDKTH

TCPPCPAPEAAGGPSVELFPPKPKDTLMISRTPEVTCVVVDVSHEDPEVKENWYVDGVEVHNA

KTKPREEQYNSTYRVVSVLTVLHQDWLNGKEYKCKVSNKALAAPIEKTISKAKGQPREPQVYT

LPPCRDELTKNQVSLWCLVKGFYPSDIAVEWESNGQPENNYKTTPPVLDSDGSFFLYSKLTVD

KSRWQQGNVFSCSVMHEALHNHYTQKSLSLSPG
``` and wherein the polypeptide of formula #2 comprises the amino acid sequence:

```
                                                    (SEQ ID NO: 81)
RNLPVATPDPGMFPCLHHSQNLLRAVSNMLQKARQTLEFYPCTSEEIDHEDITKDKTSTVEAC

LPLELTKNESCLNSRETSFITNGSCLASRKTSEMMALCLSSIYEDLKMYQVEFKTMNAKLLMD

PKRQIFLDQNMLAVIDELMQALNENSETVPQKSSLEEPDFYKTKIKLCILLHAFRIRAVTIDR

VMSYLNASGGGGSGGGGSGGGGSEPKSSDKTHTCPPCPAPEAAGGPSVELFPPKPKDTLMISR

TPEVTCVVVDVSHEDPEVKENWYVDGVEVHNAKTKPREEQYNSTYRVVSVLTVLHQDWLNGKE

YKCKVSNKALAAPIEKTISKAKGQPREPQVCTLPPSRDELTKNQVSLSCAVKGFYPSDIAVEW

ESNGQPENNYKTTPPVLDSDGSFFLVSKLTVDKSRWQQGNVFSCSVMHEALHNHYTQKSLSLS

PG
```

2. STK-022 (1947/DR1948M)

In one embodiment, the present disclosure provides a heterodimeric hIL12Fc mutein, the heterodimeric hIL12Fc mutein comprising a first polypeptide of the formula #1:

hP40M-L1$_a$-UH1-Fc1   [1]

and a second polypeptide of the formula #2:

hP35-L2$_b$-UH2-Fc2   [2]

wherein a=1 and b=1, and
wherein the polypeptide of formula #1 comprises the amino acid sequence:

```
                                                    (SEQ ID NO: 121)
IWELKKDVYVVELDWYPDAPGEMVVLTCDTPEEDGITWTLDQSSEVLGSGKTLTIQVKAAGDA

GQYTCHKGGEVLSHSLLLLHAKEDGIWSTDILKDQKEPKNKTFLRCEAKNYSGRFTCWWLTTI

STDLTFSVKSSRGSSDPQGVTCGAATLSAERVRGDNKEYEYSVECQEDSACPAAEESLPIEVM

VDAVHKLKYENYTSSFFIRDIIKPDPPKNLQLKPLKNSRQVEVSWEYPDTWSTPHSYFSLTFC

VQVQGKSKREKKDRVFTDKTSATVICRKNASISVRAQDRYYSSSWSEWASVPCSGGGGSGGGG

SEPKSSDKTHTCPPCPAPEAAGGPSVFLFPPKPKDTLMISRTPEVTCVVVDVSHEDPEVKENW

YVDGVEVHNAKTKPREEQYNSTYRVVSVLTVLHQDWLNGKEYKCKVSNKALAAPIEKTISKAK

GQPREPQVYTLPPCRDELTKNQVSLWCLVKGFYPSDIAVEWESNGQPENNYKTTPPVLDSDGS

FFLYSKLTVDKSRWQQGNVFSCSVLHEALHSHYTQKSLSLSPG
``` and wherein the polypeptide of formula #2 comprises the amino acid sequence:

(SEQ ID NO: 124)
RNLPVATPDPGMFPCLHHSQNLLRAVSNMLQKARQTLEFYPCTSEEIDHEDITKDKTSTVEAC

LPLELTKNESCLNSRETSFITNGSCLASRKTSEMMALCLSSIYEDLKMYQVEFKTMNAKLLMD

PKRQIFLDQNMLAVIDELMQALNENSETVPQKSSLEEPDFYKTKIKLCILLHAFRIRAVTIDR

VMSYLNASGGGGSGGGGSEPKSSDKTHTCPPCPAPEAAGGPSVFLFPPKPKDTLMISRTPEVT

CVVVDVSHEDPEVKENWYVDGVEVHNAKTKPREEQYNSTYRVVSVLTVLHQDWLNGKEYKCKV

SNKALAAPIEKTISKAKGQPREPQVCTLPPSRDELTKNQVSLSCAVKGFYPSDIAVEWESNGQ

PENNYKTTPPVLDSDGSFFLVSKLTVDKSRWQQGNVFSCSVLHEALHSHYTQKSLSLSPG

3. STK-023 (DR1537M/DR1536M)

In one embodiment, the present disclosure provides a heterodimeric hIL12Fc mutein, the heterodimeric hIL12Fc mutein comprising a first polypeptide of the formula #1:

hP40M-L1$_a$-UH1-Fc1     [1]

and a second polypeptide of the formula #2:

hP35-L2$_b$-UH2-Fc2     [2]

wherein a=1 and b=1, and
wherein the polypeptide of formula #1 comprises the amino acid sequence:

(SEQ ID NO: 83)
IWELKKDVYVVELDWYPDAPGEMVVLTCDTPEEDGITWTLDQSSEVLGSGKTLTIQVKAAGDA

GQYTCHKGGEVLSHSLLLLHAKEDGIWSTDILKDQKEPKNKTFLRCEAKNYSGRFTCWWLTTI

STDLTFSVKSSRGSSDPQGVTCGAATLSAERVRGDNKEYEYSVECQEDSACPAAEESLPIEVM

VDAVHKLKYENYTSSFFIRDIIKPDPPKNLQLKPLKNSRQVEVSWEYPDTWSTPHSYFSLTFC

VQVQGKSKREKKDRVFTDKTSATVICRKNASISVRAQDRYYSSSWSEWASVPCSGGGGSGGGG

SEPKSSDKTHTCPPCPAPEAAGGPSVFLFPPKPKDTLMISRTPEVTCVVVDVSHEDPEVKENW

YVDGVEVHNAKTKPREEQYNSTYRVVSVLTVLHQDWLNGKEYKCKVSNKALAAPIEKTISKAK

GQPREPQVYTLPPCRDELTKNQVSLWCLVKGFYPSDIAVEWESNGQPENNYKTTPPVLDSDGS

FFLYSKLTVDKSRWQQGNVFSCSVMHEALHNHYTQKSLSLSPG and wherein the polypeptide of formula #2 comprises the amino acid sequence:

(SEQ ID NO: 82)
RNLPVATPDPGMFPCLHHSQNLLRAVSNMLQKARQTLEFYPCTSEEIDHEDITKDKTSTVEAC

LPLELTKNESCLNSRETSFITNGSCLASRKTSEMMALCLSSIYEDLKMYQVEFKTMNAKLLMD

PKRQIFLDQNMLAVIDELMQALNENSETVPQKSSLEEPDFYKTKIKLCILLHAFRIRAVTIDR

VMSYLNASGGGGSGGGGSEPKSSDKTHTCPPCPAPEAAGGPSVFLFPPKPKDTLMISRTPEVT

CVVVDVSHEDPEVKENWYVDGVEVHNAKTKPREEQYNSTYRVVSVLTVLHQDWLNGKEYKCKV

SNKALAAPIEKTISKAKGQPREPQVCTLPPSRDELTKNQVSLSCAVKGFYPSDIAVEWESNGQ

PENNYKTTPPVLDSDGSFFLVSKLTVDKSRWQQGNVFSCSVMHEALHNHYTQKSLSLSPG.

4. DR2086M/DR1948M

In one embodiment, the present disclosure provides a heterodimeric hIL12Fc mutein, the heterodimeric hIL12Fc mutein comprising a first polypeptide of the formula #1:

hP40M-L1$_a$-UH1-Fc1     [1]

and a second polypeptide of the formula #2:

hP35-L2$_b$-UH2-Fc2     [2]

wherein a=1 and b=1, and
wherein the polypeptide of formula #1 comprises the amino acid sequence:

(SEQ ID NO: 141)
IWELKKDVYVVELDWYPDAPGEMVVLTCDTPEEDGITWTLDQSSEVLGS

GKTLTIQVKAAGDAGQYTCHKGGEVLSHSLLLLHAKEDGIWSTDILKDQ

KEPKNKTELRCEAKNYSGRFTCWWLTTISTDLTFSVKSSRGSSDPQGVT

-continued
CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSQREKKDRVFTDKTSATVICRKNASISVRAQDRYYS

SSWSEWASVPCSGGGGSGGGGSEPKSSDKTHTCPPCPAPEAAGGPSVEL

-continued

FPPKPKDTLMISRTPEVTCVVVDVSHEDPEVKENWYVDGVEVHNAKTKP

REEQYNSTYRVVSVLTVLHQDWLNGKEYKCKVSNKALAAPIEKTISKAK

GQPREPQVYTLPPCRDELTKNQVSLWCLVKGFYPSDIAVEWESNGQPEN

NYKTTPPVLDSDGSFFLYSKLTVDKSRWQQGNVFSCSVLHEALHSHYTQ

KSLSLSPG and wherein the polypeptide of formula #2 comprises the amino acid sequence:

(SEQ ID NO: 124)
RNLPVATPDPGMFPCLHHSQNLLRAVSNMLQKARQTLEFYPCTSEEIDH

EDITKDKTSTVEACLPLELTKNESCLNSRETSFITNGSCLASRKTSEMM

ALCLSSIYEDLKMYQVEFKTMNAKLLMDPKRQIFLDQNMLAVIDELMQA

LNENSETVPQKSSLEEPDFYKTKIKLCILLHAFRIRAVTIDRVMSYLNA

SGGGGSGGGGSEPKSSDKTHTCPPCPAPEAAGGPSVFLFPPKPKDTLMI

SRTPEVTCVVVDVSHEDPEVKENWYVDGVEVHNAKTKPREEQYNSTYRV

VSVLTVLHQDWLNGKEYKCKVSNKALAAPIEKTISKAKGQPREPQVCTL

PPSRDELTKNQVSLSCAVKGFYPSDIAVEWESNGQPENNYKTTPPVLDS

DGSFFLVSKLTVDKSRWQQGNVFSCSVLHEALHSHYTQKSLSLSPG.

5. DR2087M/DR1948M

In one embodiment, the present disclosure provides a heterodimeric hIL12Fc mutein, the heterodimeric hIL12Fc mutein comprising a first polypeptide of the formula #1:

hP40M-L1$_a$-UH1-Fc1     [1]

and a second polypeptide of the formula #2:

hP35-L2$_b$-UH2-Fc2     [2]

wherein a=1 and b=1, and
wherein the polypeptide of formula #1 comprises the amino acid sequence:

(SEQ ID NO: 144)
IWELKKDVYVVELDWYPDAPGEMVVLTCDTPEEDGITWTLDQSSEVLGS

GKTLTIQVKAAGDAGQYTCHKGGEVLSHSLLLLHAKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSNREKKDRVFTDKTSATVICRKNASISVRAQDRYYS

SSWSEWASVPCSGGGGSGGGGSEPKSSDKTHTCPPCPAPEAAGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALAAPIEKTISKAK

GQPREPQVYTLPPCRDELTKNQVSLWCLVKGFYPSDIAVEWESNGQPEN

NYKTTPPVLDSDGSFFLYSKLTVDKSRWQQGNVFSCSVLHEALHSHYTQ

KSLSLSPG and wherein the polypeptide of formula #2 comprises the amino acid sequence:

(SEQ ID NO: 124)
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

SGGGGSGGGGSEPKSSDKTHTCPPCPAPEAAGGPSVFLFPPKPKDTLMI

SRTPEVTCVVVDVSHEDPEVKFNWYVDGVEVHNAKTKPREEQYNSTYRV

VSVLTVLHQDWLNGKEYKCKVSNKALAAPIEKTISKAKGQPREPQVCTL

PPSRDELTKNQVSLSCAVKGFYPSDIAVEWESNGQPENNYKTTPPVLDS

DGSFFLVSKLTVDKSRWQQGNVFSCSVLHEALHSHYTQKSLSLSPG

6. STK-026 (DR2088M/DR1948M)

In one embodiment, the present disclosure provides a heterodimeric hIL12Fc mutein, the heterodimeric hIL12Fc mutein comprising a first polypeptide of the formula #1:

hP40M-L1$_a$-UH1-Fc1     [1]

and a second polypeptide of the formula #2:

hP35-L2$_b$-UH2-Fc2     [2]

wherein a=1 and b=1, and
wherein the polypeptide of formula #1 comprises the amino acid sequence:

(SEQ ID NO: 129)
IWELKKDVYVVELDWYPDAPGEMVVLTCDTPEEDGITWTLDQSSEVLGSGKTLTIQVKAAGDA

GQYTCHKGGEVLSHSLLLLHAKEDGIWSTDILKDQKEPKNKTFLRCEAKNYSGRFTCWWLTTI

STDLTFSVKSSRGSSDPQGVTCGAATLSAERVRGDNKEYEYSVECQEDSACPAAEESLPIEVM

VDAVHKLKYENYTSSFFIRDIIKPDPPKNLQLKPLKNSRQVEVSWEYPDTWSTPHSYFSLTFC

VQVQGKSGREKKDRVFTDKTSATVICRKNASISVRAQDRYYSSSWSEWASVPCSGGGGSGGGG

SEPKSSDKTHTCPPCPAPEAAGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALAAPIEKTISKAK

GQPREPQVYTLPPCRDELTKNQVSLWCLVKGFYPSDIAVEWESNGQPENNYKTTPPVLDSDGS

FFLYSKLTVDKSRWQQGNVFSCSVLHEALHSHYTQKSLSLSPG and wherein the polypeptide of formula #2 comprises the amino acid sequence:

(SEQ ID NO: 124)
```
RNLPVATPDPGMFPCLHHSQNLLRAVSNMLQKARQTLEFYPCTSEEIDHEDITKDKT
STVEACLPLELTKNESCLNSRETSFITNGSCLASRKTSFMMALCLSSIYEDLKMYQV
EFKTMNAKLLMDPKRQIFLDQNMLAVIDELMQALNFNSETVPQKSSLEEPDFYKTKI
KLCILLHAFRIRAVTIDRVMSYLNASGGGGSGGGGSEPKSSDKTHTCPPCPAPEAAG
GPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALAAPIEKTISKAKGQPREPQVCT
LPPSRDELTKNQVSLSCAVKGFYPSDIAVEWESNGQPENNYKTTPPVLDSDGSFFLV
SKLTVDKSRWQQGNVFSCSVLHEALHSHYTQKSLSLSPG.
```

7. DR2090M/DR1536M

In one embodiment, the present disclosure provides a heterodimeric hIL12Fc mutein, the heterodimeric hIL12Fc mutein comprising a first polypeptide of the formula #1:

hP40M-L1$_a$-UH1-Fc1  [1]

and a second polypeptide of the formula #2:

hP35-L2$_b$-UH2-Fc2  [2]

wherein a=1 and b=1, and
wherein the polypeptide of formula #1 comprises the amino acid sequence:

8. DR2091M/DR1536M

In one embodiment, the present disclosure provides a heterodimeric hIL12Fc mutein, the heterodimeric hIL12Fc mutein comprising a first polypeptide of the formula #1:

hP40M-L1$_a$-UH1-Fc1  [1]

and a second polypeptide of the formula #2:

hP35-L2$_b$-UH2-Fc2  [2]

wherein a=1 and b=1, and
wherein the polypeptide of formula #1 comprises the amino acid sequence:

(SEQ ID NO: 147)
```
MCHQQLVISWFSLVFLASPLVAIWELKKDVYVVELDWYPDAPGEMVVLTCDTPEEDG
ITWTLDQSSEVLGSGKTLTIQVKAAGDAGQYTCHKGGEVLSHSLLLLHAKEDGIWST
DILKDQKEPKNKTFLRCEAKNYSGRFTCWWLTTISTDLTFSVKSSRGSSDPQGVTCG
AATLSAERVRGDNKEYEYSVECQEDSACPAAEESLPIEVMVDAVHKLKYENYTSSFF
IRDIIKPDPPKNLQLKPLKNSRQVEVSWEYPDTWSTPHSYFSLTFCVQVQGKSQREK
KDRVFTDKTSATVICRKNASISVRAQDRYYSSSWSEWASVPCSGGGGSGGGGSEPKS
SDKTHTCPPCPAPEAAGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALAAPIE
KTISKAKGQPREPQVYTLPPCRDELTKNQVSLWCLVKGFYPSDIAVEWESNGQPENN
YKTTPPVLDSDGSFFLYSKLTVDKSRWQQGNVFSCSVMHEALHNHYTQKSLSLSPG
``` and wherein the polypeptide of formula #2 comprises the amino acid sequence:

(SEQ ID NO: 82)
```
RNLPVATPDPGMFPCLHHSQNLLRAVSNMLQKARQTLEFYPCTSEEIDHEDITKDKTSTVEAC
LPLELTKNESCLNSRETSFITNGSCLASRKTSFMMALCLSSIYEDLKMYQVEFKTMNAKLLMD
PKRQIFLDQNMLAVIDELMQALNFNSETVPQKSSLEEPDFYKTKIKLCILLHAFRIRAVTIDR
VMSYLNASGGGGSGGGGSEPKSSDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKV
SNKALAAPIEKTISKAKGQPREPQVCTLPPSRDELTKNQVSLSCAVKGFYPSDIAVEWESNGQ
PENNYKTTPPVLDSDGSFFLVSKLTVDKSRWQQGNVFSCSVMHEALHNHYTQKSLSLSPG
```

```
                                                     (SEQ ID NO: 150)
IWELKKDVYVVELDWYPDAPGEMVVLTCDTPEEDGITWTLDQSSEVLGSGKTLTIQV

KAAGDAGQYTCHKGGEVLSHSLLLLHAKEDGIWSTDILKDQKEPKNKTFLRCEAKNY

SGRFTCWWLTTISTDLTFSVKSSRGSSDPQGVTCGAATLSAERVRGDNKEYEYSVEC

QEDSACPAAEESLPIEVMVDAVHKLKYENYTSSFFIRDIIKPDPPKNLQLKPLKNSR

QVEVSWEYPDTWSTPHSYFSLTFCVQVQGKSNREKKDRVFTDKTSATVICRKNASIS

VRAQDRYYSSSWSEWASVPCSGGGGSGGGGSEPKSSDKTHTCPPCPAPEAAGGPSVF

LFPPKPKDTLMISRTPEVTCVVVDVSHEDPEVKFNWYVDGVEVHNAKTKPREEQYNS

TYRVVSVLTVLHQDWLNGKEYKCKVSNKALAAPIEKTISKAKGQPREPQVYTLPPCR

DELTKNQVSLWCLVKGFYPSDIAVEWESNGQPENNYKTTPPVLDSDGSFFLYSKLTV

DKSRWQQGNVFSCSVMHEALHNHYTQKSLSLSPG
``` and wherein the polypeptide of formula #2 comprises the amino acid sequence:

```
                                                      (SEQ ID NO: 82)
RNLPVATPDPGMFPCLHHSQNLLRAVSNMLQKARQTLEFYPCTSEEIDHEDITKDKTSTVEAC

LPLELTKNESCLNSRETSFITNGSCLASRKTSFMMALCLSSIYEDLKMYQVEFKTMNAKLLMD

PKRQIFLDQNMLAVIDELMQALNFNSETVPQKSSLEEPDFYKTKIKLCILLHAFRIRAVTIDR

VMSYLNASGGGGSGGGGSEPKSSDKTHTCPPCPAPEAAGGPSVFLFPPKPKDTLMISRTPEVT

CVVVDVSHEDPEVKFNWYVDGVEVHNAKTKPREEQYNSTYRVVSVLTVLHQDWLNGKEYKCKV

SNKALAAPIEKTISKAKGQPREPQVCTLPPSRDELTKNQVSLSCAVKGFYPSDIAVEWESNGQ

PENNYKTTPPVLDSDGSFFLVSKLTVDKSRWQQGNVFSCSVMHEALHNHYTQKSLSLSPG
```

9. STK-027 (DR2092M/DR1536M)

In one embodiment, the present disclosure provides a heterodimeric hIL12Fc mutein, the heterodimeric hIL12Fc mutein comprising a first polypeptide of the formula #1:

hP40M-L1$_a$-UH1-Fc1    [1]

and a second polypeptide of the formula #2:

hP35-L2$_b$-UH2-Fc2    [2]

wherein a=1 and b=1, and
wherein the polypeptide of formula #1 comprises the amino acid sequence:

```
                                                     (SEQ ID NO: 153)
IWELKKDVYVVELDWYPDAPGEMVVLTCDTPEEDGITWTLDQSSEVLGSGKTLTIQVKAAGD

AGQYTCHKGGEVLSHSLLLLHAKEDGIWSTDILKDQKEPKNKTFLRCEAKNYSGRFTCWWLT

TISTDLTFSVKSSRGSSDPQGVTCGAATLSAERVRGDNKEYEYSVECQEDSACPAAEESLPI

EVMVDAVHKLKYENYTSSFFIRDIIKPDPPKNLQLKPLKNSRQVEVSWEYPDTWSTPHSYFS

LTFCVQVQGKSGREKKDRVFTDKTSATVICRKNASISVRAQDRYYSSSWSEWASVPCSGGGG

SGGGGSEPKSSDKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALAAPIE

KTISKAKGQPREPQVYTLPPCRDELTKNQVSLWCLVKGFYPSDIAVEWESNGQPENNYKTTP

PVLDSDGSFFLYSKLTVDKSRWQQGNVFSCSVMHEALHNHYTQKSLSLSPG
``` and wherein the polypeptide of formula #2 comprises the amino acid sequence:

(SEQ ID NO: 82)
RNLPVATPDPGMFPCLHHSQNLLRAVSNMLQKARQTLEFYPCTSEEIDHEDITKDKTSTVEAC

LPLELTKNESCLNSRETSFITNGSCLASRKTSFMMALCLSSIYEDLKMYQVEFKTMNAKLLMD

PKRQIFLDQNMLAVIDELMQALNFNSETVPQKSSLEEPDFYKTKIKLCILLHAFRIRAVTIDR

VMSYLNASGGGGSGGGGSEPKSSDKTHTCPPCPAPEAAGGPSVFLFPPKPKDTLMISRTPEVT

CVVVDVSHEDPEVKFNWYVDGVEVHNAKTKPREEQYNSTYRVVSVLTVLHQDWLNGKEYKCKV

SNKALAAPIEKTISKAKGQPREPQVCTLPPSRDELTKNQVSLSCAVKGFYPSDIAVEWESNGQ

PENNYKTTPPVLDSDGSFFLVSKLTVDKSRWQQGNVFSCSVMHEALHNHYTQKSLSLSPG

10. STK-028 (DR2455M/DR1948M):

In one embodiment, the present disclosure provides a heterodimeric hIL12Fc mutein, the heterodimeric hIL12Fc mutein comprising a first polypeptide of the formula #1:

hP40M-L1$_a$-UH1-Fc1      [1]

and a second polypeptide of the formula #2:

hP35-L2$_b$-UH2-Fc2      [2]

wherein a=1 and b=1, and
wherein the polypeptide of formula #1 comprises the amino acid sequence:

11. STK-029 (DR2456M/DR1948M):

In one embodiment, the present disclosure provides a heterodimeric hIL12Fc mutein, the heterodimeric hIL12Fc mutein comprising a first polypeptide of the formula #1:

hP40M-L1$_a$-UH1-Fc1      [1]

and a second polypeptide of the formula #2:

hP35-L2$_b$-UH2-Fc2      [2]

wherein a=1 and b=1, and
wherein the polypeptide of formula #1 comprises the amino acid sequence:

(SEQ ID NO: 135)
IWELKKDVYVVELDWYPDAPGEMVVLTCDTPEEDGITWTLDQSSEVLGSGKTLTIQVKEFGD

AGQYTCHKGGEVLSHSLLLLHKKEDGIWSTDILKDQKEPKNKTFLRCEAKNYSGRFTCWWLT

TISTDLTFSVKSSRGSSDPQGVTCGAATLSAERVRGDNKEYEYSVECQEDSACPAAEESLPI

EVMVDAVHKLKYENYTSSFFIRDIIKPDPPKNLQLKPLKNSRQVEVSWEYPDTWSTPHSYFS

LTFCVQVQGKSKREKKDRVFTDKTSATVICRKNASISVRAQDRYYSSSWSEWASVPCSGGGG

SGGGGSEPKSSDKTHTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALAAPIE

KTISKAKGQPREPQVYTLPPCRDELTKNQVSLWCLVKGFYPSDIAVEWESNGQPENNYKTTP

PVLDSDGSFFLYSKLTVDKSRWQQGNVFSCSVLHEALHSHYTQKSLSLSPG and wherein the polypeptide of formula #2 comprises the amino acid sequence:

(SEQ ID NO: 124)
RNLPVATPDPGMFPCLHHSQNLLRAVSNMLQKARQTLEFYPCTSEEIDHEDITKDKT

STVEACLPLELTKNESCLNSRETSFITNGSCLASRKTSFMMALCLSSIYEDLKMYQV

EFKTMNAKLLMDPKRQIFLDQNMLAVIDELMQALNFNSETVPQKSSLEEPDFYKTKI

KLCILLHAFRIRAVTIDRVMSYLNASGGGGSGGGGSEPKSSDKTHTCPPCPAPEAAG

GPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALAAPIEKTISKAKGQPREPQVCT

LPPSRDELTKNQVSLSCAVKGFYPSDIAVEWESNGQPENNYKTTPPVLDSDGSFFLV

SKLTVDKSRWQQGNVFSCSVLHEALHSHYTQKSLSLSPG (SEQ ID NO: 138)
IWELKKDVYVVELDWYPDAPGEMVVLTCDTPEEDGITWTLDQSSEVLGSGKTLTIQVKEFGDAG

QYTCHKGGEVLSHSLLLLHKKEDGIWSTDILKDQKEPKNKTFLRCEAKNYSGRFTCWWLTTIST

DLTFSVKSSRGSSDPQGVTCGAATLSAERVRGDNKEYEYSVECQEDSACPAAEESLPIEVMVDA

VHKLKYENYTSSFFIRDIIKPDPPKNLQLKPLKNSRQVEVSWEYPDTWSTPHSYFSLTFCVQVQ

GKSGREKKDRVFTDKTSATVICRKNASISVRAQDRYYSSSWSEWASVPCSGGGGSGGGGSEPKS

SDKTHTCPPCPAPEAAGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALAAPIEKTISKAKGQPREPQ

VYTLPPCRDELTKNQVSLWCLVKGFYPSDIAVEWESNGQPENNYKTTPPVLDSDGSFFLYSKLT

VDKSRWQQGNVFSCSVLHEALHSHYTQKSLSLSPG and wherein the polypeptide of formula #2 comprises the amino acid sequence:

(SEQ ID NO: 124)
RNLPVATPDPGMFPCLHHSQNLLRAVSNMLQKARQTLEFYPCTSEEIDHEDITKDKT

STVEACLPLELTKNESCLNSRETSFITNGSCLASRKTSFMMALCLSSIYEDLKMYQV

EFKTMNAKLLMDPKRQIFLDQNMLAVIDELMQALNFNSETVPQKSSLEEPDFYKTKI

KLCILLHAFRIRAVTIDRVMSYLNASGGGGSGGGGSEPKSSDKTHTCPPCPAPEAAG

GPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALAAPIEKTISKAKGQPREPQVCT

LPPSRDELTKNQVSLSCAVKGFYPSDIAVEWESNGQPENNYKTTPPVLDSDGSFFLV

SKLTVDKSRWQQGNVFSCSVLHEALHSHYTQKSLSLSPG

Evaluation of Activity of Heterodimeric hIL12Fc Muteins

As discussed above, the heterodimeric hIL12Fc muteins of the present disclosure provide cell-type biased signaling of the downstream signal transduction mediated through the IL12 receptor compared to a reference polypeptide (e.g., wild type hIL12). In particular, the heterodimeric hIL12Fc muteins of the present disclosure retain significant hIL-12 signaling in CD8+ T cells and have decreased hIL-12 signaling in NK cells compared to a wildtype hIL-12. The selective activation of CD8+ T cells versus NK cells can be evaluated by the activation of interferon gamma (IFNγ) while providing a reduction in STAT4 signaling in NK cells.

Enhanced IFNγ In CD8+ T Cells v. NK Cells:

The heterodimeric hIL12Fc muteins of the present disclosure activate interferon gamma (IFNγ) in CD8+ T cells and have decreased IFNγ signaling in CD8+ T cells compared to the wildtype IL12. A series of experiments were performed to evaluate the IFNγ inducing effects of wt hIL12 and hIL12 proteins comprising p40 subunit E81A/F82A indicated as "2xAla", E81A/F82A/K106A indicated as "3xAla" and substitution W37A and KiH heterodimeric hIL12Fc comprising the same mutations E81A/F82A indicated as "2xAla Fc", E81A/F82A/K106A indicated as "3xAla Fc" and the substitution W37A (W37A Fc), on CD8, CD4 and NK cells, respectively. The molecules were produced recombinantly in substantial accordance with the teaching of Example 1 and evaluated for IFNγ in substantial accordance with the teaching of Example 3 herein. As illustrated by the data provided in FIG. 1, the heterodimeric hIL12Fc muteins of the present disclosure activate IFNγ in CD8+ T cells and have decreased IFNγ signaling in CD8+ T cells compared to the wildtype IL12.

Reduced STAT4 Signaling:

In some embodiments, the heterodimeric hIL12Fc muteins described herein increase STAT4 signaling in CD8+ T cells and decrease STAT4 signaling in NK cells compared to a reference polypeptide (wt hIL12). A series of experiments were performed to evaluate the effect of various IL12 muteins comprising hP40 muteins, both as proteins and as Fc fusions, of STAT4 signaling in CD8+ T cells, CD4+ T cells relative to STAT4 signaling in NK cells. The evaluation of STAT4 was performed in substantial accordance with the teaching of Example 2. The test articles evaluated were wt hIL12 and hIL12 proteins comprising a p40 subunit with the substitutions E81A/F82A indicated as "2xAla", E81A/F82A/K106A indicated as "3xAla" and KiH heterodimeric hIL12Fc constructs comprising wild type hP35 and hP40 (wt Fc), E81A/F82A indicated as "2xAla Fc", E81A/F82A/K106A indicated as "3xAla Fc" on CD8, CD4 and NK cells, respectively. The results of these experiments are provided in FIG. 2 of the attached drawings. As illustrated by the results provided in FIG. 2, the heterodimeric hIL12Fc muteins of the present disclosure provide differential STAT4 signaling on CD8+ T cells relative to NK cells. Additionally, the data provided in FIG. 2, particularly Panel A and Panel B demonstrate that the heterodimeric hIL12Fc muteins of the present disclosure act as IL12 partial agonists on T cells.

Use in the Treatment of Neoplastic Disease:

The heterodimeric hIL12Fc muteins described herein are useful in the treatment of neoplastic disease. To demonstrate the activity of the heterodimeric hIL12Fc muteins, surrogate murine IL12Fc muteins containing analogous mutations to the human molecules were generated to evaluate the effects in an MC38 mouse tumor model. A sequence alignment of the naturally occurring human and mouse p40 and p35 polypeptides are provided in FIGS. 7 and 8, respectively, of the attached drawings. A description of the heterodimeric mIL12Fc test agents used in the MC38 tumor study are summarized in the Tables 9 and 10 below:

TABLE 9

Murine IL12 Fc Polypeptide Sequences

| Name | SEQ ID No | Description |
|---|---|---|
| DR854 | 114 | mIL12 p40 mIgG2A EW LALAPG |
| DR855 | 115 | mIL12-p35-mIgG2A-RVT-LALAPG |
| DR1243 | 116 | mIL12 p40 E81A F82A mIgG2a EW LALAPG |
| DR1244 | 117 | mIL12 p40 E81A F82A K106A mIgG2a EW LALAPG |

TABLE 10

Description of murine IL12 Fc Heterodimeric Constructs

| Name | Description of Modifications | DNA Sequence | SEQ ID NO: |
|---|---|---|---|
| mIL12 | mIL12 (p35-IRES2-p40) His8 | Encoded by DR852 | 111 |
| mIL12 2xAla | mIL12 (p35-IRES2-p40 E81A F82A) His8 | Encoded by DR1022 | 112 |
| mIL12 3xAla | mIL12 (p35-IRES2-p40 E81A F82A K106A) His8 | Encoded by DR1023 | 113 |

MC38 Tumor Study 1:

Briefly, approximately $1 \times 10^6$ MC38 cells in Matrigel were implanted subcutaneously into 6-8 week old C57BL/6 mice and the tumors permitted to attain an average tumor volume at the initiation of treatment of approximately 100 mm$^3$-120 mm$^3$. The mice were separated into individual treatment groups. The mice were treated by intraperitoneal administration of the various test agents at the doses and dosing schedule indicated in the Table 11 below. In this study bodyweight (BW), an indication of toxicity, and tumor volume (TV) as an indicator of anti-tumor efficacy were measured twice per week.

TABLE 11

MC38 Tumor Model Study #1 Design

| Group | treatment | Dose [ug] | IL-12 [ug] | Treatment schedule | ROA | # of doses | Efficacy/ group |
|---|---|---|---|---|---|---|---|
| A | PBS | n/a | n/a | 2x/week | i.p. | 6 | 8 |
| B | IL12WT Fc | 1.6 | 1 | 2x/week | i.p | 6 | 8 |
| C | IL12WT Fc | 0.53 | 0.3 | 2x/week | i.p | 6 | 8 |
| D | IL12WT Fc | 0.18 | 0.1 | 2x/week | i.p | 6 | 8 |
| E | IL12WT Fc | 1.6 | 1 | 1x/week | i.p | 3 | 8 |
| F | IL12 WT-PEG10kDa | 12 | 12 | 2x/week | i.p | 6 | 8 |
| G | IL12 WT-PEG10kDa | 3 | 3 | 2x/week | i.p | 6 | 8 |
| H | IL12 2xAla Fc | 100 | 62.5 | 2x/week | i.p | 6 | 8 |
| I | IL12WT Fc | 0.8 | 0.5 | 1x/week | i.p | 3 | 5 |

Figure 5:
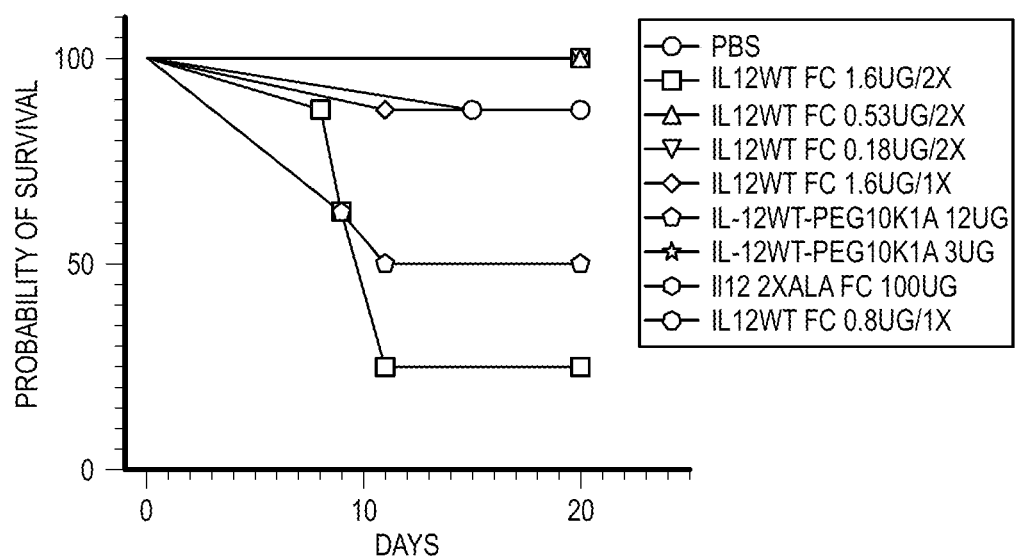
FIG. 5 provides the survival data (probability of survival on Y axis) of mice treated over time (X axis) of mice treated with various murine IL12 agents and murine IL12Fc muteins in an MC38 tumor model study as described more fully below.

The data arising from the study described above are presented in FIG. 3 (tumor volume), FIG. 4 (bodyweight), and FIG. 5 (survival) of the attached drawings. Note that the labeling of the panels in FIGS. 3 and 4 corresponds to the treatment group in Table 11 with tumor volume and bodyweight on the y-axes respectively and time (study days) is represented on the x-axes in each figure FIG. 3 provides a spider plot summary of the effect on tumor volume with respect to each animal in each study group. As demonstrated by the data presented, the murine surrogate of the heterodimeric IL12Fc mutein as described herein was effective in the control of tumor growth in this study.

FIG. 4 provides the average bodyweight of the animals during the course of the above study. Although the wild type IL12 Fc test agents evaluated in this study demonstrated an inhibition of tumor growth, the data presented in FIG. 4 indicates that such wild type IL12 Fc fusions are associated with significant toxicity as indicated by a significant loss of bodyweight (see, e.g. FIG. 4, Panels B, C, and E). In contrast, the heterodimeric IL12Fc mutein evaluated in group H comprising the 2xAla mutations in the mP40 domain did not suggest significant toxicity. This is particularly noteworthy as the IL12Fc mutein comprising the 2xAla P40 mutations was administered at a dose at more than 50 fold higher than the other wild type IL12Fc conjugates evaluated. The ability of the IL12Fc mutein comprising the 2xAla mutations to control tumor growth in the absence of significant toxicity is further supported by the data provided in FIG. 5 which indicates that all animals treated in with IL12Fc mutein comprising the 2xAla survived while there was a significant negative effect on survival in those test groups administered the wild type IL12Fc conjugates despite the apparent antitumor effect these other molecules demonstrated. Consequently, these data demonstrate that the heterodimeric IL12Fc muteins of the present disclosure are useful in the treatment of neoplastic disease and exhibit significantly lower toxicity than wild type IL12Fc conjugates that do not possess the mutations in the p40 domain of the IL12Fc conjugate.

MC38 Tumor Study 2:

A second MC38 tumor study in substantial accordance with the foregoing and the study design is provided in Table 12 was performed. In this study bodyweight (BW), an indication of toxicity, and tumor volume (TV) as an indicator of anti-tumor efficacy were measured twice per week. Mice were bled prior to the start of treatment (0 hours) and four hours, 1 day and 7 days following administration of the test agent. Some animals were taken down at days 2 and 24 post administration of the test agent for immunohistochemical evaluation and FACS analysis.

TABLE 12

MC38 Tumor Model Study #2 Design

| Group | Test Agent | Dose [ug] | Treatment schedule | # of doses | Animals Per Group |
|---|---|---|---|---|---|
| A | PBS | n/a | Daily | 7 | 8 |
| B | wt mIL12* | 1 | Daily | 7 | 8 |
| C | wt mIL12 | 1 | Daily | 7 | 8 |
| D | mIL12 2xAla | 30 | Daily | 7 | 5 |
| E | mIL12 3xAla | 30 | Daily | 7 | 5 |
| F | wt mIL12 Fc | 1.6 | 2x/week | 5 | 5 |
| G | mIL12 2xAla Fc | 48 | 2x/week | 5 | 5 |
| H | mIL12 3xAla Fc | 48 | 2x/week | 5 | 5 |
| I | IL12 WT-PEG10k1a | 1 | 2x/week | 5 | 5 |

*this wt mIL12 was produced by baculovirus expression in insect cells

Figure 6A:
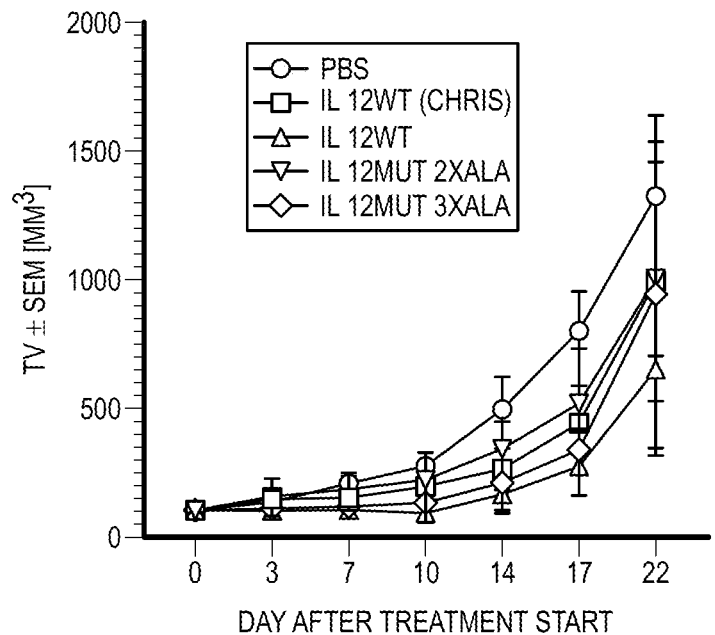
FIGS. 6A-6B provide data with respect to tumor volume (y axis) with respect to days after treatment initiation (x axis) of with mIL12 proteins in FIG. 6A and those IL12 protein subunits in a heterodimeric Fc format in FIG. 6B.
Figure 6B:
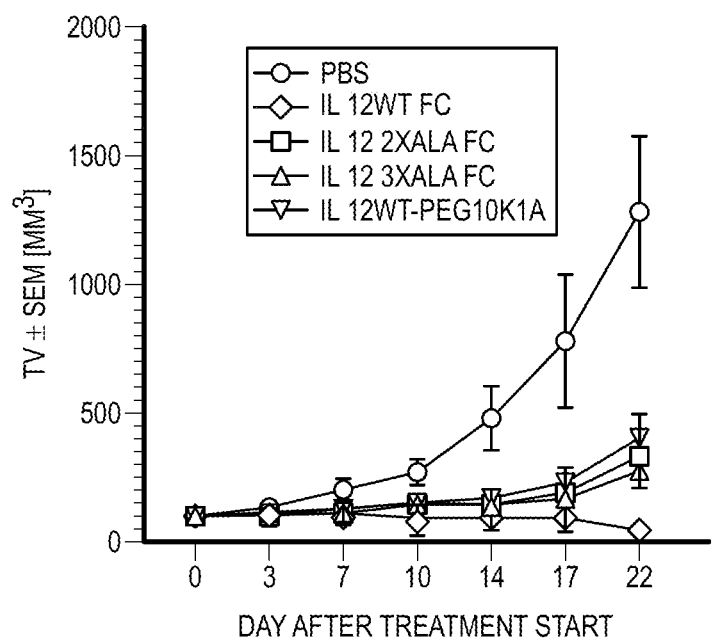

The data relating to the effects on tumor growth of these test agents and the study described in Table 12 are provided in FIG. 6 of the attached drawings. The data relating to the IL12 proteins (not conjugated to an Fc dimer) are presented in FIG. 6, Panel A and the Fc conjugated IL12 proteins is presented in FIG. 6, Panel B. A comparison of the data in FIG. 6 Panels A and B demonstrate that the IL12 molecules when conjugated to a dimeric Fc domain provide significantly improved anti-tumor efficacy relative to their non-Fc conjugated counterparts.

Figure 9A:
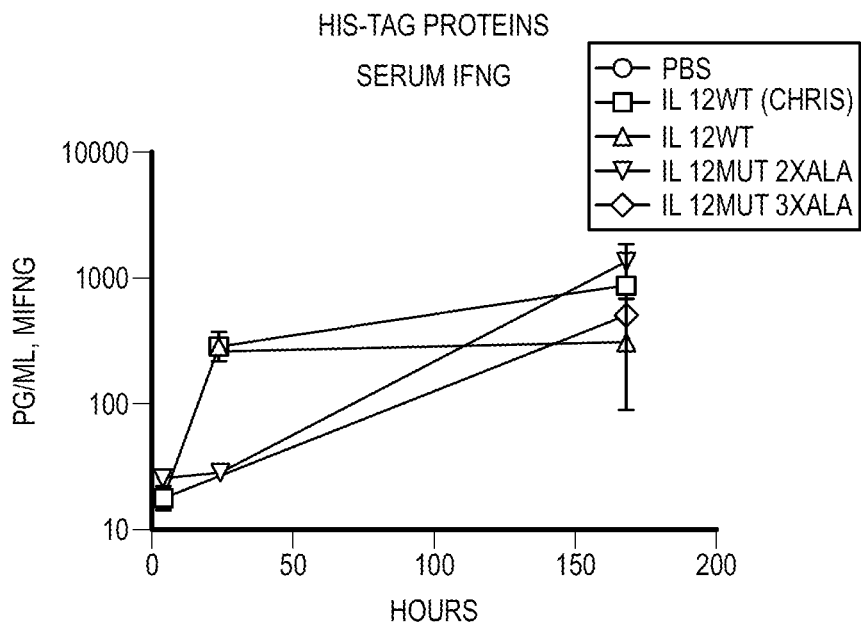
FIGS. 9A-9B provide a graphical representation of the concentration in picograms per milliliter (pg/mL) of murine interferon gamma (y-axis) measured in serum obtained from blood samples taken over time (x-axis) in the MC38 tumor model, the design of which is provided in Table 12.
Figure 9B:
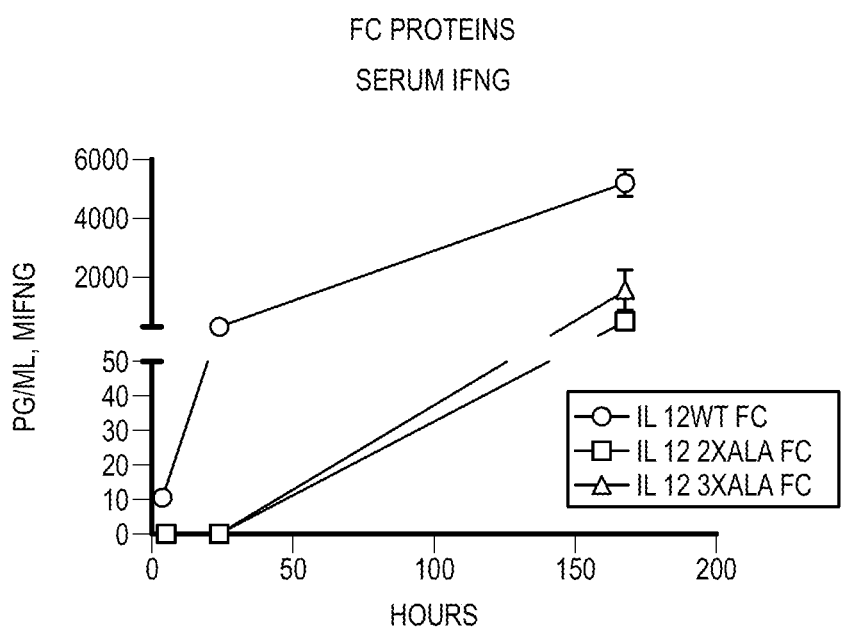

The blood samples obtained at 0 hours and 4 hours, 1 day and 7 days following administration of the test agents in treatment groups A-H were evaluated for the concentration of murine interferon gamma (mIFNg) in serum as determined by enzyme-linked immunosorbent assay (ELISA). The data obtained is presented in FIG. 9 of the attached drawings. Panel A of FIG. 9 indicates the results from treatment groups A-E (i.e., the IL12 molecules not conjugated to the Fc) and Panel B indicates the results from treatment groups F, G, and H (i.e., the IL12 molecules conjugated to the Fc). As can be seen from the data presented in FIG. 9, the Fc conjugated heterodimeric mIL12-Fc molecules comprising the amino acid substitutions (i.e., "2xAla" and "3xAla") demonstrated a significant delay in the induction of interferon gamma in relation to the other treatment groups, in particular in relation to the IL12 Fc comprising the wild type p40 sequence. This delay in the induction of IFNg results in a decrease in the acute toxicity associated with IL12 treatment.

Figure 10A:
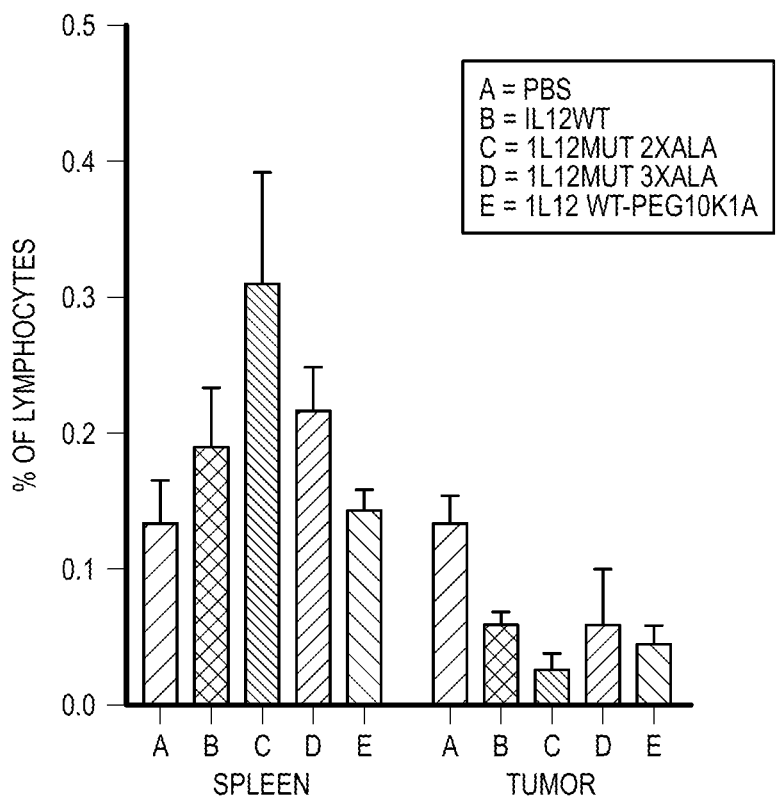
FIGS. 10-A-10C are graphical representations of the percentage of lymphocytes (y-axis) as determined by FACS analysis with respect to each of the treatment groups of Table 12 (x-axis) in spleen and tumor tissue.
Figure 10B:
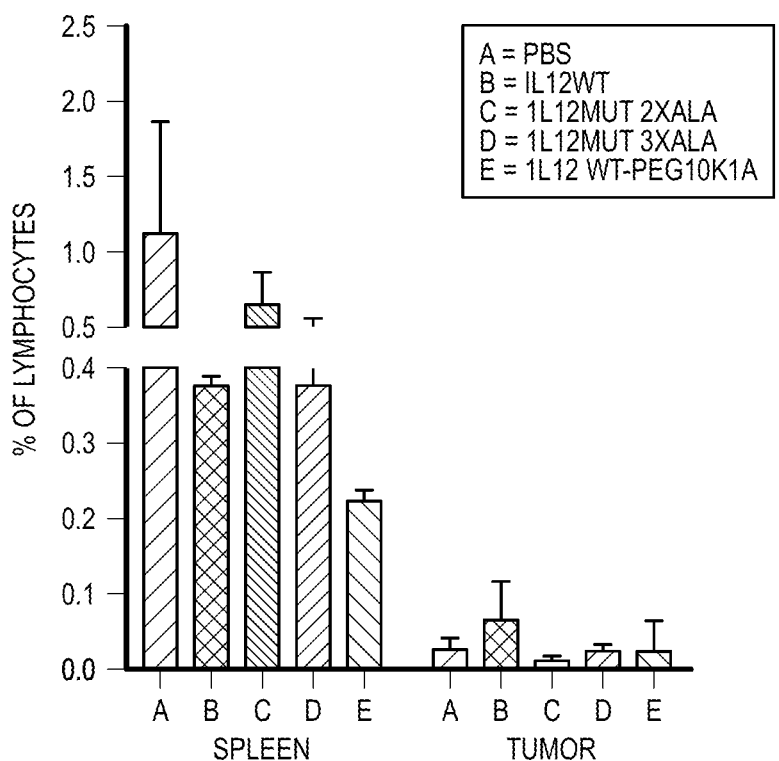
Figure 10C:
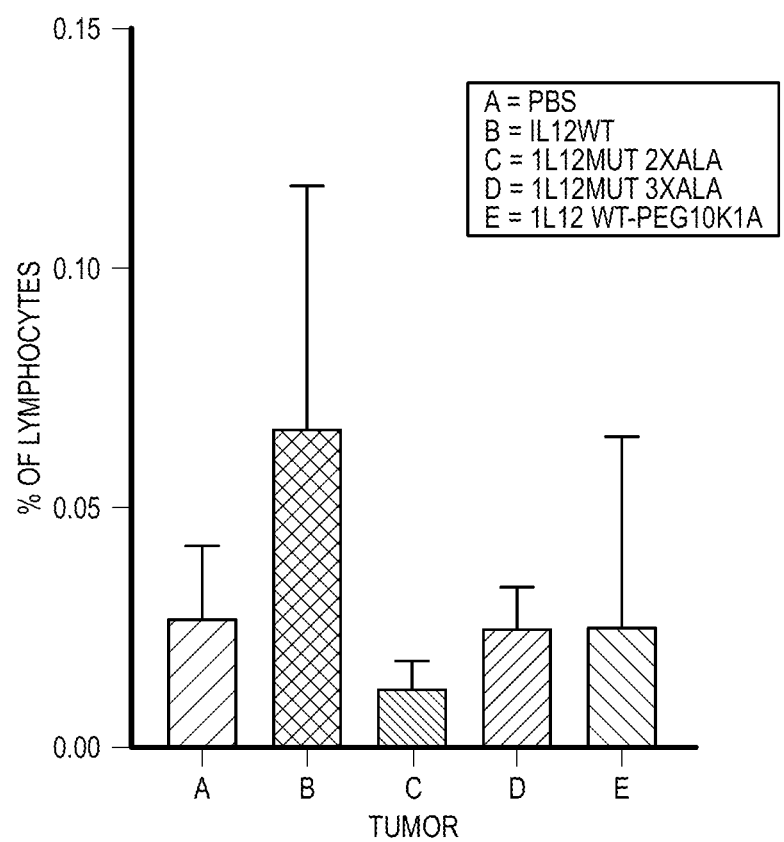

As noted, samples from this study were subjected to FACS analysis and the NK cells sorted from spleen and tumor tissues. The percentage of lymphocytes in each tissue in response to each of the treatment groups of Table 12 is provided in FIG. 10 of the attached drawings. As indicated the Fc conjugated molecules resulted in lower induction of NK cells relative to the non-Fc conjugated molecules in each tissue type. However, as shown in FIG. 10, Panel B and C (expanded view of NK frequence in tumor tissue), the Fc conjugated heterodimeric mIL12-Fc molecules comprising the P40 amino acid substitutions (i.e., "IL12 2xAla Fc" and "IL12 3xAla Fc") demonstrated a lower frequency of intratumoral NK cells relative to the heterodimeric mIL12 Fc comprising the wild type p40 sequence ("IL12 WT Fc").

Figure 11:
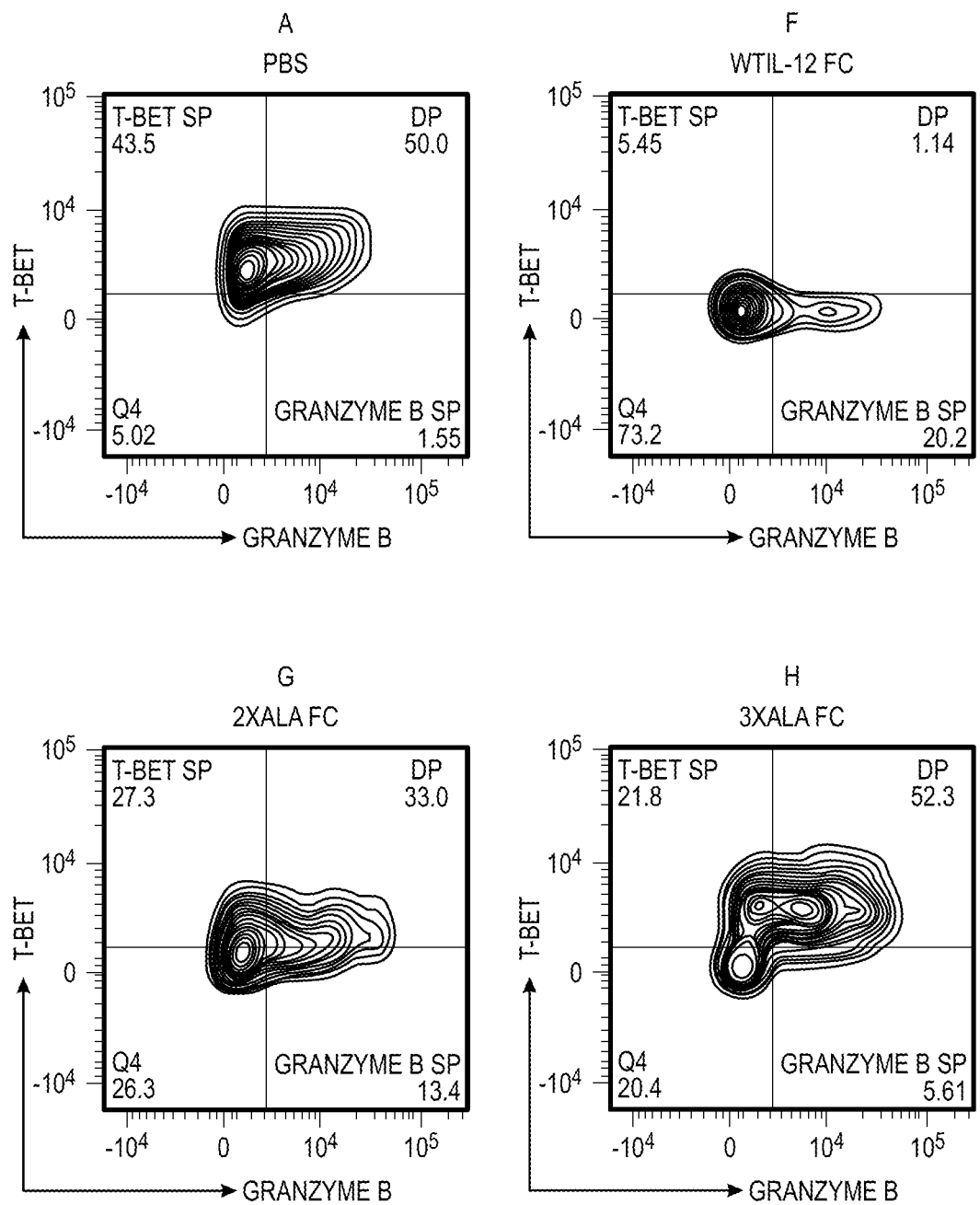
FIG. 11 provides the results of a phenotypic FACS analysis of NK cells obtained from spleen in the treatment groups and study described in Table 12. T-bet is measured on the vertical axis and intracellular Granzyme B on the horizontal axis. The graphs are labeled with the treatment groups (A, F, G and H of Table 12).

Furthermore, the phenotype of NK cells from spleen in the above study were evaluated for T-bet relative to intracellular Granzyme B. T-bet is required for NK cell effector function and NK cell cytolytic activity. The results of this analysis is provided in FIG. 11 of the attached drawings with T-bet on the vertical axis and granzyme B on the horizontal axis. As can be seen from the data presented in FIG. 10, there is a loss of Tbet+NK cells with heterodimeric mIL12 Fc comprising the wild type p40 sequence ("IL12 WT Fc") but not with the Fc conjugated heterodimeric mIL12-Fc molecules comprising the P40 amino acid substitutions (i.e., "IL12 2xAla Fc" and "IL12 3xAla Fc").

Dose Titration of mIL12 Fc Constructs in CT26 Model:

The effect of dosing at various levels of mIL12 Fc heterodimers was evaluated in a CT 26 tumor model. Briefly 6-8 week old BALB/c miles were subcutaneously implanted with approximately $0.3 \times 10^6$ CT26 mouse tumor cells in Matrigel. Mice were randomized into groups when the tumor reached an average volume of 118 $mm^3$. Treatment groups and the study design are summarized in Table 13. Bodyweight and tumor volume were measured twice per week. Some mice were sacrificed on Day 8 and day 29 of the study for FACS, IHC and serum analys. Serum PK was measured at Days 1, 8, 15, 22 and 28 of the study.

TABLE 13

CT26 Tumor Model Study Design

| Group | Test Agent | Dose [ug] | Treatment schedule | ROA | # of doses | Animals Per Group |
|---|---|---|---|---|---|---|
| A | PBS | n/a | 2x/week | i.p. | 7 | 8 |
| B | wt mIL12 Fc | 0.8 | 2x/week | i.p. | 7 | 8 |
| C | wt mIL12 Fc | 0.53 | 2x/week | i.p. | 7 | 8 |
| D | wt mIL12 Fc | 0.53 | 1x/week | i.p. | 4 | 8 |
| E | mIL12 3xAla Fc | 16 | 2x/week | i.p. | 8 | 8 |
| F | mIL12 3xAla Fc | 48 | 2x/week | i.p. | 8 | 8 |
| G | mIL12 3xAla Fc | 96 | 2x/week | i.p. | 8 | 8 |
| H | mIL12 3xAla Fc | 200 | 1x/week | i.p. | 4 | 5 |

Figure 12:
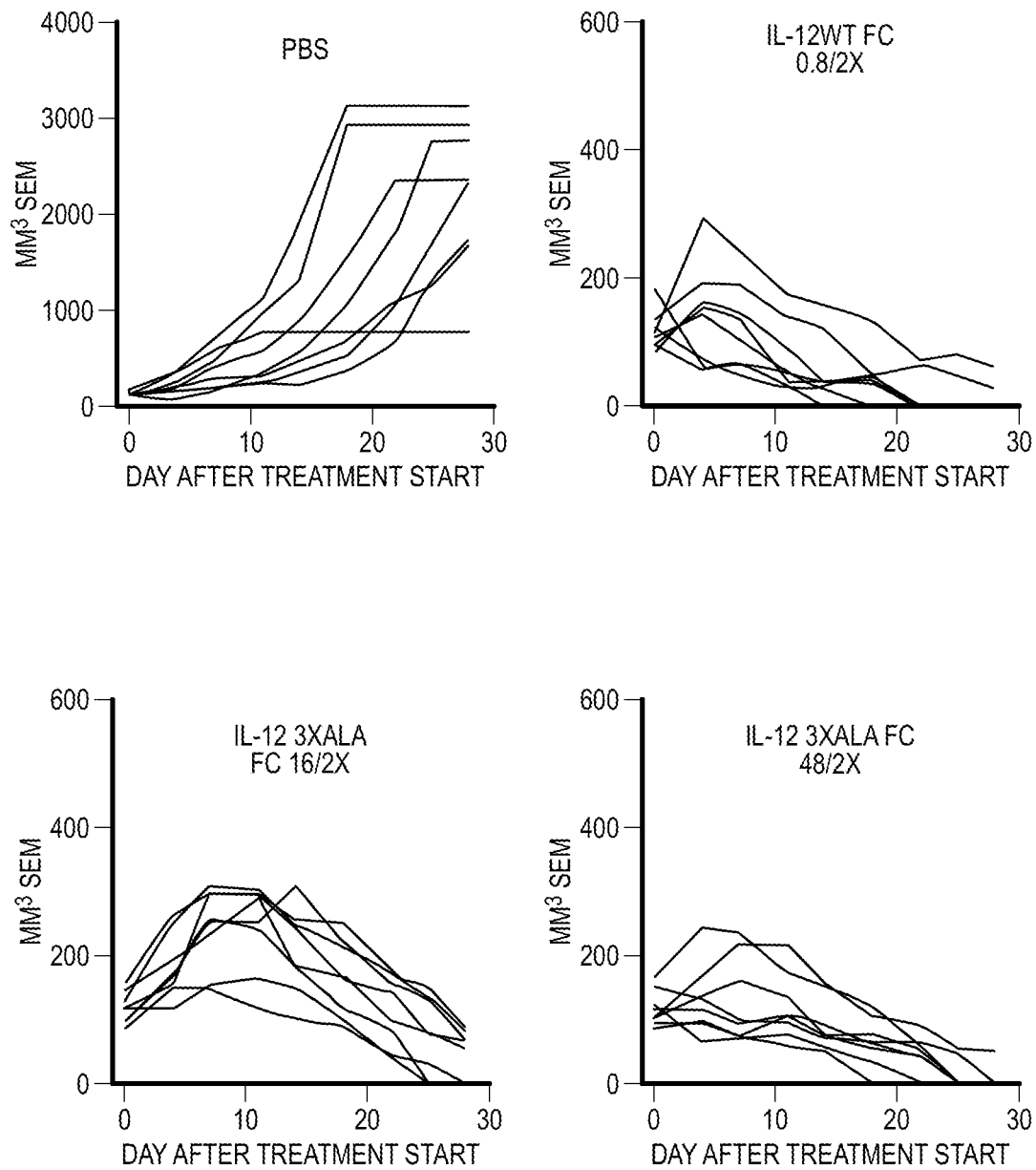
FIG. 12 provides a series of spider plots resulting from the CT26 tumor study as described herein with tumor volume provided on the vertical axis and time (study days) on the horizontal axis. Each panel of the figure indicates the test agent provide and the dosing schedule of the test agent in accordance with the study design provided in Table 13.
Figure 12:
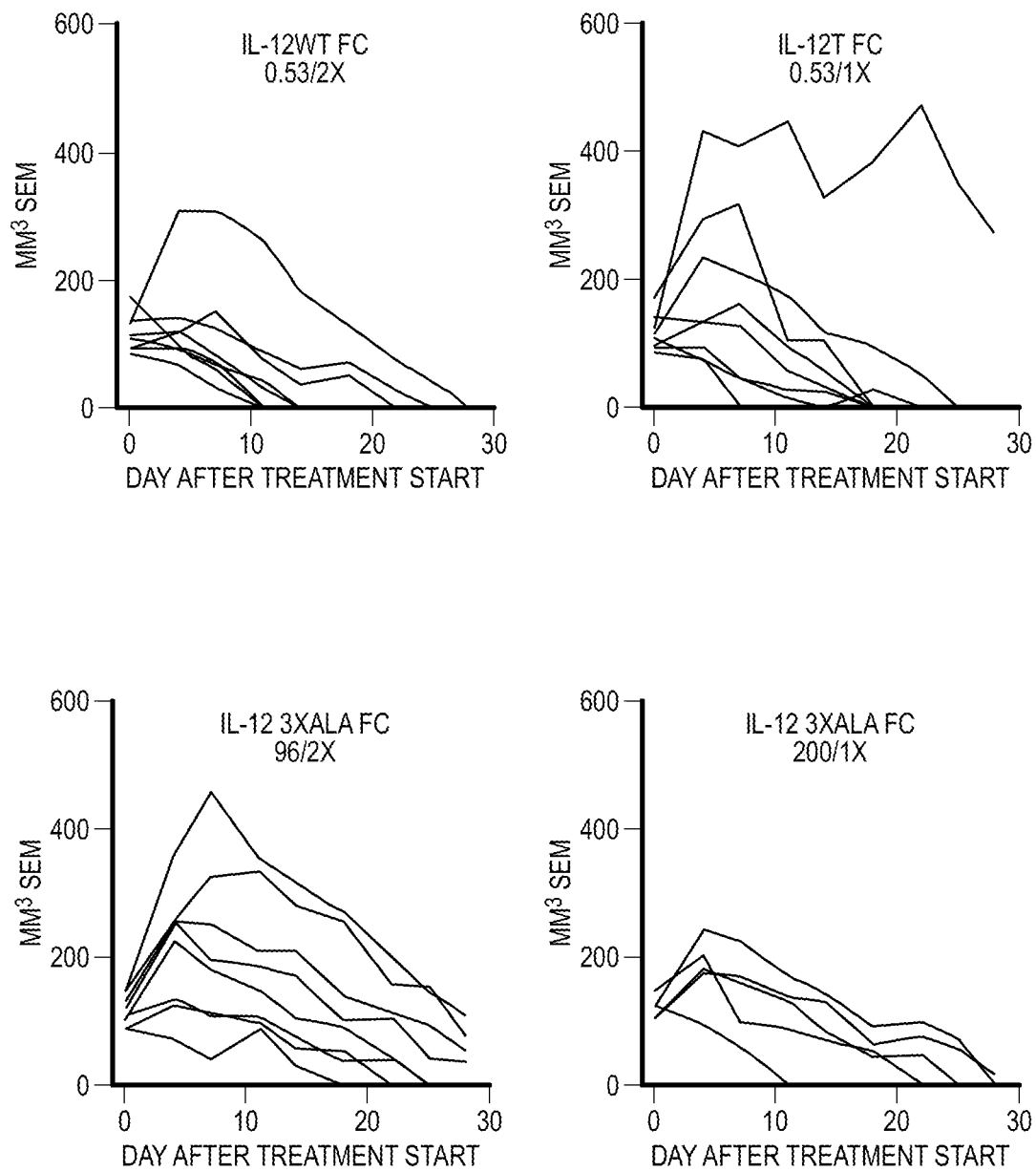
Figure 13:
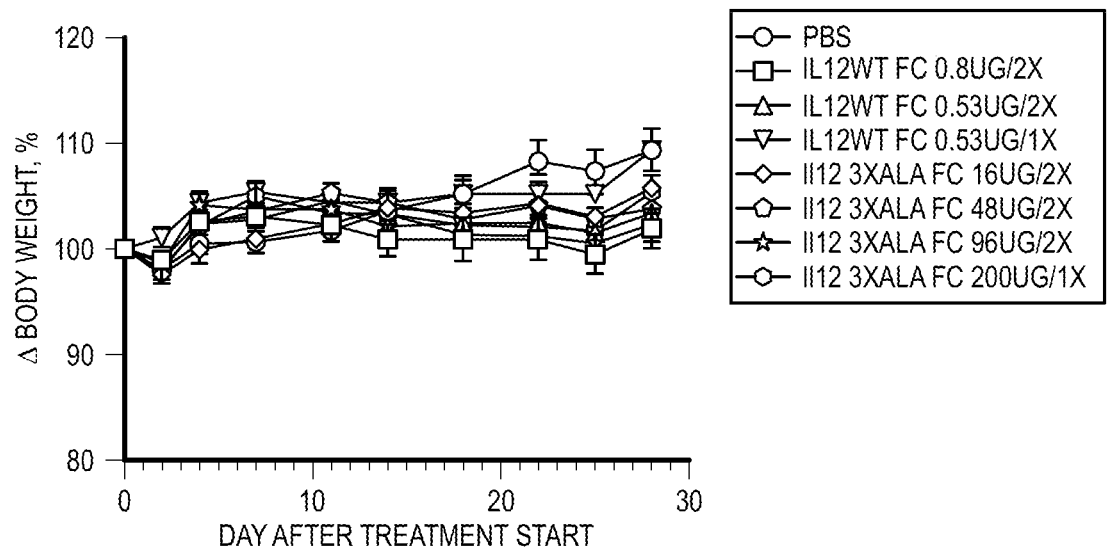
FIG. 13 provides the results of bodyweight measurements of mice evaluated in the CT26 tumor study with percent change in bodyweight on the vertical axis and time (study days) on the horizontal axis.
Figure 14:
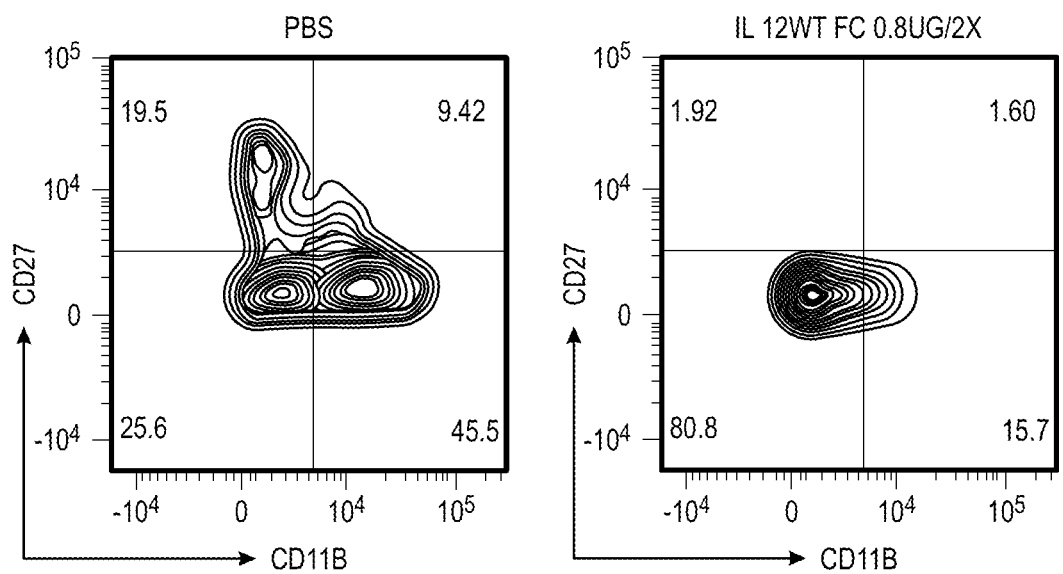
FIG. 14 provides results of a FACS analysis of cells obtained from the CT26 tumor study sorted by the presence of various markers as indicated by the arrows and various doses of test agent as indicated by the figure legends.
Figure 14:
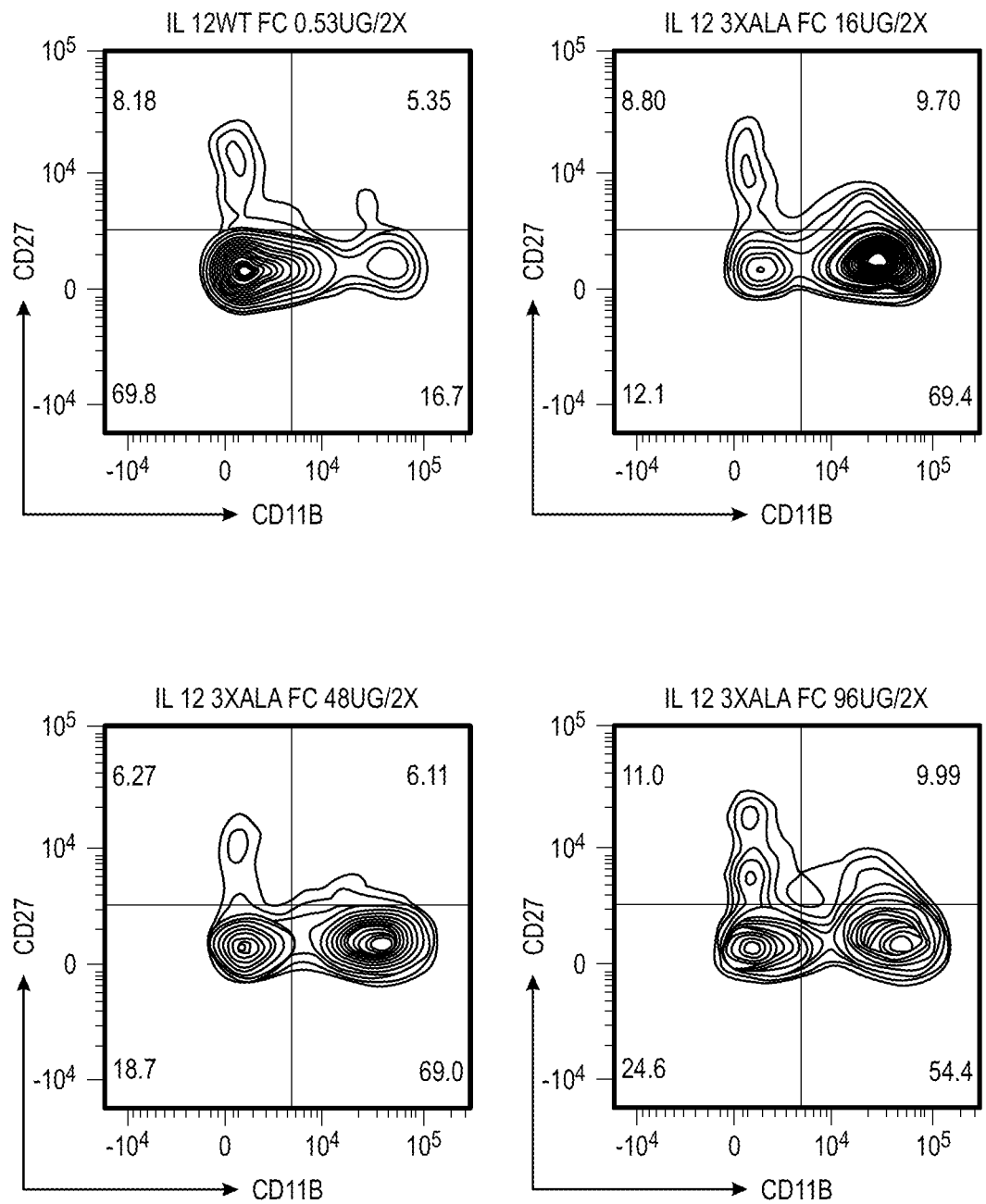
Figure 14:
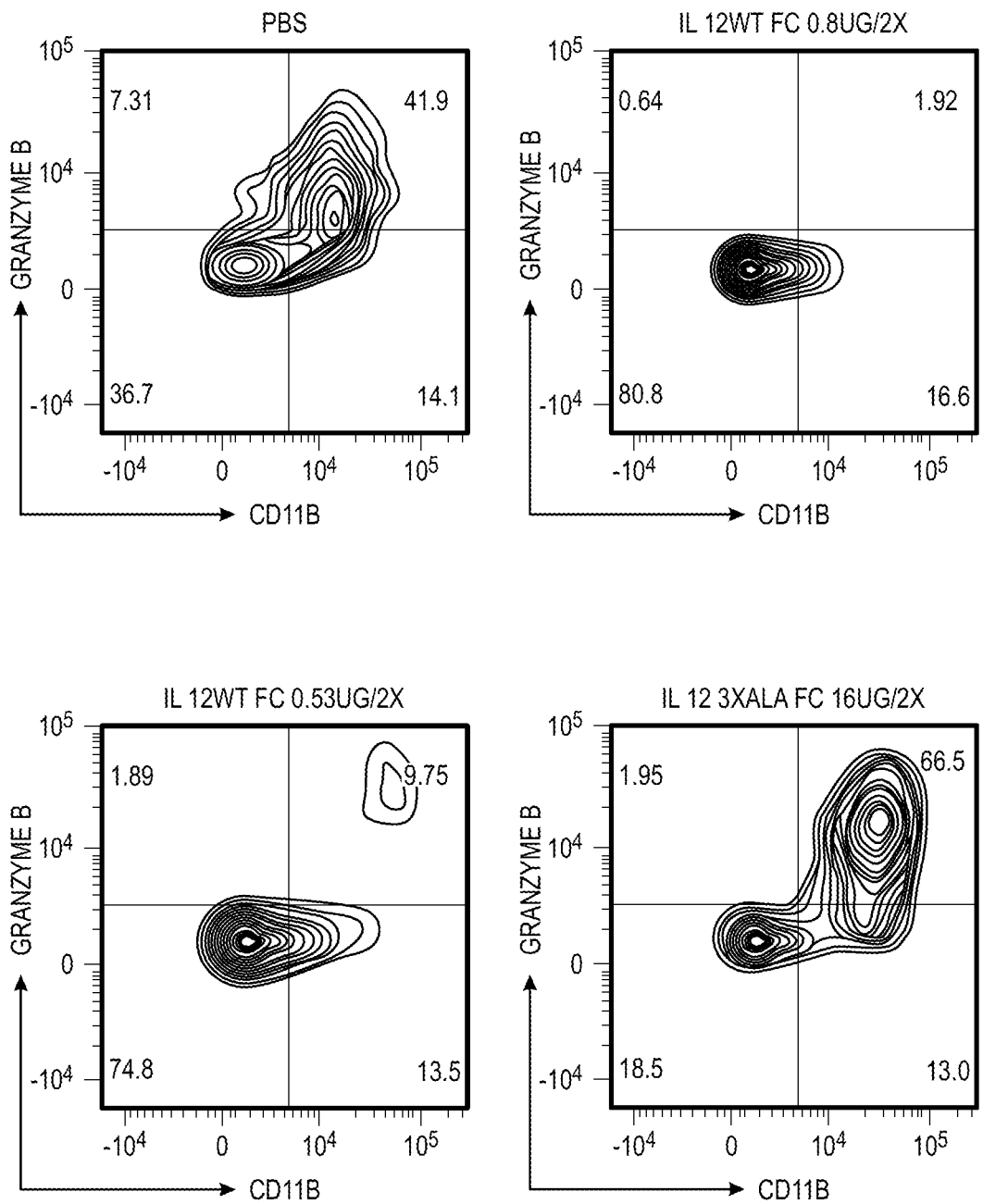
Figure 14:
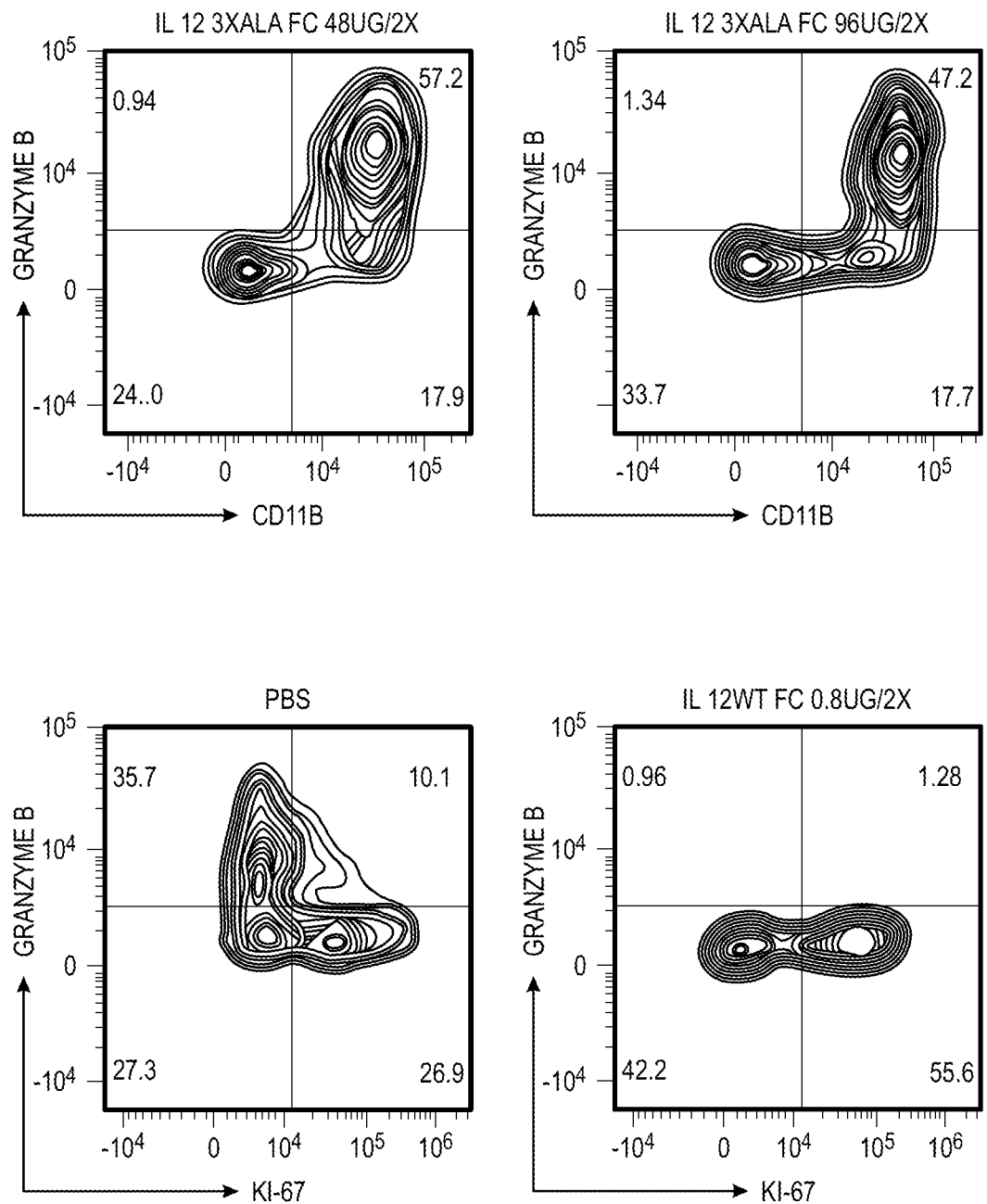
Figure 14:
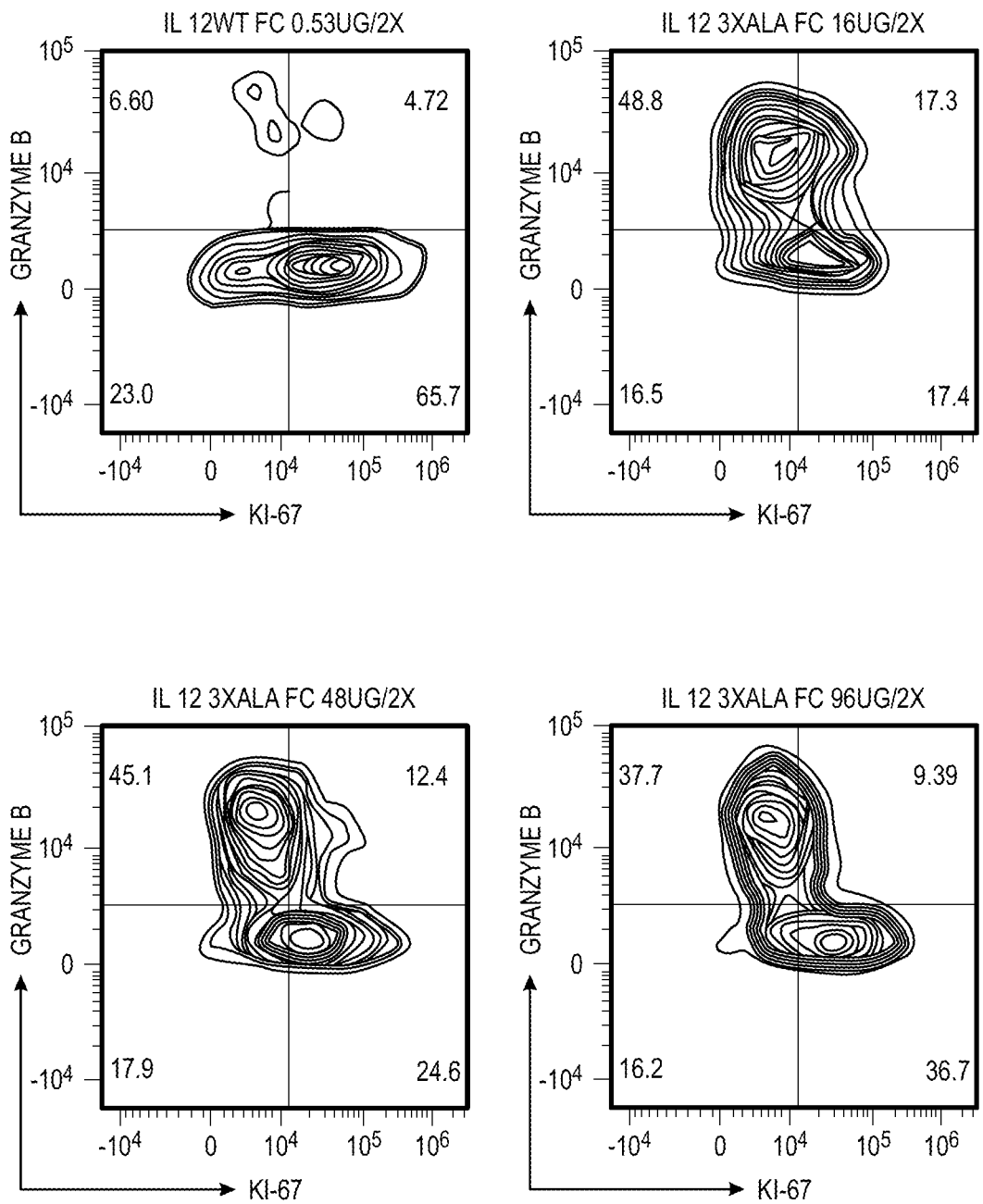

The data relating to effect on tumor growth in the above study is provided in FIGS. 12, 13, and 14 of the attached drawings. As shown in FIG. 12, the wild type IL-12WT Fc demonstrates a potent anti-tumor activity in CT26 model at 0.8 ug (0.5 ug IL-12)/dose. The IL-12 3xAla Fc leads to tumor regression with a 5-7 days delay compared to IL-12WT Fc. CT26 model appears to be more sensitive to IL-12 treatment than our in-house MC38. In FIG. 13, neither IL-12WT Fc nor IL-12 3xAla Fc lead to weight loss. In view of the toxicity observed with the test agents in the MC38 study conducted in C57BL/6 mice, the BALB/c mice appeared to be more resistant to IL-12WT Fc toxicity. FIG. 14 provides FACS analysis which indicates that wild type IL12 Fc results in NK cell degranulation but that 3xAla IL12 Fc does not substantially induce NK cell degranulation.

Evaluation of Toxicity in Combination with NK Cell Depletion Study #1 S6-21-005

A study was conducted in mice to evaluate the effect on NK cell depletion in combination with the IL12 Fc test agents. NK cells were depleted using an the NK 1.1 antibody 6-8 week old C57BL/6 treated with an NK cell depleting antibody (αNK1.1/IL12) followed by IL-12 administration. PBS or αNK1.1 was administered on days −3, 0, 3 and 7. IL12 was administered on days 0, 4, and 8 (see Table 14). Moribund mice were taken down for serum analysis and IHC. BW was measured every day. Some mice were bled and evaluated for the presence of absence of NK cells to confirm that the anti=NK1.1 antibody was depleting the NK cells. These evaluations confirmed by FACS that the antibody was indeed depleting the NK cells. The remaining surviving of the mice were taken down on day 13.

TABLE 14

NK Depletion Toxicity Model Study Design

| Group | Treatment | Treatment/ Days | Anti- NK1.1 Dose | IL-12 Dose [ug] | IL12 Schedule | IL-12 Doses | Mice |
|---|---|---|---|---|---|---|---|
| A | PBS/IL12 | −3, 0, 3, 7 | n/a | 1.6 | 2x week | 3 | 5 |
| B | PBS/IL12 | −3, 0, 3, 7 | n/a | 4.8 | 2x week | 3 | 5 |
| C | αNK1.1/IL12 | −3, 0, 3, 7 | 50 ug | 1.6 | 2x week | 3 | 5 |
| D | αNK1.1/IL12 | −3, 0, 3, 7 | 50 ug | 4.8 | 2x week | 3 | 5 |

Figure 15:
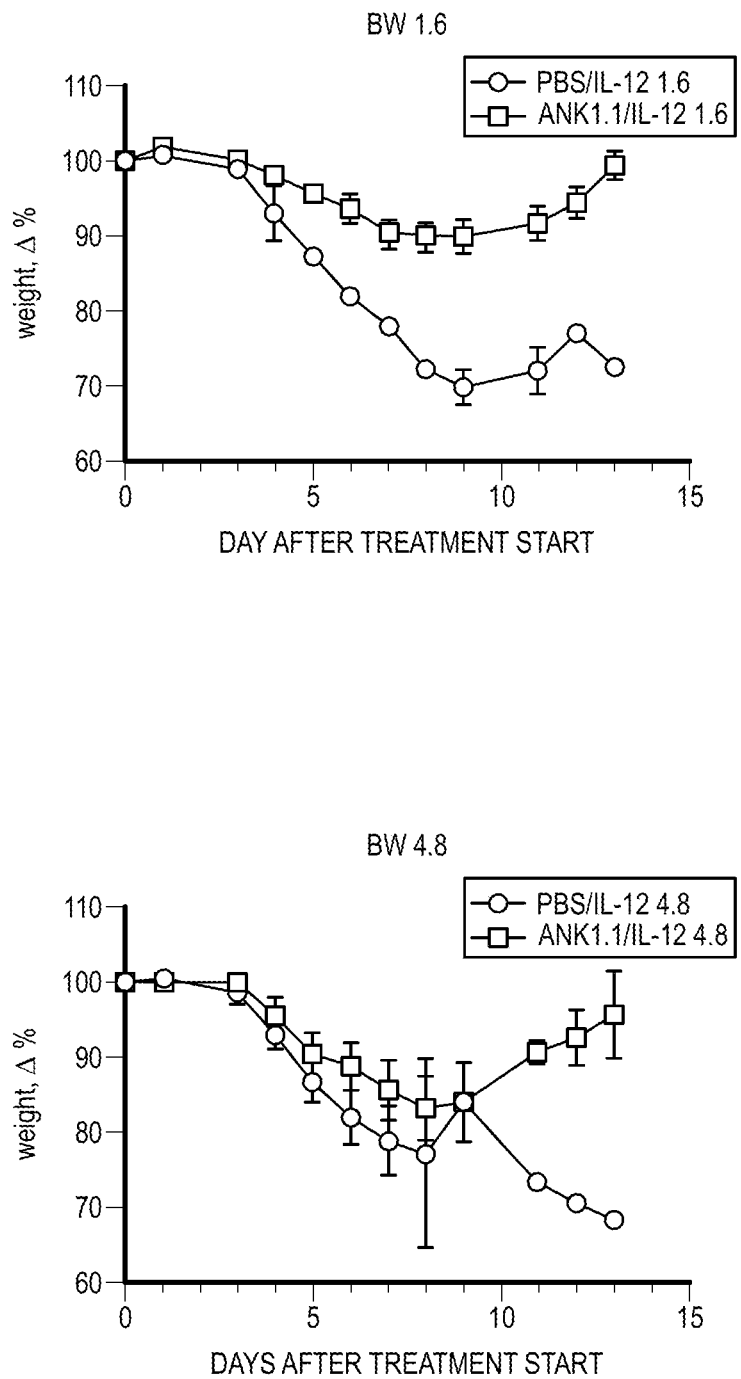
FIG. 15 provides the results of the efficacy of the various test agents indicated by the figure legends in response to depletion of NK cells in the study summarized in Table 14.
Figure 15:
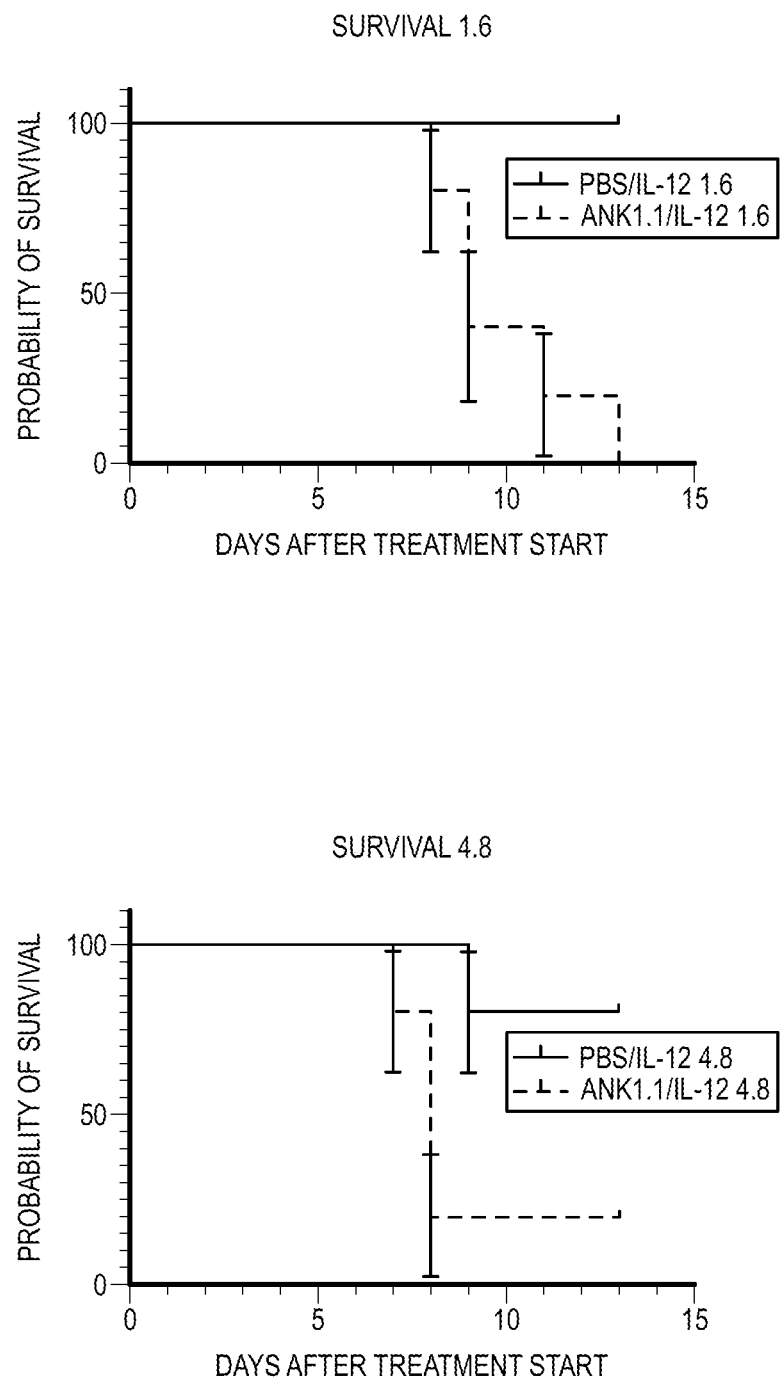

PBS/αNK1.1 was administered on days-3, 0, 3 and 7. IL12 was administered on days 0, 4, and 8. Animals were monited for bodyweight, survivable. Animals were sacrificed on day 13. The results of the study are presented in FIG. 15. As can be seen from the data presented, NK depletion alleviates toxicity as evaluated by bodyweight loss and prevents mortality after 1.6 ug IL-12WT Fc treatment. NK cell depletion it also substantially reduces mortality and morbidity in at the dose of 4.8 ug. Additionally, NK cell depletion is transient and NK cells rebound at d6 after the last NK depletion dose.

Evaluation of Antitumor Efficacy and Toxicity with NK/CD8 T Cell Depletion Study S6-21-006

A second study was conducted to evaluate the effect on NK and CD8 T-cell depletion in combination with the IL Fc test agents. In this study, 6-8 week old C57BL/6 mice were subcutaneously implanted with 1×10⁶ MC38 cells in Matrigel. Mice were randomized into groups when the tumors reached the average volume of approximately 85 mm³. Again, NK cells were depleted using an the NK 1.1 antibody. CD8 T cells were depleted. The antibodies and test agents were administered in accordance with the study design provided in Table 15 below. Mice were bled at various timepoints to confirm depletion efficiency. Tumor volume and bodyweight were measured twice weekly and the animals were sacrificed at the conclusion of the study for FACS analysis.

TABLE 15

Evaluation of Antitumor Efficacy and Toxicity with NK/CD8 TCell Depletion Study Design

| Group | Treatment | Mice | Depletion Schedule (Study Day) | IL12 Dose (ug)/Frequency (per week) | IL12 Doses Total |
|---|---|---|---|---|---|
| A | PBS | 8 | n/a | n/a | n/a |
| B | PBS + αNK1.1 | 5 | −2, 0, 3, 6, 10, 14 | n/a | n/a |
| C | PBS + αCD8 | 5 | −2, 0, 3, 6, 10, 14 | n/a | n/a |

TABLE 15-continued

Evaluation of Antitumor Efficacy and Toxicity with NK/CD8 TCell Depletion Study Design

| Group | Treatment | Mice | Depletion Schedule (Study Day) | IL12 Dose (ug)/Frequency (per week) | IL12 Doses Total |
|---|---|---|---|---|---|
| D | IL12 wt Fc | 8 | n/a | 1.6/1x | 4 |
| E | IL12 wt Fc + αNK1.1 | 8 | −2, 0, 3, 6, 10, 14 | 1.6/1x | 4 |
| F | IL12 wt Fc + αCD8 | 8 | −2, 0, 3, 6, 10, 14 | 1.6/1x | 4 |
| G | IL12 3xAla Fc | 8 | n/a | 48/2x | 8 |
| H | IL12 3xAla Fc + αNK1.1 | 8 | −2, 0, 3, 6, 10, 14 | 48/2x | 8 |
| I | IL12 3xAla Fc + αCD8 | 8 | −2, 0, 3, 6, 10, 14 | 48/2x | 8 |

Figure 16:
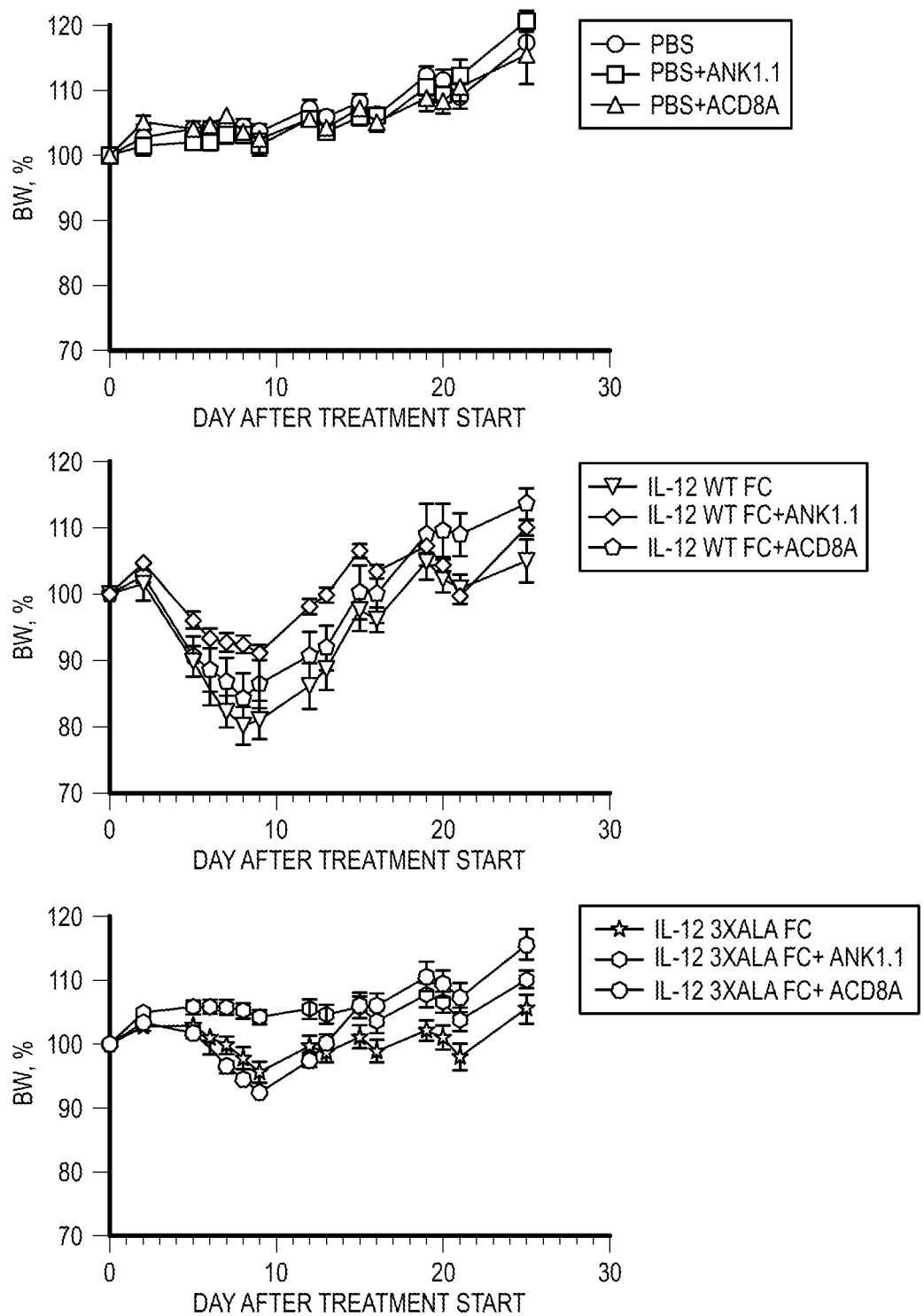
FIG. 16 provides the results of evaluation of percent change in bodyweight (vertical axis) over the course of the study (horizontal axis) in response to the various test agent conditions provided in the MC38 tumor study to evaluate the effects of NK and CD8 cell depletion as provided in detail herein, the study design of which is summarized in Table 15.
Figure 17:
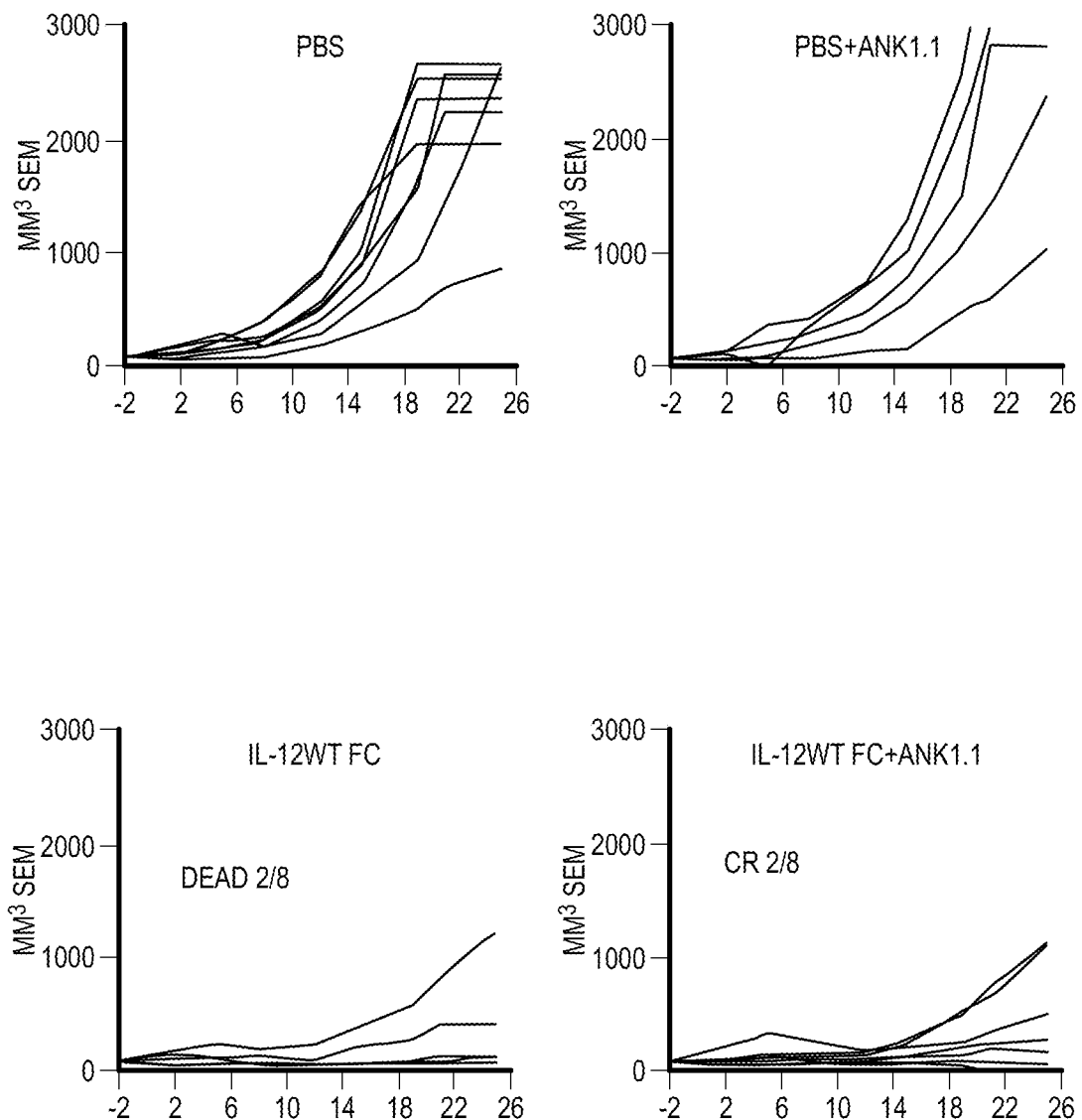
FIG. 17 provides a series of spider plots with respect to the antitumor efficacy (tumor volume on the vertical axis) over the course of the study (horizontal axis) in response to the various test conditions identified in Table 15.
Figure 17:
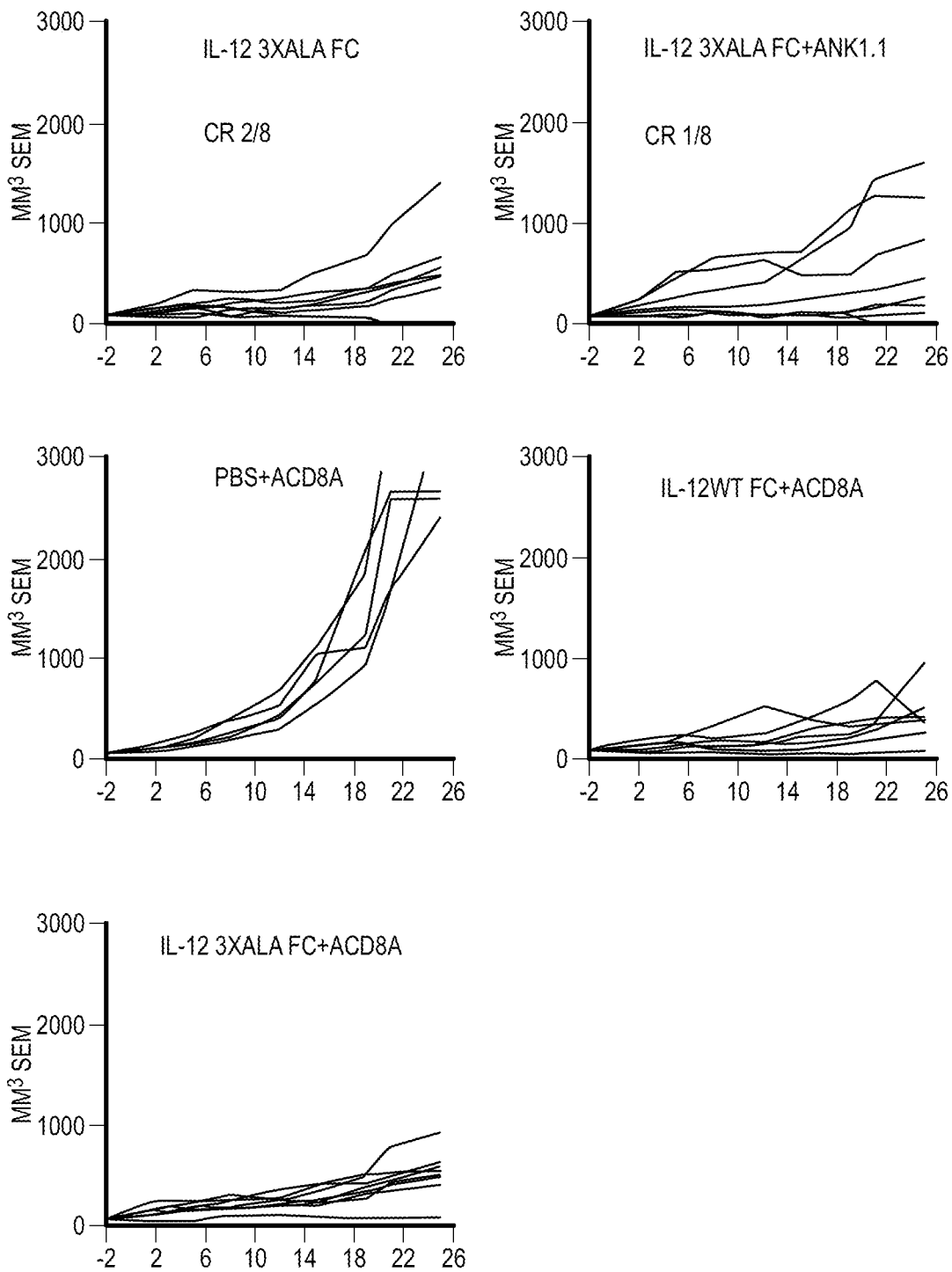

The results of the study are presented in FIGS. 16 and 17. As indicated by the data presented in FIG. 16, the depletion of NK cells does mitigate toxicity indicating that the NK cells contribute to the toxicity observed with IL12 agents. However, as shown in FIG. 17, the NK cells contribute comparatively minimally to antitumor efficacy. This data indicates that an IL12 Fc agent that having a biased activation of CD8 T cells and a reduced activation of NK cells (e.g. a heterodimeric hIL12Fc comprising a hP40M polypeptide) is efficacious in the treatment of cancers and possesses a substantially reduced toxicity relative to that observed with IL12 agents comprising a wild-type p40 polypeptide.

Evaluation of IL12 Agents in B6, RAG2 KO and RAG2/CD132 Double KO Mice

To further evaluate the activity of the hIL12 Fc muteins relative to activation of T cells versus NK cells, an antitumor efficacy study was conducted in B6 mice, RAG 2 knockout mice and RAG2/CD132 double knockout mice with the IL12 and control test agents evaluated above. B6 mice were used as a control group relative to the RAG2 knockoout (KO) mice which lack T and B cells and the RAG2/CD132 double knockout mice which lack T, B and NK cells. Briefly, the approximately 1×10$^6$ MC38 cells were implanted s.c. in Matrigel 11 days prior to the initiation of treatment (Day −11) and when the tumor volume reached approximately 120 mm$^3$ the mice were randomized into treatment groups as described in Table 16 below. The test articles and controls were administered in accordance with the schedule describe in Table 16 below. Mice were evaluated for weight loss and tumor volume twice weekly.

TABLE 16

Evaluation of IL12 Test Agents in Rag2 and Rag2/CD132 Knockout Mice

| Group | treatment | IL12 Dose [ug] | Dose regimen | ROA | Mice/ group | # IL12 doses | Genotype |
|---|---|---|---|---|---|---|---|
| A | PBS | n/a | 1x/week | i.p. | 5 | n/a | wt B6 |
| B | IL-12 WT Fc | 0.8 | 1x/week | i.p. | 5 | 4 | |
| C | IL-12 3xAla Fc | 48 | 1x/week | i.p. | 5 | 4 | |
| D | PBS | n/a | 1x/week | i.p. | 8 | n/a | Rag2 KO |
| E | IL-12 WT Fc | 0.8 | 1x/week | i.p. | 8 | 4 | |
| F | IL-12 3xAla Fc | 48 | 1x/week | i.p. | 8 | 4 | |
| G | PBS | n/a | 1x/week | i.p. | 8 | n/a | Rag2/CD132 |
| H | IL-12 WT Fc | 0.8 | 1x/week | i.p. | 8 | 4 | Double KO |
| I | IL-12 3xAla Fc | 48 | 1x/week | i.p. | 8 | 4 | |

Figure 18:
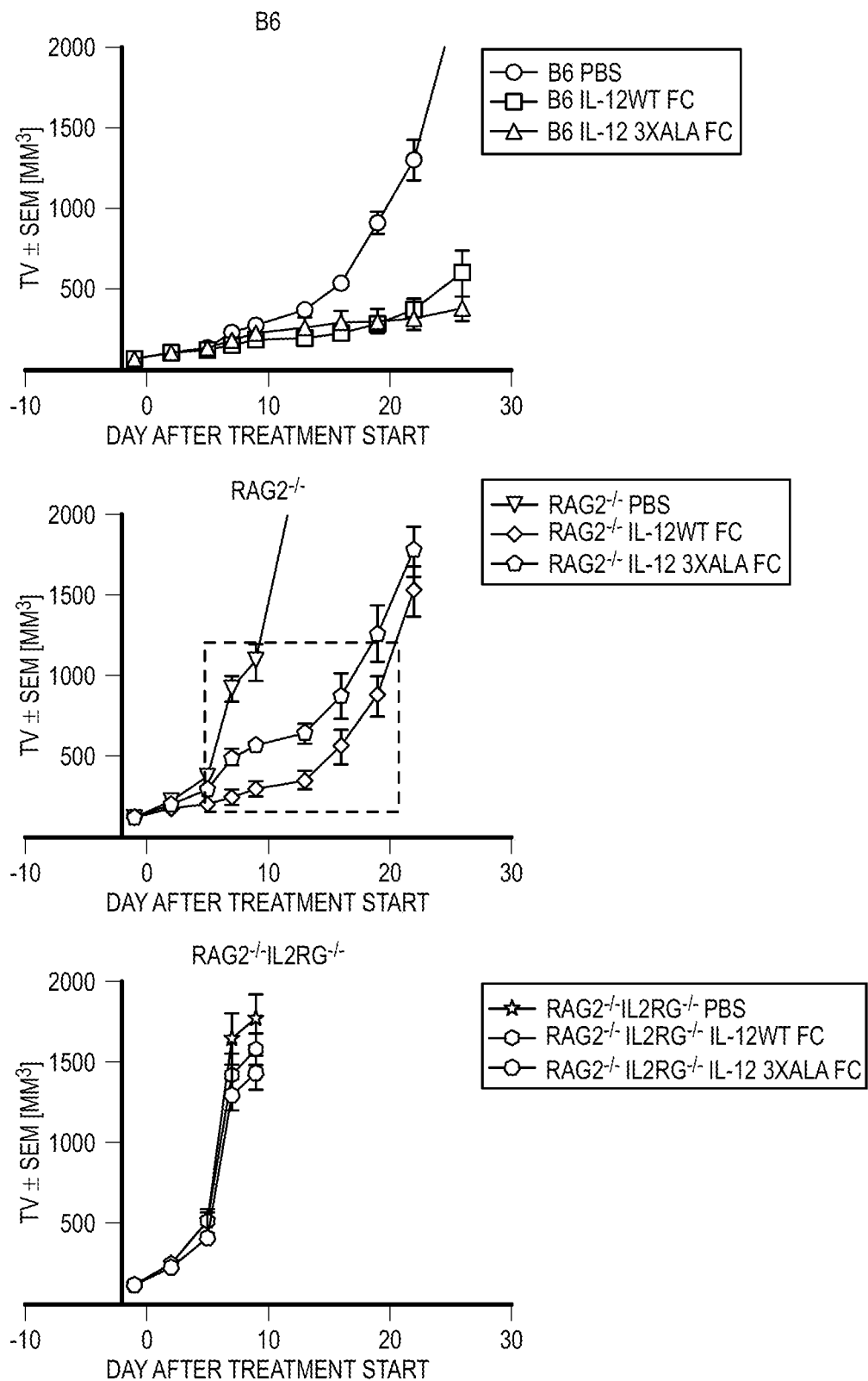
FIG. 18 provides the results of antitumor efficacy of IL12 test agents against MC38 tumors in various types of mice, B6 mice in the two figures in the first column, RAG2 knockout mice in the two figures in the second column and RAG2/CD132 double knockout mice in the third column. Tumor volume is provided on the vertical axis over the course of the study (horizontal axis). The figure legends identify the various test conditions provided in Table 15.
Figure 18:
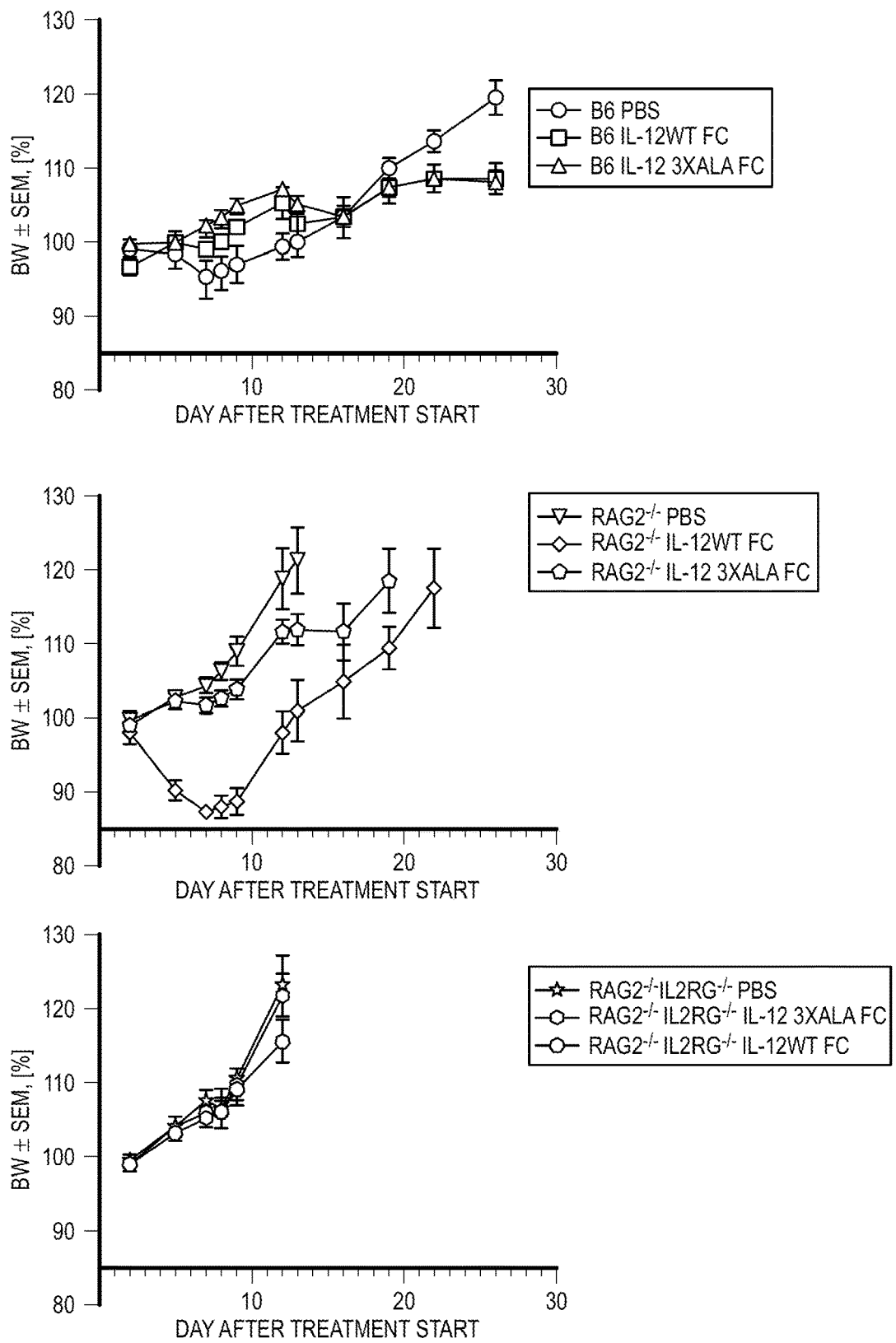

The results of this study are presented graphically in FIG. 18. As can be observed from the data, the genetic loss of T cells greatly diminishes IL-12-mediated tumor control and genetic loss of T, NK and ILCs renders mice completely resistant to IL-12. When combined with the foregoing data, these studies demonstrate that the antitumor effects of IL12 are not dependent on the presence of NK cells and that an heterodimeric IL12 Fc mutein having reduced activation of NK cells retains antitumor efficacy.

Combination Studies:

In order to evaluate that activity of the heterodimeric hIL12Fc muteins of the present disclosure in combination with supplementary therapeutic agent in the treatment of neoplastic disease, two studies were performed to evaluate the heterodimeric mIL12Fc surrogate muteins in combination with interleukin-2 and an anti-PD1 checkpoint inhibitor molecule the MC38 tumor model as previously described herein. The study design is provided in table 17 below

TABLE 17

Evaluation of mIL12 p40M Heterodimers in Combination with anti-PD1 and IL2 mutein in MC38 tumor model

| Group | treatment | Dose [ug] | regimen | ROA | Efficacy/ group | # doses |
|---|---|---|---|---|---|---|
| A | PBS | | 2x/week | i.p. | 8 | |
| B | aPD1 | 200 | 2x/week | s.c. | 8 | 6 |
| C | PEG-mREH | 10 | 2x/week | s.c. | 8 | 6 |
| D | IL-12 WT Fc | 0.8 | 1x/week | i.p. | 8 | 4 |
| E | IL-12 WT Fc/aPD-1 | 0.8/200 | 1x/week | i.p./s.c. | 8 | 4/6 |
| F | IL-12 WT Fc/PEG-mREH | 0.8/10 | 1x/week | i.p/s.c. | 8 | 4/6 |
| G | IL-12 3xAla Fc | 48 | 2x/week | i.p. | 8 | 6 |
| H | IL-12 3xAla Fc/aPD-1 | 48/200 | 2x/week | i.p./s.c. | 8 | 6/6 |
| I | IL-12 3xAla Fc/PEG-mREH | 48/10 | 2x/week | i.p/s.c. | 8 | 6/6 |

The murine IL2 mutein was developed for in vivo studies in mice to correlate activity between the rodent (mouse) and primate (human) environments for human IL2 muteins comprising amino acid substitutions at positions 18, 22 and 126 numbered in accordance with mature wild type hIL2, in particular an hIL2 mutein comprising the amino acid substitutions L18R/Q22E/Q126K. The amino acid sequence of the murine IL2 (mIL2) polypeptide used in this study is:

(SEQ ID NO: 181)
APTSSSTSSSTAEAQQQQQHLEQLRMDLEELLSRMENYRNLKLPRML

TFKFYLPKQATELKDLQCLEDELGPLRHVLDLTQSKSFQLEDAENFIS

Figure 19:
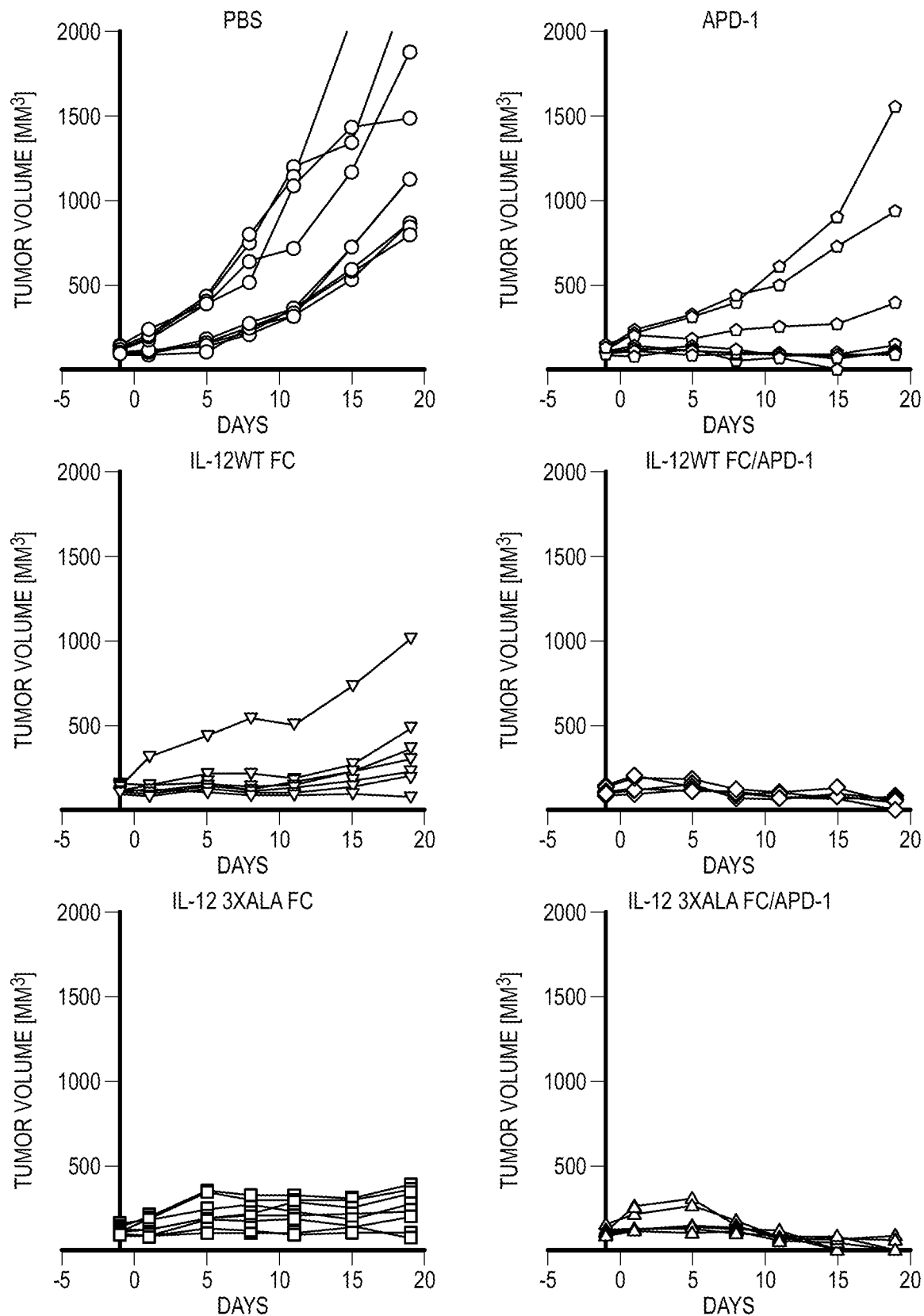
FIG. 19 provides the results of a study evaluating the anti-tumor efficacy of a heterodimeric mIL12 Fc p40M polypeptide in combination with a PD1 inhibitor in the treatment of MC38 tumors in mice. Tumor volume is provided on the vertical axis over the course of the study (horizontal axis). The figure legends correspond to the treatment groups summarized in Table 16 herein.
Figure 20:
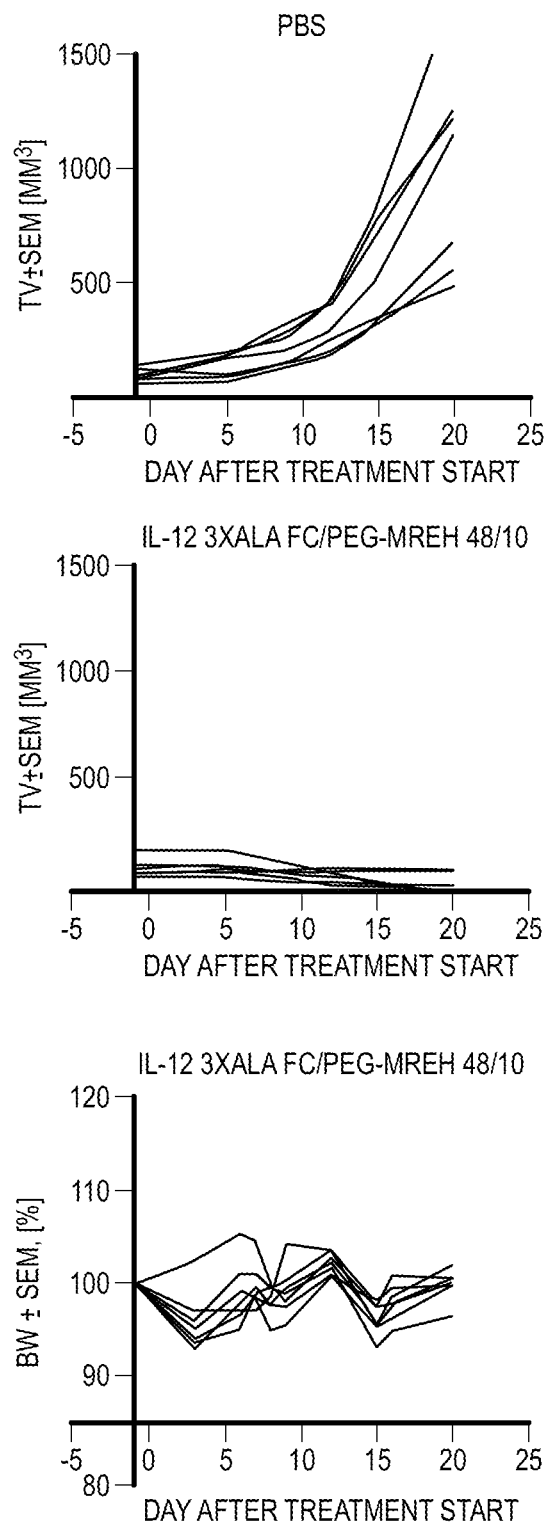
FIG. 20 provides the results of a study evaluating the anti-tumor efficacy of a heterodimeric mIL12 Fc p40M polypeptide in combination with an mIL2 mutein polypeptide in the treatment of MC38 tumors in mice. Tumor volume is provided on the vertical axis over the course of the study (horizontal axis). The figure legends correspond to the treatment groups summarized in Table 17 herein.

NIRVTVVKLKGSDNTFECQFDDESATVVDFLRRWIAFCHSIISTSPQ and is N-terminally PEGylated with a 40 kD branched chain PEG with a linker and is referred to as PEG-mREH. The results of this study are presented in FIGS. 19 (PD1) and 20 (mIL2 mutein). As can be seen from the data provided in these Figures, the combination of the heterodimeric Fc P40M mutein provides an enhanced antitumor effect in this model. In particular the combination of the heterodimeric Fc P40M mutein and the anti-PD1 antibody demonstrates a significantly enhanced effect leading to complete response. Although not indicated in Figures, it was observed that the combination heterodimeric wild type IL12 Fc and the anti-PD1 antibody was observed to alleviate the toxicity previously observed with the heterodimeric wild type IL12 Fc in this model. The foregoing data demonstrates that the heterodimeric hIL2 IL12 muteins of the present disclosure are useful in the treatment of neoplastic disease in combination with supplementary therapeutic agents, particularly IL2. IL2 muteins and checkpoint inhibitors such as anti-PD1 antibodies.

Synthesis of Heterodimeric hIL12Fc Muteins and Heterodimeric hIL23Fc Muteins

The heterodimeric hIL12Fc muteins and heterodimeric hIL23Fc muteins of the present disclosure comprise polypeptides. However, in some embodiments, heterodimeric hIL12Fc muteins and heterodimeric hIL23Fc muteins of the present disclosure comprises a non-peptidyl components such as a PEG molecule. The process for PEGylation of proteins is discussed elsewhere herein. The following is directed to the synthesis of the polypeptide components of the heterodimeric hIL12Fc muteins and heterodimeric hIL23Fc muteins of the present disclosure such including the hP40MFc, hP19Fc, and hP35Fc polypeptide subunits as well as the recombinant production of the heterodimeric hIL12Fc muteins and heterodimeric hIL23Fc muteins of the present disclosure Solid Phase Synthesis The following provides guidance to enable the solid phase and recombinant synthesis of the polypeptide hP40MFc, hP19Fc, and hP35Fc domains of the heterodimeric hIL12Fc muteins and heterodimeric hIL23Fc muteins of the present disclosure. In those embodiments where only a portion of the heterodimeric hIL12Fc mutein or heterodimeric hIL23Fc mutein is a polypeptide, it will be understood that the hP40MFc, hP19Fc, and hP35Fc polypeptidyl domain of the heterodimeric hIL12Fc mutein or heterodimeric hIL23Fc mutein are an intermediate in the process which may undergo further processing to complete the synthesis of the desired heterodimeric hIL12Fc mutein or heterodimeric hIL23Fc muteins.

The hP40MFc, hP19Fc, and hP35Fc polypeptide domains of heterodimeric hIL12Fc muteins and heterodimeric hIL23Fc muteins may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, the hP40MFc, hP19Fc, and hP35Fc polypeptide domains of heterodimeric hIL12Fc muteins and heterodimeric hIL23Fc muteins can be chemically synthesized. Chemically synthesized polypeptides are routinely generated by those of skill in the art. Chemical synthesis includes direct synthesis of a peptide by chemical means of the hP40MFc, hP19Fc, and hP35Fc polypeptide domains of heterodimeric hIL12Fc muteins and heterodimeric hIL23Fc muteins exhibiting the properties described. This method can incorporate both natural and unnatural amino acids at desired positions that facilitate linkage of particular molecules (e.g., PEG).

In some embodiments, the hP40MFc, hP19Fc, and hP35Fc polypeptide domains of heterodimeric hIL12Fc muteins and heterodimeric hIL23Fc muteins of the present disclosure may be prepared by chemical synthesis. The chemical synthesis of the hP40MFc, hP19Fc, and hP35Fc polypeptide domains of heterodimeric hIL12Fc muteins and heterodimeric hIL23Fc muteins may proceed via liquid-phase or solid-phase. Solid-phase peptide synthesis (SPPS) allows the incorporation of unnatural amino acids and/or peptide/protein backbone modification. Various forms of SPPS are available for synthesizing the hP40MFc, hP19Fc, and hP35Fc polypeptide domains of heterodimeric hIL12Fc muteins and heterodimeric hIL23Fc muteins of the present disclosure are known in the art (e.g., Ganesan A. (2006) Mini Rev. Med. Chem. 6:3-10; and Camarero J. A, et al., (2005) Protein Pept Lett. 12:723-8). In the course of chemical synthesis, the alpha functions and any reactive side chains may be protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers: hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

The hP40MFc and hp35Fc subunits of the heterodimeric hIL12Fc mutein or the hP40MFc and hp19Fc subunits of a heterodimeric hIL23Fc mutein or the complete, heterodimeric hIL12Fc muteins and heterodimeric hIL23Fc muteins of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the hP40MFc, hP19Fc, and hP35Fc Domains of the Heterodimeric hIL12Fc Mutein or Heterodimeric hIL23Fc Mutein In some embodiments, the hP40MFc, hP19Fc, and hP35Fc polypeptide domains of heterodimeric hIL12Fc mutein or heterodimeric hIL23Fc mutein are produced by recombinant methods using a nucleic acid sequence encoding the hP40MFc, hP19Fc, and hP35Fc polypeptide domains of heterodimeric hIL12Fc mutein or heterodimeric hIL23Fc mutein (or fusion proteins comprising the hP40MFc, hP19Fc, and hP35Fc polypeptide domains of heterodimeric hIL12Fc mutein or heterodimeric hIL23Fc mutein). The nucleic acid sequence encoding the desired hP40MFc, hP19Fc, and hP35Fc polypeptide domains of heterodimeric hIL12Fc mutein or heterodimeric hIL23Fc mutein can be synthesized by chemical means using an oligonucleotide synthesizer.

The nucleic acid molecules of the present disclosure are not limited to sequences that encode polypeptides; some or all of the non-coding sequences that lie upstream or downstream from a coding sequence (e.g., the coding sequence of the hP40MFc, hP19Fc, and hP35Fc polypeptide domains of heterodimeric hIL12Fc mutein or heterodimeric hIL23Fc mutein) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the hP40MFc, hP19Fc, and hP35Fc polypeptide domains of the heterodimeric hIL12Fc mutein or heterodimeric hIL23Fc mutein (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the hP40MFc, hP19Fc, and hP35Fc polypeptide domains of the heterodimeric hIL12Fc mutein or heterodimeric hIL23Fc mutein may be obtained from various commercial sources that provide custom synthesis of nucleic acid sequences. Amino acid sequence variants of the hP40MFc, hP19Fc, and hP35Fc polypeptide subunits of the heterodimeric hIL12Fc muteins and heterodimeric hIL23Fc muteins of the present disclosure are prepared by introducing appropriate nucleotide changes into the coding sequence based on the genetic code which is well known in the art. Such variations represent insertions, substitutions, and/or specified deletions of, residues as noted. Any combination of insertion, substitution, and/or specified deletion can be made to arrive at the final construct, provided that the final construct possesses the desired biological activity as defined herein.

In some embodiments, the nucleic acid sequence encoding the wild type human p40 signal peptide and the hP40MFc polypeptide is selected from the group consisting of SEQ ID NOS: 94, 97, 99, 100, 102, 105, 118, 120, 126, 128, 131, 134, 137, 140, 143, 146, 149, and 152.

In some embodiments, the nucleic acid sequence encoding the wild type human p35 signal peptide and the hP40MFc polypeptide is selected from the group consisting of SEQ ID NOS: 95, 96, 98, 103, 104, 106, and 123.

Methods for constructing a DNA sequence encoding the hP40MFc, hP19Fc, and hP35Fc polypeptide subunits of the heterodimeric hIL12Fc muteins and heterodimeric hIL23Fc muteins and expressing those sequences in a suitably transformed host include, but are not limited to, using a PCR-assisted mutagenesis technique. Mutations that consist of deletions or additions of amino acid residues to the hP40MFc, hP19Fc, and hP35Fc polypeptide subunits of the heterodimeric hIL12Fc mutein or heterodimeric hIL23Fc mutein can also be made with standard recombinant techniques. In the event of a deletion or addition, the nucleic acid molecule encoding the hP40MFc, hP19Fc, and hP35Fc polypeptide subunits of the heterodimeric hIL12Fc mutein or heterodimeric hIL23Fc muteins optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

The hP40MFc, hP19Fc, and hP35Fc polypeptide subunits of the heterodimeric hIL12Fc muteins and heterodimeric hIL23Fc muteins of the present disclosure may be produced recombinantly not only directly, but also as a fusion polypeptide with a heterologous polypeptide, e.g., a signal peptide or other polypeptide having a specific cleavage site at the N-terminus or C-terminus of the hP40MFc, hP19Fc, and hP35Fc polypeptide subunits of the heterodimeric hIL12Fc mutein or heterodimeric hIL23Fc mutein. In general, the nucleic acid sequence encoding the signal peptide may be a component of the vector, or it may be a part of the coding sequence that is inserted into the vector. If a heterologous signal peptide is employed, it is preferably a signal peptide that is recognized and processed (i.e., cleaved by a signal peptidase) by the host cell.

In some embodiments, the signal peptide is selected from the group consisting of human serum albumin signal peptide, prolactin albumin signal peptide, the human IL2 signal peptide, human trypsinogen-2, human CD-5, the human immunoglobulin kappa light chain, human azurocidin, *Gaussia* luciferase and functional derivatives thereof. Particular amino acid substitutions to increase secretion efficiency using signal peptides are described in Stern, et al. (2007) Trends in Cell and Molecular Biology 2:1-17 and Kober, et al. (2013) Biotechnol Bioeng. 1110 (4): 1164-73. Alternatively, the signal peptide may be a synthetic sequence prepared in accordance established principles. See e.g., Nielsen, et al. (1997) Protein Engineering 10 (1): 1-6 (*Identification of prokaryotic and eukaryotic signal peptides and prediction of their cleavage sites*); Bendtsen, et al (2004) J. Mol. Biol 340 (4): 783-795 (*Improved Prediction of Signal Peptides SignalP* 3.0); Petersen, et al (2011) Nature Methods 8:785-796 (*Signal P 4.0; discriminating signal peptides from transmembrane regions*).

In some embodiments, the signal peptide the hP40MFc, hP19Fc, and hP35Fc polypeptide subunits of the heterodimeric hIL12Fc mutein or heterodimeric IL23Fc mutein is the naturally occurring hP40, hP19, and hP35 signal peptide, respectively (i.e. the human hP40, hP19, and hP35 signal sequence). In some embodiments, the signal peptide of the hp35Fc sequence is the naturally occurring wild type human p35 sequence having the amino acid sequence MCPARSLLLVATLVLLDHLSLA (SEQ ID NO: 179). In some embodiments, the signal peptide of the hp40MFc sequence is the naturally occurring wild type human p40 sequence having the amino acid sequence MCHQQLVISWFSLVFLASPLVA (SEQ ID NO: 180).

The inclusion of a signal peptide depends on whether it is desired to secrete the heterodimeric hIL12Fc mutein or heterodimeric hIL23Fc mutein from the recombinant cells in which it is made. If the chosen host cells are prokaryotic, it generally is preferred that the DNA sequence not encode a signal sequence. If the host cells for expression of the heterodimeric hIL12Fc mutein or heterodimeric hIL23Fc mutein are eukaryotic, the signal peptide the hP40MFc, hP19Fc, and hP35Fc polypeptide subunits is the naturally occurring hP40, hP19, and hP35 signal peptide, respectively (i.e. the human hP40, hP19, and hP35 signal sequence). Alternatively, heterologous mammalian signal sequences may be suitable, such as signal sequences from secreted polypeptides of the same or related species, as well as viral secretory leaders, for example, the herpes simplex gD signal peptide. When the recombinant host cell is a yeast cell such as *Saccharomyces cerevisiae*, the alpha mating factor secretion signal peptide may be employed to achieve extracellular secretion of the heterodimeric hIL12Fc mutein or heterodimeric hIL23Fc mutein or one or more of the hP40MFc, hP19Fc, and hP35Fc polypeptide subunits thereof of the into the culture medium as described in Singh. U.S. Pat. No. 7,198,919 B1.

In the event the heterodimeric hIL12Fc mutein or heterodimeric hIL23Fc mutein or one or more of the hP40MFc, hP19Fc, and hP35Fc polypeptide subunits thereof are to be expressed as a chimera (e.g., a fusion protein comprising an heterodimeric hIL12Fc mutein or heterodimeric hIL23Fc mutein or the hP40MFc, hP19Fc, and hP35Fc polypeptide subunits thereof and a heterologous polypeptide sequence), the chimeric protein can be encoded by a hybrid nucleic acid molecule comprising a first sequence that encodes all or part of the polypeptide domains of heterodimeric hIL12Fc mutein or heterodimeric hIL23Fc mutein or the hP40MFc, hP19Fc, and hP35Fc polypeptide subunits thereof and a second sequence that encodes all or part of the heterologous polypeptide. For example, polypeptide domains of heterodimeric hIL12Fc mutein or heterodimeric hIL23Fc mutein or the hP40MFc, hP19Fc, and hP35Fc polypeptide subunits thereof and described herein may be fused to a chelating peptide. The incorporation of a chelating peptide facilitates purification immobilized metal affinity chromatography (IMAC) as described in Smith, et al. U.S. Pat. No. 4,569,794 issued Feb. 11, 1986. Examples of chelating polypeptides useful in the practice of the present disclosure are described in Smith, et al. supra and Dobeli, et al. U.S. Pat. No. 5,320,663 issued May 10, 1995. Particular transition metal chelating polypeptides useful in the practice of the present disclosure binding molecule are polypeptides comprising 3-6 contiguous histidine residues such as a six-histidine (His) 6 peptide and are frequently referred to in the art as "His-tags." Alternatively, a hemagglutinin tag may be incorporated into the chimeric protein to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of heterodimeric hIL12Fc mutein or heterodimeric hIL23Fc mutein. For example, the N-terminus may be linked to a targeting domain and the C-terminus linked to a hexa-histidine tag purification handle.

The amino acid sequence of the P40MFc, hP19Fc, and hP35Fc polypeptide subunits of heterodimeric hIL12Fc muteins and heterodimeric hIL23Fc muteins (or fusions/chimeras) to be expressed can be used to construct a back-translated gene. A DNA oligomer containing a nucleotide sequence coding for the P40MFc, hP19Fc, and hP35Fc polypeptide subunits of the heterodimeric hIL12Fc mutein or heterodimeric hIL23Fc mutein can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the hP40MFc, hP19Fc, and hP35Fc polypeptide subunits of the heterodimeric hIL12Fc muteins and heterodimeric hIL23Fc muteins of the present disclosure may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based online software packages that are freely available to assist in the preparation of codon optimized nucleic acid sequences.

Control Elements

The nucleic acid sequences encoding the hP40MFc and hp35Fc subunits of the heterodimeric hIL12Fc mutein (or the hP40MFc and hp19Fc subunits of the heterodimeric hIL23Fc mutein) prepared as provided above are operably linked to suitable genetic control elements that are capable of effecting expression of the polypeptide in the host cell to be transformed with the expression vector. The term "operably linked" refers to a linkage of polynucleotide elements in a functional relationship. A nucleic acid sequence is "operably linked" when it is placed into a functional relationship with another nucleic acid sequence. For example, a promoter is operably linked to a coding sequence if it controls the transcription of the polypeptide; a ribosome binding site is operably linked to a coding sequence if it is positioned to permit translation, a nucleic acid encoding signal peptide is operably linked to a nucleic acid sequence encoding such polypeptide if it is expressed as a fusion protein and participates in directing the fusion protein to the cell membrane or in secretion of the polypeptide. Typically, nucleotide sequences that are operably linked are contiguous. However, as enhancers generally function when separated from the promoter by several kilobases and intronic sequences may be of variable lengths, some polynucleotide elements may be operably linked yet physically distant and may even function in trans from a different allele or chromosome.

The specific type of control elements necessary to effect expression will depend upon the cell type to be transformed. In the practice of the present invention, the cell to be transformed is a mammalian T-cell. The term control elements refers collectively to promoter sequences, polyadenylation signals, transcription termination sequences, upstream regulatory domains, origins of replication, internal ribosome entry sites ("IRES"), enhancers, transcription enhancers to elevate the level of mRNA expression, a sequence that encodes a suitable ribosome binding site, and sequences that terminate transcription and translation which affect the replication, transcription and translation of the polypeptide coding sequence in a recipient cell. Expression vectors also usually contain an origin of replication that allows the vector to replicate independently of the host cell.

Promoter

In one embodiment, the nucleic acid sequence(s) to be expressed (e.g. encoding the hP40MFc and/or hP35Fc) is/are operably linked to a promoter sequence. The term "promoter" is used in its conventional sense to refer to a nucleotide sequence at which the initiation and rate of transcription of a coding sequence is controlled. The promoter contains the site at which RNA polymerase binds and also contains sites for the binding of regulatory factors (such as repressors or transcription factors). Promoters can be naturally occurring or synthetic. The promoter can be constitutively active, activated in response to external stimuli (inducible), active in particular cell type or cell state (tissue specific or tumor specific) promoters, and/or regulatable promoters. The term "inducible promoter" refers to promoters that facilitate transcription of the Bioactive polypeptide preferably (or solely) under certain conditions and/or in response to external chemical or other stimuli. Examples of inducible promoters are known in the scientific literature (see, e.g., Yoshida et al., Biochem. Biophys. Res. Comm., 230:426-430 (1997); Iida et al., J. Virol., 70 (9): 6054-6059 (1996); Hwang et al., J. Virol., 71 (9): 7128-7131 (1997); Lee et al., Mol. Cell. Biol., 17 (9): 5097-5105 (1997); and Dreher et al., J. Biol. Chem., 272 (46): 29364-29371 (1997). Examples of radiation inducible promoters include the EGR-1 promoter. Boothman et al., volume 138, supplement pages S68-S71 (1994).

In some embodiments, for example where the nucleic acid sequence encoding a heterodimeric hIL12 mutein (or heterodimeric hIL23 mutein) of the present disclosure (or vector comprising same) is administered to a subject, the nucleic acid sequence encoding the encoding a heterodimeric hIL12 mutein (or heterodimeric hIL23 mutein) is operably linked to a tissue specific promoter. The use of a tissue specific promoter provide for enhanced expression in particular tissue or cell types. In some embodiments the promoter is a tumor specific promoter. Tissue specific promoters and tumor specific promoters are well known in the art, e.g., pancreas specific promoters (Palmiter et al., Cell, 50:435 (1987)), liver specific promoters (Rovet et al., J. Biol. Chem., 267:20765 (1992); Lemaigne et al., J. Biol. Chem., 268:19896 (1993); Nitsch et al., Mol. Cell. Biol., 13:4494 (1993)), stomach specific promoters (Kovarik et al., J. Biol. Chem., 268:9917 (1993)), pituitary specific promoters (Rhodes et al., Genes Dev., 7:913 (1993)), and prostate specific promoters (Henderson et. al., U.S. Pat. No. 5,698, 443, issued Dec. 16, 1997). In some embodiments of the invention, the nucleic acid sequence encoding the hp35Fc and/or hP40MFc sequence is operably linked to the human cytomegalovirus (CMV) promoter.

Multicistronic Expression Constructs

When expressing a multi-subunit protein as in the practice of the present invention, each polypeptide subunit may be operably linked to an expression control sequence (monocistronic) or multiple polypeptides may be encoded by a polycistronic construct where multiple polypeptides are expressed under the control of a single expression control sequence. Examples of elements which may be employed to facilitate polycistronic expression internal ribosome entry site (IRES) elements or the foot and mouth disease virus protein 2A (FMVD2A) system. A wide variety of IRES sites are known (see e.g. Doudna J A, Sarnow P. *Translation initiation by viral internal ribosome entry sites*. In: *Translational Control in Biology and Medicine*; Mathews et al, Ed. Cold Spring Harbor, NY: Cold Spring Harbor Laboratory Press: 2007. pp. 129-154: http://www.IRESite.org). Examples of IRES elements include the picornavirus IRES of poliovirus, rhinovirus, encepahlomyocardits virus, the aphthovirus IRES of foot and mouth disease virus, the IRES cricket paralysis virus (CrPV) the hepatitis A IRES of hepatitis A virus, the hepatitis C IRES of hepatitis C virus, the pestivirus IRES of swine fever or bovine diarrhea viruses, the cripavirus IRES, and mammalian IRES elements such as the fibroblast growth factor-1 IRES, the fibroblast growth factor-2 IRES, PDGF IRES, VEGF IRES, IGF-2 IRES. The use of IRES elements typically results in significantly lower expression of the second protein of the polycistronic message. The use of the FMDV2A system results in more efficient production of the downstream proteins as the multiple proteins are first expressed as a fusion protein which contains the autoproteolytic FMDV2A domain which cleaves the polyprotein into functional subunits. Ryan and Drew (1994) EMBO J. 13 (4): 928-933. Depending on the construction of the polycistronic coding sequence, especially to facilitate restriction endonuclease sites, the use of the FMDV2A system frequently may in the addition of a small number amino acids to the carboxy terminus of the upstream protein.

In preparing a bicistronic nucleic acid sequence encoding a heterodimeric hIL23Fc mutein or heterodimeric hIL12Fc mutein, the nucleic acid sequences encoding the hP40MFc and hP19Fc subunits of the heterodimeric hIL23Fc muteins or the nucleic acid sequences encoding the hP40MFc and hP35Fc subunits of the heterodimeric hIL12Fc muteins of the present disclosure may be provided in a bicistronic expression cassette to provide for co-expression of the subunits in a mammalian host cell. In some embodiments, the present disclosure provides bicistronic nucleic acids arranged as illustrated below:

5'-hP40MFc-P2A-hP35Fc-3'
5'-hP35Fc-P2A-hP40MFc-3'
5'-hP40Fc-IRES-hP35Fc-3'
5'-hP35Fc-IRES-hP40MFc-3'
5'-hP40MFc-T2A-hP35Fc-3'
5'-hP35Fc-T2A-hP40MFc-3'
5'-hP40MFc-P2A-hP19Fc-3'
5'-hP19Fc-P2A-hP40MFc-3'
5'-hP40Fc-IRES-hP19Fc-3',
5'-hP35Fc-IRES-hP40MFc-3'.
5'-hP40Fc-T2A-hP19Fc-3', and
5'-hP35Fc-T2A-hP40MFc-3'.

Vectors

Once assembled (by synthesis, site-directed mutagenesis or another method), the nucleic acid sequence encoding the expression cassette P40MFc, hP19Fc, and hP35Fc polypeptide subunits of the polypeptide domains of heterodimeric hIL12Fc mutein or heterodimeric hIL23Fc mutein will be inserted into an vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for the hP40MFc, hP19Fc, and hP35Fc polypeptide subunits of the heterodimeric hIL12Fc muteins and heterodimeric hIL23Fc muteins of the present disclosure contain a regulatory sequence that is recognized by the host organism and is operably linked to nucleic acid sequence encoding the hP40MFc, hP19Fc, and hP35Fc polypeptide subunits of the heterodimeric hIL12Fc muteins and heterodimeric hIL23Fc muteins. The terms "regulatory control sequence." "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject hP40MFc, hP19Fc, or hP35Fc polypeptide subunit of the heterodimeric hIL12Fc mutein and heterodimeric hIL23Fc mutein, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter. PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

In some embodiments of the disclosure, the expression cassette comprising the CMV promoter and nucleic acid sequence encoding the hp35Fc and hP40MFc polypeptides is inserted into a pCDNA3.4 mammalian expression vector (Life Technologies, Carlsbad, CA). In some embodiments of the disclosure, the expression cassette comprising the CMV promoter and nucleic acid sequence encoding the hp35Fc and hP40MFc polypeptides is inserted into the multiple cloning site of the pExSyn2.0 expression vector as prepared in accordance with the teaching of Example 1.

Host Cells

The present disclosure further provides prokaryotic or eukaryotic cells that contain and express a nucleic acid molecule that encodes the hP40MFc, hP19Fc, and hP35Fc polypeptide subunits of the heterodimeric hIL12Fc muteins and heterodimeric hIL23Fc muteins. A cell of the present disclosure is a transfected cell, i.e., a cell into which a nucleic acid molecule, for example a nucleic acid molecule encoding the hP40MFc, hP19Fc, and hP35Fc polypeptide subunits of the heterodimeric hIL12Fc muteins and heterodimeric hIL23Fc muteins, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the hP40MFc, hP19Fc, and hP35Fc polypeptide subunits of the heterodimeric hIL12Fc muteins and heterodimeric hIL23Fc muteins and biologically active variants and fragments thereof can also be made in eukaryotes, such as yeast or human cells. Suitable eukaryotic host cells include insect cells (examples of Baculovirus vectors available for expression of proteins in cultured insect cells (e.g., Sf) cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M [TK-]. ATCC #CRL-2648), Expi293 cells, monkey kidney CV1 line transformed by SV40 (COS-7, ATCC CRL 1651); human embryonic kidney line (HEK293 or HEK293 cells subcloned for growth in suspension culture: baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

In some embodiments, the recombinant hP40MFc, hP19Fc, and hP35Fc polypeptide subunits of the heterodimeric hIL12Fc muteins and heterodimeric hIL23Fc muteins may be glycosylated or aglycosylated depending on the host organism used to produce the hP40MFc, hP19Fc, and hP35Fc polypeptides.

Transfection

The expression constructs of the can be introduced into host cells to thereby produce the recombinant polypeptide domains of heterodimeric hIL12Fc mutein or heterodimeric hIL23Fc mutein disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

In some embodiments, the nucleic acid sequences encoding the hp35Fc and hP40MFc are each provided a separate expression vectors which are then co-transfected into the host cell. In some embodiments, a first recombinant expression vector comprising a nucleic acid sequence encoding hp35Fc operably linked to a promoter functional in a mammalian cell and a second recombinant expression vector comprising a nucleic acid sequence encoding hP40MFc operably linked to a promoter functional in a mammalian cell are co-transfected into a mammalian host cell. In some embodiments, the promoter functional in a mammalian cell of the first and second recombinant expression vectors is the CMV promoter. In some embodiments the first and second recombinant expression vectors are pCDNA3.4 mammalian expression vectors (Life Technologies, Carlsbad, CA). In some embodiments the first and second recombinant expression vectors are pExSyn2.0 expression vectors as prepared in accordance with the teaching of Example 1.

In some embodiments, the present disclosure provides a recombinant mammalian host cell comprising a first recombinant expression vector comprising a nucleic acid sequence encoding hp35Fc operably linked to a promoter functional in the recombinant mammalian host cell and a second recombinant expression vector comprising a nucleic acid sequence encoding hP40MFc operably linked to a promoter functional in the recombinant mammalian host cell. In some embodiments, the nucleic acid sequence encoding hp35Fc and hP40MFc further encodes a signal peptide, in some embodiments. In some embodiments the signal peptide for the hP35Fc polypeptide is the wild type human p35 signal peptide (SEQ ID NO: 179). In some embodiments the signal peptide for the hP40MFc polypeptide is the wild type human p40 signal peptide (SEQ ID NO:180). In some embodiments, the nucleic acid sequence encoding the hp35Fc and hP40MFc signal peptide In some embodiments, recombinant mammalian host cell is selected from the group consisting of CHO and 293 cells. In some embodiments, the present disclosure provides a recombinant CHO cell comprising a first recombinant expression vector comprising a nucleic acid sequence encoding hp35Fc operably linked to a promoter functional in a CHO cell and a second recombinant expression vector comprising a nucleic acid sequence encoding hP40MFc operably linked to a promoter functional in a CHO cell. In some embodiments, the present disclosure provides a recombinant CHO cell comprising a first recombinant expression vector comprising a nucleic acid sequence encoding hp35Fc operably linked to a CMV promoter and a second recombinant expression vector comprising a nucleic acid sequence encoding hP40MFc operably linked to a CMV. In some embodiments the first and second recombinant expression vectors are pCDNA3.4 mammalian expression vectors (Life Technologies, Carlsbad, CA). In some embodiments the first and second recombinant expression vectors are pExSyn2.0 expression vectors as prepared in accordance with the teaching of Example 1. In some embodiments, the present disclosure provides a recombinant mammalian host cell transformed with a first expression vector comprising a nucleic acid sequence encoding a hP40M Fc selected from the group consisting of SEQ ID NOS: 80, 83, 121, 141, 144, 129, 135, 138, 147, 150, and 153 and a second expression vector comprising a nucleic acid sequence encoding a hP35 Fc selected from the group consisting of SEQ ID NOS: 81, 82, and 124.

In some embodiments, the present disclosure provides a recombinant mammalian host cell transformed with a first expression vector comprising a nucleic acid sequence encoding SEQ ID NO: 80 and a second expression vector comprising a nucleic acid sequence encoding SEQ ID NO: 81.

In some embodiments, the present disclosure provides a recombinant mammalian host cell transformed with a first expression vector comprising a nucleic acid sequence encoding SEQ ID NO: 121 and a second expression vector comprising a nucleic acid sequence encoding SEQ ID NO: 124.

In some embodiments, the present disclosure provides a recombinant mammalian host cell transformed with a first expression vector comprising a nucleic acid sequence encoding SEQ ID NO: 83 and a second expression vector comprising a nucleic acid sequence encoding SEQ ID NO: 82.

In some embodiments, the present disclosure provides a recombinant mammalian host cell transformed with a first expression vector comprising a nucleic acid sequence encoding SEQ ID NO: 141 and a second expression vector comprising a nucleic acid sequence encoding SEQ ID NO: 124.

In some embodiments, the present disclosure provides a recombinant mammalian host cell transformed with a first expression vector comprising a nucleic acid sequence encoding SEQ ID NO: 144 and a second expression vector comprising a nucleic acid sequence encoding SEQ ID NO: 124.

In some embodiments, the present disclosure provides a recombinant mammalian host cell transformed with a first expression vector comprising a nucleic acid sequence encoding SEQ ID NO: 129 and a second expression vector comprising a nucleic acid sequence encoding SEQ ID NO: 124.

In some embodiments, the present disclosure provides a recombinant mammalian host cell transformed with a first expression vector comprising a nucleic acid sequence encoding SEQ ID NO: 147 and a second expression vector comprising a nucleic acid sequence encoding SEQ ID NO:82.

In some embodiments, the present disclosure provides a recombinant mammalian host cell transformed with a first expression vector comprising a nucleic acid sequence encoding SEQ ID NO: 150 and a second expression vector comprising a nucleic acid sequence encoding SEQ ID NO: 82.

In some embodiments, the present disclosure provides a recombinant mammalian host cell transformed with a first expression vector comprising a nucleic acid sequence encoding SEQ ID NO:153 and a second expression vector comprising a nucleic acid sequence encoding SEQ ID NO: 82.

In some embodiments, the present disclosure provides a recombinant mammalian host cell transformed with a first expression vector comprising a nucleic acid sequence encoding SEQ ID NO: 135 and a second expression vector comprising a nucleic acid sequence encoding SEQ ID NO: 124.

In some embodiments, the present disclosure provides a recombinant mammalian host cell transformed with a first expression vector comprising a nucleic acid sequence encoding SEQ ID NO: 138 and a second expression vector comprising a nucleic acid sequence encoding SEQ ID NO: 124

In some embodiments, the present disclosure provides a recombinant mammalian host cell transformed with a first expression vector comprising the nucleic acid sequence of SEQ ID NO: 94 and a second expression vector comprising the nucleic acid sequence of SEQ ID NO: 95.

In some embodiments, the present disclosure provides a recombinant mammalian host cell transformed with a first expression vector comprising the nucleic acid sequence of SEQ ID NO:120 and a second expression vector comprising the nucleic acid sequence of SEQ ID NO: 123.

In some embodiments, the present disclosure provides a recombinant mammalian host cell transformed with a first expression vector comprising the nucleic acid sequence of SEQ ID NO: 97 and a second expression vector comprising the nucleic acid sequence of SEQ ID NO: 96.

In some embodiments, the present disclosure provides a recombinant mammalian host cell transformed with a first expression vector comprising the nucleic acid sequence of SEQ ID NO: 140 and a second expression vector comprising the nucleic acid sequence of SEQ ID NO: 123.

In some embodiments, the present disclosure provides a recombinant mammalian host cell transformed with a first expression vector comprising the nucleic acid sequence of SEQ ID NO: 143 and a second expression vector comprising the nucleic acid sequence of SEQ ID NO: 123.

In some embodiments, the present disclosure provides a recombinant mammalian host cell transformed with a first expression vector comprising the nucleic acid sequence of SEQ ID NO: 128 and a second expression vector comprising the nucleic acid sequence of SEQ ID NO: 123.

In some embodiments, the present disclosure provides a recombinant mammalian host cell transformed with a first expression vector comprising the nucleic acid sequence of SEQ ID NO:146 and a second expression vector comprising the nucleic acid sequence of SEQ ID NO: 96.

In some embodiments, the present disclosure provides a host cell transformed with a first expression vector comprising the nucleic acid sequence of SEQ ID NO: 149 and a second expression vector comprising the nucleic acid sequence of SEQ ID NO: 96.

In some embodiments, the present disclosure provides a recombinant mammalian host cell transformed with a first expression vector comprising the nucleic acid sequence of SEQ ID NO: 152 and a second expression vector comprising the nucleic acid sequence of SEQ ID NO: 96.

In some embodiments, the present disclosure provides a recombinant mammalian host cell transformed with a first expression vector comprising the nucleic acid sequence of SEQ ID NO: 134 and a second expression vector comprising the nucleic acid sequence of SEQ ID NO: 123.

In some embodiments, the present disclosure provides a recombinant mammalian host cell transformed with a first expression vector comprising the nucleic acid sequence of SEQ ID NO: 137 and a second expression vector comprising the nucleic acid sequence of SEQ ID NO: 123.

Cell Culture

Host cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced polypeptides can be recovered from the culture medium as a secreted polypeptide if a secretion leader sequence is employed. Alternatively, the recombinant polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of heterodimeric hIL12Fc mutein or heterodimeric hIL23Fc mutein produced by the transformed host can be purified according to any suitable method. heterodimeric hIL12Fc muteins and heterodimeric hIL23Fc muteins can be isolated from inclusion bodies generated in E. coli, or from conditioned medium from either mammalian or yeast cultures producing a given heterodimeric hIL12Fc mutein or heterodimeric hIL23Fc mutein using cation exchange, gel filtration, and or reverse phase liquid chromatography. In some embodiments, where recombinant protein is expressed with a chelating peptide, purification tag as discussed above, this purification handle may be used for isolation of the modified recombinant protein from the cell lysate or cell medium. Where the purification tag is a chelating peptide, methods for the isolation of such molecules using immobilized metal affinity chromatography are well known in the art. See, e.g., Smith, et al. U.S. Pat. No. 4,569,794.

The substantially purified forms of the heterodimeric hIL12Fc mutein or heterodimeric hIL23Fc mutein can be used, e.g., as therapeutic agents, as described herein. The biological activity of the heterodimeric hIL12Fc mutein or heterodimeric hIL23Fc mutein produced in accordance with the foregoing can be confirmed by assay using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493: 323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Pharmaceutical Formulations

In some embodiments, the heterodimeric hIL12Fc muteins or heterodimeric hIL23Fc muteins (and/or nucleic acids encoding the heterodimeric hIL12Fc muteins or heterodimeric hIL23Fc muteins and or recombinant cells incorporating a nucleic acid sequence and modified to express the heterodimeric hIL12Fc muteins or heterodimeric hIL23Fc muteins) can be incorporated into compositions, including pharmaceutical compositions. In some embodiments, the pharmaceutical composition comprises a heterodimeric hIL12Fc mutein or heterodimeric hIL23Fc mutein as described herein. Such compositions typically include the protein or nucleic acid molecule and a pharmaceutically acceptable carrier. A pharmaceutical composition is formulated to be compatible with its intended route of administration and is compatible with the therapeutic use for which the heterodimeric hIL12Fc mutein or heterodimeric hIL23Fc mutein is to be administered to the subject in need of treatment or prophylaxis.

Carriers

Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor EL™ (BASF, Parsippany, N.J.) or phosphate buffered saline (PBS).

Buffers

The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives

The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite: chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents

In many cases, it will be preferable to include isotonic agents, for example, sugars, polyalcohols such as mannitol, sorbitol, sodium chloride in the composition.

Routes of Administration

In some embodiments of the therapeutic methods of the present disclosure involve the administration of a pharmaceutical formulation comprising a heterodimeric hIL12Fc mutein or heterodimeric hIL23Fc mutein as well as nucleic acids, vectors or transformed cells comprising same, to a subject in need of treatment. In other embodiments, the therapeutic methods of the present disclosure involve the administration of a pharmaceutical formulation comprising a heterodimeric hIL12Fc mutein or heterodimeric hIL23Fc mutein described herein. Any of the pharmaceutical compositions of the present disclosure may be administered to a subject in need of treatment or prophylaxis by a variety of routes of administration, including parenteral administration, oral, topical, or inhalation routes.

Parenteral Administration

In some embodiments, the methods of the present disclosure involve the parenteral administration of a pharmaceutical formulation comprising a heterodimeric hIL12Fc mutein or heterodimeric hIL23Fc mutein (and/or nucleic acids encoding the heterodimeric hIL12Fc mutein or heterodimeric hIL23Fc mutein or recombinantly modified host cells expressing the heterodimeric hIL12Fc mutein or heterodimeric hIL23Fc mutein) to a subject in need of treatment. In some embodiments, the methods of the present disclosure involve the parenteral administration of a pharmaceutical formulation comprising a heterodimeric hIL12Fc mutein or heterodimeric hIL23Fc mutein to a subject in need of treatment. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion. The parenteral preparation can be enclosed in ampoules, disposable syringes or multiple dose vials made of glass or plastic. In one embodiment, the formulation is provided in a prefilled syringe for Oral Administration In some embodiments, the methods of the present disclosure involve the oral administration of a pharmaceutical formulation comprising a heterodimeric hIL12Fc mutein or heterodimeric hIL23Fc mutein (and/or nucleic acids encoding the heterodimeric hIL12Fc mutein or heterodimeric hIL23Fc mutein or recombinantly modified host cells expressing the heterodimeric hIL12Fc mutein or heterodimeric hIL23Fc mutein) to a subject in need of treatment. In some embodiments, the methods of the present disclosure involve the oral administration of a pharmaceutical formulation comprising a heterodimeric hIL12Fc mutein or heterodimeric hIL23Fc mutein to a subject in need of treatment. Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

Inhalation Formulations

In some embodiments, the methods of the present disclosure involve the inhaled administration of a pharmaceutical formulation comprising a heterodimeric hIL12Fc mutein or heterodimeric hIL23Fc mutein (and/or nucleic acids encoding the heterodimeric hIL12Fc mutein or heterodimeric hIL23Fc mutein or recombinantly modified host cells expressing the heterodimeric hIL12Fc mutein or heterodimeric hIL23Fc mutein) to a subject in need of treatment. In some embodiments, the methods of the present disclosure involve the inhaled administration of a pharmaceutical formulation comprising a heterodimeric hIL12Fc mutein or heterodimeric hIL23Fc mutein to a subject in need of treatment. In the event of administration by inhalation, heterodimeric hIL12Fc mutein or heterodimeric hIL23Fc mutein, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal Formulations

In some embodiments, the methods of the present disclosure involve the mucosal or transdermal administration of a pharmaceutical formulation comprising a heterodimeric hIL12Fc mutein or heterodimeric hIL23Fc mutein (and/or nucleic acids encoding the heterodimeric hIL12Fc mutein or heterodimeric hIL23Fc mutein or recombinantly modified host cells expressing the heterodimeric hIL12Fc mutein or heterodimeric hIL23Fc mutein) to a subject in need of treatment. In some embodiments, the methods of the present disclosure involve the mucosal or transdermal administration of a pharmaceutical formulation comprising a heterodimeric hIL12Fc mutein or heterodimeric hIL23Fc mutein to a subject in need of treatment. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations

In some embodiments of the method of the present disclosure, the modified hIL-12p40) polypeptide is administered to a subject in need of treatment in a formulation to provide extended release of the heterodimeric hIL12Fc mutein or heterodimeric hIL23Fc mutein. Examples of extended release formulations of the injectable compositions can be brought about by including in the composition an agent which delays absorption, for example, aluminum monostearate and gelatin. In one embodiment, the subject heterodimeric hIL12Fc mutein or heterodimeric hIL23Fc mutein or nucleic acids are prepared with carriers that will protect the heterodimeric hIL12Fc mutein or heterodimeric hIL23Fc mutein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the Modified hIL-12p40 Polypeptide

In some embodiments of the method of the present disclosure, delivery of the heterodimeric hIL12Fc mutein or heterodimeric hIL23Fc mutein to a subject in need of treatment is achieved by the administration of a nucleic acid encoding the modified heterodimeric hIL12Fc mutein or heterodimeric hIL23Fc mutein. Methods for the administration of a nucleic acid encoding the modified heterodimeric hIL12Fc mutein or heterodimeric hIL23Fc mutein to a subject is achieved by transfection or infection using methods known in the art, including but not limited to the methods described in McCaffrey et al. (Nature (2002) 418: 6893), Xia et al. (Nature Biotechnol. (2002) 20:1006-1010), or Putnam (Am. J. Health Syst. Pharm. (1996) 53:151-160 erratum at Am. J. Health Syst. Pharm. (1996) 53:325). In some embodiments, the heterodimeric hIL12Fc mutein or heterodimeric hIL23Fc mutein is administered to a subject by the administration of a pharmaceutically acceptable formulation of recombinant expression vector comprising a nucleic acid sequence encoding the heterodimeric hIL12Fc mutein or heterodimeric hIL23Fc mutein operably linked to one or more expression control sequences operable in a mammalian subject. In some embodiments, the expression control sequence may be selected that is operable in a limited range of cell types (or single cell type) to facilitate the selective expression of the modified hIL heterodimeric hIL12Fc mutein or heterodimeric hIL23Fc mutein in a particular target cell type. In one embodiment, the recombinant expression vector is a viral vector. In some embodiments, the recombinant vector is a recombinant viral vector. In some embodiments the recombinant viral vector is a recombinant adenoassociated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in the target cell type.

In some embodiments, particularly for administration of a heterodimeric hIL23Fc mutein to the subject, particular for treatment of diseases of the intestinal tract or bacterial infections in a subject, the nucleic acid encoding the heterodimeric hIL23Fc mutein may be delivered to the subject by the administration of a recombinantly modified bacteriophage vector encoding the heterodimeric hIL23Fc mutein. As used herein, the terms 'prokaryotic virus," "bacteriophage" and "phage" are used interchangeably hereinto describe any of a variety of bacterial viruses that infect and replicate within a bacterium. Bacteriophage selectively infect procaryotic cells, restricting the expression of the heterodimeric hIL23Fc mutein to procaryotic cells in the subject while avoiding expression in mammalian cells. A wide variety of bacteriophages capable of selection a broad range of bacterial cells have been identified and characterized extensively in the scientific literature. In some embodiments, the phage is modified to remove adjacent motifs (PAM). Elimination of the of Cas9 sequences from the phage genome reduces ability of the Cas9 endonuclease of the target procaryotic cell to neutralize the invading phage encoding the heterodimeric hIL23Fc mutein.

Administration of Recombinantly Modified Cells Expressing the Modified hIL-12p40 Polypeptide In some embodiments of the method of the present disclosure, delivery of the modified hIL-12p40) polypeptide to a subject in need of treatment is achieved by the administration of recombinant host cells modified to express the heterodimeric hIL12Fc mutein or heterodimeric hIL23Fc mutein, which may be administered in the therapeutic and prophylactic applications described herein. In some embodiments, the recombinant host cells are mammalian cells, e.g., human cells.

In some embodiments, the nucleic acid sequence encoding the heterodimeric hIL12Fc mutein or heterodimeric hIL23Fc mutein (or vectors comprising same) may be maintained extrachromosomally in the recombinantly modified host cell for administration. In other embodiments, the nucleic acid sequence encoding the heterodimeric hIL12Fc mutein or heterodimeric hIL23Fc mutein may be incorporated into the genome of the host cell to be administered using at least one endonuclease to facilitate incorporate insertion of a nucleic acid sequence into the genomic sequence of the cell. As used herein, the term "endonuclease" is used to refer to a wild-type or variant enzyme capable of catalyzing the cleavage of bonds between nucleic acids within a DNA or RNA molecule, preferably a DNA molecule. Endonucleases are referred to as "rare-cutting" endonucleases when such endonucleases have a polynucleotide recognition site greater than about 12 base pairs (bp) in length, more preferably of 14-55 bp. Rare-cutting endonucleases can be used for inactivating genes at a locus or to integrate transgenes by homologous recombination (HR) i.e. by inducing DNA double-strand breaks (DSBs) at a locus and insertion of exogenous DNA at this locus by gene repair mechanism. Examples of rare-cutting endonucleases include homing endonucleases (Grizot, et al (2009) Nucleic Acids Research 37 (16): 5405-5419), chimeric Zinc-Finger nucleases (ZFN) resulting from the fusion of engineered zinc-finger domains (Porteus M and Carroll D., Gene targeting using zinc finger nucleases (2005) Nature Biotechnology 23 (3): 967-973, a TALEN-nuclease, a Cas9 endonuclease from CRISPR system as or a modified restriction endonuclease to extended sequence specificity (Eisenschmidt, et al. 2005; 33 (22): 7039-7047).

Methods of Use

Treatment of Neoplastic Disease

The present disclosure provides methods of use of heterodimeric hIL12Fc muteins of the present disclosure in the treatment of subjects suffering from a neoplastic disease disorder or condition by the administration of a therapeutically effective amount of a heterodimeric hIL12Fc mutein (or nucleic acid encoding a heterodimeric hIL12Fc mutein including recombinant vectors encoding heterodimeric hIL12Fc mutein, and eucaryotic and procaryotic cells modified to express a heterodimeric hIL12Fc mutein) as described herein.

Neoplasms Amenable to Treatment:

The compositions and methods of the present disclosure are useful in the treatment of subject suffering from a neoplastic disease characterized by the presence neoplasms, including benign and malignant neoplasms, and neoplastic disease.

Examples of benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including but not limited to breast cancers; sarcomas (including but not limited to osteosarcomas and angiosarcomas and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas, astrocytomas, myelodysplastic disorders; cervical carcinoma-in-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis.

The term neoplastic disease includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic/neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML) and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease and Reed-Stemberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

In some embodiments, the present disclosure provides a method of treating a neoplastic disease by the administration of a hIL12 Fc mutein of Table 8 by the administration of a dose of the hIL12 mutein from about _____ ug/kg of bodyweight to about _____ ug/kg of bodyweight.

Combination of hIL12 Muteins with Supplementary Anti-Neoplastic Therapeutic Agents:

The present disclosure provides for the use of heterodimeric hIL12Fc muteins of the present disclosure in combination with one or more additional active anti-neoplastic agents ("supplementary agents") for the treatment of neoplastic disease. Such further combinations are referred to interchangeably as "supplementary anti-neoplastic combinations" or "supplementary anti-neoplastic combination therapy" and those therapeutic agents that are used in combination with the heterodimeric hIL12Fc mutein of the present disclosure are referred to as "supplementary anti-neoplastic agents." As used herein, the term "supplementary anti-neoplastic agents" includes anti-neoplastic agents that can be administered or introduced separately, for example, formulated separately for separate administration (e.g., as may be provided in a kit) and/or therapies that can be administered or introduced in combination with the heterodimeric hIL12Fc mutein.

Chemotherapeutic Agents:

In some embodiments, the supplementary anti-neoplastic agent is a chemotherapeutic agent. In some embodiments the supplementary agent is a "cocktail" of multiple chemotherapeutic agents. IN some embodiments the chemotherapeutic agent or cocktail is administered in combination with one or more physical methods (e.g. radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin $A_2$, cactinomycin, calicheamicin, carabicin, caminomycin, carzinophilin, chromomycins, dactinomycin, daunorubicin and derivatives such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4 (5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary anti-neoplastic agent is one or more chemical or biological agents identified in the art as useful in the treatment of neoplastic disease, including, but not limited to, a cytokines or cytokine antagonists such as INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-β1a (Avonex®), and interferon-β1b (Betaseron®) as well as combinations of one or more of the foregoing as practiced in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the heterodimeric hIL12Fc mutein is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11: S115), IDO inhibitors such as epacadostat, and oncolytic viruses such as talimogene laherparepvec (T-VEC).

Anti-Tumor Antigen Antibody Therapeutics as Supplementary Agents

In some embodiments, a "supplementary anti-neoplastic agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g. trastuzumab, pertuzumab, ado-trastuzumab emtansine), nectin-4 (e.g. enfortumab), CD79 (e.g. polatuzumab vedotin), CTLA4 (e.g. ipilumumab), CD22 (e.g. moxetumomab pasudotox), CCR4 (e.g. magamuizumab), IL23p19 (e.g. tildrakizumab), PDL1 (e.g. durvalumab, avelumab, atezolizumab), IL17a (e.g. ixekizumab), CD38 (e.g. daratumumab), SLAMF7 (e.g. elotuzumab), CD20 (e.g. rituximab, tositumomab, ibritumomab and ofatumumab), CD30 (e.g. brentuximab vedotin), CD33 (e.g. gemtuzumab ozogamicin), CD52 (e.g. alemtuzumab), EpCam, CEA, fpA33, TAG-72, CAIX, PSMA, PSA, folate binding protein, GD2 (e.g. dinuntuximab), GD3, IL6 (e.g. silutxumab) GM2, Le$^y$, VEGF (e.g. bevacizumab), VEGFR, VEGFR2 (e.g. ramucirumab), PDGFRα (e.g. olartumumab), EGFR (e.g. cetuximab, panitumumab and necitumumab), ERBB2 (e.g. trastuzumab), ERBB3, MET, IGFIR, EPHA3, TRAIL R1, TRAIL R2, RANKL RAP, tenascin, integrin αVβ3, and integrin α4β1.

In some embodiments, a therapeutic antibody is an immune checkpoint modulator for the treatment and/or prevention neoplastic disease in a subject as well as diseases, disorders or conditions associated with neoplastic disease. The term "immune checkpoint pathway" refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as "immune checkpoints." In one embodiment, the immune checkpoint pathway modulator is an antagonist of a negative immune checkpoint pathway that inhibits the binding of PD1 to PDL1 and/or PDL2 ("PD1 pathway inhibitor). The term PD1 pathway inhibitors includes monoclonal antibodies that interfere with the binding of PD1 to PDL1 and/or PDL2. Examples of commercially available PD1 pathway inhibitors useful as supplementary agents in the treatment of neoplastic disease include antibodies that interfere with the binding of PD1 to PDL1 and/or PDL2 including but not limited to nivolumab (Opdivo®, BMS-936558, MDX1106, commercially available from BristolMyers Squibb. Princeton NJ), pembrolizumab (Keytruda®MK-3475, lambrolizumab, commercially available from Merck and Company. Kenilworth NJ), and atezolizumab (Tecentriq®, Genentech/Roche, South San Francisco CA). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105. BristolMyers Squibb), and avelumab (MSB0010718C. Merck Serono/Pfizer) and SHR-1210 (Incyte). Additional antibody PD1 pathway inhibitors are described in U.S. Pat. No. 8,217,149 (Genentech. Inc) issued Jul. 10, 2012; U.S. Pat. No. 8,168, 757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011.

Examples of antibody therapeutics which are FDA approved and may be used as supplementary agents for use in the treatment of neoplastic disease include atezolizumab, olaratumab, ixekizumab, trastuzumab, infliximab, rituximab, edrecolomab, daratumumab, elotuzumab, necitumumab, dinutuximab, nivolumab, blinatumomab, pembrolizumab, pertuzumab, brentuximab vedotin, ipilimumab, ofatumumab, certolizumab pegol, catumaxomab, panitumumab, bevacizumab, ramucirumab, siltuximab, enfortumab vedotin, polatuzumab vedotin, [fam]-trastuzumab deruxtecan, cemiplimab, moxetumomab pasudotox, mogamuizumab, tildrakizumab, ibalizumab, durvalumab, inotuzumab, ozogamicin, avelumab, obinutuzumab, ado-trastuzumab emtansine, cetuximab, tositumomab-I131, ibritumomab tiuxetan, gemtuzumab, and ozogamicin.

Physical Methods

In some embodiments, a supplementary anti-neoplastic agent is one or more non-pharmacological modalities (e.g., localized radiation therapy or total body radiation therapy or surgery). By way of example, the present disclosure contemplates treatment regimens wherein a radiation phase is preceded or followed by treatment with a treatment regimen comprising a hIL12 mutein and one or more supplementary anti-neoplastic agents. In some embodiments, the present disclosure further contemplates the use of heterodimeric hIL12Fc mutein in combination with surgery (e.g. tumor resection). In some embodiments, the present disclosure further contemplates the use of a heterodimeric hIL12Fc mutein in combination with bone marrow transplantation, peripheral blood stem cell transplantation or other types of transplantation therapy.

In some embodiments, the methods of the disclosure may include the combination of the administration of a heterodimeric hIL12Fc muteins with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more activated CAR-T cells, engineered TCR cells, tumor infiltrating lymphocytes (TILs), engineered Treg cells.

CARs useful in the practice of the present invention are prepared in accordance with principles well known in the art. See e.g., Eshhaar et al. U.S. Pat. No. 7,741,465 B1 issued Jun. 22, 2010); Sadelain, et al (2013) Cancer Discovery 3 (4): 388-398: Jensen and Riddell (2015) Current Opinions in Immunology 33:9-15: Gross, et al. (1989) PNAS (USA) 86 (24): 10024-10028; Curran, et al. (2012) J Gene Med 14 (6): 405-15. Examples of commercially available CAR-T cell products include axicabtagene ciloleucel (marketed as Yescarta® commercially available from Gilead Pharmaceuticals) and tisagenlecleucel (marketed as Kymriah R commercially available from Novartis). In some embodiments, the CAR-T possesses a CAR specifically binds to a cell surface molecule associated with a tumor cell is selected from the group consisting of GD2, BCMA, CD19, CD33, CD38, CD70, GD2, IL3Rα2, CD19, mesothelin, Her2, EpCam, Muc1, ROR1, CD133, CEA, EGRFRVIII, PSCA, GPC3, Pan-ErbB and FAP Physical Methods:

In some embodiments, the supplementary anti-neoplastic agent is a anti-neoplastic physical methods including but not limited to radiotherapy, cryotherapy, hyperthermic therapy, surgery, laser ablation, and proton therapy.

Methods for Modulating hIL-12 Signaling

In another aspect, the disclosure provides methods for modulating IL-12 mediated signaling in a subject. In some embodiments, the method comprises administering to the subject an effective amount of a pharmaceutical composition to the subject, where the pharmaceutical composition comprises a heterodimeric hIL12Fc mutein described herein, a nucleic acid molecule encoding a heterodimeric hIL12Fc mutein described herein, a nucleic acid molecule encoding a heterodimeric hIL12Fc mutein described herein, or a recombinantly modified cell comprising a nucleic acid molecule encoding heterodimeric hIL12Fc mutein described herein. In some embodiments, the pharmaceutical composition comprises a pharmaceutically acceptable carrier.

In some embodiments, the method for modulating IL-12-mediated signaling in a subject comprises determining STAT4-mediated signaling in one or more cells obtained from the subject. In some embodiments, the STAT4-mediated signaling is determined by an assay selected from the group consisting of a gene expression assay, a phospho-flow signaling assay, and an enzyme-linked immunosorbent assay (ELISA). In some embodiments, the STAT4-mediated signaling in the subject is reduced by about 20% to about 100% compared to a reference level. In some embodiments, the administered composition results in a reduced capacity to induce expression of IFN-γ.

Kits

Also provided are kits comprising the heterodimeric hIL12Fc mutein or heterodimeric hIL23Fc mutein of the disclosure. In some embodiments, the kit comprises one or more components for modulating IL-12-mediated signaling in a subject, or treating a health condition in a subject in need thereof, wherein the components are selected from a hIL12Fc mutein or heterodimeric hIL23Fc mutein, a nucleic acid molecule encoding a hIL12Fc mutein or heterodimeric hIL23Fc mutein as described herein, a recombinantly modified cell comprising a nucleic acid molecule encoding hIL12Fc mutein or heterodimeric hIL23Fc mutein as described herein, or a pharmaceutical composition comprising one of more of the components. In some embodiments, the pharmaceutical composition of the kit comprises a pharmaceutically acceptable carrier.

Additional Embodiments

1. A heterodimeric hIL12Fc mutein, the heterodimeric hIL12Fc mutein comprising a first polypeptide of the formula #1:

$$hP40M\text{-}L1_a\text{-}UH1\text{-}Fc1 \quad [1]$$

and a second polypeptide of the formula #2:

$$hP35\text{-}L2_b\text{-}UH2\text{-}Fc2 \quad [2]$$

wherein:
hP35 is a polypeptide having at least 90%, alternatively at least 91%, alternatively at least 92%, alternatively at least 93%, alternatively at least 94%, alternatively at least 95%, alternatively at least 96%, alternatively at least 97%, alternatively at least 98%, or alternatively at least 99% sequence identity to SEQ ID NO:2;
hP40M is an human P40 mutein comprising one or more amino acid substitutions at positions selected from the group consisting of positions W37, P39, D40, A41, K80, E81, F82, K106, E108, D115, H216, K217, L218, and K219 numbered in accordance with wild-type pre-human P40 (SEQ ID NO:3);
L1 and L2 are GSA linkers and a and b are independently selected from 0 (absent) or 1 (present);
UH1 and UH2 are each an upper hinge domain of human immunoglobulin independently selected from the group consisting of the IgG1, IgG2, IgG3 and IgG4 upper hinge, optionally comprising the amino acid substitution C220S (EU numbering);
Fc1 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization with Fc2, and
FC2 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization with Fc1, and
wherein the polypeptide of formula 1 and the polypeptide of formula 2 are linked by at least one interchain disulfide bond.

2. The heterodimeric hIL12Fc mutein of embodiment 1 wherein hP40M has at least 70% sequence identity to SEQ ID NO:4 (e.g., at least 70%, 75%, 80%, 85%, 90%, 91%, 92%, 93%, 94%, 95%, 96%, 97%, 98%, or 99% sequence identity to SEQ ID NO:4).

3. The heterodimeric hIL12Fc mutein of embodiment 1 or 2 wherein hP40M comprises one or more amino acid substitutions at residues selected from the group consisting of W37, P39, D40, A41, K80, E81, F82, K106, E108, D115, H216, K217, L218, and K219 numbered in accordance with SEQ ID NO:3.

4. The heterodimeric hIL12Fc mutein of embodiment 3 wherein hP40M comprises the one or more amino acid substitutions selected from the group consisting of P39A, D40A, E81A, F82A, K106A, D109A, K217A, K219A.

5. The heterodimeric hIL12Fc mutein of embodiment 3 wherein hP40M comprises one or more amino acid substitutions at residues selected from the group consisting of E81, F82, K106, and K217 numbered in accordance with SEQ ID NO:3.

6. The heterodimeric hIL12Fc mutein of embodiment 1 wherein hP40M comprises two or more amino acid substitutions at residues selected from the group consisting of E81, F82, K106, and K217 numbered in accordance with SEQ ID NO:3.

7 The heterodimeric hIL12Fc mutein of embodiment 6 wherein hP40M comprises a set of amino acid substitutions selected from the group consisting of the sets of amino acid substitutions: E81A/F82A, E81K/F82A, E81L/F82A, E81H/F82A and E81S/F82A.

8. The heterodimeric hIL12Fc mutein of embodiment 1 wherein hP40M comprises three or more amino acid substitutions at residues selected from the group consisting of W37, P39, D40, A41, K80, E81, F82, K106, E108, D115, H216, K217, L218, and K219 numbered in accordance with SEQ ID NO:3.

9 The heterodimeric hIL12Fc mutein of embodiment 1 wherein hP40M comprises three or more amino acid substitutions at W37, P39, D40, A41, K80, E81, F82, K106, E108, D115, H216, K217, L218, and K219.

10. The heterodimeric hIL12Fc mutein of embodiment 9 wherein the three or more substitutions comprise a set of amino acid substitutions selected from the group consisting of the sets of amino acid substitutions: W37A/E81A/F82A; E81A/F82A/K106A; E81A/F82A/K106A/K219A, E81A/F82A/K106N, E81A/F82A/K106Q, E81A/F82A/K106T, and E81A/F82A/K106R.

11. The heterodimeric hIL12Fc mutein of embodiment 1 wherein hP40M comprises four or more amino acid substitutions at W37, P39, D40, A41, K80, E81, F82, K106, E108, D115, H216, K217, L218, and K219.

12. The heterodimeric hIL12Fc mutein of embodiment 11 wherein the four or more substitutions comprise a set of amino acid substitutions selected from the group consisting of the sets of amino acid substitutions: E81A/F82A/K106A/K217A, 81A/F82A/K106A/E108A/D115A and P39A/D40A/E81A/F82A.

13. The heterodimeric hIL12Fc mutein of embodiment 1 wherein hP40M comprises the set of amino acid substitutions E81A/F82A (SEQ ID NO:6).

14. The heterodimeric hIL12Fc mutein of embodiment 1 wherein hP40M comprises the set of amino acid substitutions E81A/F82A/K106A (SEQ ID NO:8).

15. The heterodimeric hIL12Fc mutein of embodiment 1 wherein hP40M comprises the set of amino acid substitutions E81A/F82A/K106A/K217A (SEQ ID NO:10).

16. The heterodimeric hIL12Fc mutein of any one of embodiments 1-15 wherein the binding affinity of heterodimeric hIL12Fc for the extracellular domain (ECD) of IL12Rβ1 is reduced by at least 5%, optionally by at least 10%, optionally by at least 20%, optionally by at least 30%, optionally by at least 40%, optionally by at least 50%, optionally by at least 60%, optionally by at least 70%, relative to the binding affinity of wild type hP40 (SEQ ID NO: 4) for the extracellular domain (ECD) of IL12Rβ1 as determined by surface plasmon resonance.

17. The heterodimeric hIL12Fc mutein of any one of embodiments 1-16 wherein the GSA linker is a polypeptide having 4, 5, 6, 7, 8, 9, 10, 11, 12, 13, 14, 15, 16, 17, 18, 19 or 20 amino acids comprised of amino acids selected from the group consisting of glycine, serine and alanine.

18. The heterodimeric hIL12Fc mutein of embodiment 17 wherein GSA linker is a glycine-serine polymer of the structure $(GGGGS_m)_n$, $(GGGS_m)_n$, $(GGGA_m)_n$ and $(GGGGA_m)_n$, and combinations thereof, where m, n, and o are each independently selected from 1, 2, 3 or 4.

19. The heterodimeric hIL12Fc mutein of any one of embodiments 1-18 wherein the GSA linker is a polypeptide selected from the group consisting of SEQ ID NOS: 27-79

20. The heterodimeric hIL12Fc mutein of any one of embodiments 1-19 wherein Fc1 and Fc2 is a naturally occurring upper hinge region of a human immunoglobulin selected from the UH regions of human IgG1, human IgG2, human IgG3 and human IgG4 upper hinge domains.

21. The heterodimeric hIL12Fc mutein embodiment 20 wherein upper hinge region comprises the amino acid sequence: EPKSC (SEQ ID NO: 11)

22. The heterodimeric hIL12Fc mutein embodiment 20 wherein upper hinge region comprises the amino acid sequence: EPKSS (SEQ ID NO:12)

23. The heterodimeric hIL12Fc mutein any one of embodiments 1-22 further comprising a deletion of: (a) the lysine residue at position 447 or (b) a deletion of both the glycine at position 446 and the lysine residue at position 447.

24. The heterodimeric hIL12Fc mutein of embodiment 1 wherein Fc1 and Fc2 comprise amino acid substitutions that promote heterodimerization between Fc1 and Fc2.

25. The heterodimeric hIL12Fc mutein of embodiment 24 wherein one of Fc1 and Fc2 amino acid substitutions S364H/T394F and the other comprises the amino acid substitutions Y349T/F405A.

26. The heterodimeric hIL12Fc mutein of embodiment 24 wherein one of Fc1 and Fc2 comprise amino acid substitutions T350V/L351Y/F405A/Y407V and the other comprises the amino acid substitutions T350V/T366L/K392L/T394W.

27. The heterodimeric hIL12Fc mutein of embodiment 1 wherein one of Fc1 and Fc2 comprise amino acid substitutions K360E/K409W and the other comprises the amino acid substitutions Q347R/D399V/F405T.

28. The heterodimeric hIL12Fc mutein of embodiment 1 wherein one of Fc1 and Fc2 comprise amino acid substitutions to provide a knob and the other of Fc1 and Fc2 comprises amino acid substitutions provide a hole.

29. The heterodimeric hIL12Fc mutein of embodiment 1 wherein the acid substitution to provide a knob is the T366W and the acid substitutions to provide a hole is the set of amino acid substitutions T366S/L368A/Y407V.

30. The heterodimeric hIL12Fc mutein of embodiment 1 wherein Fc1 and Fc2 are covalently linked via one or more, optionally two or more optionally three or more disulfide bonds, optionally four or more disulfide bonds between the side chains of the following groups of cystine pairs: (a) C96 of the hP35 and C199 of the hP40M; (b) between C226 of the first Fc monomer and the C226 of the second Fc monomer, (c) between C229 of the first Fc monomer and the C229 of the second Fc monomer; and (d) between S354C of the first Fc domain comprising a S354C amino acid substitution and Y349C of the second Fc domain comprising a Y349C amino acid substitution.

31. The heterodimeric hIL12Fc mutein of embodiment 1 wherein Fc1 and Fc2 are comprise one or more amino acid substitutions to reduce effector function.

32. The heterodimeric hIL12Fc mutein of embodiment 31 wherein one or both of Fc1 and Fc2 comprise the mutation selected from the group consisting of: L234E; L234A/L235A; L234A/L235A/P329A; and L234A/L235A/P329G.

33. The heterodimeric hIL12Fc mutein of any one of embodiments 1-32 wherein Fc1 and Fc2 are comprise the amino acid substitutions M428L and N434S.

34. The heterodimeric hIL12Fc mutein of any one of embodiments 1-32 wherein the Fc1 and/or Fc2 comprise one or modifications to eliminate N- or O linked glycosylation sites.

35. The heterodimeric hIL12Fc mutein of embodiments 34 wherein the modification is the amino acid substitution is selected from the group consisting of N297Q and N297G.

36. The heterodimeric hIL12Fc mutein of any one of embodiments 1-35 wherein the heterodimeric hIL12Fc mutein is PEGylated.

37. The heterodimeric hIL12Fc mutein of embodiment 36 wherein the PEG has a molecular mass greater than about 5 kDa, greater than about 10 kDa, greater than about 15 kDa, greater than about 20 kDa, greater than about 30 kDa, greater than about 40 kDa, or greater than about 50 kDa.

38. The heterodimeric hIL12Fc mutein of embodiment 36 wherein the is provided at one or both of the C220, EU Numbering) of the upper hinge region of the hP35Fc and/or the hP40MFc.

39. A nucleic acid sequence encoding a heterodimeric hIL12Fc mutein of any one of embodiments 1-38.

40. A vector comprising the nucleic acid sequence of embodiment 39.

41. A host cell transformed with a vector of embodiment 40.

42. A pharmaceutically formulation comprising as an active ingredient a heterodimeric hIL12Fc mutein of embodiments 1-38, a nucleic acid of embodiment 39, a vector of embodiment 40, or a host cell of embodiment 41.

42. A method of treating a mammal suffering from a neoplastic disease the method comprising the step of contacting the mammal with a pharmaceutical formulation of embodiment 42.

43. A heterodimeric hIL23Fc mutein, the heterodimeric hIL23Fc mutein comprising a first polypeptide of the formula #1:

hP40M-L1$_a$-UH1-Fc1      [1]

and a second polypeptide of the formula #2:

hP35-L2$_b$-UH2-Fc2      [2]

wherein:
hP19 is a polypeptide having at least 90%, alternatively at least 91%, alternatively at least 92%, alternatively at least 93%, alternatively at least 94%, alternatively at least 95%, alternatively at least 96%, alternatively at least 97%, alternatively at least 98%, or alternatively at least 99% sequence identity to SEQ ID NO:2;
hP40M is an human P40 mutein comprising one or more amino acid substitutions at positions selected from the group consisting of positions W37, P39, D40, A41, K80, E81, F82, K106, E108, D115, H216, K217, L218, and K219 numbered in accordance with wild-type pre-human P40 (SEQ ID NO:3);
L1 and L2 are GSA linkers and a and b are independently selected from 0 (absent) or 1 (present);
UH1 and UH2 are each an upper hinge domain of human immunoglobulin independently selected from the group consisting of the IgG1, IgG2, IgG3 and IgG4 upper hinge, optionally comprising the amino acid substitution C220S (EU numbering);
Fc1 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization with Fc2, and
FC2 is a polypeptide comprising the lower hinge, CH2 and CH3 domains of a human immunoglobulin selected from the group consisting of IgG1, IgG2, IgG3 and IgG4, comprising one or more amino acid substitutions promote heterodimerization with Fc1, and
wherein the polypeptide of formula 1 and the polypeptide of formula 2 are linked by at least one interchain disulfide bond.

44. The heterodimeric hIL23Fc mutein of embodiment 43 wherein hP40M has at least 70% sequence identity to SEQ ID NO:4 (e.g., at least 70%, 75%, 80%, 85%, 90%, 91%, 92%, 93%, 94%, 95%, 96%, 97%, 98%, or 99% sequence identity to SEQ ID NO:4).

45. The heterodimeric hIL23Fc mutein of embodiment 43 wherein hP40M comprises one or more amino acid substitutions at residues selected from the group consisting of W37, P39, D40, A41, K80, E81, F82, K106, E108, D115, H216, K217, L218, and K219 numbered in accordance with SEQ ID NO:3.

46. The heterodimeric hIL23Fc mutein of embodiment 3 wherein hP40M comprises the one or more amino acid substitutions selected from the group consisting of P39A, D40A, E81A, F82A, K106A, D109A, K217A, K219A.

47. The heterodimeric hIL23Fc mutein of embodiment 3 wherein hP40M comprises one or more amino acid substitutions at residues selected from the group consisting of E81, F82, K106, and K217 numbered in accordance with SEQ ID NO:3.

48. The heterodimeric hIL23Fc mutein of embodiment 43 wherein hP40M comprises two or more amino acid substitutions at residues selected from the group consisting of E81, F82, K106, and K217 numbered in accordance with SEQ ID NO:3.

49. The heterodimeric hIL23Fc mutein of embodiment 49 wherein hP40M comprises a set of amino acid substitutions selected from the group consisting of the sets of amino acid substitutions: E81A/F82A, E81K/F82A, E81L/F82A, E81H/F82A and E81S/F82A.

50. The heterodimeric hIL23Fc mutein of embodiment 43 wherein hP40M comprises three or more amino acid substitutions at residues selected from the group consisting of W37, P39, D40, A41, K80, E81, F82, K106, E108, D115, H216, K217, L218, and K219 numbered in accordance with SEQ ID NO:3.

51. 9 The heterodimeric hIL23Fc mutein of embodiment 43 wherein hP40M comprises three or more amino acid substitutions at W37, P39, D40, A41, K80, E81, F82, K106, E108, D115, H216, K217, L218, and K219.

52. The heterodimeric hIL23Fc mutein of embodiment 52 wherein the three or more substitutions comprise a set of amino acid substitutions selected from the group consisting of the sets of amino acid substitutions: W37A/E81A/F82A;

E81A/F82A/K106A; E81A/F82A/K106A/K219A, E81A/ F82A/K106N, E81A/F82A/K106Q, E81A/F82A/K106T, and E81A/F82A/K106R.

53. The heterodimeric hIL23Fc mutein of embodiment 43 wherein hP40M comprises four or more amino acid substitutions at W37, P39, D40, A41, K80, E81, F82, K106, E108, D115, H216, K217, L218, and K219.

54. The heterodimeric hIL23Fc mutein of embodiment 43 wherein the four or more substitutions comprise a set of amino acid substitutions selected from the group consisting of the sets of amino acid substitutions: E81A/F82A/K106A/ K217A, 81A/F82A/K106A/E108A/D115A and P39A/ D40A/E81A/F82A.

55. The heterodimeric hIL23Fc mutein of embodiment 43 wherein hP40M comprises the set of amino acid substitutions E81A/F82A (SEQ ID NO:6).

56. The heterodimeric hIL23Fc mutein of embodiment 43 wherein hP40M comprises the set of amino acid substitutions E81A/F82A/K106A (SEQ ID NO:8).

57. The heterodimeric hIL23Fc mutein of embodiment 43 wherein hP40M comprises the set of amino acid substitutions E81A/F82A/K106A/K217A (SEQ ID NO:10).

58. The heterodimeric hIL23Fc mutein any one of embodiments 34-58 wherein the binding affinity of heterodimeric hIL23Fc for the extracellular domain (ECD) of IL23Rβ1 is reduced by at least 5%, optionally by at least 10%, optionally by at least 20%, optionally by at least 30%, optionally by at least 40%, optionally by at least 50%, optionally by at least 60%, optionally by at least 70%, relative to the binding affinity of wild type hP40 (SEQ ID NO: 4) for the extracellular domain (ECD) of IL23Rβ1 as determined by surface plasmon resonance.

59. The heterodimeric hIL23Fc mutein of embodiment 43 wherein the GSA linker is a polypeptide having 4, 5, 6, 7, 8, 9, 10, 11, 12, 13, 14, 15, 16, 17, 18, 19 or 20 amino acids comprised of amino acids selected from the group consisting of glycine, serine and alanine.

60. The heterodimeric hIL23Fc mutein of embodiment 43 wherein GSA linker is a glycine-serine polymer of the structure $(GGGGS_m)_n$, $(GGGS_m)_n$, $(GGGA_m)_n$ and $(GGGA_m)_n$, and combinations thereof, where m, n, and o are each independently selected from 1, 2, 3 or 4.

61. The heterodimeric hIL23Fc mutein of embodiment 43 wherein the GSA linker is a polypeptide selected from the group consisting of SEQ ID NOS: 27-79.

62. The heterodimeric hIL23Fc mutein of any one of embodiments 34-61 wherein Fc1 and Fc2 is a naturally occurring upper hinge region of a human immunoglobulin selected from the UH regions of human IgG1, human IgG2, human IgG3 and human IgG4 upper hinge domains.

63. The heterodimeric hIL23Fc mutein embodiment 62 wherein upper hinge region comprises the amino acid sequence: EPKSC (SEQ ID NO: 11)

64. The heterodimeric hIL23Fc mutein embodiment 62 wherein upper hinge region comprises the amino acid sequence: EPKSS (SEQ ID NO:12)

65. The heterodimeric hIL23Fc mutein any one of embodiments 34-34 further comprising a deletion of: (a) the lysine residue at position 447 or (b) a deletion of both the glycine at position 446 and the lysine residue at position 447.

66. The heterodimeric hIL23Fc mutein of embodiment 43 wherein Fc1 and Fc2 comprise amino acid substitutions that promote heterodimerization between Fc1 and Fc2.

67. The heterodimeric hIL23Fc mutein of embodiment 66 wherein one of Fc1 and Fc2 amino acid substitutions S364H/T394F and the other comprises the amino acid substitutions Y349T/F405A.

68. The heterodimeric hIL23Fc mutein of embodiment 66 wherein one of Fc1 and Fc2 comprise amino acid substitutions T350V/L351Y/F405A/Y407V and the other comprises the amino acid substitutions T350V/T366L/K392L/T394W.

69. The heterodimeric hIL23Fc mutein of embodiment 43 wherein one of Fc1 and Fc2 comprise amino acid substitutions K360E/K409W and the other comprises the amino acid substitutions Q347R/D399V/F405T.

70. The heterodimeric hIL23Fc mutein of embodiment 43 wherein one of Fc1 and Fc2 comprise amino acid substitutions to provide a knob and the other of Fc1 and Fc2 comprises amino acid substitutions provide a hole.

71. The heterodimeric hIL23Fc mutein of embodiment 70 wherein the acid substitution to provide a knob is the T366W and the acid substitutions to provide a hole is the set of amino acid substitutions T366S/L368A/Y407V.

72. The heterodimeric hIL23Fc mutein of embodiment 43 wherein Fc1 and Fc2 are covalently linked via one or more, optionally two or more optionally three or more disulfide bonds, optionally four or more disulfide bonds between the side chains of the following groups of cystine pairs: (a) C96 of the hP19 and C199 of the hP40M; (b) between C226 of the first Fc monomer and the C226 of the second Fc monomer, (c) between C229 of the first Fc monomer and the C229 of the second Fc monomer; and (d) between S354C of the first Fc domain comprising a S354C amino acid substitution and Y349C of the second Fc domain comprising a Y349C amino acid substitution.

73. The heterodimeric hIL23Fc mutein of embodiment 43 wherein Fc1 and Fc2 are comprise one or more amino acid substitutions to reduce effector function.

74. The heterodimeric hIL23Fc mutein of embodiment 73 wherein one or both of Fc1 and Fc2 comprise the mutation selected from the group consisting of: L234E; L234A/ L235A; L234A/L235A/P329A; and L234A/L235A/P329G.

75. The heterodimeric hIL23Fc mutein of any one of embodiments 43-74 wherein Fc1 and Fc2 are comprise the amino acid substitutions M428L and N434S.

76. The heterodimeric hIL23Fc mutein of any one of embodiments 43-75 wherein the Fc1 and/or Fc2 comprise one or modifications to eliminate N- or O linked glycosylation sites.

77. The heterodimeric hIL23Fc mutein of embodiment 76 wherein the modification is the amino acid substitution is selected from the group consisting of N297Q and N297G.

78. The heterodimeric hIL23Fc mutein of any one of embodiments 43-77 wherein the heterodimeric hIL23Fc mutein is PEGylated.

79. The heterodimeric hIL23Fc mutein of embodiment 76 wherein the PEG has a molecular mass greater than about 5 kDa, greater than about 10 kDa, greater than about 15 kDa, greater than about 20 kDa, greater than about 30 kDa, greater than about 40 kDa, or greater than about 50 kDa.

80. The heterodimeric hIL23Fc mutein of embodiment 78 wherein the is provided at one or both of the C220, EU Numbering) of the upper hinge region of the hP19Fc and/or the hP40MFc.

81. A nucleic acid sequence encoding a heterodimeric hIL23Fc mutein of any one of embodiments 43-81.

82. A vector comprising the nucleic acid sequence of embodiment 81.

83. A host cell transformed with a vector of embodiment 82.

84. A pharmaceutically formulation comprising as an active ingredient a heterodimeric hIL23Fc mutein of embodiments 43-88, a nucleic acid of embodiment 81, a vector of embodiment 82, or a host cell of embodiment 83.

85. A method of treating a mammal suffering from a inflammatory or autoimmune disease the method comprising the step of contacting the mammal with a pharmaceutical formulation of embodiment 84.

Disclosed are materials, compositions, and components that can be used for, can be used in conjunction with, can be used in preparation for, or are products of the disclosed embodiments. These and other materials are disclosed herein, and it is understood that when combinations, subsets, interactions, groups, etc. of these materials are disclosed that while specific reference of each various individual and collective combinations and permutations of these compositions may not be explicitly disclosed, each is specifically contemplated and described herein. For example, if a polypeptide is disclosed and discussed and a number of modifications that can be made to the polypeptide are discussed, each and every combination of the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

All patents, patent applications and publications referred to throughout the disclosure herein are incorporated by reference in their entirety

EXAMPLES

Example 1. Recombinant Production of hIL12 Muteins

The heterodimeric IL12 muteins of the present disclosure are produced in substantial accordance with the following procedure. A pCDNA3.4 mammalian expression vector (Life Technologies, Carlsbad, CA) was modified to include additional restriction sites in the Multiple Cloning Site (MCS) and renamed pExSyn2.0. Nucleic acid sequences encoding the hP40Fc and hP40MFc polypeptides are cloned into pExSyn2.0 at the EcoRI and BamHI restriction sites, using standard molecular biology cloning techniques. A nucleic acid sequence encoding the wt hP35Fc, a Gly-Ser linker and an Hisx8 chelating peptide were cloned into the pExSyn2.0 vector at the EcoRI and BamHI using standard molecular biology cloning techniques. The vectors were DNA sequenced (MC Lab, South San Francisco, CA) to confirm identity. The vectors encoding the hP40Fc and hP35 are co-transfected into Expi293 Cells in substantial accordance with the manufacturers protocol (Life Technologies, Carlsbad, CA). The His-tagged hIL12 muteins (His-tag on p35 C-terminus) are captured using 0.1 ml Ni Sepharose excel resin (Cytiva, part #GE17371201), equilibrated in Phosphate Buffered Saline (PBS) containing 10 mM Imidazole. The muteins are eluted from the Ni resin with 0.5 ml of PBS containing 250 mM Imidazole and dialyzed into PBS. Concentrations are determined with UV absorbance at 280 nm using extinction coefficients determined from the protein sequence.

Alternatively, IL12-Fc heterodimer is produced by transfection of two constructs consisting of p35-Fc and p40-Fc monomers. DNA is produced, scaled up, and expi293 or expiCHO cells transfected as described above. The Fc-tagged IL12 complexes are captured using Protein-A resin equilibrated in PBS, and eluted from the column with 100 mM Sodium Acetate pH2.8. Elutions are neutralized and dialyzed into PBS. Further purification using standard techniques such as Size Exclusion Chromatography and/or Anion Exchange Chromatography are used to produce pure IL12-Fc heterodimer. Concentrations are determined with UV absorbance at 280 nm using extinction coefficients determined from the protein sequence.

Example 2. Human IL12 pSTAT4 Reporter Assay

To characterize the mutations' effects on pSTAT4 signaling, the HEK-Blue Human IL12 pSTAT4 Reporter Assay (Invivogen, San Diego, CA) is performed in substantial accordance with the manufacturers protocol.

Example 3. Evaluation of IFN Gamma in Isolated Human Cells

The evaluation of IFN gamma activity in isolated human PBMCs is performed in substantial accordance with the following procedure. Isolated human whole PBMCs are removed from storage in liquid nitrogen, thawed, and counted. Cells are divided into two groups from which were isolated either Pan-T Cells or Natural Killer Cells using StemCell negative isolation kits (StemCell Technologies, Cat. #17951, Cat. #19055), per manufacturer's protocol. Cells are then counted, resuspended in Complete Yssel's media (IMDM, Gibco, Cat. #122440-053) containing 0.25% w/v Human Albumin (Sigma, Cat. #A9080), 1× ITS-X (human) (Gibco, Cat. #51500056), 30 mg/L Transferrin (Roche, Cat. #10652202001), 2 mg/L PA BioXtra (Sigma, Cat. #P5585), LA-OA-Albumin (Sigma, Cat. #L9655), 1× Penicillin/Streptomycin (Gibco, Cat. #15-140-122), 1% Human Serum (Gemini, Cat. #507533011), and transferred to wells of a 96 well, flat-bottom, tissue-culture treated plate (Fisher Scientific, Cat. #FB012931). The plates used to stimulate Pan-T Cells are coated with 5 ug/mL anti-CD3 antibody (Biolegend, Cat. #300458) in Phosphate Buffered Saline (PBS) (Corning, Cat. #12-031-CV), stored overnight at 4C, and are washed prior to cell isolations. All cells are supplemented with human IL-2 and recombinant human IL-18 (R&D Systems, Cat. #9124-IL-050/CF), final concentrations 100 pM and 50 ng/mL, respectively. Pan-T Cells are additionally supplemented with 10 ug/mL anti-CD28 antibody (Biolegend, Cat. #302934), final concentration 10 ug/mL. IL-12 mutant proteins were titrated in Complete Yssel's Media at concentrations ranging from 200 nM to 2fM, 1:10 dilutions, and are added to wells in equivalent volume to previously plated cells, the final concentrations typically ranging from 100 nM to 1 fM. Cells are then incubated at 37C, 5% CO2 for 48 hours.

In the last 4 hours of incubation, cells are treated with 1:1000 Monensin (eBiosciences, Cat. #00-4505-51). After incubation, cells are washed with PBS and stained with Zombie NIR fixable viability dye (Biolegend, Cat. #423105) for 15 minutes at 4C in the dark. Cells are washed twice in pre-made FACS Buffer (BD. 554656) and are fixed in 1× Phosflow Fix Buffer I (BD. Cat. #557870), pre-heated to 37C, for 10 minutes at 37C. 5% CO2. Cells are then washed with FACS Buffer twice and permeabilized in Phosflow Perm Buffer III (BD. Cat. #558050), per manufacturer's recommendation. After permeabilization, cells are washed twice in FACS Buffer, briefly blocked with 1:10 Human TruStain FcX Fc Block (Biolegend. Cat. #422302) in FACS Buffer and then stained for with anti-IFNγ antibody (Biolegend. Cat. #506507), anti-CD4 antibody (BD. Cat. #552838), anti-CD8 antibody (BD. Cat. #563677), and anti-CD56 antibody (Biolegend. Cat. #362504) for 1 hour at room temperature, in the dark. Cells are then washed with FACS Buffer twice and resuspended in FACS Buffer containing 1% PFA (Electron Microscopy Sciences. Cat. #15710) for at least 10 minutes at 40C in the dark prior to acquisition via flow cytometry.

Example 4. Evaluation of pSTAT4 Activity in Human Cells

The evaluation of STAT4 activity in isolated human PBMCs is performed in substantial accordance with the following procedure. Human Whole PBMCs are isolated from Leukoreduction System Chambers (Stanford Blood Center) using the Erythrocyte Custom Sedimentation Kit (Miltenyi Biotec. Cat. #130)-126-357) followed by the Custom Buffy Coat/LRSC PBMC Isolation kit (Miltenyi Biotec. Cat. #130-126-448), per manufacturer's protocol. These negatively selected PBMCs are washed in warm Complete Yssel's media (IMDM. Gibco, Cat. #122440)-053) containing 0.25% w/v Human Albumin (Sigma. Cat. #A9080). 1× ITS-X (human) (Gibco. Cat. #51500056). 30 mg/L Transferrin (Roche. Cat. #10652202001). 2 mg/L PA BioXtra (Sigma. Cat. #P5585). LA-OA-Albumin (Sigma. Cat. #L9655). 1× Penicillin/Streptomycin (Gibco. Cat. #15-140-122). 1% Human Serum (Gemini, Cat. #507533011), are counted, and are transferred to a T175 tissue-culture treated flask (Nunc. Cat. #159910) at a concentration of 2E06 cells per mL. Media is supplemented with 1 ug/mL anti-CD3 antibody (Biolegend. Cat. #300458) and 1 ug/mL anti-CD28 antibody (Biolegend. Cat. #302934). Cells are incubated for 72 hours at 37C. 5% CO2.

After incubation, cells are decanted from the flask, washed twice with warm Complete Yssel's media, and allowed to rest at 37C. 5% CO2 without anti-CD3 or anti-CD28 stimulation. Loosely attached cells are detached with gentle washing and manual agitation prior to washes and rest. After resting, cells are washed with PBS and stained with Zombie NIR fixable viability dye (Biolegend, Cat. #423105) for 15 minutes at 4C in the dark. Cells are washed twice in pre-made Assay Buffer (0.5% BSA PBS) and transferred to wells of a 96 well, round-bottom, tissue-culture treated plate (Thermo Scientific, Cat. #163320) and allowed to equilibrate in a 37C, 5% CO2 incubator. After equilibration, cells are treated with an equivalent volume of 2× IL-12 mutant protein diluted in Assay Buffer at 1:10 titrations, final concentrations ranging from 1 uM to 100 fM. Cells are then incubated at 37C, 5% CO2 for 15 minutes.

After incubation, cells are fixed in an equivalent volume of pre-warmed, 1× Phosflow Lyse/Fix Buffer (BD, Cat. #558049) for 10 minutes at 37C, 5% CO2. Cells are then washed in Assay Buffer twice and permeabilized in BD Phosflow Perm Buffer III (BD, Cat. #558050), per manufacturer's recommendation. After permeabilization, cells are washed twice in FACS Buffer, briefly blocked with 1:10 Human TruStain FcX Fc Block (Biolegend, Cat. #422302) in FACS Buffer and then stained for with anti-pSTAT4 antibody (CD, Cat. #562703), anti-CD4 antibody (BD, Cat. #552838), anti-CD8 antibody (BD, Cat. #563677), anti-CD3 (Biolegend, Cat. #300415), and anti-CD56 antibody (Biolegend, Cat. #362504) for 1 hour at room temperature, in the dark. Cells are then washed with FACS Buffer twice and resuspended in FACS Buffer containing 1% PFA (Electron Microscopy Sciences, Cat. #15710) for at least 10 minutes at 4C in the dark prior to acquisition via flow cytometry.

Informal Sequence Listing

| SEQ ID NO: | Description | DNA/AA Sequence |
|---|---|---|
| 1 | Pro-hP35 (wt) Uniprot P29459 w/native signal sequence | MCPARSLLLVATLVLLDHLSLARNLPVATPDPGMFPCLHHSQNLLRAVS NMLQKARQTLEFYPCTSEEIDHEDITKDKTSTVEACLPLELTKNESCLN SRETSFITNGSCLASRKTSFMMALCLSSIYEDLKMYQVEFKTMNAKLLM DPKRQIFLDQNMLAVIDELMQALNFNSETVPQKSSLEEPDFYKTKIKLC ILLHAFRIRAVTIDRVMSYLNAS |
| 2 | Mature hP35 (wt) Uniprot P29459 (w/o signal sequence) | RNLPVATPDPGMFPCLHHSQNLLRAVSNMLQKARQTLEFYPCTSEEIDH EDITKDKTSTVEACLPLELTKNESCLNSRETSFITNGSCLASRKTSFMM ALCLSSIYEDLKMYQVEFKTMNAKLLMDPKRQIFLDQNMLAVIDELMQA LNFNSETVPQKSSLEEPDFYKTKIKLCILLHAFRIRAVTIDRVMSYLNA S |
| 3 | Pro wt hP40 Uniprot P29460 Pre-protein with native signal sequence | MCHQQLVISWFSLVFLASPLVAIWELKKDVYVVELDWYPDAPGEMVVLT CDTPEEDGITWTLDQSSEVLGSGKTLTIQVKEFGDAGQYTCHKGGEVLS HSLLLLHKKEDGIWSTDILKDQKEPKNKTFLRCEAKNYSGRFTCWWLTT ISTDLTFSVKSSRGSSDPQGVTCGAATLSAERVRGDNKEYEYSVECQED SACPAAEESLPIEVMVDAVHKLKYENYTSSFFIRDIIKPDPPKNLQLKP LKNSRQVEVSWEYPDTWSTPHSYFSLTFCVQVQGKSKREKKDRVFTDKT SATVICRKNASISVRAQDRYYSSSWSEWASVPCS |
| 4 | Mature wt hP40 Uniprot P29460 (w/o signal sequence) | IWELKKDVYVVELDWYPDAPGEMVVLTCDTPEEDGITWTLDQSSEVLGS GKTLTIQVKEFGDAGQYTCHKGGEVLSHSLLLLHKKEDGIWSTDILKDQ KEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHS YFSLTFCVQVQGKSKREKKDRVFTDKTSATVICRKNASISVRAQDRYYS SSWSEWASVPCS |

| | Informal Sequence Listing | |
|---|---|---|
| 5 | Pro-hP40 2xAla E81A F82A (w/signal sequence) | MCHQQLVISWFSLVFLASPLVAIWELKKDVYVVELDWYPDAPGEMVVLT CDTPEEDGITWTLDQSSEVLGSGKTLTIQVKAAGDAGQYTCHKGGEVLS HSLLLLHKKEDGIWSTDILKDQKEPKNKTFLRCEAKNYSGRFTCWWLTT ISTDLTFSVKSSRGSSDPQGVTCGAATLSAERVRGDNKEYEYSVECQED SACPAAEESLPIEVMVDAVHKLKYENYTSSFFIRDIIKPDPPKNLQLKP LKNSRQVEVSWEYPDTWSTPHSYFSLTFCVQVQGKSKREKKDRVFTDKT SATVICRKNASISVRAQDRYYSSSWSEWASVPCS |
| 6 | Mature hP40 2xAla E81A F82A (w/o signal sequence)) | IWELKKDVYVVELDWYPDAPGEMVVLTCDTPEEDGITWTLDQSSEVLGS GKTLTIQVKAAGDAGQYTCHKGGEVLSHSLLLLHKKEDGIWSTDILKDQ KEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHS YFSLTFCVQVQGKSKREKKDRVFTDKTSATVICRKNASISVRAQDRYYS SSWSEWASVPCS |
| 7 | Pro-hP40 (w/signal sequence) 3xAla E81A/F82A/K106A | MCHQQLVISWFSLVFLASPLVAIWELKKDVYVVELDWYPDAPGEMVVLT CDTPEEDGITWTLDQSSEVLGSGKTLTIQVKAAGDAGQYTCHKGGEVLS HSLLLLHAKEDGIWSTDILKDQKEPKNKTFLRCEAKNYSGRFTCWWLTT ISTDLTFSVKSSRGSSDPQGVTCGAATLSAERVRGDNKEYEYSVECQED SACPAAEESLPIEVMVDAVHKLKYENYTSSFFIRDIIKPDPPKNLQLKP LKNSRQVEVSWEYPDTWSTPHSYFSLTFCVQVQGKSKREKKDRVFTDKT SATVICRKNASISVRAQDRYYSSSWSEWASVPCS |
| 8 | Mature hP40 3xAla E81A F82A K106A (w/o signal sequence) | IWELKKDVYVVELDWYPDAPGEMVVLTCDTPEEDGITWTLDQSSEVLGS GKTLTIQVKAAGDAGQYTCHKGGEVLSHSLLLLHAKEDGIWSTDILKDQ KEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHS YFSLTFCVQVQGKSKREKKDRVFTDKTSATVICRKNASISVRAQDRYYS SSWSEWASVPCS |
| 9 | Pro-hP40 4xAla E81A/F82A/K106A/ K217A (w/signal sequence) | MCHQQLVISWFSLVFLASPLVAIWELKKDVYVVELDWYPDAPGEMVVLT CDTPEEDGITWTLDQSSEVLGSGKTLTIQVKAAGDAGQYTCHKGGEVLS HSLLLLHAKEDGIWSTDILKDQKEPKNKTFLRCEAKNYSGRFTCWWLTT ISTDLTFSVKSSRGSSDPQGVTCGAATLSAERVRGDNKEYEYSVECQED SACPAAEESLPIEVMVDAVHALKYENYTSSFFIRDIIKPDPPKNLQLKP LKNSRQVEVSWEYPDTWSTPHSYFSLTFCVQVQGKSKREKKDRVFTDKT SATVICRKNASISVRAQDRYYSSSWSEWASVPCS |
| 10 | Mature hP40 4xAla E81A/F82A/K106A/ K217A (w/o signal sequence) | IWELKKDVYVVELDWYPDAPGEMVVLTCDTPEEDGITWTLDQSSEVLGS GKTLTIQVKAAGDAGQYTCHKGGEVLSHSLLLLHAKEDGIWSTDILKDQ KEPKNKTFLRCEAKNYSGRFTCWWLTTISTDLTFSVKSSRGSSDPQGVT CGAATLSAERVRGDNKEYEYSVECQEDSACPAAEESLPIEVMVDAVHAL KYENYTSSFFIRDIIKPDPPKNLQLKPLKNSRQVEVSWEYPDTWSTPHS YFSLTFCVQVQGKSKREKKDRVFTDKTSATVICRKNASISVRAQDRYYS SSWSEWASVPCS |
| 11 | wt IgG1 Upper Hinge EU 216-220 | EPKSC |
| 12 | IgG1 Upper hinge w/C220S | EPKSS |
| 13 | IgG1 Lower Hinge EU 221-230 | DKTHTCPPCP |
| 14 | hIgG1 CH2 Domain EU 238-337 | >sp\|P0DOX5\|240-339 PSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKT IS |
| 15 | hIgG1 CH3 Domain EU346-442 | >sp\|P0DOX5\|348-444 PQVYTLPPSRDELTKNQVSLTCLVKGFYPSDIAVEWESNGQPENNYKTT PPVLDSDGSFFLYSKLTVDKSRWQQGNVFSCSVMHEALHNHYTQKSLS |
| 16 | wt IgG1 Fc Monomer (lower hinge/CH2/CH3) Uniprot Ref P0DOX5 EU 221-447 | Wt IGG Fc Monomer Lower Hinge/CH2/CH3 DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |

-continued

| | Informal Sequence Listing | |
|---|---|---|
| 17 | Basic Fc KNOB T366W (no upper hinge) IgG1 Fc Monomer (lower hinge/CH2/CH3 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLWC LVKGFYPSDIAVEWESNGQPENNYKTTPPVLDSDGSFFLYSKLTVDKSR WQQGNVFSCSVMHEALHNHYTQKSLSLSPGK |
| 18 | Basic Fc HOLE T366S/L368A/ Y407V (no Upper hinge) IgG1 Fc Monomer (lower hinge/CH2/CH3 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLSC AVKGFYPSDIAVEWESNGQPENNYKTTPPVLDSDGSFFLVSKLTVDKSR WQQGNVFSCSVMHEALHNHYTQKSLSLSPGK |
| 19 | Basic EPKSC UH + IgG1 Fc (LH/CH2/CH3) Knob Monomer KNOB T366W | EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLWCLVKGFYPSDIAVEWESNGQPENNYKTTPPVLDSDGSFFLYSKLT VDKSRWQQGNVFSCSVMHEALHNHYTQKSLSLSPGK |
| 20 | Basic EPKSC UH + IgG1 Fc (LH/CH2/CH3) Knob Monomer HOLE T366S/ L368A/Y407V | EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLSCAVKGFYPSDIAVEWESNGQPENNYKTTPPVLDSDGSFFLYSKLT VDKSRWQQGNVFSCSVMHEALHNHYTQKSLSLSPGK |
| 21 | C220S EPKSC UH + IgG1 Fc (LH/CH2/CH3) Knob Monomer KNOB T366W | EPKSSDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLWCLVKGFYPSDIAVEWESNGQPENNYKTTPPVLDSDGSFFLYSKLT VDKSRWQQGNVFSCSVMHEALHNHYTQKSLSLSPGK |
| 22 | C220S EPKSC UH + IgG1 Fc (LH/CH2/CH3) Knob Monomer HOLE T366S/ L368A/Y407V | EPKSSDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLSCAVKGFYPSDIAVEWESNGQPENNYKTTPPVLDSDGSFFLYSKLT VDKSRWQQGNVFSCSVMHEALHNHYTQKSLSLSPGK |
| 23 | Wt EPKSC UH + +IgG1 Fc Knob Monomer (LH/CH2/CH3) + T366W + S354C | EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPCRDELTKNQ VSLWCLVKGFYPSDIAVEWESNGQPENNYKTTPPVLDSDGSFFLYSKLT VDKSRWQQGNVFSCSVMHEALHNHYTQKSLSLSPGK |
| 24 | Wt EPKSC UH + +IgG1 Fc (LH/CH2/CH3) HOLE T366S/L368A/ Y407V + Y349C | EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVCTLPPSRDELTKNQ VSLSCAVKGFYPSDIAVEWESNGQPENNYKTTPPVLDSDGSFFLYSKLT VDKSRWQQGNVFSCSVMHEALHNHYTQKSLSLSPGK |
| 25 | C220S UH + IgG1 Fc Knob Monomer (LH/CH2/CH3) + T366W + S354C | EPKSSDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPCRDELTKNQ VSLWCLVKGFYPSDIAVEWESNGQPENNYKTTPPVLDSDGSFFLYSKLT VDKSRWQQGNVFSCSVMHEALHNHYTQKSLSLSPGK |
| 26 | C220S UH + IgG1 Fc (LH/CH2/CH3) HOLE T366S/L368A/ Y407V + Y349C | EPKSSDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVCTLPPSRDELTKNQ VSLSCAVKGFYPSDIAVEWESNGQPENNYKTTPPVLDSDGSFFLYSKLT VDKSRWQQGNVFSCSVMHEALHNHYTQKSLSLSPGK |
| 27 | (G3A)2 | GGGAGGGA |
| 28 | (G3A)4 | GGGAGGGAGGGA |
| 29 | (G3AG2)2 | GGGAGGGGGAGG |
| 30 | (G3S)3 | GGGSGGGSGGGS |
| 31 | (G3SG2)2 | GGGSGGGGGSGG |
| 32 | (G4A)2 | GGGGAGGGGA |

| Informal Sequence Listing | |
|---|---|
| 33 (G4a)3 | GGGGAGGGGAGGGGA |
| 34 (G4AG)2 | GGGGAGGGGAG |
| 35 (G4AG2)2 | GGGGAGGGGGAGG |
| 36 (G4S)2 | GGGGSGGGGS |
| 37 (G4S)3 | GGGGSGGGGSGGGGS |
| 38 (G4SG)2 | GGGGSGGGGSG |
| 39 (G4SG2)2 | GGGGSGGGGGSGG |
| 40 (G5AG)2 | GGGGGAGGGGGAG |
| 41 (G5SG)2 | GGGGGSGGGGGSG |
| 42 G2AG | GGAG |
| 43 G3A | GGGA |
| 44 G3A-G3S | GGGAGGGS |
| 45 G3A-G3S-G3A | GGGAGGGSGGGA |
| 46 G3A-G4S | GGGAGGGGS |
| 47 G3A-G4SA | GGGAGGGGA |
| 48 G3AG2 | GGGAGG |
| 49 G3AG2 G4AG | GGGAGGGGGAG |
| 50 G3S | GGGS |
| 51 G3S-G3A-GGGS | GGGSGGGAGGGS |
| 52 G3SG2 G4SG | GGGSGGGGGSG |
| 53 G4A | GGGGA |
| 54 G4A-G4S-G4A | GGGGAGGGGSGGGGA |
| 55 G4A-G4S-G4S | GGGGAGGGGSGGGGS |
| 56 G4A-G4AG | GGGGAGGGGAG |
| 57 G4A-G4S | GGGGAGGGGS |
| 58 G4A-G4SG | GGGGAGGGGSG |
| 59 G4AG | GGGGAG |
| 60 G4AG G4SG2 | GGGGAGGGGSG |
| 61 G4AG-G4AG | GGGGAGGGGAG |
| 62 G4AG-G4SG | GGGGAGGGGSG |
| 63 G4AG2 | GGGGAGG |
| 64 G4AG2 G3SG2 | GGGGAGGGGSGG |
| 65 G4S | GGGGS |
| 66 G4S-G4A-G4A | GGGGSGGGGAGGGGA |
| 67 G4S-G4A-G4S | GGGGSGGGGAGGGGS |
| 68 G4S-G4S-G4A | GGGGSGGGGSGGGGA |
| 69 G4S-G4A | GGGGSGGGGA |
| 70 G4S-G4AG | GGGGSGGGGAG |

| | Informal Sequence Listing | |
|---|---|---|
| 71 | G4S-G4SG | GGGGSGGGGSG |
| 72 | G4SG G3AG2 | GGGGSGGGGAGG |
| 73 | G4SG-G4AG | GGGGSGGGGGAG |
| 74 | G4SG-G4SG | GGGGSGGGGGSG |
| 75 | G4SG2 G5SG | GGGGSGGGGGGSG |
| 76 | G5AG | GGGGGAG |
| 77 | G5SG G4AG2 | GGGGGSGGGGAGG |
| 78 | GAG2 | GAGG |
| 79 | GSG2 | GAGG |
| 80 | DR1442M | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSEPKSSDKTHTCPPCPAPEAAGGPSVFLFPPKPKDTLM<br>ISRTPEVTCVVVDVSHEDPEVKFNWYVDGVEVHNAKTKPREEQYNSTYR<br>VVSVLTVLHQDWLNGKEYKCKVSNKALAAPIEKTISKAKGQPREPQVYT<br>LPPCRDELTKNQVSLWCLVKGFYPSDIAVEWESNGQPENNYKTTPPVLD<br>SDGSFFLYSKLTVDKSRWQQGNVFSCSVMHEALHNHYTQKSLSLSPG |
| 81 | DR1535M | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSGGGGSEPKSSDKTHTCPPCPAPEAAGGPSVFLFPPKPK<br>DTLMISRTPEVTCVVVDVSHEDPEVKFNWYVDGVEVHNAKTKPREEQYN<br>STYRVVSVLTVLHQDWLNGKEYKCKVSNKALAAPIEKTISKAKGQPREP<br>QVCTLPPSRDELTKNQVSLSCAVKGFYPSDIAVEWESNGQPENNYKTTP<br>PVLDSDGSFFLVSKLTVDKSRWQQGNVFSCSVMHEALHNHYTQKSLSLS<br>PG |
| 82 | DR1536M<br>Mature p35 Fc<br>protein | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSEPKSSDKTHTCPPCPAPEAAGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALAAPIEKTISKAKGQPREPQVCTL<br>PPSRDELTKNQVSLSCAVKGFYPSDIAVEWESNGQPENNYKTTPPVLDS<br>DGSFFLVSKLTVDKSRWQQGNVFSCSVMHEALHNHYTQKSLSLSPG |
| 83 | DR1537M<br>Mature 3xAla p40<br>Fc protein | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSGGGGSGGGGSEPKSSDKTHTCPPCPAPEAAGGPSVFL<br>FPPKPKDTLMISRTPEVTCVVVDVSHEDPEVKFNWYVDGVEVHNAKTKP<br>REEQYNSTYRVVSVLTVLHQDWLNGKEYKCKVSNKALAAPIEKTISKAK<br>GQPREPQVYTLPPCRDELTKNQVSLWCLVKGFYPSDIAVEWESNGQPEN<br>NYKTTPPVLDSDGSFFLYSKLTVDKSRWQQGNVFSCSVMHEALHNHYTQ<br>KSLSLSPG |
| 84 | DR1572M | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSEPKSCDKTHTCPPCPAPEAAGGPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALAAPIEKTISKAKGQPREPQVCTL<br>PPSRDELTKNQVSLSCAVKGFYPSDIAVEWESNGQPENNYKTTPPVLDS<br>DGSFFLVSKLTVDKSRWQQGNVFSCSVMHEALHNHYTQKSLSLSPG |

| | Informal Sequence Listing |
|---|---|
| 85 DR1573M | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSGGGGSGGGGSEPKSCDKTHTCPPCPAPEAAGGPSVFL<br>FPPKPKDTLMISRTPEVTCVVVDVSHEDPEVKFNWYVDGVEVHNAKTKP<br>REEQYNSTYRVVSVLTVLHQDWLNGKEYKCKVSNKALAAPIEKTISKAK<br>GQPREPQVYTLPPCRDELTKNQVSLWCLVKGFYPSDIAVEWESNGQPEN<br>NYKTTPPVLDSDGSFFLYSKLTVDKSRWQQGNVFSCSVMHEALHNHYTQ<br>KSLSLSPG |
| 86 DR1588M | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSEPKSSDKTHTCPPCPAPEFEGGPSVFLFPPKPKDTLM<br>ISRTPEVTCVVVDVSHEDPEVKFNWYVDGVEVHNAKTKPREEQYNSTYR<br>VVSVLTVLHQDWLNGKEYKCKVSNKALPASIEKTISKAKGQPREPQVYT<br>LPPCRDELTKNQVSLWCLVKGFYPSDIAVEWESNGQPENNYKTTPPVLD<br>SDGSFFLYSKLTVDKSRWQQGNVFSCSVMHEALHNHYTQKSLSLSPG |
| 87 DR1589M | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSGGGGSEPKSS<br>DKTHTCPPCPAPEFEGGPSVFLFPPKPKDTLMISRTPEVTCVVVDVSHE<br>DPEVKFNWYVDGVEVHNAKTKPREEQYNSTYRVVSVLTVLHQDWLNGKE<br>YKCKVSNKALPASIEKTISKAKGQPREPQVCTLPPSRDELTKNQVSLSC<br>AVKGFYPSDIAVEWESNGQPENNYKTTPPVLDSDGSFFLVSKLTVDKSR<br>WQQGNVFSCSVMHEALHNHYTQKSLSLSPG |
| 88 DR1590M | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSEPKSSDKTHTCPPCPAPEAEGAPSVELFPPKPKDTLM<br>ISRTPEVTCVVVDVSHEDPEVKENWYVDGVEVHNAKTKPREEQYNSTYR<br>VVSVLTVLHQDWLNGKEYKCKVSNKALPAPIEKTISKAKGQPREPQVYT<br>L1573LTKNQVSLWCLVKGFYPSDIAVEWESNGQPENNYKTTPPVLDSD<br>GSFFLYSKLTVDKSRWQQGNVFSCSVMHEALHNHYTQKSLSLSPG |
| 89 DR1591M | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSGGGGSEPKSSDKTHTCPPCPAPEAEGAPSVFLFPPKPK<br>DTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREP<br>QVCTLPPSRDELTKNQVSLSCAVKGFYPSDIAVEWESNGQPENNYKTTP<br>PVLDSDGSFFLVSKLTVDKSRWQQGNVFSCSVMHEALHNHYTQKSLSLS<br>PG |
| 90 DR1595M | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSGGGGSGGGGSEPKSSDKTHTCPPCPAPEAEGAPSVFL<br>FPPKPKDTLMISRTPEVTCVVVDVSHEDPEVKFNWYVDGVEVHNAKTKP<br>REEQYNSTYRVVSVLTVLHQDWLNGKEYKCKVSNKALPSSIEKTISKAK<br>GQPREPQVYTLPPCRDELTKNQVSLWCLVKGFYPSDIAVEWESNGQPEN<br>NYKTTPPVLDSDGSFFLYSKLTVDKSRWQQGNVFSCSVMHEALHNHYTQ<br>KSLSLSPG |
| 91 DR1596M | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSEPKSSDKTHTCPPCPAPEAEGAPSVFLFPPKPKDTLMI |

| | | |
|---|---|---|
| | | Informal Sequence Listing |
| | | SRTPEVTCVVVDVSHEDPEVKENWYVDGVEVHNAKTKPREEQYNSTYRV<br>VSVLTVLHQDWLNGKEYKCKVSNKALPSSIEKTISKAKGQPREPQVCTL<br>PPSRDELTKNQVSLSCAVKGFYPSDIAVEWESNGQPENNYKTTPPVLDS<br>DGSFFLVSKLTVDKSRWQQGNVFSCSVMHEALHNHYTQKSLSLSPG |
| 92 | DR1597M | IWELKKDVYVVELDWYPDAPGEMVVLTCDTPEEDGITWTLDQSSEVLGS<br>GKTLTIQVKAAGDAGQYTCHKGGEVLSHSLLLLHAKEDGIWSTDILKDQ<br>KEPKNKTFLRCEAKNYSGRFTCWWLTTISTDLTFSVKSSRGSSDPQGVT<br>CGAATLSAERVRGDNKEYEYSVECQEDSACPAAEESLPIEVMVDAVHKL<br>KYENYTSSFFIRDIIKPDPPKNLQLKPLKNSRQVEVSWEYPDTWSTPHS<br>YFSLTFCVQVQGKSKREKKDRVFTDKTSATVICRKNASISVRAQDRYYS<br>SSWSEWASVPCSGGGGSGGGGSEPKSSDKTHTCPPCPAPEAEGAPSVFL<br>FPPKPKDTLMISRTPEVTCVVVDVSHEDPEVKFNWYVDGVEVHNAKTKP<br>REEQYNSTYRVVSVLTVLHQDWLNGKEYKCKVSNKALPSSIEKTISKAK<br>GQPREPQVYTLPPCRDELTKNQVSLWCLVKGFYPSDIAVEWESNGQPEN<br>NYKTTPPVLDSDGSFFLYSKLTVDKSRWQQGNVFSCSVLHEALHSHYTQ<br>KSLSLSPG |
| 93 | DR1598M | RNLPVATPDPGMFPCLHHSQNLLRAVSNMLQKARQTLEFYPCTSEEIDH<br>EDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQA<br>LNFNSETVPQKSSLEEPDFYKTKIKLCILLHAFRIRAVTIDRVMSYLNA<br>SGGGGSGGGGSEPKSSDKTHTCPPCPAPEAEGAPSVFLFPPKPKDTLMI<br>SRTPEVTCVVVDVSHEDPEVKFNWYVDGVEVHNAKTKPREEQYNSTYRV<br>VSVLTVLHQDWLNGKEYKCKVSNKALPSSIEKTISKAKGQPREPQVCTL<br>PPSRDELTKNQVSLSCAVKGFYPSDIAVEWESNGQPENNYKTTPPVLDS<br>DGSFFLVSKLTVDKSRWQQGNVFSCSVLHEALHSHYTQKSLSLSPG |
| 94 | DNA Sequence<br>encoding<br>DR1442P | ATCTGGGAGCTGAAGAAAGACGTGTACGTGGTGGAACTGGACTGGTATC<br>CCGATGCTCCTGGCGAGATGGTGGTGCTGACCTGCGATACCCCTGAAGA<br>GGACGGCATCACCTGGACACTGGATCAGTCTAGCGAGGTGCTCGGCAGC<br>GGCAAGACCCTGACCATCCAAGTGAAAGCGGCTGGCGACGCCGGCCAGT<br>ACACCTGTCACAAAGGCGGAGAAGTGCTGAGCCACAGCCTGCTGCTGCT<br>CCACGCGAAAGAGGATGGCATTTGGAGCACCGACATCCTGAAGGACCAG<br>AAAGAGCCCAAGAACAAGACCTTCCTGAGATGCGAGGCCAAGAACTACA<br>GCGGCCGGTTCACATGTTGGTGGCTGACCACCATCAGCACCGACCTGAC<br>CTTCAGCGTGAAGTCCAGCAGAGGCAGCAGTGATCCTCAGGGCGTTACA<br>TGTGGCGCTGCCACACTGTCTGCCGAAAGAGTGCGGGGCGACAACAAAG<br>AATACGAGTACAGCGTGGAATGCCAAGAGGACAGCGCCTGTCCAGCCGC<br>CGAAGAGTCTCTGCCTATCGAAGTGATGGTGGACGCCGTGCACAAGCTG<br>AAGTACGAGAACTACACCTCCAGCTTTTTCATCCGGGACATCATCAAGC<br>CCGATCCTCCAAAGAACCTGCAGCTGAAGCCTCTGAAGAACAGCAGACA<br>GGTGGAAGTGTCCTGGGAGTACCCCGACACCTGGTCTACACCCCACAGC<br>TACTTCAGCCTGACCTTTTGCGTGCAAGTGCAGGGCAAGTCCAAGCGCG<br>AGAAAAAGGACCGGGTGTTCACCGACAAGACCAGCGCCACCGTGATCTG<br>CAGAAAGAACGCCAGCATCAGCGTCAGAGCCCAGGATCGGTACTACAGC<br>AGCTCTTGGAGCGAGTGGGCCTCGGTACCATGTAGCGAACCAAAATCAT<br>CAGACAAGACCCACACCTGTCCTCCATGTCCTGCTCCAGAAGCTGCTGG<br>GGGCCCTTCCGTGTTTCTGTTCCCTCCAAAGCCTAAGGACACCCTGATG<br>ATCTCTCGGACCCCTGAAGTGACCTGCGTGGTGGTGGATGTGTCTCACG<br>AAGATCCAGAAGTGAAGTTCAATTGGTACGTGGACGGCGTGGAAGTGCA<br>CAACGCCAAGACCAAGCCTAGAGAGGAACAGTACAACTCCACCTACAGA<br>GTGGTGTCCGTGCTGACCGTGCTGCACCAGGATTGGCTGAACGGCAAAG<br>AGTACAAGTGCAAGGTGTCCAACAAGGCCCTGGCCGCTCCCATCGAAAA<br>GACCATCTCTAAGGCCAAGGGCCAGCCTCGGGAACCCCAGGTTTACACA<br>CTGCCTCCATGCCGGGATGAGCTGACCAAGAACCAGGTGTCCCTGTGGT<br>GCCTGGTCAAGGGCTTCTACCCTTCCGATATCGCCGTGGAATGGGAGAG<br>CAATGGCCAGCCTGAGAACAACTACAAGACAACCCCTCCTGTGCTGGAC<br>TCCGACGGCTCATTCTTCCTGTACTCCAAGCTGACAGTGGACAAGTCCA<br>GATGGCAGCAGGGCAACGTGTTCTCCTGCTCCGTGATGCACGAAGCTTT<br>GCACAATCACTACACACAGAAGTCCCTGTCTCTGTCCCCTGGC |
| 95 | DNA Sequence<br>encoding<br>DR1535P | AGAAACCTGCCAGTGGCCACGCCTGATCCTGGCATGTTTCCTTGTCTGC<br>ACCACAGCCAGAACCTGCTGAGAGCCGTGTCCAACATGCTGCAGAAGGC<br>CAGACAGACCCTCGAGTTCTACCCCTGCACCAGCGAGGAAATCGACCAC<br>GAGGACATCACCAAGGACAAGACCAGCACCGTGGAAGCCTGCCTGCCTC<br>TGGAACTGACCAAGAACGAGAGCTGCCTGAACAGCAGAGAGACAAGCTT<br>CATCACCAACGGCTCTTGCCTGGCCTCCAGAAAGACCTCCTTCATGATG<br>GCCCTGTGCCTGAGCAGCATCTACGAGGACCTGAAGATGTACCAGGTCG<br>AGTTCAAGACCATGAACGCCAAGCTGCTGATGGACCCCAAGCGGCAGAT<br>CTTCCTGGACCAGAATATGCTGGCCGTGATCGACGAGCTGATGCAGGCC<br>CTGAACTTCAACAGCGAGACAGTGCCCCAGAAGTCCAGCCTGGAAGAAC<br>CCGACTTCTACAAGACCAAGATCAAGCTGTGCATCCTGCTGCACGCCTT<br>CCGGATCAGAGCCGTGACCATCGACAGAGTGATGAGCTACCTGAACGCC<br>AGCGGAGGCGGAGGATCCGGCGGAGGTGGAAGTGGCGGAGGCGGATCTG<br>AACCAAAATCATCAGACAAGACCCACACCTGTCCTCCATGTCCTGCTCC<br>AGAAGCTGCTGGGGGCCCCTCCGTTTTTCTGTTCCCACCTAAGCCTAAG |

| | | |
|---|---|---|
| | | GACACCCTGATGATCTCTCGGACCCCTGAAGTGACCTGCGTGGTGGTGG<br>ATGTGTCTCACGAAGATCCCGAAGTGAAGTTCAATTGGTACGTGGACGG<br>CGTGGAAGTGCACAACGCCAAGACCAAGCCTAGAGAGGAACAGTACAAC<br>TCCACCTACAGAGTGGTGTCCGTGCTGACCGTGCTGCACCAGGATTGGC<br>TGAACGGCAAAGAGTACAAGTGCAAGGTGTCCAACAAGGCCCTGGCCGC<br>TCCTATCGAAAAGACCATCTCCAAGGCCAAGGGCCAGCCTAGGGAACCC<br>CAGGTTTGCACCCTGCCTCCAAGCCGGGATGAGCTGACCAAGAACCAGG<br>TGTCCCTGTCCTGTGCCGTGAAGGGCTTCTACCCTTCCGATATCGCCGT<br>GGAATGGGAGAGCAATGGCCAGCCTGAGAACAACTACAAGACAACCCCT<br>CCTGTGCTGGACTCCGACGGCTCATTCTTCCTGGTGTCCAAGCTGACAG<br>TGGACAAGTCCAGATGGCAGCAGGGCAACGTGTTCTCCTGCTCCGTGAT<br>GCACGAAGCTTTGCACAACCACTACACCCAGAAGTCCCTGTCTCTGAGC<br>CCTGGA |
| 96 | Nucleic acid<br>sequence<br>encoding<br>DR1536P<br>SEQ ID NO: 125 | ATGTGCCCTGCCAGATCTCTGCTGCTGGTGGCTACACTGGTGCTGCTGG<br>ATCATCTGAGCCTGGCCAGAAACCTGCCAGTGGCCACGCCTGATCCTGG<br>CATGTTTCCTTGTCTGCACCACAGCCAGAACCTGCTGAGAGCCGTGTCC<br>AACATGCTGCAGAAGGCCAGACAGACCCTCGAGTTCTACCCCTGCACCA<br>GCGAGGAAATCGACCACGAGGACATCACCAAGGACAAGACCAGCACCGT<br>GGAAGCCTGCCTGCCTCTGGAACTGACCAAGAACGAGAGCTGCCTGAAC<br>AGCAGAGAGACAAGCTTCATCACCAACGGCTCTTGCCTGGCCTCCAGAA<br>AGACCTCCTTCATGATGGCCCTGTGCCTGAGCAGCATCTACGAGGACCT<br>GAAGATGTACCAGGTCGAGTTCAAGACCATGAACGCCAAGCTGCTGATG<br>GACCCCAAGCGGCAGATCTTCCTGGACCAGAATATGCTGGCCGTGATCG<br>ACGAGCTGATGCAGGCCCTGAACTTCAACAGCGAGACAGTGCCCCAGAA<br>GTCCAGCCTGGAAGAACCCGACTTCTACAAGACCAAGATCAAGCTGTGC<br>ATCCTGCTGCACGCCTTCCGGATCAGAGCCGTGACCATCGACAGAGTGA<br>TGAGCTACCTGAACGCCAGCGGAGGCGGAGGATCCGGCGGAGGCGGATC<br>TGAACCAAAATCATCAGACAAGACCCACACCTGTCCTCCATGTCCTGCT<br>CCAGAAGCTGCTGGGGGCCCCTCCGTTTTTCTGTTCCCACCTAAGCCTA<br>AGGACACCCTGATGATCTCTCGGACCCCTGAAGTGACCTGCGTGGTGGT<br>GGATGTGTCTCACGAAGATCCCGAAGTGAAGTTCAATTGGTACGTGGAC<br>GGCGTGGAAGTGCACAACGCCAAGACCAAGCCTAGAGAGGAACAGTACA<br>ACTCCACCTACAGAGTGGTGTCCGTGCTGACCGTGCTGCACCAGGATTG<br>GCTGAACGGCAAAGAGTACAAGTGCAAGGTGTCCAACAAGGCCCTGGCC<br>GCTCCTATCGAAAAGACCATCTCCAAGGCCAAGGGCCAGCCTAGGGAAC<br>CCCAGGTTTGCACCCTGCCTCCAAGCCGGGATGAGCTGACCAAGAACCA<br>GGTGTCCCTGTCCTGTGCCGTGAAGGGCTTCTACCCTTCCGATATCGCC<br>GTGGAATGGGAGAGCAATGGCCAGCCTGAGAACAACTACAAGACAACCC<br>CTCCTGTGCTGGACTCCGACGGCTCATTCTTCCTGGTGTCCAAGCTGAC<br>AGTGGACAAGTCCAGATGGCAGCAGGGCAACGTGTTCTCCTGCTCCGTG<br>ATGCACGAAGCTTTGCACAACCACTACACCCAGAAGTCCCTGTCTCTGA<br>GCCCTGGA |
| 97 | Nucleic acid<br>sequence<br>encoding<br>DR1537P | ATGTGTCACCAGCAGCTGGTCATCAGCTGGTTCAGCCTGGTGTTCCTGG<br>CCTCTCCTCTGGTGGCCATCTGGGAGCTGAAGAAAGACGTGTACGTGGT<br>GGAACTGGACTGGTATCCCGATGCTCCTGGCGAGATGGTGGTGCTGACC<br>TGCGATACCCCTGAAGAGGACGGCATCACCTGGACACTGGATCAGTCTA<br>GCGAGGTGCTCGGCAGCGGCAAGACCCTGACCATCCAAGTGAAAGCGGC<br>TGGCGACGCCGGCCAGTACACCTGTCACAAAGGCGGAGAAGTGCTGAGC<br>CACAGCCTGCTGCTGCTCCACGCGAAAGAGGATGGCATTTGGAGCACCG<br>ACATCCTGAAGGACCAGAAAGAGCCCAAGAACAAGACCTTCCTGAGATG<br>CGAGGCCAAGAACTACAGCGGCCGGTTCACATGTTGGTGGCTGACCACC<br>ATCAGCACCGACCTGACCTTCAGCGTGAAGTCCAGCAGAGGCAGCAGTG<br>ATCCTCAGGGCGTTACATGTGGCGCTGCCACACTGTCTGCCGAAAGAGT<br>GCGGGGCGACAACAAAGAATACGAGTACAGCGTGGAATGCCAAGAGGAC<br>AGCGCCTGTCCAGCCGCCGAAGAGTCTCTGCCTATCGAAGTGATGGTGG<br>ACGCCGTGCACAAGCTGAAGTACGAGAACTACACCTCCAGCTTTTTCAT<br>CCCGGGACATCATCAAGCCCGATCCTCCAAAGAACCTGCAGCTGAAGCCT<br>CTGAAGAACAGCAGACAGGTGGAAGTGTCCTGGGAGTACCCCGACACCT<br>GGTCTACACCCCACAGCTACTTCAGCCTGACCTTTTGCGTGCAAGTGCA<br>GGGCAAGTCCAAGCGCGAGAAAAAGGACCGGGTGTTCACCGACAAGACC<br>AGCGCCACCGTGATCTGCAGAAAGAACGCCAGCATCAGCGTCAGAGCCC<br>AGGATCGGTACTACAGCAGCTCTTGGAGCGAGTGGGCCTCGGTACCATG<br>TAGCGGAGGCGGAGGATCCGGCGGAGGCGGATCTGAACCAAAATCATCA<br>GACAAGACCCACACCTGTCCTCCATGTCCTGCTCCAGAAGCTGCTGGGG<br>GCCCTTCCGTGTTTCTGTTCCCTCCAAAGCCTAAGGACACCCTGATGAT<br>CTCTCGGACCCCTGAAGTGACCTGCGTGGTGGTGGATGTGTCTCACGAA<br>GATCCAGAAGTGAAGTTCAATTGGTACGTGGACGGCGTGGAAGTGCACA<br>ACGCCAAGACCAAGCCTAGAGAGGAACAGTACAACTCCACCTACAGAGT<br>GGTGTCCGTGCTGACCGTGCTGCACCAGGATTGGCTGAACGGCAAAGAG<br>TACAAGTGCAAGGTGTCCAACAAGGCCCTGGCCGCTCCCATCGAAAAGA<br>CCATCTCTAAGGCCAAGGGCCAGCCTCGGGAACCCCAGGTTTACACACT<br>GCCTCCATGCCGGGATGAGCTGACCAAGAACCAGGTGTCCCTGTGGTGC<br>CTGGTCAAGGGCTTCTACCCTTCCGATATCGCCGTGGAATGGGAGAGCA<br>ATGGCCAGCCTGAGAACAACTACAAGACAACCCCTCCTGTGCTGGACTC<br>CGACGGCTCATTCTTCCTGTACTCCAAGCTGACAGTGGACAAGTCCAGA |

| | Informal Sequence Listing | |
|---|---|---|
| | | TGGCAGCAGGGCAACGTGTTCTCCTGCTCCGTGATGCACGAAGCTTTGC |
| | | ACAATCACTACACACAGAAGTCCCTGTCTCTGTCCCTGGC |
| 98 | DNA Sequence encoding DR1572P | AGAAACCTGCCAGTGGCCACGCCTGATCCTGGCATGTTTCCTTGTCTGC ACCACAGCCAGAACCTGCTGAGAGCCGTGTCCAACATGCTGCAGAAGGC CAGACAGACCCTCGAGTTCTACCCCTGCACCAGCGAGGAAATCGACCAC GAGGACATCACCAAGGACAAGACCAGCACCGTGGAAGCCTGCCTGCCTC TGGAACTGACCAAGAACGAGAGCTGCCTGAACAGCAGAGAGACAAGCTT CATCACCAACGGCTCTTGCCTGGCCTCCAGAAAGACCTCCTTCATGATG GCCCTGTGCCTGAGCAGCATCTACGAGGACCTGAAGATGTACCAGGTCG AGTTCAAGACCATGAACGCCAAGCTGCTGATGGACCCCAAGCGGCAGAT CTTCCTGGACCAGAATATGCTGGCCGTGATCGACAGCTGATGCAGGCC CTGAACTTCAACAGCGAGACAGTGCCCCAGAAGTCCAGCCTGGAAGAAC CCGACTTCTACAAGACCAAGATCAAGCTGTGCATCCTGCTGCACGCCTT CCGGATCAGAGCCGTGACCATCGACAGAGTGATGAGCTACCTGAACGCC AGCGGAGGCGGAGGATCCGGCGGAGGCGGATCTGAACCAAAATCATGTG ACAAGACCCACACCTGTCCTCCATGTCCTGCTCCAGAAGCTGCTGGGGG CCCCTCCGTTTTTCTGTTCCCACCTAAGCCTAAGGACACCCTGATGATC TCTCGGACCCCTGAAGTGACCTGCGTGGTGGTGGATGTGTCTCACGAAG ATCCCGAAGTGAAGTTCAATTGGTACGTGGACGGCGTGGAAGTGCACAA CGCCAAGACCAAGCCTAGAGAGGAACAGTACAACTCCACCTACAGAGTG GTGTCCGTGCTGACCGTGCTGCACCAGGATTGGCTGAACGGCAAAGAGT ACAAGTGCAAGGTGTCCAACAAGGCCCTGGCCGCTCCTATCGAAAAGAC CATCTCCAAGGCCAAGGGCCAGCCTAGGGAACCCCAGGTTTGCACCCTG CCTCCAAGCCGGGATGAGCTGACCAAGAACCAGGTGTCCCTGTCCTGTG CCGTGAAGGGCTTCTACCCTTCCGATATCGCCGTGGAATGGGAGAGCAA TGGCCAGCCTGAGAACAACTACAAGACAACCCCTCCTGTGCTGGACTCC GACGGCTCATTCTTCCTGGTGTCCAAGCTGACAGTGGACAAGTCCAGAT GGCAGCAGGGCAACGTGTTCTCCTGCTCCGTGATGCACGAAGCTTTGCA CAACCACTACACCCAGAAGTCCCTGTCTCTGAGCCCTGGA |
| 99 | DNA Sequence encoding DR1573P | ATCTGGGAGCTGAAGAAAGACGTGTACGTGGTGGAACTGGACTGGTATC CCGATGCTCCTGGCGAGATGGTGGTGCTGACCTGCGATACCCCTGAAGA GGACGGCATCACCTGGACACTGGATCAGTCTAGCGAGGTGCTCGGCAGC GGCAAGACCCTGACCATCCAAGTGAAAGCGGCTGGCGACGCCGGCCAGT ACACCTGTCACAAAGGCGGAGAAGTGCTGAGCCACAGCCTGCTGCTGCT CCACGCGAAAGAGGATGGCATTTGGAGCACCGACATCCTGAAGGACCAG AAAGAGCCCAAGAACAAGACCTTCCTGAGATGCGAGGCCAAGAACTACA GCGGCCGGTTCACATGTTGGTGGCTGACCACCATCAGCACCGACCTGAC CTTCAGCGTGAAGTCCAGCAGAGGCAGCAGTGATCCTCAGGGCGTTACA TGTGGCGCTGCCACACTGTCTGCCGAAAGAGTGCGGGGCGACAACAAAG AATACGAGTACAGCGTGGAATGCCAAGAGGACAGCGCCTGTCCAGCCGC CGAAGAGTCTCTGCCTATCGAAGTGATGGTGGACGCCGTGCACAAGCTG AAGTACGAGAACTACACCTCCAGCTTTTTCATCCGGGACATCATCAAGC CCGATCCTCCAAAGAACCTGCAGCTGAAGCCTCTGAAGAACAGCAGACA GGTGGAAGTGTCCTGGGAGTACCCCGACACCTGGTCTACACCCCACAGC TACTTCAGCCTGACCTTTTGCGTGCAAGTGCAGGGCAAGTCCAAGCGCG AGAAAAAGGACCGGGTGTTCACCGACAAGACCAGCGCCACCGTGATCTG CAGAAAGAACGCCAGCATCAGCGTCAGAGCCCAGGATCGGTACTACAGC AGCTCTTGGAGCGAGTGGGCCTCGGTACCATGTAGCGGAGGCGGAGGAT CCGGCGGAGGCGGATCTGAACCAAAATCATGTGACAAGACCCACACCTG TCCTCCATGTCCTGCTCCAGAAGCTGCTGGGGGCCCTTCCGTGTTTCTG TTCCCTCCAAAGCCTAAGGACACCCTGATGATCTCTCGGACCCCTGAAG TGACCTGCGTGGTGGTGGATGTGTCTCACGAAGATCCAGAAGTGAAGTT CAATTGGTACGTGGACGGCGTGGAAGTGCACAACGCCAAGACCAAGCCT AGAGAGGAACAGTACAACTCCACCTACAGAGTGGTGTCCGTGCTGACCG TGCTGCACCAGGATTGGCTGAACGGCAAAGAGTACAAGTGCAAGGTGTC CAACAAGGCCCTGGCCGCTCCCATCGAAAAGACCATCTCTAAGGCCAAG GGCCAGCCTCGGGAACCCCAGGTTTACACACTGCCTCCATGCCGGGATG AGCTGACCAAGAACCAGGTGTCCCTGTGGTGCCTGGTCAAGGGCTTCTA CCCTTCCGATATCGCCGTGGAATGGGAGAGCAATGGCCAGCCTGAGAAC AACTACAAGACAACCCCTCCTGTGCTGGACTCCGACGGCTCATTCTTCC TGTACTCCAAGCTGACAGTGGACAAGTCCAGATGGCAGCAGGGCAACGT GTTCTCCTGCTCCGTGATGCACGAAGCTTTGCACAATCACTACACACAG AAGTCCCTGTCTCTGTCCCTGGC |
| 100 | DNA Sequence encoding DR1588P | ATCTGGGAGCTGAAGAAAGACGTGTACGTGGTGGAACTGGACTGGTATC CCGATGCTCCTGGCGAGATGGTGGTGCTGACCTGCGATACCCCTGAAGA GGACGGCATCACCTGGACACTGGATCAGTCTAGCGAGGTGCTCGGCAGC GGCAAGACCCTGACCATCCAAGTGAAAGCGGCTGGCGACGCCGGCCAGT ACACCTGTCACAAAGGCGGAGAAGTGCTGAGCCACAGCCTGCTGCTGCT CCACGCGAAAGAGGATGGCATTTGGAGCACCGACATCCTGAAGGACCAG AAAGAGCCCAAGAACAAGACCTTCCTGAGATGCGAGGCCAAGAACTACA GCGGCCGGTTCACATGTTGGTGGCTGACCACCATCAGCACCGACCTGAC CTTCAGCGTGAAGTCCAGCAGAGGCAGCAGTGATCCTCAGGGCGTTACA TGTGGCGCTGCCACACTGTCTGCCGAAAGAGTGCGGGGCGACAACAAAG AATACGAGTACAGCGTGGAATGCCAAGAGGACAGCGCCTGTCCAGCCGC |

| | | |
|---|---|---|
| | | CGAAGAGTCTCTGCCTATCGAAGTGATGGTGGACGCCGTGCACAAGCTG<br>AAGTACGAGAACTACACCTCCAGCTTTTTCATCCGGGACATCATCAAGC<br>CCGATCCTCCAAAGAACCTGCAGCTGAAGCCTCTGAAGAACAGCAGACA<br>GGTGGAAGTGTCCTGGGAGTACCCCGACACCTGGTCTACACCCCACAGC<br>TACTTCAGCCTGACCTTTTGCGTGCAAGTGCAGGGCAAGTCCAAGCGCG<br>AGAAAAAGGACCGGGTGTTCACCGACAAGACCAGCGCCACCGTGATCTG<br>CAGAAAGAACGCCAGCATCAGCGTCAGAGCCCAGGATCGGTACTACAGC<br>AGCTCTTGGAGCGAGTGGGCCTCGGTACCATGTAGCGAACCAAAATCAT<br>CAGACAAGACCCACACCTGTCCTCCATGTCCTGCTCCAGAATTTGAAGG<br>GGGCCCTTCCGTGTTTCTGTTCCCTCCAAAGCCTAAGGACACCCTGATG<br>ATCTCTCGGACCCCTGAAGTGACCTGCGTGGTGGTGGATGTGTCTCACG<br>AAGATCCAGAAGTGAAGTTCAATTGGTACGTGGACGGCGTGGAAGTGCA<br>CAACGCCAAGACCAAGCCTAGAGAGGAACAGTACAACTCCACCTACAGA<br>GTGGTGTCCGTGCTGACCGTGCTGCACCAGGATTGGCTGAACGGCAAAG<br>AGTACAAGTGCAAGGTGTCCAACAAGGCCCTGCCCGCTTCCATCGAAAA<br>GACCATCTCTAAGGCCAAGGGCCAGCCTCGGGAACCCCAGGTTTACACA<br>CTGCCTCCATGCCGGGATGAGCTGACCAAGAACCAGGTGTCCTGTGGT<br>GCCTGGTCAAGGGCTTCTACCCTTCCGATATCGCCGTGGAATGGGAGAG<br>CAATGGCCAGCCTGAGAACAACTACAAGACAACCCCTCCTGTGCTGGAC<br>TCCGACGGCTCATTCTTCCTGTACTCCAAGCTGACAGTGGACAAGTCCA<br>GATGGCAGCAGGGCAACGTGTTCTCCTGCTCCGTGATGCACGAAGCTTT<br>GCACAATCACTACACACAGAAGTCCCTGTCTCTGTCCCCTGGC |
| 101 | DNA Sequence encoding DR1589P | AGAAACCTGCCAGTGGCCACGCCTGATCCTGGCATGTTTCCTTGTCTGC<br>ACCACAGCCAGAACCTGCTGAGAGCCGTGTCCAACATGCTGCAGAAGGC<br>CAGACAGACCCTCGAGTTCTACCCCTGCACCAGCGAGGAAATCGACCAC<br>GAGGACATCACCAAGGACAAGACCAGCACCGTGGAAGCCTGCCTGCCTC<br>TGGAACTGACCAAGAACGAGAGCTGCCTGAACAGCAGAGAGACAAGCTT<br>CATCACCAACGGCTCTTGCCTGGCCTCCAGAAAGACCTCCTTCATGATG<br>GCCCTGTGCCTGAGCAGCATCTACGAGGACCTGAAGATGTACCAGGTCG<br>AGTTCAAGACCATGAACGCCAAGCTGCTGATGGACCCCAAGCGGCAGAT<br>CTTCCTGGACCAGAATATGCTGGCCGTGATCGACGAGCTGATGCAGGCC<br>CTGAACTTCAACAGCGAGACAGTGCCCCAGAAGTCCAGCCTGGAAGAAC<br>CCGACTTCTACAAGACCAAGATCAAGCTGTGCATCCTGCTGCACGCCTT<br>CCGGATCAGAGCCGTGACCATCGACAGAGTGATGAGCTACCTGAACGCC<br>AGCGGAGGCGGAGGATCCGGCGGAGGTGGAAGTGGCGGAGGCGGATCTG<br>AACCAAAATCATCAGACAAGACCCACACCTGTCCTCCATGTCCTGCTCC<br>AGAATTTGAAGGGGGCCCCTCCGTTTTTCTGTTCCCACCTAAGCCTAAG<br>GACACCCTGATGATCTCTCGGACCCCTGAAGTGACCTGCGTGGTGGTGG<br>ATGTGTCTCACGAAGATCCCGAAGTGAAGTTCAATTGGTACGTGGACGG<br>CGTGGAAGTGCACAACGCCAAGACCAAGCCTAGAGAGGAACAGTACAAC<br>TCCACCTACAGAGTGGTGTCCGTGCTGACCGTGCTGCACCAGGATTGGC<br>TGAACGGCAAAGAGTACAAGTGCAAGGTGTCCAACAAGGCCCTGCCCGC<br>TTCTATCGAAAAGACCATCTCCAAGGCCAAGGGCCAGCCTAGGGAACCC<br>CAGGTTTGCACCCTGCCTCCAAGCCGGGATGAGCTGACCAAGAACCAGG<br>TGTCCCTGTCCTGTGCCGTGAAGGGCTTCTACCCTTCCGATATCGCCGT<br>GGAATGGGAGAGCAATGGCCAGCCTGAGAACAACTACAAGACAACCCCT<br>CCTGTGCTGGACTCCGACGGCTCATTCTTCCTGGTGTCCAAGCTGACAG<br>TGGACAAGTCCAGATGGCAGCAGGGCAACGTGTTCTCCTGCTCCGTGAT<br>GCACGAAGCTTTGCACAACCACTACACCCAGAAGTCCCTGTCTCTGAGC<br>CCTGGA |
| 102 | DNA Sequence encoding DR1590P | ATCTGGGAGCTGAAGAAAGACGTGTACGTGGTGGAACTGGACTGGTATC<br>CCGATGCTCCTGGCGAGATGGTGGTGCTGACCTGCGATACCCCTGAAGA<br>GGACGGCATCACCTGGACACTGGATCAGTCTAGCGAGGTGCTCGGCAGC<br>GGCAAGACCCTGACCATCCAAGTGAAAGCGGCTGGCGACGCCGGCCAGT<br>ACACCTGTCACAAAGGCGGAGAAGTGCTGAGCCACAGCCTGCTGCTGCT<br>CCACGCGAAAGAGGATGGCATTTGGAGCACCGACATCCTGAAGGACCAG<br>AAAGAGCCCAAGAACAAGACCTTCCTGAGATGCGAGGCCAAGAACTACA<br>GCGGCCGGTTCACATGTTGGTGGCTGACCACCATCAGCACCGACCTGAC<br>CTTCAGCGTGAAGTCCAGCAGAGGCAGCAGTGATCCTCAGGGCGTTACA<br>TGTGGCGCTGCCACACTGTCTGCCGAAAGAGTGCGGGGCGACAACAAAG<br>AATACGAGTACAGCGTGGAATGCCAAGAGGACAGCGCCTGTCCAGCCGC<br>CGAAGAGTCTCTGCCTATCGAAGTGATGGTGGACGCCGTGCACAAGCTG<br>AAGTACGAGAACTACACCTCCAGCTTTTTCATCCGGGACATCATCAAGC<br>CCGATCCTCCAAAGAACCTGCAGCTGAAGCCTCTGAAGAACAGCAGACA<br>GGTGGAAGTGTCCTGGGAGTACCCCGACACCTGGTCTACACCCCACAGC<br>TACTTCAGCCTGACCTTTTGCGTGCAAGTGCAGGGCAAGTCCAAGCGCG<br>AGAAAAAGGACCGGGTGTTCACCGACAAGACCAGCGCCACCGTGATCTG<br>CAGAAAGAACGCCAGCATCAGCGTCAGAGCCCAGGATCGGTACTACAGC<br>AGCTCTTGGAGCGAGTGGGCCTCGGTACCATGTAGCGAACCAAAATCAT<br>CAGACAAGACCCACACCTGTCCTCCATGTCCTGCTCCAGAAGCTGAAGG<br>GGCCCCTTCCGTGTTTCTGTTCCCTCCAAAGCCTAAGGACACCCTGATG<br>ATCTCTCGGACCCCTGAAGTGACCTGCGTGGTGGTGGATGTGTCTCACG<br>AAGATCCAGAAGTGAAGTTCAATTGGTACGTGGACGGCGTGGAAGTGCA<br>CAACGCCAAGACCAAGCCTAGAGAGGAACAGTACAACTCCACCTACAGA<br>GTGGTGTCCGTGCTGACCGTGCTGCACCAGGATTGGCTGAACGGCAAAG |

| | | |
|---|---|---|
| 103 | DNA Sequence encoding DR1591P | AGTACAAGTGCAAGGTGTCCAACAAGGCCCTGCCCGCTCCCATCGAAAA<br>GACCATCTCTAAGGCCAAGGGCCAGCCTCGGGAACCCCAGGTTTACACA<br>CTGCCTCCATGCCGGGATGAGCTGACCAAGAACCAGGTGTCCCTGTGGT<br>GCCTGGTCAAGGGCTTCTACCCTTCCGATATCGCCGTGGAATGGGAGAG<br>CAATGGCCAGCCTGAGAACAACTACAAGACAACCCCTCCTGTGCTGGAC<br>TCCGACGGCTCATTCTTCCTGTACTCCAAGCTGACAGTGGACAAGTCCA<br>GATGGCAGCAGGGCAACGTGTTCTCCTGCTCCGTGATGCACGAAGCTTT<br>GCACAATCACTACACACAGAAGTCCCTGTCTCTGTCCCCTGGC |
| 103 | DNA Sequence encoding DR1591P | AGAAACCTGCCAGTGGCCACGCCTGATCCTGGCATGTTTCCTTGTCTGC<br>ACCACAGCCAGAACCTGCTGAGAGCCGTGTCCAACATGCTGCAGAAGGC<br>CAGACAGACCCTCGAGTTCTACCCCTGCACCAGCGAGGAAATCGACCAC<br>GAGGACATCACCAAGGACAAGACCAGCACCGTGGAAGCCTGCCTGCCTC<br>TGGAACTGACCAAGAACGAGAGCTGCCTGAACAGCAGAGAGACAAGCTT<br>CATCACCAACGGCTCTTGCCTGGCCTCCAGAAAGACCTCCTTCATGATG<br>GCCCTGTGCCTGAGCCAGCATCTACGAGGACCTGAAGATGTACCAGGTCG<br>AGTTCAAGACCATGAACGCCAAGCTGCTGATGGACCCCAAGCGGCAGAT<br>CTTCCTGGACCAGAATATGCTGGCCGTGATCGACGAGCTGATGCAGGCC<br>CTGAACTTCAACAGCGAGACAGTGCCCCAGAAGTCCAGCCTGGAAGAAC<br>CCGACTTCTACAAGACCAAGATCAAGCTGTGTCATCCTGCTGCACGCCTT<br>CCGGATCAGAGCCGTGACCATCGACAGAGTGATGAGCTACCTGAACGCC<br>AGCGGAGGCGGAGGATCCGGCGGAGGTGGAAGTGGCGGAGGCGGATCTG<br>AACCAAAATCATCAGACAAGACCCACACCTGTCCTCCATGTCCTGCTCC<br>AGAAGCTGAAGGGGCTCCCTCCGTTTTTCTGTTCCCACCTAAGCCTAAG<br>GACACCCTGATGATCTCTCGGACCCCTGAAGTGACCTGCGTGGTGGTGG<br>ATGTGTCTCACGAAGATCCCGAAGTGAAGTTCAATTGGTACGTGGACGG<br>CGTGGAAGTGCACAACGCCAAGACCAAGCCTAGAGAGGAACAGTACAAC<br>TCCACCTACAGAGTGGTGTCCGTGCTGACCGTGCTGCACCAGGATTGGC<br>TGAACGGCAAAGAGTACAAGTGCAAGGTGTCCAACAAGGCCCTGCCCGC<br>TCCTATCGAAAAGACCATCTCCAAGGCCAAGGGCCAGCCTAGGGAACCC<br>CAGGTTTGCACCCTGCCTCCAAGCCGGGATGAGCTGACCAAGAACCAGG<br>TGTCCCTGTCCTGTGCCGTGAAGGGCTTCTACCCTTCCGATATCGCCGT<br>GGAATGGGAGAGCAATGGCCAGCCTGAGAACAACTACAAGACAACCCCT<br>CCTGTGCTGGACTCCGACGGCTCATTCTTCCTGGTGTCCAAGCTGACAG<br>TGGACAAGTCCAGATGGCAGCAGGGCAACGTGTTCTCCTGCTCCGTGAT<br>GCACGAAGCTTTGCACAACCACTACACCCAGAAGTCCCTGTCTCTGAGC<br>CCTGGA |
| 104 | DNA Sequence encoding DR1596P | AGAAACCTGCCAGTGGCCACGCCTGATCCTGGCATGTTTCCTTGTCTGC<br>ACCACAGCCAGAACCTGCTGAGAGCCGTGTCCAACATGCTGCAGAAGGC<br>CAGACAGACCCTCGAGTTCTACCCCTGCACCAGCGAGGAAATCGACCAC<br>GAGGACATCACCAAGGACAAGACCAGCACCGTGGAAGCCTGCCTGCCTC<br>TGGAACTGACCAAGAACGAGAGCTGCCTGAACAGCAGAGAGACAAGCTT<br>CATCACCAACGGCTCTTGCCTGGCCTCCAGAAAGACCTCCTTCATGATG<br>GCCCTGTGCCTGAGCAGCATCTACGAGGACCTGAAGATGTACCAGGTCG<br>AGTTCAAGACCATGAACGCCAAGCTGCTGATGGACCCCAAGCGGCAGAT<br>CTTCCTGGACCAGAATATGCTGGCCGTGATCGACGAGCTGATGCAGGCC<br>CTGAACTTCAACAGCGAGACAGTGCCCCAGAAGTCCAGCCTGGAAGAAC<br>CCGACTTCTACAAGACCAAGATCAAGCTGTGTCATCCTGCTGCACGCCTT<br>CCGGATCAGAGCCGTGACCATCGACAGAGTGATGAGCTACCTGAACGCC<br>AGCGGAGGCGGAGGATCCGGCGGAGGTGGAAGTGAACCAAAATCATCAG<br>ACAAGACCCACACCTGTCCTCCATGTCCTGCTCCAGAAGCTGAAGGGGC<br>TCCCTCCGTTTTTCTGTTCCCACCTAAGCCTAAGGACACCCTGATGATC<br>TCTCGGACCCCTGAAGTGACCTGCGTGGTGGTGGATGTGTCTCACGAAG<br>ATCCCGAAGTGAAGTTCAATTGGTACGTGGACGGCGTGGAAGTGCACAA<br>CGCCAAGACCAAGCCTAGAGAGGAACAGTACAACTCCACCTACAGAGTG<br>GTGTCCGTGCTGACCGTGCTGCACCAGGATTGGCTGAACGGCAAAGAGT<br>ACAAGTGCAAGGTGTCCAACAAGGCCCTGCCCTCTTCTATCGAAAAGAC<br>CATCTCCAAGGCCAAGGGCCAGCCTAGGGAACCCCAGGTTTGCACCCTG<br>CCTCCAAGCCGGGATGAGCTGACCAAGAACCAGGTGTCCCTGTCCTGTG<br>CCGTGAAGGGCTTCTACCCTTCCGATATCGCCGTGGAATGGGAGAGCAA<br>TGGCCAGCCTGAGAACAACTACAAGACAACCCCTCCTGTGCTGGACTCC<br>GACGGCTCATTCTTCCTGGTGTCCAAGCTGACAGTGGACAAGTCCAGAT<br>GGCAGCAGGGCAACGTGTTCTCCTGCTCCGTGATGCACGAAGCTTTGCA<br>CAACCACTACACCCAGAAGTCCCTGTCTCTGAGCCCTGGA |
| 105 | DNA Sequence encoding DR1597P | ATCTGGGAGCTGAAGAAAGACGTGTACGTGGTGGAACTGGACTGGTATC<br>CCGATGCTCCTGGCGAGATGGTGGTGCTGACCTGCGATACCCCTGAAGA<br>GGACGGCATCACCTGGACACTGGATCAGTCTAGCGAGGTGCTCGGCAGC<br>GGCAAGACCCTGACCATCCAAGTGAAAGCGGCTGGCGACGCCGGCCAGT<br>ACACCTGTCACAAAGGCGGAGAAGTGCTGAGCCACAGCCTGCTGCTGCT<br>CCACGCGAAAGAGGATGGCATTTGGAGCACCGACATCCTGAAGGACCAG<br>AAAGAGCCCAAGAACAAGACCTTCCTGAGATGCGAGGCCAAGAACTACA<br>GCGGCCGGTTCACATGTTGGTGGCTGACCACCATCAGCACCGACCTGAC<br>CTTCAGCGTGAAGTCCAGCAGAGGCAGCAGTGATCCTCAGGGCGTTACA<br>TGTGGCGCTGCCACACTGTCTGCCGAAAGAGTGCGGGGCGACAACAAAG<br>AATACGAGTACAGCGTGGAATGCCAAGAGGACAGCGCCTGTCCAGCCGC |

| | | |
|---|---|---|
| | | CGAAGAGTCTCTGCCTATCGAAGTGATGGTGGACGCCGTGCACAAGCTG<br>AAGTACGAGAACTACACCTCCAGCTTTTTCATCCGGGACATCATCAAGC<br>CCGATCCTCCAAAGAACCTGCAGCTGAAGCCTCTGAAGAACAGCAGACA<br>GGTGGAAGTGTCCTGGGAGTACCCCGACACCTGGTCTACACCCCACAGC<br>TACTTCAGCCTGACCTTTTGCGTGCAAGTGCAGGGCAAGTCCAAGCGCG<br>AGAAAAAGGACCGGGTGTTCACCGACAAGACCAGCGCCACCGTGATCTG<br>CAGAAAGAACGCCAGCATCAGCGTCAGAGCCCAGGATCGGTACTACAGC<br>AGCTCTTGGAGCGAGTGGGCCTCGGTACCATGTAGCGGAGGCGGAGGAT<br>CCGGCGGAGGTGGAAGTGAACCAAAATCATCAGACAAGACCCACACCTG<br>TCCTCCATGTCCTGCTCCAGAAGCTGAAGGGGCCCCTTCCGTGTTTCTG<br>TTCCCTCCAAAGCCTAAGGACACCCTGATGATCTCTCGGACCCCTGAAG<br>TGACCTGCGTGGTGGTGGATGTGTCTCACGAAGATCCAGAAGTGAAGTT<br>CAATTGGTACGTGGACGGCGTGGAAGTGCACAACGCCAAGACCAAGCCT<br>AGAGAGGAACAGTACAACTCCACCTACAGAGTGGTGTCCGTGCTGACCG<br>TGCTGCACCAGGATTGGCTGAACGGCAAAGAGTACAAGTGCAAGGTGTC<br>CAACAAGGCCCTGCCCTCTTCCATCGAAAAGACCATCTCTAAGGCCAAG<br>GGCCAGCCTCGGGAACCCCAGGTTTACACACTGCCTCCATGCCGGGATG<br>AGCTGACCAAGAACCAGGTGTCCCTGTGGTGCCTGGTCAAGGGCTTCTA<br>CCCCTTCCGATATCGCCGTGGAATGGGAGAGCAATGGCCAGCCTGAGAAC<br>AACTACAAGACAACCCCTCCTGTGCTGGACTCCGACGGCTCATTCTTCC<br>TGTACTCCAAGCTGACAGTGGACAAGTCCAGATGGCAGCAGGGCAACGT<br>GTTCTCCTGCTCCGTGTTGCACGAAGCTTTGCACTCTCACTACACACAG<br>AAGTCCCTGTCTCTGTCCCCTGGC |
| 106 | DNA Sequence<br>encoding<br>DR1598P | AGAAACCTGCCAGTGGCCACGCCTGATCCTGGCATGTTTCCTTGTCTGC<br>ACCACAGCCAGAACCTGCTGAGAGCCGTGTCCAACATGCTGCAGAAGGC<br>CAGACAGACCCTCGAGTTCTACCCCTGCACCAGCGAGGAAATCGACCAC<br>GAGGACATCACCAAGGACAAGACCAGCACCGTGGAAGCCTGCCTGCCTC<br>TGGAACTGACCAAGAACGAGAGCTGCCTGAACAGCAGAGAGACAAGCTT<br>CATCACCAACGGCTCTTGCCTGGCCTCCAGAAAGACCTCCTTCATGATG<br>GCCCTGTGCCTGAGCAGCATCTACGAGGACCTGAAGATGTACCAGGTCG<br>AGTTCAAGACCATGAACGCCAAGCTGCTGATGGACCCCAAGCGGCAGAT<br>CTTCCTGGACCAGAATATGCTGGCCGTGATCGACGAGCTGATGCAGGCC<br>CTGAACTTCAACAGCGAGACAGTGCCCCAGAAGTCCAGCCTGGAAGAAC<br>CCGACTTCTACAAGACCAAGATCAAGCTGTGCATCCTGCTGCACGCCTT<br>CCGGATCAGAGCCGTGACCATCGACAGAGTGATGAGCTACCTGAACGCC<br>AGCGGAGGCGGAGGATCCGGCGGAGGTGGAAGTGAACCAAAATCATCAG<br>ACAAGACCCACACCTGTCCTCCATGTCCTGCTCCAGAAGCTGAAGGGGC<br>TCCCTCCGTTTTTCTGTTCCCACCTAAGCCTAAGGACACCCTGATGATC<br>TCTCGGACCCCTGAAGTGACCTGCGTGGTGGTGGATGTGTCTCACGAAG<br>ATCCCGAAGTGAAGTTCAATTGGTACGTGGACGGCGTGGAAGTGCACAA<br>CGCCAAGACCAAGCCTAGAGAGGAACAGTACAACTCCACCTACAGAGTG<br>GTGTCCGTGCTGACCGTGCTGCACCAGGATTGGCTGAACGGCAAAGAGT<br>ACAAGTGCAAGGTGTCCAACAAGGCCCTGCCCTCTTCTATCGAAAAGAC<br>CATCTCCAAGGCCAAGGGCCAGCCTAGGGAACCCCAGGTTTGCACCCTG<br>CCTCCAAGCCGGGATGAGCTGACCAAGAACCAGGTGTCCCTGTCCTGTG<br>CCGTGAAGGGCTTCTACCCTTCCGATATCGCCGTGGAATGGGAGAGCAA<br>TGGCCAGCCTGAGAACAACTACAAGACAACCCCTCCTGTGCTGGACTCC<br>GACGGCTCATTCTTCCTGGTGTCCAAGCTGACAGTGGACAAGTCCAGAT<br>GGCAGCAGGGCAACGTGTTCTCCTGCTCCGTGCTGCACGAAGCTTTGCA<br>CTCCCACTACACCCAGAAGTCCCTGTCTCTGAGCCCTGGA |
| 107 | Pro-mP35 (wt)<br>Uniprot P43431<br>w/native signal<br>sequence | MCQSRYLLFLATLALLNHLSLARVIPVSGPARCLSQSRNLLKTTDDMVK<br>TAREKLKHYSCTAEDIDHEDITRDQTSTLKTCLPLELHKNESCLATRET<br>SSTTRGSCLPPQKTSLMMTLCLGSIYEDLKMYQTEFQAINAALQNHNHQ<br>QIILDKGMLVAIDELMQSLNHNGETLRQKPPVGEADPYRVKMKLCILLH<br>AFSTRVVTINRVMGYLSSA |
| 108 | Mature mP35 (wt)<br>Uniprot P43431<br>(w/o signal<br>sequence) | RVIPVSGPARCLSQSRNLLKTTDDMVKTAREKLKHYSCTAEDIDHEDIT<br>RDQTSTLKTCLPLELHKNESCLATRETSSTTRGSCLPPQKTSLMMTLCL<br>GSIYEDLKMYQTEFQAINAALQNHNHQQIILDKGMLVAIDELMQSLNHN<br>GETLRQKPPVGEADPYRVKMKLCILLHAFSTRVVTINRVMGYLSSA |
| 109 | Pro wt mP40<br>Uniprot Q3ZAX5<br>Pre-protein<br>with native<br>signal<br>sequence | MCPQKLTISWFAIVLLVSPLMAMWELEKDVYVVEVDWTPDAPGETVNLT<br>CDTPEEDDITWTSDQRHGVIGSGKTLTITVKEFLDAGQYTCHKGGETLS<br>HSHLLLHKKENGIWSTEILKNFKNKTFLKCEAPNYSGRFTCSWLVQRNM<br>DLKFNIKSSSSSPDSRAVTCGMASLSAEKVTLDQRDYEKYSVSCQEDVT<br>CPTAEETLPIELALEARQQNKYENYSTSFFIRDIIKPDPPKNLQMKPLK<br>NSQVEVSWEYPDSWSTPHSYFSLKFFVRIQRKKEKMKETEEGCNQKGAF<br>LVEKTSTEVQCKGGNVCVQAQDRYYNSSCSKWACVPCRVRS |

| | | |
|---|---|---|
| 110 | Mature wt mP40 Uniprot Q3ZAX5 (w/o signal sequence) | MWELEKDVYVVEVDWTPDAPGETVNLTCDTPEEDDITWTSDQRHGVIGS GKTLTITVKEFLDAGQYTCHKGGETLSHSHLLLHKKENGIWSTEILKNF KNKTFLKCEAPNYSGRFTCSWLVQRNMDLKFNIKSSSSSPDSRAVTCGM ASLSAEKVTLDQRDYEKYSVSCQEDVTCPTAEETLPIELALEARQQNKY ENYSTSFFIRDIIKPDPPKNLQMKPLKNSQVEVSWEYPDSWSTPHSYFS LKFFVRIQRKKEKMKETEEGCNQKGAFLVEKTSTEVQCKGGNVCVQAQD RYYNSSCSKWACVPCRVRS |
| 111 | DR852 DNA sequence encoding mIL12 (p35-IRES2-p40) His8 | AGAGTGATCCCCGTGTCTGGACCTGCCAGATGTCTGAGCCAGTCCAGAA ACCTGCTGAAAACCACCGACGACATGGTCAAGACCGCCAGAGAGAAGCT GAAGCACTACAGCTGCACCGCCGAGGACATCGACCACGAGGATATCACC AGGGACCAGACCAGCACACTGAAAACCTGCCTGCCTCTGGAACTGCACA AGAACGAGAGCTGCCTGGCCACCAGAGAGACAAGCAGCACAACAAGAGG CAGCTGTCTGCCTCCTCAGAAAACCAGCCTGATGATGACCCTGTGCCTG GGCAGCATCTACGAGGACCTGAAGATGTACCAGACCGAGTTCCAGGCCA TCAACGCCGCTCTGCAGAACCACAACCACCAGCAGATCATCCTGGACAA GGGCATGCTGGTGGCTATCGACGAGCTGATGCAGAGCCTGAACCACAAT GGCGAGACACTGCGGCAGAAGCCTCCAGTTGGAGAGGCCGATCCTTACA GAGTGAAGATGAAGCTGTGCATCCTGCTGCACGCCTTCAGCACCAGAGT GGTCACCATCAACAGAGTGATGGGCTACCTGAGCAGCGCCTGATAAGCT AGCCCCCTCTCCCTCCCCCCCCCCTAACGTTACTGGCCGAAGCCGCTTG GAATAAGGCCGGTGTGCGTTTGTCTATATGTTATTTTCCACCATATTGC CGTCTTTTGGCAATGTGAGGGCCCGGAAACCTGGCCCTGTCTTCTTGAC GAGCATTCCTAGGGGTCTTTCCCCTCTCGCCAAAGGAATGCAAGGTCTG TTGAATGTCGTGAAGGAAGCAGTTCCTCTGGAAGCTTCTTGAAGACAAA CAACGTCTGTAGCGACCCTTTGCAGGCAGCGGAACCCCCCACCTGGCGA CAGGTGCCTCTGCGGCAAAAGCCACGTGTATAAGATACACCTGCAAAG GCGGCACAACCCCAGTGCCACGTTGTGAGTTGGATAGTTGTGGAAAGAG TCAAATGGCTCTCCTCAAGCGTATTCAACAAGGGGCTGAAGGATGCCCA GAAGGTACCCCATTGTATGGGATCTGATCTGGGGCCTCGGTGCACATGC ACGGGGACGTGGTTTTCCTTTGAAAAACACGATGATAATATGGCCACAA TTTACATGTGTTTAGTCGAGGTTAAAAAAACGTCTAGGCCCCCCGAACC CCATGTGCCCTCAGAAGCTGACCATCAGTTGGTTCGCCATCGTGCTGCT GGTGTCCCCACTGATGGCCATGTGGGAGCTTGAGAAGGACGTGTACGTG GTGGAAGTGGACTGGACCCCTGATGCTCCTGGCGAGACAGTGAACCTGA CCTGCGATACCCCTGAAGAGGACGACATCACCTGGACCAGCGACCAGAG ACATGGCGTGATCGGCTCTGGCAAGACCCTGACAATTACCGTGAAAGAG TTCCTGGACGCCGGCCAGTACACCTGTCACAAAGGCGGAGAGACACTGA GCCACTCTCATCTGCTGCTGCACAAGAAAGAGAACGGCATCTGGTCCAC CGAGATCCTGAAGAACTTCAAGAACAAGACCTTCCTGAAGTGCGAGGCC CCTAACTACAGCGGCAGATTCACCTGTAGCTGGCTGGTGCAGCGGAACA TGGACCTGAAGTTCAACATCAAGTCCTCCAGCAGCAGCCCCGACAGCAG AGCTGTGACATGTGGCATGGCTTCTCTGAGCGCCGAGAAAGTGACCCTG GATCAGCGGGACTACGAGAAGTACAGCGTGTCCTGCCAAGAGGACGTGA CCTGTCCTACCGCCGAGGAAACACTGCCTATCGAGCTGGCCCTGGAAGC CCGGCAGCAGAACAAATACGAGAACTACTCCACCAGCTTTTTCATCCGG GACATCATCAAGCCCGATCCTCCAAAGAACCTGCAGATGAAGCCTCTGA AGAACAGCCAGGTCGAGGTGTCCTGGGAGTACCCCGATAGCTGGTCTAC CCCTCACAGCTACTTCAGCCTGAAATTCTTCGTGCGCATCCAGCGCAAG AAAGAAAAGATGAAGGAAACCGAGGAAGGCTGCAACCAGAAAGGGGCCT TCCTGGTGGAAAAGACCAGCACCGAGGTGCAGTGCAAAGGCGGCAATGT TTGTGTGCAGGCCCAGGATCGGTACTACAACAGCAGCTGTAGCAAGTGG GCCTGCGTGCCATGTAGAGTCCGGAGTCACCACCATCATCACCATCACC AC |
| 112 | DNA Sequence Encoding DR1022P mIL12 (p35-IRES2-p40 E81A F82A) His8 | AGAGTGATCCCCGTGTCTGGACCTGCCAGATGTCTGAGCCAGTCCAGAA ACCTGCTGAAAACCACCGACGACATGGTCAAGACCGCCAGAGAGAAGCT GAAGCACTACAGCTGCACCGCCGAGGACATCGACCACGAGGATATCACC AGGGACCAGACCAGCACACTGAAAACCTGCCTGCCTCTGGAACTGCACA AGAACGAGAGCTGCCTGGCCACCAGAGAGACAAGCAGCACAACAAGAGG CAGCTGTCTGCCTCCTCAGAAAACCAGCCTGATGATGACCCTGTGCCTG GGCAGCATCTACGAGGACCTGAAGATGTACCAGACCGAGTTCCAGGCCA TCAACGCCGCTCTGCAGAACCACAACCACCAGCAGATCATCCTGGACAA GGGCATGCTGGTGGCTATCGACGAGCTGATGCAGAGCCTGAACCACAAT GGCGAGACACTGCGGCAGAAGCCTCCAGTTGGAGAGGCCGATCCTTACA GAGTGAAGATGAAGCTGTGCATCCTGCTGCACGCCTTCAGCACCAGAGT GGTCACCATCAACAGAGTGATGGGCTACCTGAGCAGCGCCTGATAAGCT AGCCCCCTCTCCCTCCCCCCCCCCTAACGTTACTGGCCGAAGCCGCTTG GAATAAGGCCGGTGTGCGTTTGTCTATATGTTATTTTCCACCATATTGC CGTCTTTTGGCAATGTGAGGGCCCGGAAACCTGGCCCTGTCTTCTTGAC GAGCATTCCTAGGGGTCTTTCCCCTCTCGCCAAAGGAATGCAAGGTCTG TTGAATGTCGTGAAGGAAGCAGTTCCTCTGGAAGCTTCTTGAAGACAAA CAACGTCTGTAGCGACCCTTTGCAGGCAGCGGAACCCCCCACCTGGCGA CAGGTGCCTCTGCGGCAAAAGCCACGTGTATAAGATACACCTGCAAAG GCGGCACAACCCCAGTGCCACGTTGTGAGTTGGATAGTTGTGGAAAGAG GAAGGTACCCCATTGTATGGGATCTGATCTGGGGCCTCGGTGCACATGC TCAAATGGCTCTCCTCAAGCGTATTCAACAAGGGGCTGAAGGATGCCCA |

| | Informal Sequence Listing | |
|---|---|---|
| | | ACGGGGACGTGGTTTTCCTTTGAAAAACACGATGATAATATGGCCACAA<br>TTTACATGTGTTTAGTCGAGGTTAAAAAAACGTCTAGGCCCCCCGAACC<br>CCATGTGCCCTCAGAAGCTGACCATCAGTTGGTTCGCCATCGTGCTGCT<br>GGTGTCCCCACTGATGGCCATGTGGGAGCTTGAGAAGGACGTGTACGTG<br>GTGGAAGTGGACTGGACCCCTGATGCTCCTGGCGAGACAGTGAACCTGA<br>CCTGCGATACCCCTGAAGAGGACGACATCACCTGGACCAGCGACCAGAG<br>ACATGGCGTGATCGGCTCTGGCAAGACCCTGACAATTACCGTGAAAGCG<br>GCCCTGGACGCCGGCCAGTACACCTGTCACAAAGGCGGAGAGACACTGA<br>GCCACTCTCATCTGCTGCTGCACAAGAAAGAGAACGGCATCTGGTCCAC<br>CGAGATCCTGAAGAACTTCAAGAACAAGACCTTCCTGAAGTGCGAGGCC<br>CCTAACTACAGCGGCAGATTCACCTGTAGCTGGCTGGTGCAGCGGAACA<br>TGGACCTGAAGTTCAACATCAAGTCCTCCAGCAGCAGCCCCGACAGCAG<br>AGCTGTGACATGTGGCATGGCTTCTCTGAGCGCCGAGAAAGTGACCCTG<br>GATCAGCGGGACTACGAGAAGTACAGCGTGTCCTGCCAAGAGGACGTGA<br>CCTGTCCTACCGCCGAGGAAACACTGCCTATCGAGCTGGCCCTGGAAGC<br>CCGGCAGCAGAACAAATACGAGAACTACTCCACCAGCTTTTTCATCCGG<br>GACATCATCAAGCCCGATCCTCCAAAGAACCTGCAGATGAAGCCTCTGA<br>AGAACAGCCAGGTCGAGGTGTCCTGGGAGTACCCCGATAGCTGGTCTAC<br>CCCTCACAGCTACTTCAGCCTGAAATTCTTCGTGCGCATCCAGCGCAAG<br>AAAGAAAAGATGAAGGAAACCGAGGAAGGCTGCAACCAGAAAGGGGCCT<br>TCCTGGTGGAAAAGACCAGCACCGAGGTGCAGTGCAAAGGCGGCAATGT<br>TTGTGTGCAGGCCCAGGATCGGTACTACAACAGCAGCTGTAGCAAGTGG<br>GCCTGCGTGCCATGTAGAGTCCGGAGTCACCACCATCATCACCATCACC<br>AC |
| 113 | DNA Sequence<br>Encoding DR1023P<br>mIL12 (p35-<br>IRES2-p40 E81A<br>F82A K106A) His8 | AGAGTGATCCCCGTGTCTGGACCTGCCAGATGTCTGAGCCAGTCCAGAA<br>ACCTGCTGAAAACCACCGACGACATGGTCAAGACCGCCAGAGAGAAGCT<br>GAAGCACTACAGCTGCACCGCCGAGGACATCGACCACGAGGATATCACC<br>AGGGACCAGACCAGCACACTGAAAACCTGCCTGCCTCTGGAACTGCACA<br>AGAACGAGAGCTGCCTGGCCACCAGAGAGACAAGCAGCACAACAAGAGG<br>CAGCTGTCTGCCTCCTCAGAAAACCAGCCTGATGATGACCCTGTGCCTG<br>GGCAGCATCTACGAGGACCTGAAGATGTACCAGACCGAGTTCCAGGCCA<br>TCAACGCCGCTCTGCAGAACCACAACCACCAGCAGATCATCCTGGACAA<br>GGGCATGCTGGTGGCTATCGACGAGCTGATGCAGAGCCTGAACCACAAT<br>GGCGAGACACTGCGGCAGAAGCCTCCAGTTGGAGAGGCCGATCCTTACA<br>GAGTGAAGATGAAGCTGTGCATCCTGCTGCACGCCTTCAGCACCAGAGT<br>GGTCACCATCAACAGAGTGATGGGCTACCTGAGCAGCGCCTGATAAGCT<br>AGCCCCCTCTCCCTCCCCCCCCCTAACGTTACTGGCCGAAGCCGCTTG<br>GAATAAGGCCGGTGTGCGTTTGTCTATATGTTATTTTCCACCATATTGC<br>CGTCTTTTGGCAATGTGAGGGCCCGGAAACCTGGCCCTGTCTTCTTGAC<br>GAGCATTCCTAGGGGTCTTTCCCCTCTCGCCAAAGGAATGCAAGGTCTG<br>TTGAATGTCGTGAAGGAAGCAGTTCCTCTGGAAGCTTCTTGAAGACAAA<br>CAACGTCTGTAGCGACCCTTTGCAGGCAGCGGAACCCCCCACCTGGCGA<br>CAGGTGCCTCTGCGGCAAAAGCCACGTGTATAAGATACACCTGCAAAG<br>GCGGCACAACCCCAGTGCCACGTTGTGAGTTGGATAGTTGTGGAAAGAG<br>CCATGTGCCCTCAGAAGCTGACCATCAGTTGGTTCGCCATCGTGCTGCT<br>GAAGGTACCCCATTGTATGGGATCTGATCTGGGGCCTCGGTGCACATGC<br>ACGGGGACGTGGTTTTCCTTTGAAAAACACGATGATAATATGGCCACAA<br>GTGGAAGTGGACTGGACCCCTGATGCTCCTGGCGAGACAGTGAACCTGA<br>TCAAATGGCTCTCCTCAAGCGTATTCAACAAGGGGCTGAAGGATGCCCA<br>GGTGTCCCCACTGATGGCCATGTGGGAGCTTGAGAAGGACGTGTACGTG<br>TTTACATGTGTTTAGTCGAGGTTAAAAAAACGTCTAGGCCCCCCGAACC<br>CCTGCGATACCCCTGAAGAGGACGACATCACCTGGACCAGCGACCAGAG<br>ACATGGCGTGATCGGCTCTGGCAAGACCCTGACAATTACCGTGAAAGCG<br>GCCCTGGACGCCGGCCAGTACACCTGTCACAAAGGCGGAGAGACACTGA<br>GCCACTCTCATCTGCTGCTGCACGCGAAAGAGAACGGCATCTGGTCCAC<br>CGAGATCCTGAAGAACTTCAAGAACAAGACCTTCCTGAAGTGCGAGGCC<br>CCTAACTACAGCGGCAGATTCACCTGTAGCTGGCTGGTGCAGCGGAACA<br>TGGACCTGAAGTTCAACATCAAGTCCTCCAGCAGCAGCCCCGACAGCAG<br>AGCTGTGACATGTGGCATGGCTTCTCTGAGCGCCGAGAAAGTGACCCTG<br>GATCAGCGGGACTACGAGAAGTACAGCGTGTCCTGCCAAGAGGACGTGA<br>CCTGTCCTACCGCCGAGGAAACACTGCCTATCGAGCTGGCCCTGGAAGC<br>CCGGCAGCAGAACAAATACGAGAACTACTCCACCAGCTTTTTCATCCGG<br>GACATCATCAAGCCCGATCCTCCAAAGAACCTGCAGATGAAGCCTCTGA<br>AGAACAGCCAGGTCGAGGTGTCCTGGGAGTACCCCGATAGCTGGTCTAC<br>CCCTCACAGCTACTTCAGCCTGAAATTCTTCGTGCGCATCCAGCGCAAG<br>AAAGAAAAGATGAAGGAAACCGAGGAAGGCTGCAACCAGAAAGGGGCCT<br>TCCTGGTGGAAAAGACCAGCACCGAGGTGCAGTGCAAAGGCGGCAATGT<br>TTGTGTGCAGGCCCAGGATCGGTACTACAACAGCAGCTGTAGCAAGTGG<br>GCCTGCGTGCCATGTAGAGTCCGGAGTCACCACCATCATCACCATCACC<br>AC |
| 114 | DR854<br>mIL12 p40<br>mIgG2A<br>EW LALA PG | MWELEKDVYVVEVDWTPDAPGETVNLTCDTPEEDDITWTSDQRHGVIGS<br>GKTLTITVKEFLDAGQYTCHKGGETLSHSHLLLHKKENGIWSTEILKNF<br>KNKTFLKCEAPNYSGRFTCSWLVQRNMDLKFNIKSSSSSPDSRAVTCGM<br>ASLSAEKVTLDQRDYEKYSVSCQEDVTCPTAEETLPIELALEARQQNKY<br>ENYSTSFFIRDIIKPDPPKNLQMKPLKNSQVEVSWEYPDSWSTPHSYFS |

| | | |
|---|---|---|
| | | LKFFVRIQRKKEKMKETEEGCNQKGAFLVEKTSTEVQCKGGNVCVQAQD<br>RYYNSSCSKWACVPCRVRSPRGPTIKPCPPCKCPAPNAAGGPSVFIFPP<br>KIKDVLMISLSPIVTCVVVDVSEDDPDVQISWFVNNVEVHTAQTQTHRE<br>DYNSTLRVVSALPIQHQDWMSGKEFKCKVNNKDLGAPIERTISKPKGSV<br>RAPQVYVLPPPEEEMTEKQVTLTCMVTDFMPEDIYVEWTNNGKTELNYK<br>NTEPVLDSDGSYFMYSWLRVEKKNWVERNSYSCSVVHEGLHNHHTTKSF<br>SRTPG |
| 115 | DR855<br>mIL12-p35-<br>mIgG2A-RVT-<br>LALAPG | RVIPVSGPARCLSQSRNLLKTTDDMVKTAREKLKHYSCTAEDIDHEDIT<br>RDQTSTLKTCLPLELHKNESCLATRETSSTTRGSCLPPQKTSLMMTLCL<br>GSIYEDLKMYQTEFQAINAALQNHNHQQIILDKGMLVAIDELMQSLNHN<br>GETLRQKPPVGEADPYRVKMKLCILLHAFSTRVVTINRVMGYLSSAGGG<br>GSGGGGSGGGGSPRGPTIKPCPPCKCPAPNAAGGPSVFIFPPKIKDVLM<br>ISLSPIVTCVVVDVSEDDPDVQISWFVNNVEVHTAQTQTHREDYNSTLR<br>VVSALPIQHQDWMSGKEFKCKVNNKDLGAPIERTISKPKGSVRAPRVYV<br>LPPPEEEMTKKQVTLTCMVTDFMPEDIYVEWTNNGKTELNYKNTEPVLV<br>SDGSYTMYSKLRVEKKNWVERNSYSCSVVHEGLHNHHTTKSFSRTPG |
| 116 | DR1243P<br>mIL12 p40 E81A<br>F82A mIgG2a EW<br>LALA PG | MWELEKDVYVVEVDWTPDAPGETVNLTCDTPEEDDITWTSDQRHGVIGS<br>GKTLTITVKAALDAGQYTCHKGGETLSHSHLLLHKKENGIWSTEILKNF<br>KNKTFLKCEAPNYSGRFTCSWLVQRNMDLKFNIKSSSSSPDSRAVTCGM<br>ASLSAEKVTLDQRDYEKYSVSCQEDVTCPTAEETLPIELALEARQQNKY<br>ENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQD<br>RYYNSSCSKWACVPCRVRSPRGPTIKPCPPCKCPAPNAAGGPSVFIFPP<br>KIKDVLMISLSPIVTCVVVDVSEDDPDVQISWFVNNVEVHTAQTQTHRE<br>DYNSTLRVVSALPIQHQDWMSGKEFKCKVNNKDLGAPIERTISKPKGSV<br>RAPQVYVLPPPEEEMTEKQVTLTCMVTDFMPEDIYVEWTNNGKTELNYK<br>NTEPVLDSDGSYFMYSWLRVEKKNWVERNSYSCSVVHEGLHNHHTTKSF<br>SRTPG |
| 117 | DR1244P<br>mIL12 p40 E81A<br>F82A K106A<br>mIgG2a EW LALA<br>PG | MWELEKDVYVVEVDWTPDAPGETVNLTCDTPEEDDITWTSDQRHGVIGS<br>GKTLTITVKAALDAGQYTCHKGGETLSHSHLLLHAKENGIWSTEILKNF<br>KNKTFLKCEAPNYSGRFTCSWLVQRNMDLKFNIKSSSSSPDSRAVTCGM<br>ASLSAEKVTLDQRDYEKYSVSCQEDVTCPTAEETLPIELALEARQQNKY<br>ENYSTSFFIRDIIKPDPPKNLQMKPLKNSQVEVSWEYPDSWSTPHSYFS<br>LKFFVRIQRKKEKMKETEEGCNQKGAFLVEKTSTEVQCKGGNVCVQAQD<br>RYYNSSCSKWACVPCRVRSPRGPTIKPCPPCKCPAPNAAGGPSVFIFPP<br>KIKDVLMISLSPIVTCVVVDVSEDDPDVQISWFVNNVEVHTAQTQTHRE<br>DYNSTLRVVSALPIQHQDWMSGKEFKCKVNNKDLGAPIERTISKPKGSV<br>RAPQVYVLPPPEEEMTEKQVTLTCMVTDFMPEDIYVEWTNNGKTELNYK<br>NTEPVLDSDGSYFMYSWLRVEKKNWVERNSYSCSVVHEGLHNHHTTKSF<br>SRTPG |
| 118 | DNA Sequence<br>encoding<br>DR1595P | ATCTGGGAGCTGAAGAAAGACGTGTACGTGGTGGAACTGGACTGGTATCCC<br>GATGCTCCTGGCGAGATGGTGGTGCTGACCTGCGATACCCCTGAAGAGGAC<br>GGCATCACCTGGACACTGGATCAGTCTAGCGAGGTGCTCGGCAGCGGCAAG<br>ACCCTGACCATCCAAGTGAAAGCGGCTGGCGACGCCGGCCAGTACACCTGT<br>CACAAAGGCGGAGAAGTGCTGAGCCACAGCCTGCTGCTGCTCCACGCGAAA<br>GAGGATGGCATTTGGAGCACCGACATCCTGAAGGACCAGAAAGAGCCCAAG<br>AACAAGACCTTCCTGAGATGCGAGGCCAAGAACTACAGCGGCCGGTTCACA<br>TGTTGGTGGCTGACCACCATCAGCACCGACCTGACCTTCAGCGTGAAGTCC<br>AGCAGAGGCAGCAGTGATCCTCAGGGCGTTACATGTGGCGCTGCCACACTG<br>TCTGCCGAAAGAGTGCGGGCGACAACAAAGAATACGAGTACAGCGTGGAA<br>TGCCAAGAGGACAGCGCCTGTCCAGCCGCCGAAGAGTCTCTGCCTATCGAA<br>GTGATGGTGGACGCCGTGCACAAGCTGAAGTACGAGAACTACACCTCCAGC<br>TTTTTCATCCGGGACATCATCAAGCCCGATCCTCCAAAGAACCTGCAGCTG<br>AAGCCTCTGAAGAACAGCAGACAGGTGGAAGTGTCCTGGGAGTACCCCGAC<br>ACCTGGTCTACACCCCACAGCTACTTCAGCCTGACCTTTTGCGTGCAAGTG<br>CAGGGCAAGTCCAAGCGCGAGAAAAAGGACCGGGTGTTCACCGACAAGACC<br>AGCGCCACCGTGATCTGCAGAAAGAACGCCAGCATCAGCGTCAGAGCCCAG<br>GATCGGTACTACAGCAGCTCTTGGAGCGAGTGGGCCTCGGTACCATGTAGC<br>GGAGGCGGAGGATCCGGCGGAGGTGGAAGTGAACCAAAATCATCAGACAAG<br>ACCCACACCTGTCCTCCATGTCCTGCTCCAGAAGCTGAAGGGGCCCCTTCC<br>GTGTTTCTGTTCCCTCCAAAGCCTAAGGACACCCTGATGATCTCTCGGACC<br>CCTGAAGTGACCTGCGTGGTGGTGGATGTGTCTCACGAAGATCCAGAAGTG<br>AAGTTCAATTGGTACGTGGACGGCGTGGAAGTGCACAACGCCAAGACCAAG<br>CCTAGAGAGGAACAGTACAACTCCACCTACAGAGTGGTGTCCGTGCTGACC<br>GTGCTGCACCAGGATTGGCTGAACGGCAAAGAGTACAAGTGCAAGGTGTCC |

-continued

| | Informal Sequence Listing |
|---|---|
| | AACAAGGCCCTGCCCTCTTCCATCGAAAAGACCATCTCTAAGGCCAAGGGC<br>CAGCCTCGGGAACCCCAGGTTTACACACTGCCTCCATGCCGGGATGAGCTG<br>ACCAAGAACCAGGTGTCCCTGTGGTGCCTGGTCAAGGGCTTCTACCCTTCC<br>GATATCGCCGTGGAATGGGAGAGCAATGGCCAGCCTGAGAACAACTACAAG<br>ACAACCCCTCCTGTGCTGGACTCCGACGGCTCATTCTTCCTGTACTCCAAG<br>CTGACAGTGGACAAGTCCAGATGGCAGCAGGGCAACGTGTTCTCCTGCTCC<br>GTGATGCACGAAGCTTTGCACAATCACTACACACAGAAGTCCCTGTCTCTG<br>TCCCCTGGC |

| SEQ<br>ID | Name/Description | Amino Acid or Nucleotide Sequence |
|---|---|---|
| 119 | DR1947P<br>(3xAla p40 Fc<br>pre-protein) | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVLHEALHSHYTQKSLSLSPG |
| 120 | Nucleic acid<br>sequence<br>encoding<br>DR1947P | ATGTGTCACCAGCAGCTGGTCATCAGCTGGTTCAGCCTGGTGTTCCTGGCCT<br>CTCCTCTGGTGGCCATCTGGGAGCTGAAGAAAGACGTGTACGTGGTGGAACT<br>GGACTGGTATCCCGATGCTCCTGGCGAGATGGTGGTGCTGACCTGCGATACC<br>CCTGAAGAGGACGGCATCACCTGGACACTGGATCAGTCTAGCGAGGTGCTCG<br>GCAGCGGCAAGACCCTGACCATCCAAGTGAAAGCGGCTGGCGACGCCGGCCA<br>GTACACCTGTCACAAAGGCGGAGAAGTGCTGAGCCACAGCCTGCTGCTGCTC<br>CACGCGAAAGAGGATGGCATTTGGAGCACCGACATCCTGAAGGACCAGAAAG<br>AGCCCAAGAACAAGACCTTCCTGAGATGCGAGGCCAAGAACTACAGCGGCCG<br>GTTCACATGTTGGTGGCTGACCACCATCAGCACCGACCTGACCTTCAGCGTG<br>AAGTCCAGCAGAGGCAGCAGTGATCCTCAGGGCGTTACATGTGGCGCTGCCA<br>CACTGTCTGCCGAAAGAGTGCGGGGCGACAACAAAGAATACGAGTACAGCGT<br>GGAATGCCAAGAGGACAGCGCCTGTCCAGCCGCCGAAGAGTCTCTGCCTATC<br>GAAGTGATGGTGGACGCCGTGCACAAGCTGAAGTACGAGAACTACACCTCCA<br>GCTTTTTCATCCGGGACATCATCAAGCCCGATCCTCCAAAGAACCTGCAGCT<br>GAAGCCTCTGAAGAACAGCAGACAGGTGGAAGTGTCCTGGGAGTACCCCGAC<br>ACCTGGTCTACACCCCACAGCTACTTCAGCCTGACCTTTTGCGTGCAAGTGC<br>AGGGCAAGTCCAAGCGCGAGAAAAAGGACCGGGTGTTCACCGACAAGACCAG<br>CGCCACCGTGATCTGCAGAAAGAACGCCAGCATCAGCGTCAGAGCCCAGGAT<br>CGGTACTACAGCAGCTCTTGGAGCGAGTGGGCCTCGGTACCATGTAGCGGAG<br>GCGGAGGATCCGGCGGAGGTGGAAGTGAACCAAAATCATCAGACAAGACCCA<br>CACCTGTCCTCCATGTCCTGCTCCAGAAGCTGCAGGGGGCCCTTCCGTGTTT<br>CTGTTCCCTCCAAAGCCTAAGGACACCCTGATGATCTCTCGGACCCCTGAAG<br>TGACCTGCGTGGTGGTGGATGTGTCTCACGAAGATCCAGAAGTGAAGTTCAA<br>TTGGTACGTGGACGGCGTGGAAGTGCACAACGCCAAGACCAAGCCTAGAGAG<br>GAACAGTACAACTCCACCTACAGAGTGGTGTCCGTGCTGACCGTGCTGCACC<br>AGGATTGGCTGAACGGCAAAGAGTACAAGTGCAAGGTGTCCAACAAGGCCCT<br>GGCCGCTCCCATCGAAAAGACCATCTCTAAGGCCAAGGGCCAGCCTCGGGAA<br>CCCCAGGTTTACACACTGCCTCCATGCCGGGATGAGCTGACCAAGAACCAGG<br>TGTCCCTGTGGTGCCTGGTCAAGGGCTTCTACCCTTCCGATATCGCCGTGGA<br>ATGGGAGAGCAATGGCCAGCCTGAGAACAACTACAAGACAACCCCTCCTGTG<br>CTGGACTCCGACGGCTCATTCTTCCTGTACTCCAAGCTGACAGTGGACAAGT<br>CCAGATGGCAGCAGGGCAACGTGTTCTCCTGCTCCGTGTTGCACGAAGCTTT<br>GCACTCTCACTACACACAGAAGTCCCTGTCTCTGTCCCCTGGC |
| 121 | DR1947M<br>Mature 3xAla<br>p40 Fc protein | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSK<br>REKKDRVFTDKTSATVICRKNASISVRAQDRYYSSSWSEWASVPCSGGGGSG<br>GGGSEPKSSDKTHTCPPCPAPEAAGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALAAPIEKTISKAKGQPREPQVYTLPPCRDELTKNQVSLWC<br>LVKGFYPSDIAVEWESNGQPENNYKTTPPVLDSDGSFFLYSKLTVDKSRWQQ<br>GNVFSCSVLHEALHSHYTQKSLSLSPG |
| 122 | DR1948P<br>Wt P35 Fc<br>precursor<br>(signal<br>sequence<br>underlined) | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD<br>QNMLAVIDELMQALNFNSETVPQKSSLEEPDFYKTKIKLCILLHAFRIRAVT<br>IDRVMSYLNASGGGGSGGGGSEPKSSDKTHTCPPCPAPEAAGGPSVFLFPPK<br>PKDTLMISRTPEVTCVVVDVSHEDPEVKFNWYVDGVEVHNAKTKPREEQYNS<br>TYRVVSVLTVLHQDWLNGKEYKCKVSNKALAAPIEKTISKAKGQPREPQVCT |

| | | |
|---|---|---|
| | | LPPSRDELTKNQVSLSCAVKGFYPSDIAVEWESNGQPENNYKTTPPVLDSDG<br>SFFLVSKLTVDKSRWQQGNVFSCSVLHEALHSHYTQKSLSLSPG |
| 123 | Nucleic acid<br>sequence<br>encoding<br>DR1948P | ATGTGCCCTGCCAGATCTCTGCTGCTGGTGGCTACACTGGTGCTGCTGGATC<br>ATCTGAGCCTGGCCAGAAACCTGCCAGTGGCCACGCCTGATCCTGGCATGTT<br>TCCTTGTCTGCACCACAGCCAGAACCTGCTGAGAGCCGTGTCCAACATGCTG<br>CAGAAGGCCAGACAGACCCTCGAGTTCTACCCCTGCACCAGCGAGGAAATCG<br>ACCACGAGGACATCACCAAGGACAAGACCAGCACCGTGGAAGCCTGCCTGCC<br>TCTGGAACTGACCAAGAACGAGAGCTGCCTGAACAGCAGAGAGACAAGCTTC<br>ATCACCAACGGCTCTTGCCTGGCCTCCAGAAAGACCTCCTTCATGATGGCCC<br>TGTGCCTGAGCAGCATCTACGAGGACCTGAAGATGTACCAGGTCGAGTTCAA<br>GACCATGAACGCCAAGCTGCTGATGGACCCCAAGCGGCAGATCTTCCTGGAC<br>CAGAATATGCTGGCCGTGATCGACGAGCTGATGCAGGCCCTGAACTTCAACA<br>GCGAGACAGTGCCCCAGAAGTCCAGCCTGGAAGAACCCGACTTCTACAAGAC<br>CAAGATCAAGCTGTGCATCCTGCTGCACGCCTTCCGGATCAGAGCCGTGACC<br>ATCGACAGAGTGATGAGCTACCTGAACGCCAGCGGAGGCGGAGGATCCGGCG<br>GAGGTGGAAGTGAACCAAAATCATCAGACAAGACCCACACCTGTCCTCCATG<br>TCCTGCTCCAGAAGCTGCAGGGGGTCCCTCCGTTTTTCTGTTCCCACCTAAG<br>CCTAAGGACACCCTGATGATCTCTCGGACCCCTGAAGTGACCTGCGTGGTGG<br>TGGATGTGTCTCACGAAGATCCCGAAGTGAAGTTCAATTGGTACGTGGACGG<br>CGTGGAAGTGCACAACGCCAAGACCAAGCCTAGAGAGGAACAGTACAACTCC<br>ACCTACAGAGTGGTGTCCGTGCTGACCGTGCTGCACCAGGATTGGCTGAACG<br>GCAAAGAGTACAAGTGCAAGGTGTCCAACAAGGCCCTGGCCGCTCCTATCGA<br>AAAGACCATCTCCAAGGCCAAGGGCCAGCCTAGGGAACCCCAGGTTTGCACC<br>CTGCCTCCAAGCCGGGATGAGCTGACCAAGAACCAGGTGTCCCTGTCCTGTG<br>CCGTGAAGGGCTTCTACCCTTCCGATATCGCCGTGGAATGGGAGAGCAATGG<br>CCAGCCTGAGAACAACTACAAGACAACCCCTCCTGTGCTGGACTCCGACGGC<br>TCATTCTTCCTGGTGTCCAAGCTGACAGTGGACAAGTCCAGATGGCAGCAGG<br>GCAACGTGTTCTCCTGCTCCGTGCTGCACGAAGCTTTGCACTCCCACTACAC<br>CCAGAAGTCCCTGTCTCTGAGCCCTGGA |
| 124 | DR1948M<br>Mature wt hP35<br>Fc protein<br>without signal<br>peptide | RNLPVATPDPGMFPCLHHSQNLLRAVSNMLQKARQTLEFYPCTSEEIDHEDI<br>TKDKTSTVEACLPLELTKNESCLNSRETSFITNGSCLASRKTSFMMALCLSS<br>IYEDLKMYQVEFKTMNAKLLMDPKRQIFLDQNMLAVIDELMQALNFNSETVP<br>QKSSLEEPDFYKTKIKLCILLHAFRIRAVTIDRVMSYLNASGGGGSGGGGSE<br>PKSSDKTHTCPPCPAPEAAGGPSVFLFPPKPKDTLMISRTPEVTCVVVDVSH<br>EDPEVKFNWYVDGVEVHNAKTKPREEQYNSTYRVVSVLTVLHQDWLNGKEYK<br>CKVSNKALAAPIEKTISKAKGQPREPQVCTLPPSRDELTKNQVSLSCAVKGF<br>YPSDIAVEWESNGQPENNYKTTPPVLDSDGSFFLVSKLTVDKSRWQQGNVFS<br>CSVLHEALHSHYTQKSLSLSPG |
| 125 | DR1536P<br>Wt P35 Fc<br>precursor<br>protein | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD<br>QNMLAVIDELMQALNFNSETVPQKSSLEEPDFYKTKIKLCILLHAFRIRAVT<br>IDRVMSYLNASGGGGSGGGGSEPKSSDKTHTCPPCPAPEAAGGPSVFLFPPK<br>PKDTLMISRTPEVTCVVVDVSHEDPEVKFNWYVDGVEVHNAKTKPREEQYNS<br>TYRVVSVLTVLHQDWLNGKEYKCKVSNKALAAPIEKTISKAKGQPREPQVCT<br>LPPSRDELTKNQVSLSCAVKGFYPSDIAVEWESNGQPENNYKTTPPVLDSDG<br>SFFLVSKLTVDKSRWQQGNVFSCSVMHEALHNHYTQKSLSLSPG |
| 126 | DR1537P<br>(3xAla p40 Fc<br>pre-protein) | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 127 | DR2088P<br>3xAla p40Fc<br>precursor<br>protein | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSGREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVLHEALHSHYTQKSLSLSPG |

-continued

| | | |
|---|---|---|
| Informal Sequence Listing | | |
| 128 | Nucleic acid sequence encoding DR2088P | ATGTGTCACCAGCAGCTGGTCATCAGCTGGTTCAGCCTGGTGTTCCTGGCCT<br>CTCCTCTGGTGGCCATCTGGGAGCTGAAGAAAGACGTGTACGTGGTGGAACT<br>GGACTGGTATCCCGATGCTCCTGGCGAGATGGTGGTGCTGACCTGCGATACC<br>CCTGAAGAGGACGGCATCACCTGGACACTGGATCAGTCTAGCGAGGTGCTCG<br>GCAGCGGCAAGACCCTGACCATCCAAGTGAAAGCGGCTGGCGACGCCGGCCA<br>GTACACCTGTCACAAAGGCGGAGAAGTGCTGAGCCACAGCCTGCTGCTGCTC<br>CACGCGAAAGAGGATGGCATTTGGAGCACCGACATCCTGAAGGACCAGAAAG<br>AGCCCAAGAACAAGACCTTCCTGAGATGCGAGGCCAAGAACTACAGCGGCCG<br>GTTCACATGTTGGTGGCTGACCACCATCAGCACCGACCTGACCTTCAGCGTG<br>AAGTCCAGCAGAGGCAGCAGTGATCCTCAGGGCGTTACATGTGGCGCTGCCA<br>CACTGTCTGCCGAAAGAGTGCGGGGCGACAACAAAGAATACGAGTACAGCGT<br>GGAATGCCAAGAGGACAGCGCCTGTCCAGCCGCCGAAGAGTCTCTGCCTATC<br>GAAGTGATGGTGGACGCCGTGCACAAGCTGAAGTACGAGAACTACACCTCCA<br>GCTTTTTCATCCGGGACATCATCAAGCCCGATCCTCCAAAGAACCTGCAGCT<br>GAAGCCTCTGAAGAACAGCAGACAGGTGGAAGTGTCCTGGGAGTACCCCGAC<br>ACCTGGTCTACACCCCACAGCTACTTCAGCCTGACCTTTTGCGTGCAAGTGC<br>AGGGCAAGTCCGGGCGCGAGAAAAAGGACCGGGTGTTCACCGACAAGACCAG<br>CGCCACCGTGATCTGCAGAAAGAACGCCAGCATCAGCGTCAGAGCCCAGGAT<br>CGGTACTACAGCAGCTCTTGGAGCGAGTGGGCCTCGGTACCATGTAGCGGAG<br>GCGGAGGATCCGGCGGAGGTGGAAGTGAACCAAAATCATCAGACAAGACCCA<br>CACCTGTCCTCCATGTCCTGCTCCAGAAGCTGCAGGGGCCCTTCCGTGTTT<br>CTGTTCCCTCCAAAGCCTAAGGACACCCTGATGATCTCTCGGACCCCTGAAG<br>TGACCTGCGTGGTGGTGGATGTGTCTCACGAAGATCCAGAAGTGAAGTTCAA<br>TTGGTACGTGGACGGCGTGGAAGTGCACAACGCCAAGACCAAGCCTAGAGAG<br>GAACAGTACAACTCCACCTACAGAGTGGTGTCCGTGCTGACCGTGCTGCACC<br>AGGATTGGCTGAACGGCAAAGAGTACAAGTGCAAGGTGTCCAACAAGGCCCT<br>GGCCGCTCCCATCGAAAAGACCATCTCTAAGGCCAAGGGCCAGCCTCGGGAA<br>CCCCAGGTTTACACACTGCCTCCATGCCGGGATGAGCTGACCAAGAACCAGG<br>TGTCCCTGTGGTGCCTGGTCAAGGGCTTCTACCCTTCCGATATCGCCGTGGA<br>ATGGGAGAGCAATGGCCAGCCTGAGAACAACTACAAGACAACCCCTCCTGTG<br>CTGGACTCCGACGGCTCATTCTTCCTGTACTCCAAGCTGACAGTGGACAAGT<br>CCAGATGGCAGCAGGGCAACGTGTTCTCCTGCTCCGTGTTGCACGAAGCTTT<br>GCACTCTCACTACACACAGAAGTCCCTGTCTCTGTCCCCTGGC |
| 129 | DR2088M Mature 3xAla p40 Fc protein | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCSGGGGSG<br>GGGSEPKSSDKTHTCPPCPAPEAAGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALAAPIEKTISKAKGQPREPQVYTLPPCRDELTKNQVSLWC<br>LVKGFYPSDIAVEWESNGQPENNYKTTPPVLDSDGSFFLYSKLTVDKSRWQQ<br>GNVFSCSVLHEALHSHYTQKSLSLSPG |
| 130 | DR2092P 3xAla p40Fc precursor protein | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSGREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 131 | Nucleic acid sequence encoding DR2092P | ATGTGTCACCAGCAGCTGGTCATCAGCTGGTTCAGCCTGGTGTTCCTGGCCT<br>CTCCTCTGGTGGCCATCTGGGAGCTGAAGAAAGACGTGTACGTGGTGGAACT<br>GGACTGGTATCCCGATGCTCCTGGCGAGATGGTGGTGCTGACCTGCGATACC<br>CCTGAAGAGGACGGCATCACCTGGACACTGGATCAGTCTAGCGAGGTGCTCG<br>GCAGCGGCAAGACCCTGACCATCCAAGTGAAAGCGGCTGGCGACGCCGGCCA<br>GTACACCTGTCACAAAGGCGGAGAAGTGCTGAGCCACAGCCTGCTGCTGCTC<br>CACGCGAAAGAGGATGGCATTTGGAGCACCGACATCCTGAAGGACCAGAAAG<br>AGCCCAAGAACAAGACCTTCCTGAGATGCGAGGCCAAGAACTACAGCGGCCG<br>GTTCACATGTTGGTGGCTGACCACCATCAGCACCGACCTGACCTTCAGCGTG<br>AAGTCCAGCAGAGGCAGCAGTGATCCTCAGGGCGTTACATGTGGCGCTGCCA<br>CACTGTCTGCCGAAAGAGTGCGGGGCGACAACAAAGAATACGAGTACAGCGT<br>GGAATGCCAAGAGGACAGCGCCTGTCCAGCCGCCGAAGAGTCTCTGCCTATC<br>GAAGTGATGGTGGACGCCGTGCACAAGCTGAAGTACGAGAACTACACCTCCA<br>GCTTTTTCATCCGGGACATCATCAAGCCCGATCCTCCAAAGAACCTGCAGCT<br>GAAGCCTCTGAAGAACAGCAGACAGGTGGAAGTGTCCTGGGAGTACCCCGAC<br>ACCTGGTCTACACCCCACAGCTACTTCAGCCTGACCTTTTGCGTGCAAGTGC<br>AGGGCAAGTCCGGGCGCGAGAAAAAGGACCGGGTGTTCACCGACAAGACCAG<br>CGCCACCGTGATCTGCAGAAAGAACGCCAGCATCAGCGTCAGAGCCCAGGAT<br>CGGTACTACAGCAGCTCTTGGAGCGAGTGGGCCTCGGTACCATGTAGCGGAG |

| | | |
|---|---|---|
| | | Informal Sequence Listing |
| | | GCGGAGGATCCGGCGGAGGCGGATCTGAACCAAAATCATCAGACAAGACCCA<br>CACCTGTCCTCCATGTCCTGCTCCAGAAGCTGCTGGGGGCCCTTCCGTGTTT<br>CTGTTCCCTCCAAAGCCTAAGGACACCCTGATGATCTCTCGGACCCCTGAAG<br>TGACCTGCGTGGTGGTGGATGTGTCTCACGAAGATCCAGAAGTGAAGTTCAA<br>TTGGTACGTGGACGGCGTGGAAGTGCACAACGCCAAGACCAAGCCTAGAGAG<br>GAACAGTACAACTCCACCTACAGAGTGGTGTCCGTGCTGACCGTGCTGCACC<br>AGGATTGGCTGAACGGCAAAGAGTACAAGTGCAAGGTGTCCAACAAGGCCCT<br>GGCCGCTCCCATCGAAAAGACCATCTCTAAGGCCAAGGGCCAGCCTCGGGAA<br>CCCCAGGTTTACACACTGCCTCCATGCCGGGATGAGCTGACCAAGAACCAGG<br>TGTCCCTGTGGTGCCTGGTCAAGGGCTTCTACCCTTCCGATATCGCCGTGGA<br>ATGGGAGAGCAATGGCCAGCCTGAGAACAACTACAAGACAACCCCTCCTGTG<br>CTGGACTCCGACGGCTCATTCTTCCTGTACTCCAAGCTGACAGTGGACAAGT<br>CCAGATGGCAGCAGGGCAACGTGTTCTCCTGCTCCGTGATGCACGAAGCTTT<br>GCACAATCACTACACACAGAAGTCCCTGTCTCTGTCCCCTGGC |
| 132 | DR2092M<br>Mature 3xAla<br>p40Fc protein | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCSGGGGSG<br>GGGSEPKSSDKTHTCPPCPAPEAAGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALAAPIEKTISKAKGQPREPQVYTLPPCRDELTKNQVSLWC<br>LVKGFYPSDIAVEWESNGQPENNYKTTPPVLDSDGSFFLYSKLTVDKSRWQQ<br>GNVFSCSVMHEALHNHYTQKSLSLSPG |
| 133 | DR2455P<br>3xAla p40Fc<br>precursor<br>protein | MCHQQLVISWFSLVFLASPLVAIWELKKDVYVVELDWYPDAPGEMVVLTCDT<br>PEEDGITWTLDQSSEVLGSGKTLTIQVKEFGDAGQYTCHKGGEVLSHSLLLL<br>HKKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVLHEALHSHYTQKSLSLSPG |
| 134 | Nucleic acid<br>sequence<br>encoding<br>DR2455P | ATGTGCCATCAACAGCTTGTTATCAGCTGGTTCTCATTGGTCTTCCTGGCAA<br>GCCCACTGGTGGCAATCTGGGAACTGAAGAAAGACGTGTACGTAGTGGAACT<br>GGACTGGTATCCTGACGCTCCTGGGGAGATGGTCGTTCTGACCTGCGATACC<br>CCGGAAGAGGATGGAATTACCTGGACCCTCGACCAGTCTTCAGAAGTGCTGG<br>GCAGCGGAAAAACACTGACCATTCAGGTGAAGGAGTTCGGCGATGCCGGACA<br>GTACACCTGCCATAAGGGTGGCGAAGTGTTGTCCCATAGCTTGCTGCTCCTG<br>CATAAAAAGGAGGACGGAATCTGGAGCACCGACATTCTGAAGGACCAGAAGG<br>AACCAAAGAACAAACATTTCTGCGTTGCGAGGCGAAAAACTACTCTGGCCG<br>CTTCACCTGTTGGTGGCTGACAACCATCAGCACCGATCTGACCTTCTCCGTG<br>AAGTCCTCACGCGGCTCCAGCGATCCTCAGGGTGTTACTTGCGGAGCTGCAA<br>CGCTTAGTGCGGAAAGAGTGAGGGGTGATAACAAGGAATACGAATACTCCGT<br>GGAATGTCAGGAAGATAGCGCCTGCCCTGCTGCCGAGGAATCATTGCCAATC<br>GAGGTGATGGTGGACGCCGTGCATAAGCTGAAGTACGAAAATTACACGAGCA<br>GTTTTTTCATTCGCGATATCATTAAGCCAGACCCTCCCAAAAACTTGCAGCT<br>GAAGCCTCTGAAGAACAGTAGGCAGGTCGAGGTTTCTTGGGAATACCCGGAT<br>ACTTGGTCCACCCCTCACAGCTATTTTTCCTTGACGTTCTGCGTCCAGGTGC<br>AAGGCAAGTCCAAGCGGGAAAAAAAGGACAGGGTGTTTACCGATAAGACTAG<br>CGCCACTGTGATTTGCCGTAAAAACGCTAGTATTTCCGTGCGTGCCCAAGAC<br>CGCTACTATAGCTCCAGCTGGTCCGAGTGGGCCAGCGTTCCCTGTTCCGGCG<br>GTGGGGGCTCCGGCGGTGGCGGTTCCGAGCCTAAGAGTAGCGACAAGACTCA<br>CACCTGTCCCCTTGTCCCGCGCCGGAGGCCGCTGGAGGTCCTTCAGTATTC<br>CTGTTTCCTCCAAAGCCTAAAGATACCCTGATGATCTCTCGCACGCCAGAGG<br>TTACTTGCGTGGTAGTGGACGTATCCCACGAAGATCCTGAAGTCAAGTTCAA<br>CTGGTACGTCGATGGAGTGGAGGTGCATAACGCTAAGACAAAACCAAGAGAG<br>GAACAGTACAACTCTACATACCGGGTTGTGTCCGTGCTGACAGTGCTGCACC<br>AAGACTGGCTTAATGGCAAAGAGTATAAGTGCAAAGTCTCTAACAAAGCCCT<br>GGCCGCCCCCATTGAAAAGACTATTAGCAAAGCTAAGGGCCAACCGAGGGAG<br>CCACAGGTTTACACGCTGCCTCCATGCCGTGACGAACTCACCAAGAATCAGG<br>TGTCCCTGTGGTGTTTGGTGAAAGGCTTTTACCCCAGCGATATCGCCGTGGA<br>GTGGGAGAGCAATGGCCAGCCTGAAAATAACTATAAAACAACCCCACCCGTG<br>CTGGACAGTGACGGTTCCTTCTTTTTGTATTCTAAGCTGACCGTGGACAAAA<br>GCAGGTGGCAACAGGGAAACGTCTTTTCTTGCAGTGCTGCACGAGGCCCT<br>CCACTCTCACTATACGCAGAAGTCTCTGTCTCTGTCCCCAGGC |
| 135 | DR2455M<br>3xAla p40Fc<br>mature protein | IWELKKDVYVVELDWYPDAPGEMVVLTCDTPEEDGITWTLDQSSEVLGSGKT<br>LTIQVKEFGDAGQYTCHKGGEVLSHSLLLLHKKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR |

| | | |
|---|---|---|
| 136 | DR2456P p40 LALA PA K282G | MCHQQLVISWFSLVFLASPLVAIWELKKDVYVVELDWYPDAPGEMVVLTCDT<br>PEEDGITWTLDQSSEVLGSGKTLTIQVKEFGDAGQYTCHKGGEVLSHSLLLL<br>HKKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSGREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVESCSVLHEALHSHYTQKSLSLSPG |
| 137 | Nucleic acid sequence encoding DR2456P | ATGTGCCATCAACAGCTCGTTATCAGCTGGTTCTCTCTTGTGTTCCTTGCTT<br>CCCCTCTTGTGGCAATTTGGGAGCTTAAAAAGGACGTTTACGTAGTGGAGCT<br>GGACTGGTATCCAGACGCGCCGGGTGAGATGGTAGTGTTGACCTGTGACACC<br>CCAGAAGAGGACGGAATCACCTGGACATTGGATCAGAGTTCGAGGTGCCTCG<br>GCAGCGGCAAGACACTGACCATCCAGGTGAAAGAATTTGGTGACGCCGGTCA<br>ATACACTTGTCACAAGGGTGGCGAGGTGTTGTCTCACTCCCTTCTGCTCCTT<br>CATAAAAAGGAAGACGGCATCTGGAGTACGGACATCCTGAAGGACCAGAAGG<br>AGCCTAAGAATAAGACCTTCCTGCGTTGCGAGGCCAAGAACTACTCTGGCCG<br>CTTTACTTGTTGGTGGCTCACAACTATCTCAACCGACCTGACCTTTTCTGTA<br>AAAAGCTCTCGGGGCAGCTCCGATCCTCAGGGTGTTACTTGCGGGGCAGCCA<br>CCCTGAGCGCCGAGCGTGTGCGCGGCGACAATAAAGAGTACGAATACTCTGT<br>TGAGTGTCAGGAGGACTCAGCTTGCCCCGCAGCGGAAGAGTCTTTGCCTATC<br>GAGGTCATGGTGGACGCCGTGCATAAGCTGAAATACGAGAATTATACAAGCT<br>CATTCTTTATCCGTGATATTATCAAGCCCGATCCCCCGAAGAATCTCCAGCT<br>GAAACCCCTGAAGAACTCCCGCCAGGTCGAGGTGAGCTGGGAGTACCCCGAT<br>ACCTGGAGTACTCCCCACAGCTATTTCAGTCTCACCTTTTGCGTGCAGGTGC<br>AGGGAAAGTCTGGTCGCGAGAAGAAAGATCGCGTATTTACCGATAAGACCAG<br>TGCTACTGTCATTTGCCGCAAAAACGCGAGCATCTCCGTTCGCGCTCAGGAC<br>CGCTACTATTCTAGCTCATGGTCAGAGTGGGCCAGTGTACCTTGTAGCGGCG<br>GAGGGGGTAGCGGTGGCGGTGGCTCCGAGCCCAAAAGTAGCGACAAGACACA<br>CACCTGTCCCCCTTGCCCGGCTCCCGAGGCCGCTGGAGGCCCCTCCGTATTC<br>CTTTTTCCCCCGAAGCCTAAGGACACCCTTATGATCTCTCGTACCCCTGAGG<br>TGACTTGCGTTGTCGTTGATGTCAGCCACGAAGATCCAGAGGTGAAGTTCAA<br>CTGGTATGTCGATGGCGTTGAGGTCCATAACGCTAAAACAAAGCCCAGGGAG<br>GAACAGTATAACTCCACTTACCGCGTCGTGTCCGTTCTGACAGTATTGCATC<br>AAGATTGGCTGAACGGCAAGGAGTACAAGTCAAGGTCTCAAACAAGGCCTT<br>GGCAGCTCCTATTGAGAAGACCATCAGCAAGGCGAAGGGACAGCCTCGGGAA<br>CCCCAGGTCTACACGCTGCCCCCTTGCCGCGATGAACTCACTAAAAATCAGG<br>TGTCCCTGTGGTGCCTCGTGAAGGGATTCTACCCTAGCGATATTGCTGTGGA<br>ATGGGAAAGCAACGGTCAGCCTGAAAACAATTACAAGACAACTCCACCTGTC<br>TTGGATTCAGATGGCAGCTTTTTCCTGTACTCCAAGCTCACCGTGGACAAGT<br>CCCGTTGGCAACAGGGTAACGTGTTTTCTTGCAGCGTTCTTCACGAAGCCCT<br>GCACTCCCATTATACTCAGAAGTCCTTGTCACTTTCACCTGGG |
| 138 | DR2456M 3xAla p40Fc mature protein | IWELKKDVYVVELDWYPDAPGEMVVLTCDTPEEDGITWTLDQSSEVLGSGKT<br>LTIQVKEFGDAGQYTCHKGGEVLSHSLLLLHKKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCSGGGGSG<br>GGGSEPKSSDKTHTCPPCPAPEAAGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALAAPIEKTISKAKGQPREPQVYTLPPCRDELTKNQVSLWC<br>LVKGFYPSDIAVEWESNGQPENNYKTTPPVLDSDGSFFLYSKLTVDKSRWQQ<br>GNVFSCSVLHEALHSHYTQKSLSLSPG |
| 139 | DR2086P precursor with signal human p40 E81A F82A K106A K260Q hIgG1 KiH knob C220S LALAPA S354C M428L N434S DelK447 | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSQREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVLHEALHSHYTQKSLSLSPG |

| | | |
|---|---|---|
| Informal Sequence Listing | | |
| 140 | Nucleic Acid Sequence encoding DR2086P | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSQREKKDRVFTDKTSATVICRKNASISVRAQD RYYSSSWSEWASVPCSGGGGSGGGGSEPKSSDKTHTCPPCPAPEAAGGPSVF LFPPKPKDTLMISRTPEVTCVVVDVSHEDPEVKFNWYVDGVEVHNAKTKPRE EQYNSTYRVVSVLTVLHQDWLNGKEYKCKVSNKALAAPIEKTISKAKGQPRE PQVYTLPPCRDELTKNQVSLWCLVKGFYPSDIAVEWESNGQPENNYKTTPPV LDSDGSFFLYSKLTVDKSRWQQGNVFSCSVLHEALHSHYTQKSLSLSPG |
| 141 | DR2086M human p40 E81A F82A K106A K260Q hIgG1 KiH knob C220S LALAPA S354C M428L N434S DelK447 | IWELKKDVYVVELDWYPDAPGEMVVLTCDTPEEDGITWTLDQSSEVLGSGKT LTIQVKAAGDAGQYTCHKGGEVLSHSLLLLHAKEDGIWSTDILKDQKEPKNK TFLRCEAKNYSGRFTCWWLTTISTDLTFSVKSSRGSSDPQGVTCGAATLSAE RVRGDNKEYEYSVECQEDSACPAAEESLPIEVMVDAVHKLKYENYTSSFFIR DIIKPDPPKNLQLKPLKNSRQVEVSWEYPDTWSTPHSYFSLTFCVQVQGKSQ REKKDRVFTDKTSATVICRKNASISVRAQDRYYSSSWSEWASVPCSGGGGSG GGGSEPKSSDKTHTCPPCPAPEAAGGPSVFLFPPKPKDTLMISRTPEVTCVV VDVSHEDPEVKFNWYVDGVEVHNAKTKPREEQYNSTYRVVSVLTVLHQDWLN GKEYKCKVSNKALAAPIEKTISKAKGQPREPQVYTLPPCRDELTKNQVSLWC LVKGFYPSDIAVEWESNGQPENNYKTTPPVLDSDGSFFLYSKLTVDKSRWQQ GNVFSCSVLHEALHSHYTQKSLSLSPG |
| 142 | DR2087P precursor with signal human p40 E81A F82A K106A K260N hIgG1 KiH knob C220S LALAPA S354C M428L N434S DelK447 | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSNREKKDRVFTDKTSATVICRKNASISVRAQD RYYSSSWSEWASVPCSGGGGSGGGGSEPKSSDKTHTCPPCPAPEAAGGPSVF LFPPKPKDTLMISRTPEVTCVVVDVSHEDPEVKENWYVDGVEVHNAKTKPRE EQYNSTYRVVSVLTVLHQDWLNGKEYKCKVSNKALAAPIEKTISKAKGQPRE PQVYTLPPCRDELTKNQVSLWCLVKGFYPSDIAVEWESNGQPENNYKTTPPV LDSDGSFFLYSKLTVDKSRWQQGNVFSCSVLHEALHSHYTQKSLSLSPG |
| 143 | Nucleic Acid Sequence encoding DR2087P | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSNREKKDRVFTDKTSATVICRKNASISVRAQD RYYSSSWSEWASVPCSGGGGSGGGGSEPKSSDKTHTCPPCPAPEAAGGPSVF LFPPKPKDTLMISRTPEVTCVVVDVSHEDPEVKFNWYVDGVEVHNAKTKPRE EQYNSTYRVVSVLTVLHQDWLNGKEYKCKVSNKALAAPIEKTISKAKGQPRE PQVYTLPPCRDELTKNQVSLWCLVKGFYPSDIAVEWESNGQPENNYKTTPPV LDSDGSFFLYSKLTVDKSRWQQGNVFSCSVLHEALHSHYTQKSLSLSPG |
| 144 | DR2087M Mature human p40 E81A F82A K106A K260N hIgG1 KiH knob C220S LALAPA S354C M428L N434S DelK447 | IWELKKDVYVVELDWYPDAPGEMVVLTCDTPEEDGITWTLDQSSEVLGSGKT LTIQVKAAGDAGQYTCHKGGEVLSHSLLLLHAKEDGIWSTDILKDQKEPKNK TFLRCEAKNYSGRFTCWWLTTISTDLTFSVKSSRGSSDPQGVTCGAATLSAE RVRGDNKEYEYSVECQEDSACPAAEESLPIEVMVDAVHKLKYENYTSSFFIR DIIKPDPPKNLQLKPLKNSRQVEVSWEYPDTWSTPHSYFSLTFCVQVQGKSN REKKDRVFTDKTSATVICRKNASISVRAQDRYYSSSWSEWASVPCSGGGGSG GGGSEPKSSDKTHTCPPCPAPEAAGGPSVFLFPPKPKDTLMISRTPEVTCVV VDVSHEDPEVKFNWYVDGVEVHNAKTKPREEQYNSTYRVVSVLTVLHQDWLN GKEYKCKVSNKALAAPIEKTISKAKGQPREPQVYTLPPCRDELTKNQVSLWC LVKGFYPSDIAVEWESNGQPENNYKTTPPVLDSDGSFFLYSKLTVDKSRWQQ GNVFSCSVLHEALHSHYTQKSLSLSPG |
| 145 | DR2090P precursor with signal human p40 E81A F82A K106A K260Q hIgG1 KiH knob C220S LALAPA S354C DelK447 | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSQREKKDRVFTDKTSATVICRKNASISVRAQD RYYSSSWSEWASVPCSGGGGSGGGGSEPKSSDKTHTCPPCPAPEAAGGPSVF LFPPKPKDTLMISRTPEVTCVVVDVSHEDPEVKENWYVDGVEVHNAKTKPRE EQYNSTYRVVSVLTVLHQDWLNGKEYKCKVSNKALAAPIEKTISKAKGQPRE PQVYTLPPCRDELTKNQVSLWCLVKGFYPSDIAVEWESNGQPENNYKTTPPV LDSDGSFFLYSKLTVDKSRWQQGNVFSCSVMHEALHNHYTQKSLSLSPG |
| 146 | Nucleic Acid Sequence encoding DR2090P | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI |

| | | |
|---|---|---|
| | | EVMVDAVHKLKYENYTSSFFIRDIIKPDPPKNLQLKPLKNSRQVEVSWEYPD<br>TWSTPHSYFSLTFCVQVQGKSQREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 147 | DR2090M<br>mature<br>human p40 E81A<br>F82A K106A K260Q<br>hIgG1 KiH knob<br>C220S LALAPA<br>S354C DelK447 | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSQREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 148 | DR2091P<br>precursor with<br>signal<br>human p40 E81A<br>F82A K106A K260N<br>hIgG1 KiH knob<br>C220S LALAPA<br>S354C DelK447 | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSNREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVESCSVMHEALHNHYTQKSLSLSPG |
| 149 | Nucleic Acid<br>Sequence<br>encoding DR2091P | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSNREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 150 | DR2091M<br>mature<br>human p40 E81A<br>F82A K106A K260N<br>hIgG1 KiH knob<br>C220S LALAPA<br>S354C DelK447 | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSN<br>REKKDRVFTDKTSATVICRKNASISVRAQDRYYSSSWSEWASVPCSGGGGSG<br>GGGSEPKSSDKTHTCPPCPAPEAAGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALAAPIEKTISKAKGQPREPQVYTLPPCRDELTKNQVSLWC<br>LVKGFYPSDIAVEWESNGQPENNYKTTPPVLDSDGSFFLYSKLTVDKSRWQQ<br>GNVFSCSVMHEALHNHYTQKSLSLSPG |
| 151 | DR2092P<br>precursor with<br>signal<br>human p40 E81A<br>F82A K106A K260G<br>hIgG1 KiH knob<br>C220S LALAPA<br>S354C DelK447 | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSGREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 152 | Nucleic Acid<br>Sequence<br>encoding DR2092P | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSGREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE |

| | Informal Sequence Listing |
|---|---|
| | PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 153 DR2092M<br>human p40 E81A<br>F82A K106A K260G<br>hIgG1 KiH knob<br>C220S LALAPA<br>S354C DelK447 | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCSGGGGSG<br>GGGSEPKSSDKTHTCPPCPAPEAAGGPSVFLFPPKPKDTLMISRTPEVTCVV<br>VDVSHEDPEVKFNWYVDGVEVHNAKTKPREEQYNSTYRVVSVLTVLHQDWLN<br>GKEYKCKVSNKALAAPIEKTISKAKGQPREPQVYTLPPCRDELTKNQVSLWC<br>LVKGFYPSDIAVEWESNGQPENNYKTTPPVLDSDGSFFLYSKLTVDKSRWQQ<br>GNVFSCSVMHEALHNHYTQKSLSLSPG |
| 154 DR1535P<br>Precursor | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD<br>QNMLAVIDELMQALNENSETVPQKSSLEEPDFYKTKIKLCILLHAFRIRAVT<br>IDRVMSYLNASGGGGSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVCTLPPSRDELTKNQVSLSCAVKGFYPSDIAVEWESNGQPENNYKTTPPV<br>LDSDGSFFLVSKLTVDKSRWQQGNVFSCSVMHEALHNHYTQKSLSLSPG |
| 155 hP40<br>E81A/F82A/<br>K106A/K282G | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 156 hP40<br>E81A/F82A/<br>K106A/K282A, | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRADNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 157 hP40<br>E81A/F82A/<br>K106A/K282N | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRNDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 158 hP40<br>E81A/F82A/<br>K106A/K282Q | IWELKKDVYVVELDWYPDAPGEMVVLTCDTPEEDGITWTLDQSSEVLGSGKT<br>LTIQVKAAGDAGQYTCHKGGEVLSHSLLLLHAKEDGIWSTDILKDQKEPKNK<br>TFLRCEAKNYSGRFTCWWLTTISTDLTFSVKSSRGSSDPQGVTCGAATLSAE<br>RVRQDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 159 hP40<br>E81A/F82A/K282G | IWELKKDVYVVELDWYPDAPGEMVVLTCDTPEEDGITWTLDQSSEVLGSGKT<br>LTIQVKAAGDAGQYTCHKGGEVLSHSLLLLHKKEDGIWSTDILKDQKEPKNK<br>TFLRCEAKNYSGRFTCWWLTTISTDLTFSVKSSRGSSDPQGVTCGAATLSAE<br>RVRGDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 160 hP40<br>E81A/F82A/K282A | IWELKKDVYVVELDWYPDAPGEMVVLTCDTPEEDGITWTLDQSSEVLGSGKT<br>LTIQVKAAGDAGQYTCHKGGEVLSHSLLLLHKKEDGIWSTDILKDQKEPKNK<br>TFLRCEAKNYSGRFTCWWLTTISTDLTFSVKSSRGSSDPQGVTCGAATLSAE<br>RVRADNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 161 hP40<br>E81A/F82A/K282N | IWELKKDVYVVELDWYPDAPGEMVVLTCDTPEEDGITWTLDQSSEVLGSGKT<br>LTIQVKAAGDAGQYTCHKGGEVLSHSLLLLHKKEDGIWSTDILKDQKEPKNK<br>TFLRCEAKNYSGRFTCWWLTTISTDLTFSVKSSRGSSDPQGVTCGAATLSAE<br>RVRNDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 162 E81A/F82A/K282Q | IWELKKDVYVVELDWYPDAPGEMVVLTCDTPEEDGITWTLDQSSEVLGSGKT<br>LTIQVKAAGDAGQYTCHKGGEVLSHSLLLLHKKEDGIWSTDILKDQKEPKNK<br>TFLRCEAKNYSGRFTCWWLTTISTDLTFSVKSSRGSSDPQGVTCGAATLSAE |

| | | |
|---|---|---|
| | | RVRQDNKEYEYSVECQEDSACPAAEESLPIEVMVDAVHKLKYENYTSSFFIR<br>DIIKPDPPKNLQLKPLKNSRQVEVSWEYPDTWSTPHSYFSLTFCVQVQGKSG<br>REKKDRVFTDKTSATVICRKNASISVRAQDRYYSSSWSEWASVPCS |
| 163 | DR1442P | MCHQQLVISWFSLVELASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSEPKSSDKTHTCPPCPAPEAAGGPSVFLFPPKPKDTL<br>MISRTPEVTCVVVDVSHEDPEVKFNWYVDGVEVHNAKTKPREEQYNSTYRVV<br>SVLTVLHQDWLNGKEYKCKVSNKALAAPIEKTISKAKGQPREPQVYTLPPCR<br>DELTKNQVSLWCLVKGFYPSDIAVEWESNGQPENNYKTTPPVLDSDGSFFLY<br>SKLTVDKSRWQQGNVFSCSVMHEALHNHYTQKSLSLSPG |
| 164 | DR1535P | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD<br>QNMLAVIDELMQALNFNSETVPQKSSLEEPDFYKTKIKLCILLHAFRIRAVT<br>IDRVMSYLNASGGGGSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVCTLPPSRDELTKNQVSLSCAVKGFYPSDIAVEWESNGQPENNYKTTPPV<br>LDSDGSFFLVSKLTVDKSRWQQGNVFSCSVMHEALHNHYTQKSLSLSPG |
| 165 | DR1536P | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD<br>QNMLAVIDELMQALNFNSETVPQKSSLEEPDFYKTKIKLCILLHAFRIRAVT<br>IDRVMSYLNASGGGGSGGGGSEPKSSDKTHTCPPCPAPEAAGGPSVFLEPPK<br>PKDTLMISRTPEVTCVVVDVSHEDPEVKFNWYVDGVEVHNAKTKPREEQYNS<br>TYRVVSVLTVLHQDWLNGKEYKCKVSNKALAAPIEKTISKAKGQPREPQVCT<br>LPPSRDELTKNQVSLSCAVKGFYPSDIAVEWESNGQPENNYKTTPPVLDSDG<br>SFFLVSKLTVDKSRWQQGNVFSCSVMHEALHNHYTQKSLSLSPG |
| 166 | DR1537P | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSGGGGSGGGGSEPKSSDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 167 | DR1572P | MCPARSLLLVATLVLLDHLSLARNLPVATPDPGMFPCLHHSQNLLRAVSNML<br>QKARQTLEFYPCTSEEIDHEDITKDKTSTVEACLPLELTKNESCLNSRETSF<br>ITNGSCLASRKTSFMMALCLSSIYEDLKMYQVEFKTMNAKLLMDPKRQIFLD<br>QNMLAVIDELMQALNFNSETVPQKSSLEEPDFYKTKIKLCILLHAFRIRAVT<br>IDRVMSYLNASGGGGSGGGGSEPKSCDKTHTCPPCPAPEAAGGPSVFLFPPK<br>PKDTLMISRTPEVTCVVVDVSHEDPEVKFNWYVDGVEVHNAKTKPREEQYNS<br>TYRVVSVLTVLHQDWLNGKEYKCKVSNKALAAPIEKTISKAKGQPREPQVCT<br>LPPSRDELTKNQVSLSCAVKGFYPSDIAVEWESNGQPENNYKTTPPVLDSDG<br>SFFLVSKLTVDKSRWQQGNVFSCSVMHEALHNHYTQKSLSLSPG |
| 168 | DR1573P | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSGGGGSGGGGSEPKSCDKTHTCPPCPAPEAAGGPSVF<br>LFPPKPKDTLMISRTPEVTCVVVDVSHEDPEVKFNWYVDGVEVHNAKTKPRE<br>EQYNSTYRVVSVLTVLHQDWLNGKEYKCKVSNKALAAPIEKTISKAKGQPRE<br>PQVYTLPPCRDELTKNQVSLWCLVKGFYPSDIAVEWESNGQPENNYKTTPPV<br>LDSDGSFFLYSKLTVDKSRWQQGNVFSCSVMHEALHNHYTQKSLSLSPG |
| 169 | DR1588P | MCHQQLVISWFSLVFLASPLVAIWELKKDVYVVELDWYPDAPGEMVVLTCDT<br>PEEDGITWTLDQSSEVLGSGKTLTIQVKAAGDAGQYTCHKGGEVLSHSLLLL<br>HAKEDGIWSTDILKDQKEPKNKTFLRCEAKNYSGRFTCWWLTTISTDLTFSV<br>KSSRGSSDPQGVTCGAATLSAERVRGDNKEYEYSVECQEDSACPAAEESLPI<br>EVMVDAVHKLKYENYTSSFFIRDIIKPDPPKNLQLKPLKNSRQVEVSWEYPD<br>TWSTPHSYFSLTFCVQVQGKSKREKKDRVFTDKTSATVICRKNASISVRAQD<br>RYYSSSWSEWASVPCSEPKSSDKTHTCPPCPAPEFEGGPSVFLFPPKPKDTL |

| | Informal Sequence Listing |
|---|---|
| | MISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPCR DELTKNQVSLWCLVKGFYPSDIAVEWESNGQPENNYKTTPPVLDSDGSFFLY SKLTVDKSRWQQGNVFSCSVMHEALHNHYTQKSLSLSPG |
| 170 DR1589P | MCPARSLLLVATLVLLDHLSLARNLPVATPDPGMFPCLHHSQNLLRAVSNML QKARQTLEFYPCTSEEIDHEDITKDKTSTVEACLPLELTKNESCLNSRETSF ITNGSCLASRKTSFMMALCLSSIYEDLKMYQVEFKTMNAKLLMDPKRQIFLD QNMLAVIDELMQALNFNSETVPQKSSLEEPDFYKTKIKLCILLHAFRIRAVT IDRVMSYLNASGGGGSGGGGSGGGGSEPKSS DKTHTCPPCPAPEFEGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPASIEKTISKAKGQPREPQVCTLPPSRDELTKNQVSLSCAVKGFYPSD IAVEWESNGQPENNYKTTPPVLDSDGSFFLVSKLTVDKSRWQQGNVFSCSVM HEALHNHYTQKSLSLSPG |
| 171 DR1590P | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSKREKKDRVFTDKTSATVICRKNASISVRAQD RYYSSSWSEWASVPCSEPKSSDKTHTCPPCPAPEAEGAPSVFLFPPKPKDTL MISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTL1573 LTKNQVSLWCLVKGFYPSDIAVEWESNGQPENNYKTTPPVLDSDGSFFLYSK LTVDKSRWQQGNVFSCSVMHEALHNHYTQKSLSLSPG |
| 172 DR1591P | MCPARSLLLVATLVLLDHLSLARNLPVATPDPGMFPCLHHSQNLLRAVSNML QKARQTLEFYPCTSEEIDHEDITKDKTSTVEACLPLELTKNESCLNSRETSF ITNGSCLASRKTSFMMALCLSSIYEDLKMYQVEFKTMNAKLLMDPKRQIFLD QNMLAVIDELMQALNFNSETVPQKSSLEEPDFYKTKIKLCILLHAFRIRAVT IDRVMSYLNASGGGGSGGGGSGGGGSEPKSSDKTHTCPPCPAPEAEGAPSVF LFPPKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQPRE PQVCTLPPSRDELTKNQVSLSCAVKGFYPSDIAVEWESNGQPENNYKTTPPV LDSDGSFFLVSKLTVDKSRWQQGNVFSCSVMHEALHNHYTQKSLSLSPG |
| 173 DR1595P | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSKREKKDRVFTDKTSATVICRKNASISVRAQD RYYSSSWSEWASVPCSGGGGSGGGGSEPKSSDKTHTCPPCPAPEAEGAPSVF LFPPKPKDTLMISRTPEVTCVVVDVSHEDPEVKFNWYVDGVEVHNAKTKPRE EQYNSTYRVVSVLTVLHQDWLNGKEYKCKVSNKALPSSIEKTISKAKGQPRE PQVYTLPPCRDELTKNQVSLWCLVKGFYPSDIAVEWESNGQPENNYKTTPPV LDSDGSFFLYSKLTVDKSRWQQGNVFSCSVMHEALHNHYTQKSLSLSPG |
| 174 DR1596P | MCPARSLLLVATLVLLDHLSLARNLPVATPDPGMFPCLHHSQNLLRAVSNML QKARQTLEFYPCTSEEIDHEDITKDKTSTVEACLPLELTKNESCLNSRETSF ITNGSCLASRKTSFMMALCLSSIYEDLKMYQVEFKTMNAKLLMDPKRQIFLD QNMLAVIDELMQALNFNSETVPQKSSLEEPDFYKTKIKLCILLHAFRIRAVT IDRVMSYLNASGGGGSGGGGSEPKSSDKTHTCPPCPAPEAEGAPSVFLFPPK PKDTLMISRTPEVTCVVVDVSHEDPEVKFNWYVDGVEVHNAKTKPREEQYNS TYRVVSVLTVLHQDWLNGKEYKCKVSNKALPSSIEKTISKAKGQPREPQVCT LPPSRDELTKNQVSLSCAVKGFYPSDIAVEWESNGQPENNYKTTPPVLDSDG SFFLVSKLTVDKSRWQQGNVFSCSVMHEALHNHYTQKSLSLSPG |
| 175 DR1597P | MCHQQLVISWFSLVFLASPLVAIWELKKDVYVVELDWYPDAPGEMVVLTCDT PEEDGITWTLDQSSEVLGSGKTLTIQVKAAGDAGQYTCHKGGEVLSHSLLLL HAKEDGIWSTDILKDQKEPKNKTFLRCEAKNYSGRFTCWWLTTISTDLTFSV KSSRGSSDPQGVTCGAATLSAERVRGDNKEYEYSVECQEDSACPAAEESLPI EVMVDAVHKLKYENYTSSFFIRDIIKPDPPKNLQLKPLKNSRQVEVSWEYPD TWSTPHSYFSLTFCVQVQGKSKREKKDRVFTDKTSATVICRKNASISVRAQD RYYSSSWSEWASVPCSGGGGSGGGGSEPKSSDKTHTCPPCPAPEAEGAPSVF LFPPKPKDTLMISRTPEVTCVVVDVSHEDPEVKFNWYVDGVEVHNAKTKPRE EQYNSTYRVVSVLTVLHQDWLNGKEYKCKVSNKALPSSIEKTISKAKGQPRE PQVYTLPPCRDELTKNQVSLWCLVKGFYPSDIAVEWESNGQPENNYKTTPPV LDSDGSFFLYSKLTVDKSRWQQGNVFSCSVLHEALHSHYTQKSLSLSPG |
| 176 DR1598P | MCPARSLLLVATLVLLDHLSLARNLPVATPDPGMFPCLHHSQNLLRAVSNML QKARQTLEFYPCTSEEIDHEDITKDKTSTVEACLPLELTKNESCLNSRETSF ITNGSCLASRKTSFMMALCLSSIYEDLKMYQVEFKTMNAKLLMDPKRQIFLD QNMLAVIDELMQALNFNSETVPQKSSLEEPDFYKTKIKLCILLHAFRIRAVT IDRVMSYLNASGGGGSGGGGSEPKSSDKTHTCPPCPAPEAEGAPSVFLFPPK |

| | | |
|---|---|---|
| | | PKDTLMISRTPEVTCVVVDVSHEDPEVKFNWYVDGVEVHNAKTKPREEQYNS<br>TYRVVSVLTVLHQDWLNGKEYKCKVSNKALPSSIEKTISKAKGQPREPQVCT<br>LPPSRDELTKNQVSLSCAVKGFYPSDIAVEWESNGQPENNYKTTPPVLDSDG<br>SFFLVSKLTVDKSRWQQGNVFSCSVLHEALHSHYTQKSLSLSPG |
| 177 | Human p19P<br>Precursor<br>Wild type<br>UniProt Ref:<br>Q9NPF7 | MLGSRAVMLLLLLPWTAQGRAVPGGSSPAWTQCQQLSQKLCTLAWSAHPLVG<br>HMDLREEGDEETTNDVPHIQCGDGCDPQGLRDNSQFCLQRIHQGLIFYEKLL<br>GSDIFTGEPSLLPDSPVGQLHASLLGLSQLLQPEGHHWETQQIPSLSPSQPW<br>QRLLLRFKILRSLQAFVAVAARVFAHGAATLSP |
| 178 | Human P19M<br>Mature<br>Wild type p19<br>UniProt Ref:<br>Q9NPF7 | RAVPGGSSPAWTQCQQLSQKLCTLAWSAHPLVGHMDLREEGDEETTNDVPHI<br>QCGDGCDPQGLRDNSQFCLQRIHQGLIFYEKLLGSDIFTGEPSLLPDSPVGQ<br>LHASLLGLSQLLQPEGHHWETQQIPSLSPSQPWQRLLLRFKILRSLQAFVAV<br>AARVFAHGAATLSP |
| 179 | Wild type human<br>p35 signal<br>peptide | MCPARSLLLVATLVLLDHLSLA |
| 180 | Wild type human<br>p40 signal<br>peptide | MCHQQLVISWFSLVFLASPLVA |
| 181 | mREH | APTSSSTSSSTAEAQQQQQHLEQLRMDLEELLSRMENYRNLKLPRMLTFKFY<br>LPKQATELKDLQCLEDELGPLRHVLDLTQSKSFQLEDAENFISNIRVTVVKL<br>KGSDNTFECQFDDESATVVDFLRRWIAFCHSIISTSPQ |

We claim:

1. A heterodimeric hIL12Fc mutein, the heterodimeric hIL12Fc mutein comprising a first polypeptide having the sequence of any one of SEQ ID NOS: 80, 83, 85, 86, 88, 90, 92, 121, 129, 132, 135, 138, 141, 144, 147, 150, and 153; and
   a second polypeptide having the sequence of any one of SEQ ID NOS: 81, 82, 84, 87, 89, 91, 93, and 124.

2. The heterodimeric hIL12Fc mutein of claim 1, wherein the first polypeptide has the sequence of SEQ ID NO: 80 and the second polypeptide has the sequence of SEQ ID NO: 81.

3. The heterodimeric hIL12Fc mutein of claim 1, wherein the first polypeptide has the sequence of SEQ ID NO: 121 and the second polypeptide has the sequence of SEQ ID NO: 124.

4. The heterodimeric hIL12Fc mutein of claim 1, wherein the first polypeptide has the sequence of SEQ ID NO: 83 and the second polypeptide has the sequence of SEQ ID NO: 82.

5. The heterodimeric hIL12Fc mutein of claim 1, wherein the first polypeptide has the sequence of SEQ ID NO: 141 and the second polypeptide has the sequence of SEQ ID NO: 124.

6. The heterodimeric hIL12Fc mutein of claim 1, wherein the first polypeptide has the sequence of SEQ ID NO: 144 and the second polypeptide has the sequence of SEQ ID NO: 124.

7. The heterodimeric hIL12Fc mutein of claim 1, wherein the first polypeptide has the sequence of SEQ ID NO: 129 and the second polypeptide has the sequence of SEQ ID NO: 124.

8. The heterodimeric hIL12Fc mutein of claim 1, wherein the first polypeptide has the sequence of SEQ ID NO: 147 and the second polypeptide has the sequence of SEQ ID NO: 82.

9. The heterodimeric hIL12Fc mutein of claim 1, wherein the first polypeptide has the sequence of SEQ ID NO: 150 and the second polypeptide has the sequence of SEQ ID NO: 82.

10. The heterodimeric hIL12Fc mutein of claim 1, wherein the first polypeptide has the sequence of SEQ ID NO: 153 and the second polypeptide has the sequence of SEQ ID NO: 82.

11. The heterodimeric hIL12Fc mutein of claim 1, wherein the first polypeptide has the sequence of SEQ ID NO: 135 and the second polypeptide has the sequence of SEQ ID NO: 124.

12. The heterodimeric hIL12Fc mutein of claim 1, wherein the first polypeptide has the sequence of SEQ ID NO: 138 and the second polypeptide has the sequence of SEQ ID NO: 124.

13. The heterodimeric hIL12Fc mutein of claim 1, wherein the first polypeptide and the second polypeptide are linked by at least one interchain disulfide bond.

14. The heterodimeric hIL12Fc mutein of claim 1, wherein the heterodimeric hIL12Fc mutein is PEGylated.

15. A pharmaceutically acceptable formulation comprising as an active ingredient a heterodimeric hIL12Fc mutein of claim 1.

* * * * *

SEQUENCE LISTING

```
Sequence total quantity: 181
SEQ ID NO: 1             moltype = AA  length = 219
FEATURE                  Location/Qualifiers
REGION                   1..219
                         note = Description of sequence: Pro-hP35 (wt) Uniprot
                          P29459 w/native signal sequence
source                   1..219
                         mol_type = protein
                         organism = synthetic construct
SEQUENCE: 1
MCPARSLLLV ATLVLLDHLS LARNLPVATP DPGMFPCLHH SQNLLRAVSN MLQKARQTLE  60
FYPCTSEEID HEDITKDKTS TVEACLPLEL TKNESCLNSR ETSFITNGSC LASRKTSFMM  120
ALCLSSIYED LKMYQVEFKT MNAKLLMDPK RQIFLDQNML AVIDELMQAL NFNSETVPQK  180
SSLEEPDFYK TKIKLCILLH AFRIRAVTID RVMSYLNAS                        219

SEQ ID NO: 2             moltype = AA  length = 197
FEATURE                  Location/Qualifiers
REGION                   1..197
                         note = Description of sequence: Mature hP35 (wt) Uniprot
                          P29459 (w/o signal sequence)
source                   1..197
                         mol_type = protein
                         organism = synthetic construct
SEQUENCE: 2
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                197

SEQ ID NO: 3             moltype = AA  length = 328
FEATURE                  Location/Qualifiers
REGION                   1..328
                         note = Description of sequence: Pro wt hP40 Uniprot P29460
                          Pre-protein with native signal sequence
source                   1..328
                         mol_type = protein
                         organism = synthetic construct
SEQUENCE: 3
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
```

```
LQLKPLKNSR QVEVSWEYPD TWSTPHSYFS LTFCVQVQGK SKREKKDRVF TDKTSATVIC   300
RKNASISVRA QDRYYSSSWS EWASVPCS                                     328

SEQ ID NO: 4            moltype = AA  length = 306
FEATURE                 Location/Qualifiers
REGION                  1..306
                        note = Description of sequence: Mature wt hP40 Uniprot
                        P29460 (w/o signal sequence)
source                  1..306
                        mol_type = protein
                        organism = synthetic construct
SEQUENCE: 4
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                             306

SEQ ID NO: 5            moltype = AA  length = 328
FEATURE                 Location/Qualifiers
REGION                  1..328
                        note = Description of sequence: Pro-hP40 2xAla E81A F82A
                        (w/ signal sequence)
source                  1..328
                        mol_type = protein
                        organism = synthetic construct
SEQUENCE: 5
MCHQQLVISW FSLVFLASPL VAIWELKKDV YVVELDWYPD APGEMVVLTC DTPEEDGITW   60
TLDQSSEVLG SGKTLTIQVK AAGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                     328

SEQ ID NO: 6            moltype = AA  length = 306
FEATURE                 Location/Qualifiers
REGION                  1..306
                        note = Description of sequence: Mature hP40 2xAla E81A F82A
                        (w/o signal sequence))
source                  1..306
                        mol_type = protein
                        organism = synthetic construct
SEQUENCE: 6
IWELKKDVYV VELDWYPDAP GEMVVLTCDT PEEDGITWTL DQSSEVLGSG KTLTIQVKAA   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                             306

SEQ ID NO: 7            moltype = AA  length = 328
FEATURE                 Location/Qualifiers
REGION                  1..328
                        note = Description of sequence: Pro-hP40 (w/signal
                        sequence) 3xAla E81A/F82A/K106A
source                  1..328
                        mol_type = protein
                        organism = synthetic construct
SEQUENCE: 7
MCHQQLVISW FSLVFLASPL VAIWELKKDV YVVELDWYPD APGEMVVLTC DTPEEDGITW   60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                     328

SEQ ID NO: 8            moltype = AA  length = 306
FEATURE                 Location/Qualifiers
REGION                  1..306
                        note = Description of sequence: Mature hP40 3xAla E81A F82A
                        K106A (w/o signal sequence)
source                  1..306
                        mol_type = protein
                        organism = synthetic construct
SEQUENCE: 8
IWELKKDVYV VELDWYPDAP GEMVVLTCDT PEEDGITWTL DQSSEVLGSG KTLTIQVKAA   60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
```

```
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCS                                                               306

SEQ ID NO: 9            moltype = AA   length = 328
FEATURE                 Location/Qualifiers
REGION                  1..328
                        note = Description of sequence: Pro-hP40 4xAla
                        E81A/F82A/K106A/ K217A (w/ signal sequence)
source                  1..328
                        mol_type = protein
                        organism = synthetic construct
SEQUENCE: 9
MCHQQLVISW FSLVFLASPL VAIWELKKDV YVVELDWYPD APGEMVVLTC DTPEEDGITW     60
TLDQSSEVLG SGKTLTIQVK AAGDAGQYTC HKGGEVLSHS LLLLHAKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAHALKY ENYTSSFFIR DIIKPDPPKN     240
LQLKPLKNSR QVEVSWEYPD TWSTPHSYFS LTFCVQVQGK SKREKKDRVF TDKTSATVIC    300
RKNASISVRA QDRYYSSSWS EWASVPCS                                       328

SEQ ID NO: 10           moltype = AA   length = 306
FEATURE                 Location/Qualifiers
REGION                  1..306
                        note = Description of sequence: Mature hP40 4xAla
                        E81A/F82A/K106A/ K217A (w/o signal sequence)
source                  1..306
                        mol_type = protein
                        organism = synthetic construct
SEQUENCE: 10
IWELKKDVYV VELDWYPDAP GEMVVLTCDT PEEDGITWTL DQSSEVLGSG KTLTIQVKAA     60
GDAGQYTCHK GGEVLSHSLL LLHAKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHALKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCS                                                               306

SEQ ID NO: 11           moltype = AA   length = 5
FEATURE                 Location/Qualifiers
REGION                  1..5
                        note = Description of sequence: wt IgG1 Upper Hinge EU
                        216-220
source                  1..5
                        mol_type = protein
                        organism = synthetic construct
SEQUENCE: 11
EPKSC                                                                  5

SEQ ID NO: 12           moltype = AA   length = 5
FEATURE                 Location/Qualifiers
REGION                  1..5
                        note = Description of sequence: IgG1 Upper hinge w/C220S
source                  1..5
                        mol_type = protein
                        organism = synthetic construct
SEQUENCE: 12
EPKSS                                                                  5

SEQ ID NO: 13           moltype = AA   length = 10
FEATURE                 Location/Qualifiers
REGION                  1..10
                        note = Description of sequence: IgG1 Lower Hinge EU 221-230
source                  1..10
                        mol_type = protein
                        organism = synthetic construct
SEQUENCE: 13
DKTHTCPPCP                                                            10

SEQ ID NO: 14           moltype = AA   length = 100
FEATURE                 Location/Qualifiers
REGION                  1..100
                        note = Description of sequence: hIgG1 CH2 Domain EU 238-337
                        sp-P0DOX5-240-339
source                  1..100
                        mol_type = protein
                        organism = synthetic construct
SEQUENCE: 14
PSVFLFPPKP KDTLMISRTP EVTCVVVDVS HEDPEVKFNW YVDGVEVHNA KTKPREEQYN     60
STYRVVSVLT VLHQDWLNGK EYKCKVSNKA LPAPIEKTIS                           100
```

-continued

```
SEQ ID NO: 15            moltype = AA  length = 97
FEATURE                  Location/Qualifiers
REGION                   1..97
                         note = Description of sequence: hIgG1 CH3 Domain EU346-442
                         sp-P0DOX5-348-444
source                   1..97
                         mol_type = protein
                         organism = synthetic construct
SEQUENCE: 15
PQVYTLPPSR DELTKNQVSL TCLVKGFYPS DIAVEWESNG QPENNYKTTP PVLDSDGSFF    60
LYSKLTVDKS RWQQGNVFSC SVMHEALHNH YTQKSLS                             97

SEQ ID NO: 16            moltype = AA  length = 227
FEATURE                  Location/Qualifiers
REGION                   1..227
                         note = Description of sequence: wt IgG1 Fc Monomer (lower
                         hinge/CH2/CH3) Uniprot Ref P0DOX5 EU 221-447
source                   1..227
                         mol_type = protein
                         organism = synthetic construct
SEQUENCE: 16
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 17            moltype = AA  length = 227
FEATURE                  Location/Qualifiers
REGION                   1..227
                         note = Description of sequence: Basic Fc KNOB T366W (no
                         upper hinge) IgG1 Fc Monomer (lower hinge/CH2/CH3
source                   1..227
                         mol_type = protein
                         organism = synthetic construct
SEQUENCE: 17
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 18            moltype = AA  length = 227
FEATURE                  Location/Qualifiers
REGION                   1..227
                         note = Description of sequence: Basic Fc HOLE
                         T366S/L368A/Y407V (no Upper hinge) IgG1 Fc Monomer (lower
                         hinge/CH2/CH3
source                   1..227
                         mol_type = protein
                         organism = synthetic construct
SEQUENCE: 18
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 19            moltype = AA  length = 232
FEATURE                  Location/Qualifiers
REGION                   1..232
                         note = Description of sequence: Basic EPKSC UH + IgG1 Fc
                         (LH/CH2/CH3) Knob Monomer KNOB T366W
source                   1..232
                         mol_type = protein
                         organism = synthetic construct
SEQUENCE: 19
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL WCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 20            moltype = AA  length = 232
FEATURE                  Location/Qualifiers
REGION                   1..232
                         note = Description of sequence: Basic EPKSC UH + IgG1 Fc
                         (LH/CH2/CH3) Knob Monomer HOLE T366S/L368A/Y407V
source                   1..232
                         mol_type = protein
                         organism = synthetic construct
SEQUENCE: 20
EPKSCDKTHT CPPCPAPELL GGPSVFLFPP KPKDTLMISR TPEVTCVVVD VSHEDPEVKF    60
```

```
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL SCAVKGFYPS DIAVEWESNG QPENNYKTTP    180
PVLDSDGSFF LVSKLTVDKS RWQQGNVFSC SVMHEALHNH YTQKSLSLSP GK           232

SEQ ID NO: 21            moltype = AA   length = 232
FEATURE                  Location/Qualifiers
REGION                   1..232
                         note = Description of sequence: C220S EPKSC UH + IgG1 Fc
                         (LH/CH2/CH3) Knob Monomer KNOB T366W
source                   1..232
                         mol_type = protein
                         organism = synthetic construct
SEQUENCE: 21
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL WCLVKGFYPS DIAVEWESNG QPENNYKTTP    180
PVLDSDGSFF LYSKLTVDKS RWQQGNVFSC SVMHEALHNH YTQKSLSLSP GK           232

SEQ ID NO: 22            moltype = AA   length = 232
FEATURE                  Location/Qualifiers
REGION                   1..232
                         note = Description of sequence: C220S EPKSC UH + IgG1 Fc
                         (LH/CH2/CH3) Knob Monomer HOLE T366S/L368A/Y407V
source                   1..232
                         mol_type = protein
                         organism = synthetic construct
SEQUENCE: 22
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL SCAVKGFYPS DIAVEWESNG QPENNYKTTP    180
PVLDSDGSFF LVSKLTVDKS RWQQGNVFSC SVMHEALHNH YTQKSLSLSP GK           232

SEQ ID NO: 23            moltype = AA   length = 232
FEATURE                  Location/Qualifiers
REGION                   1..232
                         note = Description of sequence: Wt EPKSC UH + +IgG1 Fc Knob
                         Monomer (LH/CH2/CH3) + T366W + S354C
source                   1..232
                         mol_type = protein
                         organism = synthetic construct
SEQUENCE: 23
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPCR DELTKNQVSL WCLVKGFYPS DIAVEWESNG QPENNYKTTP    180
PVLDSDGSFF LYSKLTVDKS RWQQGNVFSC SVMHEALHNH YTQKSLSLSP GK           232

SEQ ID NO: 24            moltype = AA   length = 232
FEATURE                  Location/Qualifiers
REGION                   1..232
                         note = Description of sequence: Wt EPKSC UH + + IgG1 Fc
                         (LH/CH2/CH3) HOLE T366S/L368A/Y407V + Y349C
source                   1..232
                         mol_type = protein
                         organism = synthetic construct
SEQUENCE: 24
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVCTLPPSR DELTKNQVSL SCAVKGFYPS DIAVEWESNG QPENNYKTTP    180
PVLDSDGSFF LVSKLTVDKS RWQQGNVFSC SVMHEALHNH YTQKSLSLSP GK           232

SEQ ID NO: 25            moltype = AA   length = 232
FEATURE                  Location/Qualifiers
REGION                   1..232
                         note = Description of sequence: C220S UH +IgG1 Fc Knob
                         Monomer (LH/CH2/CH3) + T366W + S354C
source                   1..232
                         mol_type = protein
                         organism = synthetic construct
SEQUENCE: 25
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPCR DELTKNQVSL WCLVKGFYPS DIAVEWESNG QPENNYKTTP    180
PVLDSDGSFF LYSKLTVDKS RWQQGNVFSC SVMHEALHNH YTQKSLSLSP GK           232

SEQ ID NO: 26            moltype = AA   length = 232
FEATURE                  Location/Qualifiers
REGION                   1..232
                         note = Description of sequence: C220S UH + IgG1 Fc
                         (LH/CH2/CH3) HOLE T366S/L368A/Y407V + Y349C
```

```
source                  1..232
                        mol_type = protein
                        organism = synthetic construct
SEQUENCE: 26
EPKSSDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVCTLPPSR DELTKNQVSL SCAVKGFYPS DIAVEWESNG QPENNYKTTP  180
PVLDSDGSFF LVSKLTVDKS RWQQGNVFSC SVMHEALHNH YTQKSLSLSP GK          232

SEQ ID NO: 27           moltype = AA  length = 8
FEATURE                 Location/Qualifiers
REGION                  1..8
                        note = Description of sequence: (G3A)2
source                  1..8
                        mol_type = protein
                        organism = synthetic construct
SEQUENCE: 27
GGGAGGGA                                                             8

SEQ ID NO: 28           moltype = AA  length = 12
FEATURE                 Location/Qualifiers
REGION                  1..12
                        note = Description of sequence: (G3A)4
source                  1..12
                        mol_type = protein
                        organism = synthetic construct
SEQUENCE: 28
GGGAGGGAGG GA                                                       12

SEQ ID NO: 29           moltype = AA  length = 12
FEATURE                 Location/Qualifiers
REGION                  1..12
                        note = Description of sequence: (G3AG2)2
source                  1..12
                        mol_type = protein
                        organism = synthetic construct
SEQUENCE: 29
GGGAGGGGGA GG                                                       12

SEQ ID NO: 30           moltype = AA  length = 12
FEATURE                 Location/Qualifiers
REGION                  1..12
                        note = Description of sequence: (G3S)3
source                  1..12
                        mol_type = protein
                        organism = synthetic construct
SEQUENCE: 30
GGGSGGGSGG GS                                                       12

SEQ ID NO: 31           moltype = AA  length = 12
FEATURE                 Location/Qualifiers
REGION                  1..12
                        note = Description of sequence: (G3SG2)2
source                  1..12
                        mol_type = protein
                        organism = synthetic construct
SEQUENCE: 31
GGGSGGGGGS GG                                                       12

SEQ ID NO: 32           moltype = AA  length = 10
FEATURE                 Location/Qualifiers
REGION                  1..10
                        note = Description of sequence: (G4A)2
source                  1..10
                        mol_type = protein
                        organism = synthetic construct
SEQUENCE: 32
GGGGAGGGGA                                                          10

SEQ ID NO: 33           moltype = AA  length = 15
FEATURE                 Location/Qualifiers
REGION                  1..15
                        note = Description of sequence: (G4a)3
source                  1..15
                        mol_type = protein
                        organism = synthetic construct
SEQUENCE: 33
GGGGAGGGGA GGGGA                                                    15
```

```
SEQ ID NO: 34              moltype = AA  length = 12
FEATURE                    Location/Qualifiers
REGION                     1..12
                           note = Description of sequence: (G4AG)2
source                     1..12
                           mol_type = protein
                           organism = synthetic construct
SEQUENCE: 34
GGGGAGGGGG AG                                                              12

SEQ ID NO: 35              moltype = AA  length = 14
FEATURE                    Location/Qualifiers
REGION                     1..14
                           note = Description of sequence: (G4AG2)2
source                     1..14
                           mol_type = protein
                           organism = synthetic construct
SEQUENCE: 35
GGGGAGGGGG GAGG                                                            14

SEQ ID NO: 36              moltype = AA  length = 10
FEATURE                    Location/Qualifiers
REGION                     1..10
                           note = Description of sequence: (G4S)2
source                     1..10
                           mol_type = protein
                           organism = synthetic construct
SEQUENCE: 36
GGGGSGGGGS                                                                 10

SEQ ID NO: 37              moltype = AA  length = 15
FEATURE                    Location/Qualifiers
REGION                     1..15
                           note = Description of sequence: (G4S)3
source                     1..15
                           mol_type = protein
                           organism = synthetic construct
SEQUENCE: 37
GGGGSGGGGS GGGGS                                                           15

SEQ ID NO: 38              moltype = AA  length = 12
FEATURE                    Location/Qualifiers
REGION                     1..12
                           note = Description of sequence: (G4SG)2
source                     1..12
                           mol_type = protein
                           organism = synthetic construct
SEQUENCE: 38
GGGGSGGGGG SG                                                              12

SEQ ID NO: 39              moltype = AA  length = 14
FEATURE                    Location/Qualifiers
REGION                     1..14
                           note = Description of sequence: (G4SG2)2
source                     1..14
                           mol_type = protein
                           organism = synthetic construct
SEQUENCE: 39
GGGGSGGGGG GSGG                                                            14

SEQ ID NO: 40              moltype = AA  length = 14
FEATURE                    Location/Qualifiers
REGION                     1..14
                           note = Description of sequence: (G5AG)2
source                     1..14
                           mol_type = protein
                           organism = synthetic construct
SEQUENCE: 40
GGGGGAGGGG GGAG                                                            14

SEQ ID NO: 41              moltype = AA  length = 14
FEATURE                    Location/Qualifiers
REGION                     1..14
                           note = Description of sequence: (G5SG)2
source                     1..14
                           mol_type = protein
                           organism = synthetic construct
SEQUENCE: 41
GGGGGSGGGG GGSG                                                            14
```

```
SEQ ID NO: 42            moltype = AA   length = 4
FEATURE                  Location/Qualifiers
REGION                   1..4
                         note = Description of sequence: G2AG
source                   1..4
                         mol_type = protein
                         organism = synthetic construct
SEQUENCE: 42
GGAG                                                                        4

SEQ ID NO: 43            moltype = AA   length = 4
FEATURE                  Location/Qualifiers
REGION                   1..4
                         note = Description of sequence: G3A
source                   1..4
                         mol_type = protein
                         organism = synthetic construct
SEQUENCE: 43
GGGA                                                                        4

SEQ ID NO: 44            moltype = AA   length = 8
FEATURE                  Location/Qualifiers
REGION                   1..8
                         note = Description of sequence: G3A-G3S
source                   1..8
                         mol_type = protein
                         organism = synthetic construct
SEQUENCE: 44
GGGAGGGS                                                                    8

SEQ ID NO: 45            moltype = AA   length = 12
FEATURE                  Location/Qualifiers
REGION                   1..12
                         note = Description of sequence: G3A-G3S- G3A
source                   1..12
                         mol_type = protein
                         organism = synthetic construct
SEQUENCE: 45
GGGAGGGSGG GA                                                              12

SEQ ID NO: 46            moltype = AA   length = 9
FEATURE                  Location/Qualifiers
REGION                   1..9
                         note = Description of sequence: G3A-G4S
source                   1..9
                         mol_type = protein
                         organism = synthetic construct
SEQUENCE: 46
GGGAGGGGS                                                                   9

SEQ ID NO: 47            moltype = AA   length = 9
FEATURE                  Location/Qualifiers
REGION                   1..9
                         note = Description of sequence: G3A-G4SA
source                   1..9
                         mol_type = protein
                         organism = synthetic construct
SEQUENCE: 47
GGGAGGGGA                                                                   9

SEQ ID NO: 48            moltype = AA   length = 6
FEATURE                  Location/Qualifiers
REGION                   1..6
                         note = Description of sequence: G3AG2
source                   1..6
                         mol_type = protein
                         organism = synthetic construct
SEQUENCE: 48
GGGAGG                                                                      6

SEQ ID NO: 49            moltype = AA   length = 12
FEATURE                  Location/Qualifiers
REGION                   1..12
                         note = Description of sequence: G3AG2 G4AG
source                   1..12
                         mol_type = protein
                         organism = synthetic construct
SEQUENCE: 49
```

```
GGGAGGGGGG AG                                                               12

SEQ ID NO: 50           moltype = AA  length = 4
FEATURE                 Location/Qualifiers
REGION                  1..4
                        note = Description of sequence: G3S
source                  1..4
                        mol_type = protein
                        organism = synthetic construct
SEQUENCE: 50
GGGS                                                                         4

SEQ ID NO: 51           moltype = AA  length = 12
FEATURE                 Location/Qualifiers
REGION                  1..12
                        note = Description of sequence: G3S-G3A-GGGS
source                  1..12
                        mol_type = protein
                        organism = synthetic construct
SEQUENCE: 51
GGGSGGGAGG GS                                                               12

SEQ ID NO: 52           moltype = AA  length = 12
FEATURE                 Location/Qualifiers
REGION                  1..12
                        note = Description of sequence: G3SG2 G4SG
source                  1..12
                        mol_type = protein
                        organism = synthetic construct
SEQUENCE: 52
GGGSGGGGGG SG                                                               12

SEQ ID NO: 53           moltype = AA  length = 5
FEATURE                 Location/Qualifiers
REGION                  1..5
                        note = Description of sequence: G4A
source                  1..5
                        mol_type = protein
                        organism = synthetic construct
SEQUENCE: 53
GGGGA                                                                        5

SEQ ID NO: 54           moltype = AA  length = 15
FEATURE                 Location/Qualifiers
REGION                  1..15
                        note = Description of sequence: G4A- G4S- G4A
source                  1..15
                        mol_type = protein
                        organism = synthetic construct
SEQUENCE: 54
GGGGAGGGGS GGGGA                                                            15

SEQ ID NO: 55           moltype = AA  length = 15
FEATURE                 Location/Qualifiers
REGION                  1..15
                        note = Description of sequence: G4A- G4S- G4S
source                  1..15
                        mol_type = protein
                        organism = synthetic construct
SEQUENCE: 55
GGGGAGGGGS GGGGS                                                            15

SEQ ID NO: 56           moltype = AA  length = 11
FEATURE                 Location/Qualifiers
REGION                  1..11
                        note = Description of sequence: G4A-G4AG
source                  1..11
                        mol_type = protein
                        organism = synthetic construct
SEQUENCE: 56
GGGGAGGGGA G                                                                11

SEQ ID NO: 57           moltype = AA  length = 10
FEATURE                 Location/Qualifiers
REGION                  1..10
                        note = Description of sequence: G4A-G4S
source                  1..10
                        mol_type = protein
                        organism = synthetic construct
```

```
SEQUENCE: 57
GGGGAGGGGS                                                                     10

SEQ ID NO: 58           moltype = AA  length = 11
FEATURE                 Location/Qualifiers
REGION                  1..11
                        note = Description of sequence: G4A-G4SG
source                  1..11
                        mol_type = protein
                        organism = synthetic construct
SEQUENCE: 58
GGGGAGGGGS G                                                                   11

SEQ ID NO: 59           moltype = AA  length = 6
FEATURE                 Location/Qualifiers
REGION                  1..6
                        note = Description of sequence: G4AG
source                  1..6
                        mol_type = protein
                        organism = synthetic construct
SEQUENCE: 59
GGGGAG                                                                          6

SEQ ID NO: 60           moltype = AA  length = 12
FEATURE                 Location/Qualifiers
REGION                  1..12
                        note = Description of sequence: G4AG G4SG2
source                  1..12
                        mol_type = protein
                        organism = synthetic construct
SEQUENCE: 60
GGGGAGGGGG SG                                                                  12

SEQ ID NO: 61           moltype = AA  length = 12
FEATURE                 Location/Qualifiers
REGION                  1..12
                        note = Description of sequence: G4AG-G4AG
source                  1..12
                        mol_type = protein
                        organism = synthetic construct
SEQUENCE: 61
GGGGAGGGGG AG                                                                  12

SEQ ID NO: 62           moltype = AA  length = 12
FEATURE                 Location/Qualifiers
REGION                  1..12
                        note = Description of sequence: G4AG-G4SG
source                  1..12
                        mol_type = protein
                        organism = synthetic construct
SEQUENCE: 62
GGGGAGGGGG SG                                                                  12

SEQ ID NO: 63           moltype = AA  length = 7
FEATURE                 Location/Qualifiers
REGION                  1..7
                        note = Description of sequence: G4AG2
source                  1..7
                        mol_type = protein
                        organism = synthetic construct
SEQUENCE: 63
GGGGAGG                                                                         7

SEQ ID NO: 64           moltype = AA  length = 13
FEATURE                 Location/Qualifiers
REGION                  1..13
                        note = Description of sequence: G4AG2 G3SG2
source                  1..13
                        mol_type = protein
                        organism = synthetic construct
SEQUENCE: 64
GGGGAGGGGG SGG                                                                 13

SEQ ID NO: 65           moltype = AA  length = 5
FEATURE                 Location/Qualifiers
REGION                  1..5
                        note = Description of sequence: G4S
source                  1..5
                        mol_type = protein
```

```
                              organism = synthetic construct
SEQUENCE: 65
GGGGS                                                                    5

SEQ ID NO: 66            moltype = AA  length = 15
FEATURE                  Location/Qualifiers
REGION                   1..15
                         note = Description of sequence: G4S- G4A- G4A
source                   1..15
                         mol_type = protein
                         organism = synthetic construct
SEQUENCE: 66
GGGGSGGGGA GGGGA                                                        15

SEQ ID NO: 67            moltype = AA  length = 15
FEATURE                  Location/Qualifiers
REGION                   1..15
                         note = Description of sequence: G4S- G4A- G4S
source                   1..15
                         mol_type = protein
                         organism = synthetic construct
SEQUENCE: 67
GGGGSGGGGA GGGGS                                                        15

SEQ ID NO: 68            moltype = AA  length = 15
FEATURE                  Location/Qualifiers
REGION                   1..15
                         note = Description of sequence: G4S- G4S- G4A
source                   1..15
                         mol_type = protein
                         organism = synthetic construct
SEQUENCE: 68
GGGGSGGGGS GGGGA                                                        15

SEQ ID NO: 69            moltype = AA  length = 10
FEATURE                  Location/Qualifiers
REGION                   1..10
                         note = Description of sequence: G4S-G4A
source                   1..10
                         mol_type = protein
                         organism = synthetic construct
SEQUENCE: 69
GGGGSGGGGA                                                              10

SEQ ID NO: 70            moltype = AA  length = 11
FEATURE                  Location/Qualifiers
REGION                   1..11
                         note = Description of sequence: G4S-G4AG
source                   1..11
                         mol_type = protein
                         organism = synthetic construct
SEQUENCE: 70
GGGGSGGGGA G                                                            11

SEQ ID NO: 71            moltype = AA  length = 11
FEATURE                  Location/Qualifiers
REGION                   1..11
                         note = Description of sequence: G4S-G4SG
source                   1..11
                         mol_type = protein
                         organism = synthetic construct
SEQUENCE: 71
GGGGSGGGGS G                                                            11

SEQ ID NO: 72            moltype = AA  length = 12
FEATURE                  Location/Qualifiers
REGION                   1..12
                         note = Description of sequence: G4SG G3AG2
source                   1..12
                         mol_type = protein
                         organism = synthetic construct
SEQUENCE: 72
GGGGSGGGGA GG                                                           12

SEQ ID NO: 73            moltype = AA  length = 12
FEATURE                  Location/Qualifiers
REGION                   1..12
                         note = Description of sequence: G4SG-G4AG
source                   1..12
```

```
                      mol_type = protein
                      organism = synthetic construct
SEQUENCE: 73
GGGGSGGGGG AG                                                        12

SEQ ID NO: 74         moltype = AA   length = 12
FEATURE               Location/Qualifiers
REGION                1..12
                      note = Description of sequence: G4SG-G4SG
source                1..12
                      mol_type = protein
                      organism = synthetic construct
SEQUENCE: 74
GGGGSGGGGG SG                                                        12

SEQ ID NO: 75         moltype = AA   length = 13
FEATURE               Location/Qualifiers
REGION                1..13
                      note = Description of sequence: G4SG2 G5SG
source                1..13
                      mol_type = protein
                      organism = synthetic construct
SEQUENCE: 75
GGGGSGGGGG GSG                                                       13

SEQ ID NO: 76         moltype = AA   length = 7
FEATURE               Location/Qualifiers
REGION                1..7
                      note = Description of sequence: G5AG
source                1..7
                      mol_type = protein
                      organism = synthetic construct
SEQUENCE: 76
GGGGGAG                                                              7

SEQ ID NO: 77         moltype = AA   length = 14
FEATURE               Location/Qualifiers
REGION                1..14
                      note = Description of sequence: G5SG G4AG2
source                1..14
                      mol_type = protein
                      organism = synthetic construct
SEQUENCE: 77
GGGGGSGGGG GAGG                                                      14

SEQ ID NO: 78         moltype = AA   length = 4
FEATURE               Location/Qualifiers
REGION                1..4
                      note = Description of sequence: GAG2
source                1..4
                      mol_type = protein
                      organism = synthetic construct
SEQUENCE: 78
GAGG                                                                 4

SEQ ID NO: 79         moltype = AA   length = 4
FEATURE               Location/Qualifiers
REGION                1..4
                      note = Description of sequence: GSG2
source                1..4
                      mol_type = protein
                      organism = synthetic construct
SEQUENCE: 79
GAGG                                                                 4

SEQ ID NO: 80         moltype = AA   length = 537
FEATURE               Location/Qualifiers
REGION                1..537
                      note = Description of sequence: DR1442M
source                1..537
                      mol_type = protein
                      organism = synthetic construct
SEQUENCE: 80
IWELKKDVYV VELDWYPDAP GEMVVLTCDT PEEDGITWTL DQSSEVLGSG KTLTIQVKAA     60
GDAGQYTCHK GGEVLSHSLL LLHAKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSEPKS SDKTHTCPPC PAPEAAGGPS VFLFPPKPKD TLMISRTPEV TCVVVDVSHE    360
```

```
DPEVKFNWYV DGVEVHNAKT KPREEQYNST YRVVSVLTVL HQDWLNGKEY KCKVSNKALA  420
APIEKTISKA KGQPREPQVY TLPPCRDELT KNQVSLWCLV KGFYPSDIAV EWESNGQPEN  480
NYKTTPPVLD SDGSFFLYSK LTVDKSRWQQ GNVFSCSVMH EALHNHYTQK SLSLSPG     537

SEQ ID NO: 81            moltype = AA   length = 443
FEATURE                  Location/Qualifiers
REGION                   1..443
                         note = Description of sequence: DR1535M
source                   1..443
                         mol_type = protein
                         organism = synthetic construct
SEQUENCE: 81
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSGGG GSEPKSSDKT HTCPPCPAPE AAGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALAAPIE KTISKAKGQP REPQVCTLPP SRDELTKNQV  360
SLSCAVKGFY PSDIAVEWES NGQPENNYKT TPPVLDSDGS FFLVSKLTVD KSRWQQGNVF  420
SCSVMHEALH NHYTQKSLSL SPG                                         443

SEQ ID NO: 82            moltype = AA   length = 438
FEATURE                  Location/Qualifiers
REGION                   1..438
                         note = Description of sequence: DR1536M Mature p35 Fc
                          protein
source                   1..438
                         mol_type = protein
                         organism = synthetic construct
SEQUENCE: 82
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSEPK SSDKTHTCPP CPAPEAAGGP SVFLFPPKPK  240
DTLMISRTPE VTCVVVDVSH EDPEVKFNWY VDGVEVHNAK TKPREEQYNS TYRVVSVLTV  300
LHQDWLNGKE YKCKVSNKAL AAPIEKTISK AKGQPREPQV CTLPPSRDEL TKNQVSLSCA  360
VKGFYPSDIA VEWESNGQPE NNYKTTPPVL DSDGSFFLVS KLTVDKSRWQ QGNVFSCSVM  420
HEALHNHYTQ KSLSLSPG                                               438

SEQ ID NO: 83            moltype = AA   length = 547
FEATURE                  Location/Qualifiers
REGION                   1..547
                         note = Description of sequence: DR1537M Mature 3xAla p40 Fc
                          protein
source                   1..547
                         mol_type = protein
                         organism = synthetic construct
SEQUENCE: 83
IWELKKDVYV VELDWYPDAP GEMVVLTCDT PEEDGITWTL DQSSEVLGSG KTLTIQVKAA   60
GDAGQYTCHK GGEVLSHSLL LLHAKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSEPKS SDKTHTCPPC PAPEAAGGPS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALA APIEKTISKA KGQPREPQVY TLPPCRDELT KNQVSLWCLV KGFYPSDIAV  480
EWESNGQPEN NYKTTPPVLD SDGSFFLYSK LTVDKSRWQQ GNVFSCSVMH EALHNHYTQK  540
SLSLSPG                                                           547

SEQ ID NO: 84            moltype = AA   length = 438
FEATURE                  Location/Qualifiers
REGION                   1..438
                         note = Description of sequence: DR1572M
source                   1..438
                         mol_type = protein
                         organism = synthetic construct
SEQUENCE: 84
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASGGG GSGGGGSEPK SCDKTHTCPP CPAPEAAGGP SVFLFPPKPK  240
DTLMISRTPE VTCVVVDVSH EDPEVKFNWY VDGVEVHNAK TKPREEQYNS TYRVVSVLTV  300
LHQDWLNGKE YKCKVSNKAL AAPIEKTISK AKGQPREPQV CTLPPSRDEL TKNQVSLSCA  360
VKGFYPSDIA VEWESNGQPE NNYKTTPPVL DSDGSFFLVS KLTVDKSRWQ QGNVFSCSVM  420
HEALHNHYTQ KSLSLSPG                                               438

SEQ ID NO: 85            moltype = AA   length = 547
FEATURE                  Location/Qualifiers
REGION                   1..547
```

```
                        note = Description of sequence: DR1573M
source                  1..547
                        mol_type = protein
                        organism = synthetic construct
SEQUENCE: 85
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSEPKS CDKTHTCPPC PAPEAAGGPS VFLFPPKPKD TLMISRTPEV   360
TCVVVDVSHE DPEVKFNWYV DGVEVHNAKT KPREEQYNST YRVVSVLTVL HQDWLNGKEY   420
KCKVSNKALA APIEKTISKA KGQPREPQVY TLPPCRDELT KNQVSLWCLV KGFYPSDIAV   480
EWESNGQPEN NYKTTPPVLD SDGSFFLYSK LTVDKSRWQQ GNVFSCSVMH EALHNHYTQK   540
SLSLSPG                                                             547

SEQ ID NO: 86           moltype = AA   length = 537
FEATURE                 Location/Qualifiers
REGION                  1..537
                        note = Description of sequence: DR1588M
source                  1..537
                        mol_type = protein
                        organism = synthetic construct
SEQUENCE: 86
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSEPKS SDKTHTCPPC PAPEFEGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
ASIEKTISKA KGQPREPQVY TLPPCRDELT KNQVSLWCLV KGFYPSDIAV EWESNGQPEN   480
NYKTTPPVLD SDGSFFLYSK LTVDKSRWQQ GNVFSCSVMH EALHNHYTQK SLSLSPG      537

SEQ ID NO: 87           moltype = AA   length = 443
FEATURE                 Location/Qualifiers
REGION                  1..443
                        note = Description of sequence: DR1589M
source                  1..443
                        mol_type = protein
                        organism = synthetic construct
SEQUENCE: 87
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSGGG GSEPKSSDKT HTCPPCPAPE FEGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPASIE KTISKAKGQP REPQVCTLPP SRDELTKNQV   360
SLSCAVKGFY PSDIAVEWES NGQPENNYKT TPPVLDSDGS FFLVSKLTVD KSRWQQGNVF   420
SCSVMHEALH NHYTQKSLSL SPG                                           443

SEQ ID NO: 88           moltype = AA   length = 531
FEATURE                 Location/Qualifiers
REGION                  1..531
                        note = Description of sequence: DR1590M
source                  1..531
                        mol_type = protein
                        organism = synthetic construct
SEQUENCE: 88
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSEPKS SDKTHTCPPC PAPEAEGAPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVY TLLTKNQVSL WCLVKGFYPS DIAVEWESNG QPENNYKTTP   480
PVLDSDGSFF LYSKLTVDKS RWQQGNVFSC SVMHEALHNH YTQKSLSLSP G            531

SEQ ID NO: 89           moltype = AA   length = 443
FEATURE                 Location/Qualifiers
REGION                  1..443
                        note = Description of sequence: DR1591M
source                  1..443
                        mol_type = protein
                        organism = synthetic construct
SEQUENCE: 89
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
```

```
AKLLMDPKRQ IFLDQNMLAV IDELMQALNF NSETVPQKSS LEEPDFYKTK IKLCILLHAF    180
RIRAVTIDRV MSYLNASGGG GSGGGGSGGG GSEPKSSDKT HTCPPCPAPE AEGAPSVFLF    240
PPKPKDTLMI SRTPEVTCVV VDVSHEDPEV KFNWYVDGVE VHNAKTKPRE EQYNSTYRVV    300
SVLTVLHQDW LNGKEYKCKV SNKALPAPIE KTISKAKGQP REPQVCTLPP SRDELTKNQV    360
SLSCAVKGFY PSDIAVEWES NGQPENNYKT TPPVLDSDGS FFLVSKLTVD KSRWQQGNVF    420
SCSVMHEALH NHYTQKSLSL SPG                                           443

SEQ ID NO: 90           moltype = AA  length = 547
FEATURE                 Location/Qualifiers
REGION                  1..547
                        note = Description of sequence: DR1595M
source                  1..547
                        mol_type = protein
                        organism = synthetic construct
SEQUENCE: 90
IWELKKDVYV VELDWYPDAP GEMVVLTCDT PEEDGITWTL DQSSEVLGSG KTLTIQVKAA     60
GDAGQYTCHK GGEVLSHSLL LLHAKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSEPKS SDKTHTCPPC PAPEAEGAPS VFLFPPKPKD TLMISRTPEV    360
TCVVVDVSHE DPEVKFNWYV DGVEVHNAKT KPREEQYNST YRVVSVLTVL HQDWLNGKEY    420
KCKVSNKALP SSIEKTISKA KGQPREPQVY TLPPCRDELT KNQVSLWCLV KGFYPSDIAV    480
EWESNGQPEN NYKTTPPVLD SDGSFFLYSK LTVDKSRWQQ GNVFSCSVMH EALHNHYTQK    540
SLSLSPG                                                              547

SEQ ID NO: 91           moltype = AA  length = 438
FEATURE                 Location/Qualifiers
REGION                  1..438
                        note = Description of sequence: DR1596M
source                  1..438
                        mol_type = protein
                        organism = synthetic construct
SEQUENCE: 91
RNLPVATPDP GMFPCLHHSQ NLLRAVSNML QKARQTLEFY PCTSEEIDHE DITKDKTSTV     60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSEPK SSDKTHTCPP CPAPEAEGAP SVFLFPPKPK    240
DTLMISRTPE VTCVVVDVSH EDPEVKFNWY VDGVEVHNAK TKPREEQYNS TYRVVSVLTV    300
LHQDWLNGKE YKCKVSNKAL PSSIEKTISK AKGQPREPQV CTLPPSRDEL TKNQVSLSCA    360
VKGFYPSDIA VEWESNGQPE NNYKTTPPVL DSDGSFFLVS KLTVDKSRWQ QGNVFSCSVM    420
HEALHNHYTQ KSLSLSPG                                                  438

SEQ ID NO: 92           moltype = AA  length = 547
FEATURE                 Location/Qualifiers
REGION                  1..547
                        note = Description of sequence: DR1597M
source                  1..547
                        mol_type = protein
                        organism = synthetic construct
SEQUENCE: 92
IWELKKDVYV VELDWYPDAP GEMVVLTCDT PEEDGITWTL DQSSEVLGSG KTLTIQVKAA     60
GDAGQYTCHK GGEVLSHSLL LLHAKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSEPKS SDKTHTCPPC PAPEAEGAPS VFLFPPKPKD TLMISRTPEV    360
TCVVVDVSHE DPEVKFNWYV DGVEVHNAKT KPREEQYNST YRVVSVLTVL HQDWLNGKEY    420
KCKVSNKALP SSIEKTISKA KGQPREPQVY TLPPCRDELT KNQVSLWCLV KGFYPSDIAV    480
EWESNGQPEN NYKTTPPVLD SDGSFFLYSK LTVDKSRWQQ GNVFSCSVLH EALHSHYTQK    540
SLSLSPG                                                              547

SEQ ID NO: 93           moltype = AA  length = 438
FEATURE                 Location/Qualifiers
REGION                  1..438
                        note = Description of sequence: DR1598M
source                  1..438
                        mol_type = protein
                        organism = synthetic construct
SEQUENCE: 93
RNLPVATPDP GMFPCLHHSQ NLLRAVSNML QKARQTLEFY PCTSEEIDHE DITKDKTSTV     60
EACLPLELTK NESCLNSRET SFITNGSCLA SRKTSFMMAL CLSSIYEDLK MYQVEFKTMN    120
AKLLMDPKRQ IFLDQNMLAV IDELMQALNF NSETVPQKSS LEEPDFYKTK IKLCILLHAF    180
RIRAVTIDRV MSYLNASGGG GSGGGGSEPK SSDKTHTCPP CPAPEAEGAP SVFLFPPKPK    240
DTLMISRTPE VTCVVVDVSH EDPEVKFNWY VDGVEVHNAK TKPREEQYNS TYRVVSVLTV    300
LHQDWLNGKE YKCKVSNKAL PSSIEKTISK AKGQPREPQV CTLPPSRDEL TKNQVSLSCA    360
VKGFYPSDIA VEWESNGQPE NNYKTTPPVL DSDGSFFLVS KLTVDKSRWQ QGNVFSCSVL    420
HEALHSHYTQ KSLSLSPG                                                  438
```

| SEQ ID NO: 94 | moltype = DNA length = 1611 |
| --- | --- |
| FEATURE | Location/Qualifiers |
| misc_feature | 1..1611 |
| | note = Description of sequence: DNA Sequence encoding DR1442P |
| source | 1..1611 |
| | mol_type = other DNA |
| | organism = synthetic construct |

SEQUENCE: 94

```
atctgggagc tgaagaaaga cgtgtacgtg gtggaactgg actggtatcc cgatgctcct   60
ggcgagatgg tggtgctgac ctgcgatacc cctgaagagg acggcatcac ctggacactg  120
gatcagtcta gcgaggtgct cggcagcggc aagaccctga ccatccaagt gaaagcggct  180
ggcgacgccg ccagtacac ctgtcacaaa ggcggagaag tgctgagcca cagcctgctg  240
ctgctccacg cgaaagagga tggcatttgg agcaccgaca tcctgaagga ccagaaagag  300
cccaagaaca agaccttcct gagatgcgag gccaagaact acagcggccg gttcacatgt  360
tggtggctga ccaccatcag caccgacctg accttcagcg tgaagtccag cagaggcagc  420
agtgatcctc agggcgttac atgtggcgct gccacactgt ctgccgaaag agtgcggggc  480
gacaacaaag aatacgagta cagcgtggaa tgccaagagg cagcgcctg tccagcgcc  540
gaagagtctc tgcctatcga agtgatggtg gacgccgtgc acaagctgaa gtacgagaac  600
tacacctcca gcttttcat ccgggacatc atcaagcccg atcctccaaa gaacctgcag  660
ctgaagcctc tgaagaacag cagacaggtg gaagtgtcct gggagtaccc cgacacctgg  720
tctacacccc acagctactt cagcctgacc ttttgcgtgc aagtgcaggg caagtccaag  780
cgcgagaaaa aggaccgggt gttcaccgac aagaccagcg ccaccgtgat ctgcagaaag  840
aacgccagca tcagcgtcag agcccaggat cggtactaca gcagctcttg gagcgagtgg  900
gcctcggtac catgtagcga accaaaatca tcagacaaga cccacacctg tcctccatgt  960
cctgctccag aagctgctgg gggccttcc gtgtttctgt tccctccaaa gcctaaggac 1020
accctgatga tctctcggac ccctgaagtg acctgcgtgg tggtggatgt gtctcacgaa 1080
gatccagaag tgaagttcaa ttggtacgtg gacggcgtgg aagtgcacaa cgccaagacc 1140
aagcctagag aggaacagta caactccacc tacagagtgg tgtccgtgct gaccgtgctg 1200
caccaggatt ggctgaacgg caaagagtac aagtgcaaga tgtccaacaa ggccctgccc 1260
gctcccatcg aaaagaccat ctctaaggcc aagggccagc ctcgggaacc ccagttttac 1320
acactgcctc catgccggga tgagctgacc aagaaccagg tgtccctgtg tgcctggtc 1380
aagggcttct acccttccga tatcgccgtg aatgggaga gcaatggcca gcctgagaac 1440
aactacaaga caacccctcc tgtgctggac tccgacggct cattcttcct gtactccaag 1500
ctgacagtgg acaagtccag atggcagcag ggcaacgtgt tctcctgctc cgtgatgcac 1560
gaagctttgc acaatcacta cacacagaag tcccctgtct tgtcccctgg c           1611
```

| SEQ ID NO: 95 | moltype = DNA length = 1329 |
| --- | --- |
| FEATURE | Location/Qualifiers |
| misc_feature | 1..1329 |
| | note = Description of sequence: DNA Sequence encoding DR1535P |
| source | 1..1329 |
| | mol_type = other DNA |
| | organism = synthetic construct |

SEQUENCE: 95

```
agaaacctgc cagtggccac gcctgatcct ggcatgtttc cttgtctgca ccacagccag   60
aacctgctga gagccgtgtc caacatgctg cagaaggcca gacagaccct cgagttctac  120
ccctgcacca gcgaggaaat cgaccacgag gacatcacca aggacaagac cagcaccgtg  180
gaagcctgcc tgcctctgga actgaccaag aacgagagct gcctgaacag cagagagaca  240
agcttcatca ccaacggctc ttgcctggcc tccagaaaga cctcctttca gatgcccatg  300
tgcctgagca gcatctacga ggacctgaag atgtaccagg tcgagttcaa gaccatgaac  360
gccaagctgc tgatggaccc caagcggcag atcttcctgg accagaatat gctggccgtg  420
atcgacgagc tgatgcaggc cctgaacttc aacagcgaga cagtgcccca agagtccagc  480
ctggaagaac ccgacttcta caagaccaag atcaagctgt gcatcctgct gcacgccttc  540
cggatcagag ccgtgaccat cgacagagtg atgagctacc tgaacgccag cggaggcgga  600
ggatccggcg gaggtggaag tggcggaggc ggatctgaac caaaatcatc agacaagacc  660
cacacctgtc ctccatgtcc tgctccagaa gctgctgggg gcccctccgt ttttctgttc  720
ccacctaagc ctaaggacac cctgatgatc tctcggaccc ctgaagtgac ctgcgtggtg  780
gtggatgtgt ctcacgaaga tcccgaagtg aagttcaatt ggtacgtgga cggcgtggaa  840
gtgcacaacg ccaagaccaa gcctagagag aacagtaca actccaccta cagagtggt  900
tccgtgctga ccgtgctgca ccaggattgg ctgaacggca agagtacaa gtgcaaggtg  960
tccaacaagg ccctggccgc tcctatcgaa aagaccatct ccaaggccaa gggccagcct 1020
agggaacccc aggtttgcac cctgcctcca agccgggatg aactgaccaa gaaccaggtg 1080
tccctgtcct gtgccgtgaa gggcttctac ccttccgata tcgccgtgga atgggagagc 1140
aatggccagc tgagaacaa ctacaagaca cccctcctg tgctgactc cgacggctca 1200
ttcttcctgt gtccaagct gacagtggac aagtccagat ggcagcaggg caacgtgttc 1260
tcctgctccg tgatgcacga agctttgcac aaccactaca cccagaagtc cctgtctctg 1320
agccctgga                                                           1329
```

| SEQ ID NO: 96 | moltype = DNA length = 1380 |
| --- | --- |
| FEATURE | Location/Qualifiers |
| misc_feature | 1..1380 |
| | note = Description of sequence: Nucleic acid sequence encoding DR1536P SEQ ID NO: 125 |
| source | 1..1380 |
| | mol_type = other DNA |
| | organism = synthetic construct |

SEQUENCE: 96

```
atgtgccctg ccagatctct gctgctggtg gctacactgg tgctgctgga tcatctgagc   60
ctggccagaa acctgccagt ggccacgcct gatcctggca tgtttccttg tctgcaccac  120
agccagaacc tgctgagagc cgtgtccaac atgctgcaga aggccagaca gaccctcgag  180
ttctacccct gcaccagcga ggaaatcgac acgaggaca tcaccaagga caagaccagc  240
accgtggaag cctgcctgcc tctggaactg accaagaacg agagctgcct gaacagcaga  300
gagacaagct tcatcaccaa cggctcttgc ctggcctcca gaaagacctc cttcatgatg  360
gccctgtgcc tgagcagcat ctacgaggac ctgaagatgt accaggtcga gttcaagacc  420
atgaacgcca agctgctgat ggaccccaag cggcagatct tcctggacca gaatatgctg  480
gccgtgatcg acgagctgat gcaggccctg aacttcaaca gcgagacagt gccccagaag  540
tccagcctgg aagaacccga cttctacaag accaagatca agctgtgcat cctgctgcac  600
gccttccgga tcagagccgt gaccatcgac agagtgatga gctacctgaa cgccagcgga  660
ggcggaggat ccggcggagg cggatctgaa ccaaaatcat cagacaagac ccacacctgt  720
cctccatgtc ctgctccaga agctgctggg ggccctccg tttttctgtt cccacctaag  780
cctaaggaca ccctgatgat ctctcggacc cctgaagtga cctgcgtggt ggtggatgtg  840
tctcacgaag atcccgaagt gaagttcaat tggtacgtgg acggcgtgga agtgcacaac  900
gccaagacca gcctagaga ggaacagtac aactccacct cagagtggt gtccgtgctg  960
accgtgctgc accaggattg gctgaacggc aaagagtaca agtgcaaggt gtccaacaag 1020
gccctggccg ctcctatcga aaagaccatc tccaaggccg agggccagcc tagggaaccc 1080
caggtttgca ccctgcctcc aagccgggat gagctgacca gaaccaggt gtccctgtcc 1140
tgtgccgtga agggcttcta ccccttccgat atcgccgtgg aatgggagag caatggccag 1200
cctgagaaca actacaagac aacccctcct gtgctggact ccgacggctc attcttcctg 1260
tgtccaagc tgacagtgga caagtccaga tggcagcagg gcaacgtgtt ctcctgctcc 1320
gtgatgcacg aagctttgca caaccactac acccagaagt ccctgtctct gagccctgga 1380

SEQ ID NO: 97            moltype = DNA   length = 1707
FEATURE                  Location/Qualifiers
misc_feature             1..1707
                         note = Description of sequence: Nucleic acid sequence
                         encoding DR1537P
source                   1..1707
                         mol_type = other DNA
                         organism = synthetic construct
SEQUENCE: 97
atgtgtcacc agcagctggt catcagctgg ttcagcctgg tgttcctggc ctctcctctg   60
gtggccatct gggagctgaa gaaagacgtg tacgtggtgg aactggactg gtatcccgat  120
gctcctggcg agatggtggt gctgacctgc gataccctg aagaggacgg catcacctgg  180
acactggatc agtctagcga ggtgctcggc agcggcaaga ccctgaccat ccaagtgaaa  240
gcggctggcg acgccggcca gtacacctgt cacaaaggcg agaagtgct gagccacagc  300
ctgctgctgc tccacgcgaa agaggatggc atttggaacg ccgacatcct gaaggaccag  360
aaagagccca gaacaagac cttcctgaga tgcgaggcca agaactcag cggccggttc  420
acatgttggt ggctgaccac catcagcacc gacctgacct tcagcgtgaa gtccagcaga  480
ggcagcagtg atcctcaggg cgttacatgt ggcgctgcca cactgtctgc cgaaagagtg  540
cggggcgaca acaaagaata cgagtacagc gtggaatgcc aagaggacag cgcctgtcca  600
gccgccgaag agtctctgcc tatcgaagtg atggtggacg ccgtgcacaa gctgaagtac  660
gagaactaca cctccagctt tttcatccgg gacatcatca agcccgatcc tccaaagaac  720
ctgcagctga agcctctgaa gaacagcaga caggtggaag tgtcctggga gtaccccgac  780
acctggctca caccccacag ctacttcagc ctgaccttt gcgtgcaagt gcagggcaag  840
tccaagcgcg agaaaaagga ccgggtgttc accgacaaga ccagcgccac cgtgatctgc  900
agaaagaacg ccagcatcag cgtcagagcc caggatcgt actacagcag ctcttggagc  960
gagtgggcct cggtaccatg tagcggagc ggaggatccg gcggaggcgg atctgaacca 1020
aaatcatcag acaagaccca cacctgtcct ccatgtcctg ctccagaagc tgctggggga 1080
ccttccgtgt ttctgttccc tccaaagcct aaggacaccc tgatgatctc tcggaccct 1140
gaagtgacct gcgtggtggt ggatgtgtct cacgaagatc cagaagtgaa gttcaattgg 1200
tacgtggacg gcgtggaagt gcacaacgcc aagaccaagc ctagagagga acagtacaac 1260
tccacctaca gtgggtgtc cgtgctgacc gtgctgcacc aggattggct gaacggcaaa 1320
gagtacaagt gcaaggtgtc caacaaggcc ctgccgctc ccatcgaaaa gaccatctct 1380
aaggccaagg gccagcctcg ggaacccag gtttacacac tgcctccatg ccgggatgag 1440
ctgaccaaga accaggtgtc cctgtggtgc tggtcaagg gcttctaccc ttccgatatc 1500
gccgtggaat gggagagcaa tggccagcct gagaacaact acaagacaac cctcctgtg 1560
ctggactccg acggctcatt cttcctgtac tccaagctga cagtggacaa gtccagatgg 1620
cagcagggca acgtgttctc ctgctccgtg atgcacgaag ctttgcacaa tcactacaca 1680
cagaagtccc tgtctctgtc ccctggc                                     1707

SEQ ID NO: 98            moltype = DNA   length = 1314
FEATURE                  Location/Qualifiers
misc_feature             1..1314
                         note = Description of sequence: DNA Sequence encoding
                         DR1572P
source                   1..1314
                         mol_type = other DNA
                         organism = synthetic construct
SEQUENCE: 98
agaaacctgc cagtggccac gcctgatcct ggcatgtttc cttgtctgca ccacagccag   60
aacctgctga gccgtgtc caacatgctg cagaaggcca gacagaccct cgagttctac  120
ccctgcacca gcgaggaaat cgaccacgag gacatcacca aggacaagac cagcaccgtg  180
gaagcctgcc tgcctctgga actgaccaag aacgagagct gcctgaacag cagagagaca  240
agcttcatca ccaacggctc ttgcctgcc tccagaaaga cctccttcat gatggccctg  300
tgcctgagca gcatctacga ggacctgaag atgtaccagg tcgagttcaa gaccatgaac  360
gccaagctgc tgatggaccc caagcggcag atcttcctgg accagaatat gctggccgtg  420
```

```
atcgacgagc tgatgcaggc cctgaacttc aacagcgaga cagtgcccca gaagtccagc    480
ctggaagaac ccgacttcta caagaccaag atcaagctgt gcatcctgct gcacgccttc    540
cggatcagag ccgtgaccat cgacagagtg atgagctacc tgaacgccag cggaggcgga    600
ggatccggcg gaggcggatc tgaaccaaaa tcatgtgaca agacccacac ctgtcctcca    660
tgtcctgctc cagaagctgc tggggggcccc tccgttttc tgttcccacc taagcctaag    720
gacaccctga tgatctctcg gacccctgaa gtgacctgcg tggtggtgga tgtgtctcac    780
gaagatcccg aagtgaagtt caattggtac gtggacggcg tggaagtgca aacgccaag     840
accaagccta gagaggaaca gtacaactcc acctacagag tggtgtccgt gctgaccgtg    900
ctgcaccagg attggctgaa cggcaaagag tacaagtgca aggtgtccaa caaggccctg    960
gccgctccta tcgaaaagac catctccaag gccaaggcc agcctaggga accccaggtt     1020
tgcaccctgc ctccaagccg ggatgagctg accaagaacc aggtgtccct gtcctgtgcc    1080
gtgaagggct tctacccttc cgatatcgcc gtggaatggg agagcaatgg ccagcctgag    1140
aacaactaca agacaacccc tcctgtgctg gactccgacg gctcattctt cctggtgtcc    1200
aagctgacag tggacaagtc cagatgcag cagggcaacg tgttctcctg ctccgtgatg     1260
cacgaagctt tgcacaacca ctacacccag aagtccctgt ctctgagccc tgga          1314

SEQ ID NO: 99            moltype = DNA   length = 1641
FEATURE                  Location/Qualifiers
misc_feature             1..1641
                         note = Description of sequence: DNA Sequence encoding
                         DR1573P
source                   1..1641
                         mol_type = other DNA
                         organism = synthetic construct
SEQUENCE: 99
atctgggagc tgaagaaaga cgtgtacgtg gtggaactgg actggtatcc cgatgctcct     60
ggcgagatgg tggtgctgac ctgcgatacc cctgaagagg acggcatcac ctggacactg    120
gatcagtcta gcgaggtgct cggcagcggc aagaccctga ccatccaagt gaaagcggct    180
ggcgacgccg ccagtacac ctgtcacaaa ggcgagaag tgctgagcca cagcctgctg      240
ctgctccacg cgaaagagga tggcatttgg agcaccgaca tcctgaagga ccagaaagag    300
cccaagaaca agaccttcct gagatgcgag gccaagaact acagcggccg gttcacatgt    360
tggtggctga ccaccatcag caccgacctg accttcagcg tgaagtccag cagaggcagc    420
agtgatcctc agggcgttac atgtggcgct gccacactgt ctgccgaaag agtgcggggc    480
gacaacaaag aatacgagta cagcgtggaa tgccaagagg acagcgcctg tccagccgcc    540
gaagagtctc tgcctatcga agtgatggtg gacgccgtgc acaagctgaa gtacgagaac    600
tacacctcca gcttttttcat ccgggacatc atcaagcccg atcctccaaa gaacctgcag    660
ctgaagcctc tgaagaacag cagacaggtg gaagtgtcct gggagtaccc cgacacctgg    720
tctacaccc acagctactt cagcctgacc ttttgcgtgc aagtgcaggg caagtccaag     780
cgcgagaaaa aggaccgggt gttcaccgac aagaccagcg ccaccgtgat ctgcagaaag    840
aacgccagca tcagcgtcag agcccaggat cggtactaca gcagctcttg gagcgagtgg    900
gcctcggtac catgtagcgg aggcggagga tccggcggag gcggatctga accaaaatca    960
tgtgacaaga cccacacctg tcctccatgt cctgctccag aagctgctgg ggggccttcc    1020
gtgtttcttgt tccctccaaa gcctaaggac accctgatga tctctcggac ccctgaaggt   1080
acctgcgtgg tggtggatgt gtctcacgaa gatccagaa tgaagttcaa ttggtacgtg    1140
gacggcgtgg aagtgcacaa cgccaagacc aagcctagag gaacagta caactccacc     1200
tacagagtgg tgtccgtgct gaccgtgctg caccaggatt ggctgaacgg caaagagtac    1260
aagtgcaaag tgtccaacaa ggcctggcc gctcccatcg aaaagaccat ctctaaggcc    1320
aagggccagc ctcgggaacc ccaggtttac acactgcctc catgccggga tgagctgacc    1380
aagaaccagg tgtccctgtg gtgcctggtc aagggcttct acccttccga tatcgccgtg    1440
gaatgggaga gcaatggcca gcctgagaac aactacaaga caacccctcc tgtgctggac    1500
tccgacggct cattcttcct gtactccaag ctgacagtgg acaagtccag atggcagcag    1560
ggcaacgtgt tctcctcgc cgtgatgcac gaagctttgc acaatcacta cacacagaag    1620
tccctgtctc tgtccctgg c                                                 1641

SEQ ID NO: 100           moltype = DNA   length = 1611
FEATURE                  Location/Qualifiers
misc_feature             1..1611
                         note = Description of sequence: DNA Sequence encoding
                         DR1588P
source                   1..1611
                         mol_type = other DNA
                         organism = synthetic construct
SEQUENCE: 100
atctgggagc tgaagaaaga cgtgtacgtg gtggaactgg actggtatcc cgatgctcct     60
ggcgagatgg tggtgctgac ctgcgatacc cctgaagagg acggcatcac ctggacactg    120
gatcagtcta gcgaggtgct cggcagcggc aagaccctga ccatccaagt gaaagcggct    180
ggcgacgccg ccagtacac ctgtcacaaa ggcgagaag tgctgagcca cagcctgctg      240
ctgctccacg cgaaagagga tggcatttgg agcaccgaca tcctgaagga ccagaaagag    300
cccaagaaca agaccttcct gagatgcgag gccaagaact acagcggccg gttcacatgt    360
tggtggctga ccaccatcag caccgacctg accttcagcg tgaagtccag cagaggcagc    420
agtgatcctc agggcgttac atgtggcgct gccacactgt ctgccgaaag agtgcggggc    480
gacaacaaag aatacgagta cagcgtggaa tgccaagagg acagcgcctg tccagccgcc    540
gaagagtctc tgcctatcga agtgatggtg gacgccgtgc acaagctgaa gtacgagaac    600
tacacctcca gcttttttcat ccgggacatc atcaagcccg atcctccaaa gaacctgcag    660
ctgaagcctc tgaagaacag cagacaggtg gaagtgtcct gggagtaccc cgacacctgg    720
tctacaccc acagctactt cagcctgacc ttttgcgtgc aagtgcaggg caagtccaag     780
cgcgagaaaa aggaccgggt gttcaccgac aagaccagcg ccaccgtgat ctgcagaaag    840
aacgccagca tcagcgtcag agcccaggat cggtactaca gcagctcttg gagcgagtgg    900
gcctcggtac catgtagcga accaaaatca tcagacaaga cccacacctg tcctccatgt    960
```

```
cctgctccag aatttgaagg gggcccttcc gtgtttctgt tccctccaaa gcctaaggac   1020
accctgatga tctctcggac ccctgaagtg acctgcgtgg tggtggatgt gtctcacgaa   1080
gatccagaag tgaagttcaa ttggtacgtg gacggcgtgg aagtgcacaa cgccaagacc   1140
aagcctagag aggaacagta caactccacc tacagagtgg tgtccgtgct gaccgtgctg   1200
caccaggatt ggctgaacgg caaagagtac aagtgcaagg tgtccaacaa ggccctgccc   1260
gcttccatcg aaaagaccat ctctaaggcc aagggccagc ctcgggaacc ccaggtttac   1320
acactgcctc catgccggga tgagctgacc aagaaccagg tgtccctgtg gtgcctggtc   1380
aagggcttct acccttccga tatcgccgtg gaatgggaga gcaatggcca gcctgagaac   1440
aactacaaga caacccctcc tgtgctggac tccgacggct cattcttcct gtactccaag   1500
ctgacagtgg acaagtccag atggcagcag ggcaacgtgt tctcctgctc cgtgatgcac   1560
gaagctttgc acaatcacta cacacagaag tccctgtctc tgtccctgg c              1611

SEQ ID NO: 101        moltype = DNA  length = 1329
FEATURE               Location/Qualifiers
misc_feature          1..1329
                      note = Description of sequence: DNA Sequence encoding
                      DR1589P
source                1..1329
                      mol_type = other DNA
                      organism = synthetic construct
SEQUENCE: 101
agaaacctgc cagtggccac gcctgatcct ggcatgtttc cttgtctgca ccacagccag    60
aacctgctga gagccgtgtc caacatgctg cagaaggcca gacagaccct cgagttctac   120
ccctgcacca gcgaggaaat cgaccacgag gacatcacca aggacaagac cagcaccgtg   180
gaagcctgcc tgcctctgga actgaccaag aacgagagct gcctgaacag cagagagaca   240
agcttcatca ccaacggctc ttgcctggcc tccagaaaga cctccttcat gatggccctg   300
tgcctgagca gcatctacga ggacctgaag atgtaccagg tcgagttcaa gaccatgaac   360
gccaagctgc tgatggaccc caagcggcag atcttcctgg accagaatat gctggccgtg   420
atcgacgagc tgatgcaggc cctgaacttc aacagcgaga cagtgcccca gaagtccagc   480
ctggaagaac ccgacttcta caagaccaag atcaagctgc tgcatcctgc tgcacgcctt c   540
cggatcagag ccgtgaccat cgacagagtg atgagctacc tgaacgccag cggaggcgga   600
ggatccggcg gaggtggaag tggcggaggc ggatctgaac caaaatcatc agacaagacc   660
cacacctgtc ctccatgtcc tgctccagaa tttgaagggg gccctccgt ttttctgttc    720
ccacctaagc ctaaggacac cctgatgatc tctcggacac ctgaagtgac ctgcgtggtg   780
gtggatgtgt ctcacgaaga tcccgaagtg aagttcaatt ggtacgtgga cggcgtggtg   840
gtgcacaacg ccaagaccaa gcctagagag gaacagtaca actccaccta cagagtggtg   900
tccgtgctga ccgtgctgca ccaggattgg ctgaacggca agagtacaa gtgcaaggtg     960
tccaacaagg ccctgcccgc ttctatcgaa aagaccatct ccaaggccaa gggccagcct   1020
agggaacccc aggtttgcac cctgcctcca agcagggatg agctgaccaa gaaccaggtg   1080
tccctgtcct gtgccgtgaa gggcttctac ccttccgata tcgccgtgga atgggagagc   1140
aatggccagc ctgagaacaa ctacaagaca ccccctcctg tgctgactc cgacggctca    1200
ttcttcctgg tgtccaagct gacagtggac aagtccagat ggcagcaggg caacgtgttc   1260
tcctgctccg tgatgcacga agctttgcac aaccactaca cccagaagtc cctgtctctg   1320
agccctgga                                                            1329

SEQ ID NO: 102        moltype = DNA  length = 1611
FEATURE               Location/Qualifiers
misc_feature          1..1611
                      note = Description of sequence: DNA Sequence encoding
                      DR1590P
source                1..1611
                      mol_type = other DNA
                      organism = synthetic construct
SEQUENCE: 102
atctgggagc tgaagaaaga cgtgtacgtg gtggaactgg actggtatcc cgatgctcct    60
ggcgagatgg tggtgctgac ctgcgatacc cctgaagagg acggcatcac ctggacactg   120
gatcagtcta gcgaggtgct cggcagcggc aagaccctga ccatccaagt gaaagcggct   180
ggcgacgccg ccagtacac ctgtcacaaa ggcgagaag tgctgagcca cagcctgctg     240
ctgctccacg cgaaagagga tggcattgg agcaagacca tcctgaagga cacagaaagag   300
cccaagaaca agaccttcct gagatgcgag gccaagaact acagcggccg gttcacatgt   360
tggtggctga ccaccatcag caccgacctg accttcagcg tgaagtccag cagaggcagc   420
agtgatcctc agggcgttac atgtggcgct gccacactgt ctgccgaaag agtgcggggc   480
gacaacaaag aatacgagta cagcgtggaa tgccaagagg acagcgcctg tccagccgcc   540
gaagagtctc tgcctatcga agtgatggtg gacgccgtgc acaagctgaa gtacgagaac   600
tacacctcca gcttttttat ccgggacatc atcaagcccg atcctccaaa gaacctgcag   660
ctgaagcctc tgaagaacag cagacaggtg gaagtgtcct gggagtaccc cgacacctgg   720
tctacacccc acagctactt cagcctgacc ttttgcgtgc aagtgcaggg caagtccaag   780
cgcgagaaaa aggaccgggt gttcaccgac aagaccagcg ccaccgtgat ctgcagaaag   840
aacgccagca tcagcgtcag agccccaggt cggtactaca gcagcttgt gagcgagttg    900
gcctcggtac catgtagcga accaaaatca tcagacaaga cccacacctg tcctccatgt   960
cctgctccag aagctgaagg ggcccttcc gtgtttctgt tccctccaaa gcctaaggac    1020
accctgatga tctctcggac ccctgaagtg acctgcgtgg tggtggatgt gtctcacgaa   1080
gatccagaag tgaagttcaa ttggtacgtg gacggcgtgg aagtgcacaa cgccaagacc   1140
aagcctagag aggaacagta caactccacc tacagagtgg tgtccgtgct gaccgtgctg   1200
caccaggatt ggctgaacgg caaagagtac aagtgcaagg tgtccaacaa ggccctgccc   1260
gctcccatcg aaaagaccat ctctaaggcc aagggccagc ctcgggaacc ccaggtttac   1320
acactgcctc catgccggga tgagctgacc aagaaccagg tgtccctgtg gtgcctggtc   1380
aagggcttct acccttccga tatcgccgtg gaatgggaga gcaatggcca gcctgagaac   1440
aactacaaga caacccctcc tgtgctggac tccgacggct cattcttcct gtactccaag   1500
```

```
ctgacagtgg acaagtccag atggcagcag ggcaacgtgt tctcctgctc cgtgatgcac   1560
gaagctttgc acaatcacta cacacagaag tccctgtctc tgtccctgg c             1611

SEQ ID NO: 103          moltype = DNA  length = 1329
FEATURE                 Location/Qualifiers
misc_feature            1..1329
                        note = Description of sequence: DNA Sequence encoding
                        DR1591P
source                  1..1329
                        mol_type = other DNA
                        organism = synthetic construct
SEQUENCE: 103
agaaacctgc cagtggccac gcctgatcct ggcatgtttc cttgtctgca ccacagccag   60
aacctgctga gagccgtgtc caacatgctg cagaaggcca gacagaccct cgagttctac   120
ccctgcacca gcgaggaaat cgaccacgag gacatcacca aggacaagac cagcaccgtg   180
gaagcctgcc tgcctctgga actgaccaag aacgagagct gcctgaacag cagagagaca   240
agcttcatca ccaacggctc ttgcctggcc tccagaaaga cctccttcat gatggccctg   300
tgcctgagca gcatctacga ggacctgaag atgtaccagg tcgagttcaa gaccatgaac   360
gccaagctgc tgatggaccc caagcggcag atcttcctgg accagaatat gctggccgtg   420
atcgacgagc tgatgcaggc cctgaacttc aacagcgaga cagtgcccca gaagtccagc   480
ctggaagaac ccgacttcta caagaccaag atcaagctgt gcatcctgct gcacgccttc   540
cggatcagag ccgtgaccat cgacagagtg atgagctacc tgaacgccag cggaggcgga   600
ggatccggcg gaggtggaag tggcggaggc ggatctgaac caaaatcatc agacaagacc   660
cacacctgtc ctccatgtcc tgctccagaa gctgaagggg ctccctccgt ttttctgttc   720
ccacctaagc ctaaggacac cctgatgatc tctcggaccc ctgaagtgac ctgcgtggtg   780
gtggatgtgt ctcacgaaga tcccgaagtg aagttcaatt ggtacgtgga cggcgtggaa   840
gtgcacaacg ccaagaccaa gcctagagag aacagtaca actccaccta cagagtggtg   900
tccgtgctga ccgtgctgca ccaggattgg ctgaacggca agagtacaa gtgcaaggtg   960
tccaacaagg ccctgcccgc tcctatcgaa aagaccatct ccaaggccaa gggccagcct   1020
agggaacccc aggtttgcac cctgcctcca agccgggatg agctgaccaa gaaccaggtg   1080
tccctgtcct gtgccgtgaa gggcttctac ccttccgata tcgccgtgga atgggagagc   1140
aatggccagc tgagaacaa ctacaagaca ccctcctg tgctggactc cgacggctca    1200
ttcttcctgt tgtccaagct gacagtggac aagtccagat ggcagcaggg caacgtgttc   1260
tcctgctccg tgatgcacga agctttgcac aaccactaca cccagaagtc cctgtctctg   1320
agccctgga                                                           1329

SEQ ID NO: 104          moltype = DNA  length = 1314
FEATURE                 Location/Qualifiers
misc_feature            1..1314
                        note = Description of sequence: DNA Sequence encoding
                        DR1596P
source                  1..1314
                        mol_type = other DNA
                        organism = synthetic construct
SEQUENCE: 104
agaaacctgc cagtggccac gcctgatcct ggcatgtttc cttgtctgca ccacagccag   60
aacctgctga gagccgtgtc caacatgctg cagaaggcca gacagaccct cgagttctac   120
ccctgcacca gcgaggaaat cgaccacgag gacatcacca aggacaagac cagcaccgtg   180
gaagcctgcc tgcctctgga actgaccaag aacgagagct gcctgaacag cagagagaca   240
agcttcatca ccaacggctc ttgcctggcc tccagaaaga cctccttcat gatggccctg   300
tgcctgagca gcatctacga ggacctgaag atgtaccagg tcgagttcaa gaccatgaac   360
gccaagctgc tgatggaccc caagcggcag atcttcctgg accagaatat gctggccgtg   420
atcgacgagc tgatgcaggc cctgaacttc aacagcgaga cagtgcccca gaagtccagc   480
ctggaagaac ccgacttcta caagaccaag atcaagctgt gcatcctgct gcacgccttc   540
cggatcagag ccgtgaccat cgacagagtg atgagctacc tgaacgccag cggaggcgga   600
ggatccggcg gaggtggaag tgaaccaaaa tcatcagaca gaccccacac ctgtcctcca   660
tgtcctgctc cagaagctga aggggctccc tccgtttttc tgttcccacc taagcctaag   720
gacaccctga tgatctctcg gacccctgaa gtgacctgcg tggtggtgga tgtgtctcac   780
gaagatcccg aagtgaagtt caattggtac gtggacggcg tggaagtgca caacgccaag   840
accaagccta gagagaacta caactcc acctacagagt tggtgtccgt gctgaccgtg   900
ctgcaccagg attggctgaa cggcaaagag tacaagtgca aggtgtccaa caaggccctg   960
cccctcttcta tcgaaaagac catctccaag gccaagggcc agcctaggga accccaggtt   1020
tgcaccctgc ctccaagccg ggatgagctg accaagaacc aggtgtccct gtcctgtgcc   1080
gtgaagggct tctacccttc cgatatcgcc gtggaatggg agagcaatgg ccagctgag   1140
aacaactaca agacaacccc tcctgtgctg gactccgacg gctcattctt cctggtgtcc   1200
aagctgacag tggacaagtc cagatggcag cagggcaacg tgttctcctg ctccgtgatg   1260
cacgaagctt tgcacaacca ctacacccag aagtccctgt ctctgagccc tgga         1314

SEQ ID NO: 105          moltype = DNA  length = 1641
FEATURE                 Location/Qualifiers
misc_feature            1..1641
                        note = Description of sequence: DNA Sequence encoding
                        DR1597P
source                  1..1641
                        mol_type = other DNA
                        organism = synthetic construct
SEQUENCE: 105
atctgggagc tgaagaaaga cgtgtacgtg gtggaactgg actggtatcc cgatgctcct   60
ggcgagatgg tggtgctgac ctgcgatacc cctgaagagg acggcatcac ctggacactg   120
```

-continued

```
gatcagtcta gcgaggtgct cggcagcggc aagaccctga ccatccaagt gaaagcggct   180
ggcgacgccg gccagtacac ctgtcacaaa ggcggagaag tgctgagcca cagcctgctg   240
ctgctccacg cgaaagagga tggcatttgg agcaccgaca tcctgaagga ccagaaagag   300
cccaagaaca agaccttcct gagatgcgag gccaagaact acagcggccg gttcacatgt   360
tggtggctga ccaccatcag caccgacctg accttccgtg tgaagtccag cagaggcagc   420
agtgatcctc agggcgttac atgtggcgct gccacactgt ctgccgaaag agtgcggggc   480
gacaacaaag aatacgagta cagcgtggaa tgccaagagg acagcgcctg tccagccgcc   540
gaaagtctc  tgcctatcga agtgatggtg gacgccgtgc acaagctgaa gtacgagaac   600
tacacctcca gcttttttcat ccgggacatc atcaagcccg atcctccaaa gaacctgcag   660
ctgaagcctc tgaagaacag cagacaggtg gaagtgtcct gggagtaccc cgacacctgg   720
tctacacccc acagctactt cagcctgacc ttttgcgtgc aagtgcaggg caagtccaag   780
cgcgagaaaa aggaccgggt gttcaccgac aagaccagcg ccaccgtgat ctgcagaaag   840
aacgccagca tcagcgtcag agcccaggat cggtactaca gcagctcttg gagcgagtgg   900
gcctcggtac catgtagcgg aggcggagga tccggcggag gtggaagtga accaaaatca   960
tcagacaaga cccacacctg tcctccatgt cctgctccag aagctgaagg ggccccttcc  1020
gtgtttctgt tccctccaaa gcctaaggac accctgatga tctctcggac ccctgaagtg  1080
acctgcgtgg tggtggatgt gtctcacgaa gatccagaag tgaagttcaa ttggtacgtg  1140
gacggcgtgg aagtgcacaa cgccaagacc aagcctagag aggaacagta caactgcacc  1200
tacagagtgg tgtccgtgct gaccgtgctg caccaggatt ggctgaacgg caaagagtac  1260
aagtgcaagg tgtccaacaa ggccctgccc tcttccatcg aaaagaccat ctctaaggcc  1320
aagggccagc ctcgggaacc ccaggtttac acactgcctc catgccggga tgagctgacc  1380
aagaaccaga tgtccctgtg gtgcctggtc aagggcttct accttccga tatcgccgtg  1440
gaatgggaga gcaatggcca gcctgagaac aactacaaga caacccctcc tgtgctggac  1500
tccgacggct cattcttcct gtactccaag ctgacagtgg acaagtccag atggcagcag  1560
ggcaacgtgt tctcctgctc cgtgttgcac gaagctttgc actctcacta cacacagaag  1620
tccctgtctc tgtcccctgg c                                            1641

SEQ ID NO: 106          moltype = DNA  length = 1314
FEATURE                 Location/Qualifiers
misc_feature            1..1314
                        note = Description of sequence: DNA Sequence encoding
                        DR1598P
source                  1..1314
                        mol_type = other DNA
                        organism = synthetic construct
SEQUENCE: 106
agaaacctgc cagtggccac gcctgatcct ggcatgtttc cttgtctgca ccacagccag    60
aacctgctga gagccgtgtc caacatgctg cagaaggcca gacagaccct cgagttctac   120
ccctgcacca gcgaggaaat cgaccacgag gacatccaca aggacaagac cagcaccgtg   180
gaagcctgcc tgcctctgga actgaccaag aacgagagct gcctgaacag cagagagaca   240
agcttcatca ccaacggctc ttgcctggcc tccagaaaga cctcctttcat gatggccctg   300
tgcctgagca gcatctacga ggacctgaag atgtaccagg tcgagttcaa gaccatgaac   360
gccaagctgc tgatggaccc caagcggcag atcttcctgg accagaatat gctggccgtg   420
atcgacgagc tgatgcaggc cctgaacttc aacagcgaga cagtgcccca gaagtccagc   480
ctggaagaac ccgacttcta caagaccaag atcaagctgt gcatcctgct gcacgccttc   540
cggatcagag ccgtgaccat cgacagagtg atgagctacc tgaacgccag cggaggcgga   600
ggatccggcg gaggtggaag tgaaccaaaa tcatcagaca agacccacac ctgtcctcca   660
tgtcctgctc cagaagctga aggggctccc tccgtttttc tgttcccacc taagcctaag   720
gacaccctga tgatctctcg gacccctgaa gtgacctgcg tggtggtgga tgtgtctcac   780
gaagatccag aagtgaagtt caattggtac gtggacggcg tggaagtgca caacgccaag   840
accaagccta gagaggaaca gtacaactcc acctacagtg tggtccgt gctgaccgtg   900
ctgcaccagg attggctgaa cggcaaagag tacaagtgca aggtgtccaa caaggccctg   960
ccctcttcta tcgaaaagac catctccaag gccaagggcc agcctaggga accccaggtt  1020
tgcacccctgc ctccaagccg ggatgagctg accaagaacc aggtgtccct gtcctgtgcc  1080
gtgaagggct tctacccttc cgatatcgcc gtggaatggg agagcaatgg ccagcctgag  1140
aacaactaca agacaaccc tcctgtgctg gactccgacg gctcattctt cctggtgtcc  1200
aagctgacag tggacaagtc cagatggcag cagggcaacg tgttctcctg ctccgtgctg  1260
cacgaagctt tgcactccca ctacacccag aagtccctgt ctctgagccc tgga        1314

SEQ ID NO: 107          moltype = AA  length = 215
FEATURE                 Location/Qualifiers
REGION                  1..215
                        note = Description of sequence: Pro-mP35 (wt) Uniprot
                        P43431 w/native signal sequence
source                  1..215
                        mol_type = protein
                        organism = synthetic construct
SEQUENCE: 107
MCQSRYLLFL ATALLNHLS LARVIPVSGP ARCLSQSRNL LKTTDDMVKT AREKLKHYSC    60
TAEDIDHEDI TRDQTSTLKT CLPLELHKNE SCLATRETSS TTRGSCLPPQ KTSLMMTLCL  120
GSIYEDLKMY QTEFQAINAA LQNHNHQQII LDKGMLVAID ELMQSLNHNG ETLRQKPPVG  180
EADPYRVKMK LCILLHAFST RVVTINRVMG YLSSA                             215

SEQ ID NO: 108          moltype = AA  length = 193
FEATURE                 Location/Qualifiers
REGION                  1..193
                        note = Description of sequence: Mature mP35 (wt) Uniprot
                        P43431 (w/o signal sequence)
source                  1..193
```

```
                            mol_type = protein
                            organism = synthetic construct
SEQUENCE: 108
RVIPVSGPAR CLSQSRNLLK TTDDMVKTAR EKLKHYSCTA EDIDHEDITR DQTSTLKTCL     60
PLELHKNESC LATRETSSTT RGSCLPPQKT SLMMTLCLGS IYEDLKMYQT EFQAINAALQ    120
NHNHQQIILD KGMLVAIDEL MQSLNHNGET LRQKPPVGEA DPYRVKMKLC ILLHAFSTRV    180
VTINRVMGYL SSA                                                      193

SEQ ID NO: 109          moltype = AA  length = 335
FEATURE                 Location/Qualifiers
REGION                  1..335
                        note = Description of sequence: Pro wt mP40 Uniprot Q3ZAX5
                         Pre-protein with native signal sequence
source                  1..335
                        mol_type = protein
                        organism = synthetic construct
SEQUENCE: 109
MCPQKLTISW FAIVLLVSPL MAMWELEKDV YVVEVDWTPD APGETVNLTC DTPEEDDITW     60
TSDQRHGVIG SGKTLTITVK EFLDAGQYTC HKGGETLSHS HLLLHKKENG IWSTEILKNF    120
KNKTFLKCEA PNYSGRFTCS WLVQRNMDLK FNIKSSSSSP DSRAVTCGMA SLSAEKVTLD    180
QRDYEKYSVS CQEDVTCPTA EETLPIELAL EARQQNKYEN YSTSFFIRDI IKPDPPKNLQ    240
MKPLKNSQVE VSWEYPDSWS TPHSYFSLKF FVRIQRKKEK MKETEEGCNQ KGAFLVEKTS    300
TEVQCKGGNV CVQAQDRYYN SSCSKWACVP CRVRS                              335

SEQ ID NO: 110          moltype = AA  length = 313
FEATURE                 Location/Qualifiers
REGION                  1..313
                        note = Description of sequence: Mature wt mP40 Uniprot
                         Q3ZAX5 (w/o signal sequence)
source                  1..313
                        mol_type = protein
                        organism = synthetic construct
SEQUENCE: 110
MWELEKDVYV VEVDWTPDAP GETVNLTCDT PEEDDITWTS DQRHGVIGSG KTLTITVKEF     60
LDAGQYTCHK GGETLSHSHL LLHKKENGIW STEILKNFKN KTFLKCEAPN YSGRFTCSWL    120
VQRNMDLKFN IKSSSSPDS RAVTCGMASL SAEKVTLDQR DYEKYSVSCQ EDVTCPTAEE    180
TLPIELALEA RQQNKYENYS TSFFIRDIIK PDPPKNLQMK PLKNSQVEVS WEYPDSWSTP    240
HSYFSLKFFV RIQRKKEKMK ETEEGCNQKG AFLVEKTSTE VQCKGGNVCV QAQDRYYNSS    300
CSKWACVPCR VRS                                                      313

SEQ ID NO: 111          moltype = DNA  length = 2207
FEATURE                 Location/Qualifiers
misc_feature            1..2207
                        note = Description of sequence: DR852 DNA sequence encoding
                         mIL12 (p35-IRES2-p40) His8
source                  1..2207
                        mol_type = other DNA
                        organism = synthetic construct
SEQUENCE: 111
agagtgatcc ccgtgtctgg acctgccaga tgtctgagcc agtccagaaa cctgctgaaa     60
accaccgacg acatggtcaa gaccgccaga gagaagctga agcactacag ctgcaccgcc    120
gaggacatcg accacgagga tatcaccagg accagaccca gcacactgaa aacctgcctg    180
cctctggaac tgcacaagaa cgagagctgc ctggccacca gagagacaag cagcacaaca    240
agaggcagct gtctgcctcc tcagaaaacc agcctgatga tgaccctgtg cctgggcagc    300
atctacgagg acctgaagat gtaccagacc gagttccagg ccatcaacgc cgctctgcag    360
aaccacaacc accagcagat catcctggac aagggcatgc tggtggctat cgacgagctg    420
atgcagagcc tgaaccacaa tggcgagaca ctgcggcaga gcctccagt ggagagggcc    480
gatccttaca gagtgaagat gaagctgtgc atcctgctgc acgccttcag caccagagtg    540
gtcaccatca acagagtgat gggctacctg agcagcgcct gataagctag ccccctctcc    600
ctccccccc cctaacgtta ctggccaaag ccgcttgaa taaggccggt gtgcgtttgt     660
ctatatgtta ttttccacca tattgccgtc ttttggcaat gtgagggccc ggaaacctgg    720
ccctgtcttc ttgacgagca ttcctagggg tcttt
```

```
tggccctgga agcccggcag cagaacaaat acgagaacta ctccaccagc ttttcatcc    1860
gggacatcat caagcccgat cctccaaaga acctgcagat gaagcctctg aagaacagcc    1920
aggtcgaggt gtcctgggag taccccgata gctggtctac ccctcacagc tacttcagcc    1980
tgaaattctt cgtgcgcatc cagcgcaaga agaaaaagat gaaggaaacc gaggaaggct    2040
gcaaccagaa aggggccttc ctggtggaaa agaccagcag cgaggtgcag tgcaaaggcg    2100
gcaatgtttg tgtgcaggcc caggatcggt actacaacag cagctgtagc aagtgggcct    2160
gcgtgccatg tagagtccgg agtcaccacc atcatcacca tcaccac                 2207

SEQ ID NO: 112          moltype = DNA  length = 2207
FEATURE                 Location/Qualifiers
misc_feature            1..2207
                        note = Description of sequence: DNA Sequence Encoding
                        DR1022P mIL12 (p35-IRES2-p40 E81A F82A) His8
source                  1..2207
                        mol_type = other DNA
                        organism = synthetic construct
SEQUENCE: 112
agagtgatcc ccgtgtctgg acctgccaga tgtctgagcc agtccagaaa cctgctgaaa    60
accaccgacg acatggtcaa gaccgccaga gagaagctga agcactacag ctgcaccgcc    120
gaggacatcg accacgagga tatcaccagg gaccagacca gcacactgaa aacctgcctg    180
cctctggaac tgcacaagaa cgagagctgc ctggccacca gagagacaag cagcacaaca    240
agaggcagct gtctgcctcc tcagaaaacc agcctgatga tgcctctgtg cctgggcagc    300
atctacgagg acctgaagat gtaccagacc gagttccagg ccatcaacgc cgctctgcag    360
aaccacaacc accagcagat catcctggac aagggcatgc tggtggctat cgacgagctg    420
atgcagagcc tgaaccacaa tggcgagaca ctgcggcaga agcctccagt ggagaggcc    480
gatccttaca gagtgaagat gaagctgtgc atcctgctgc acgccttcag caccagagtg    540
gtcaccatca acagagtgat gggctacctg agcagcgcct gataagctag ccccctctcc    600
ctcccccccc cctaacgtta ctggccgaag ccgcttggaa taaggccggt gtgcgtttgt    660
ctatatgtta ttttccacca tattgccgtc ttttggcaat gtgagggccc ggaaacctgg    720
ccctgtcttc ttgacgagca ttcctagggg tcttccccct ctcgccaaag gaatgcaagg    780
tctgttgaat gtcgtgaagg aagcagttcc tctggaagct tcttgaagac aaacaacgtc    840
tgtagcgacc ctttgcaggc agcggaaccc cccacctggc gacaggtgcc tctgcggcca    900
aaagccacgt gtataagata cacctgcaaa ggcggcacaa ccccagtgcc acgttgtgag    960
ttggatagtt gtggaaagag tcaaatggct tcctctagta gtattcaaca aggggctgaa    1020
ggatgcccag aaggtacccc attgtatggg atctgatctg gggcctcggt gcacatgctt    1080
tacatgtgtt tagtcgaggt taaaaaaacg tctaggcccc ccgaaccacg gggacgtggt    1140
tttcctttga aaaacacgat gataatatgg ccacaaccat gtgccctcag aagctgacca    1200
tcagttggtt cgccatcgtg ctgctggtgt ccccactgat ggccatgtgg gagcttgaga    1260
aggacgtgta cgtggtggaa gtggactgga ccccgtactg tcctggcgag acagtgaacc    1320
tgacctgcga tacccctgaa gaggacgaca tcacctggac cagcgaccag agacatggcg    1380
tgatcggctc tggcaagacc ctgacaatta ccgtgaaagc ggccctggac gccggccagt    1440
acacctgtca caaggcggag agacactgac gccactctca tctgctgctg cacaagaaag    1500
agaacggcat ctggtccacc gagatcctga agaacttcaa gaacaagacc ttcctgaagt    1560
gcgaggcccc taactacagc ggcagattca cctgtagctg gctggtgcag cggaacatgg    1620
acctgaagtt caacatcaag tcctccagca gcagccccga cagcagagct gtgacatgtg    1680
gcatggcttc tctgagcgcc gagaaagtga ccctggatca gcgggactac gagaagtaca    1740
gcgtgtcctg ccaagaggac gtgacctgtc ctaccgacga ggaaacactg cctatcgagc    1800
tggccctgga agcccggcag cagaacaaat acgagaacta ctccaccagc ttttcatcc    1860
gggacatcat caagcccgat cctccaaaga acctgcagat gaagcctctg aagaacagcc    1920
aggtcgaggt gtcctgggag taccccgata gctggtctac ccctcacagc tacttcagcc    1980
tgaaattctt cgtgcgcatc cagcgcaaga agaaaaagat gaaggaaacc gaggaaggct    2040
gcaaccagaa aggggccttc ctggtggaaa agaccagcag cgaggtgcag tgcaaaggcg    2100
gcaatgtttg tgtgcaggcc caggatcggt actacaacag cagctgtagc aagtgggcct    2160
gcgtgccatg tagagtccgg agtcaccacc atcatcacca tcaccac                 2207

SEQ ID NO: 113          moltype = DNA  length = 2207
FEATURE                 Location/Qualifiers
misc_feature            1..2207
                        note = Description of sequence: DNA Sequence Encoding
                        DR1023P mIL12 (p35-IRES2-p40 E81A F82A K106A) His8
source                  1..2207
                        mol_type = other DNA
                        organism = synthetic construct
SEQUENCE: 113
agagtgatcc ccgtgtctgg acctgccaga tgtctgagcc agtccagaaa cctgctgaaa    60
accaccgacg acatggtcaa gaccgccaga gagaagctga agcactacag ctgcaccgcc    120
gaggacatcg accacgagga tatcaccagg gaccagacca gcacactgaa aacctgcctg    180
cctctggaac tgcacaagaa cgagagctgc ctggccacca gagagacaag cagcacaaca    240
agaggcagct gtctgcctcc tcagaaaacc agcctgatga tgcctctgtg cctgggcagc    300
atctacgagg acctgaagat gtaccagacc gagttccagg ccatcaacgc cgctctgcag    360
aaccacaacc accagcagat catcctggac aagggcatgc tggtggctat cgacgagctg    420
atgcagagcc tgaaccacaa tggcgagaca ctgcggcaga agcctccagt ggagaggcc    480
gatccttaca gagtgaagat gaagctgtgc atcctgctgc acgccttcag caccagagtg    540
gtcaccatca acagagtgat gggctacctg agcagcgcct gataagctag ccccctctcc    600
ctcccccccc cctaacgtta ctggccgaag ccgcttggaa taaggccggt gtgcgtttgt    660
ctatatgtta ttttccacca tattgccgtc ttttggcaat gtgagggccc ggaaacctgg    720
ccctgtcttc ttgacgagca ttcctagggg tcttccccct ctcgccaaag gaatgcaagg    780
tctgttgaat gtcgtgaagg aagcagttcc tctggaagct tcttgaagac aaacaacgtc    840
tgtagcgacc ctttgcaggc agcggaaccc cccacctggc gacaggtgcc tctgcggcca    900
```

```
aaagccacgt gtataagata cacctgcaaa ggcggcacaa ccccagtgcc acgttgtgag    960
ttggatagtt gtggaaagag tcaaatggct ctcctcaagc gtattcaaca aggggctgaa   1020
ggatgcccag aaggtacccc attgtatggg atctgatctg gggcctcggt gcacatgctt   1080
tacatgtgtt tagtcgaggt taaaaaaacg tctaggcccc ccgaaccacg gggacgtggt   1140
tttcctttga aaaacacgat gataaatatg ccacaaccat gtgccctcag aagctgacca   1200
tcagttggtt cgccatcgtg ctgctggtgt ccccactgat ggccatgtgg gagcttgaga   1260
aggacgtgta cgtggtggaa gtggactgga ccccctgatgc tcctggcgag acagtgaacc   1320
tgacctgcga taccccctgaa gaggacgaca tcacctggac cagcgaccag agacatggcg   1380
tgatcggctc tggcaagacc ctgacaatta ccgtgaaagc cgtctggaac gccggccagt   1440
acacctgtca caaggcggga gagacactga gccactctca tctgctgctg cacgcgaagt   1500
agaacggcat ctggtccacc gagatcctga agaacttcaa gaacaagacc ttcctgaagt   1560
gcgaggcccc taactacagc ggcagattca cctgtagctg gctggtgcag cggaacatgg   1620
acctgaagtt caacatcaag tcctccagca gcagccccga cagcagagct gtgacatgtg   1680
gcatgcgcttc tctgagcgcc gagaaagtga ccctggatca gcgggactac gagaagtaca   1740
gcgtgtcctg ccaagaggac gtgacctgtc ctaccgccga ggaaacactg cctatcgagc   1800
tggccctgga agcccggcag cagaacaaat acgagaacta ctccaccagc ttttcatcc    1860
gggacatcat caagcccgat cctccaaaga acctgcagat gaagcctctg aagaacagcc   1920
aggtcgaggt gtcctgggag taccccgata gctggtctac ccctcacagc tacttcagcc   1980
tgaaattctt cgtgcgcatc cagcgcaaga agaaaaagat gaaggaaacc gaggaaggct   2040
gcaaccagaa aggggccttc ctggtggaaa agaccagcac cgaggtgcag tgcaagggcg   2100
gcaatgtttg tgtgcaggcc caggatcggt actacaacag cagctgtagc aagtgggcct   2160
gcgtgccatg tagagtccgg agtcaccacc atcatcacca tcaccac              2207

SEQ ID NO: 114           moltype = AA  length = 544
FEATURE                  Location/Qualifiers
REGION                   1..544
                         note = Description of sequence: DR854 mIL12 p40 mIgG2A EW
                         LALA PG
source                   1..544
                         mol_type = protein
                         organism = synthetic construct
SEQUENCE: 114
MWELEKDVYV VEVDWTPDAP GETVNLTCDT PEEDDITWTS DQRHGVIGSG KTLTITVKEF    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG AFLVEKTSTE VQCKGGNVCV QAQDRYYNSS   300
CSKWACVPCR VRSPRGPTIK PCPPCKCPAP NAAGGPSVFI FPPKIKDVLM ISLSPIVTCV   360
VVDVSEDDPD VQISWFVNNV EVHTAQTQTH REDYNSTLRV VSALPIQHQD WMSGKEFKCK   420
VNNKDLGAPI ERTISKPKGS VRAPQVYVLP PPEEEMTEKQ VTLTCMVTDF MPEDIYVEWT   480
NNGKTELNYK NTEPVLDSDG SYFMYSWLRV EKKNWVERNS YSCSVVHEGL HNHHTTKSFS   540
RTPG                                                               544

SEQ ID NO: 115           moltype = AA  length = 439
FEATURE                  Location/Qualifiers
REGION                   1..439
                         note = Description of sequence: DR855
                         mIL12-p35-mIgG2A-RVT-LALAPG
source                   1..439
                         mol_type = protein
                         organism = synthetic construct
SEQUENCE: 115
RVIPVSGPAR CLSQSRNLLK TTDDMVKTAR EKLKHYSCTA EDIDHEDITR DQTSTLKTCL    60
PLELHKNESC LATRETSSTT RGSCLPPQKT SLMMTLCLGS IYEDLKMYQT EFQAINAALQ   120
NHNHQQIILD KGMLVAIDEL MQSLNHNGET LRQKPPVGEA DPYRVKMKLC ILLHAFSTRV   180
VTINRVMGYL SSAGGGGSGG GGSGGGGSPR GPTIKPCPPC KCPAPNAAGG PSVFIFPPKI   240
KDVLMISLSP IVTCVVVDVS EDDPDVQISW FVNNVEVHTA QTQTHREDYN STLRVVSALP   300
IQHQDWMSGK EFKCKVNNKD LGAPIERTIS KPKGSVRAPR VYVLPPPEEE MTKKQVTLTC   360
MVTDFMPEDI YVEWTNNGKT ELNYKNTEPV LVSDGSYTMY SKLRVEKKNW VERNSYSCSV   420
VHEGLHNHHT TKSFSRTPG                                               439

SEQ ID NO: 116           moltype = AA  length = 544
FEATURE                  Location/Qualifiers
REGION                   1..544
                         note = Description of sequence: DR1243P mIL12 p40 E81A F82A
                         mIgG2a EW LALA PG
source                   1..544
                         mol_type = protein
                         organism = synthetic construct
SEQUENCE: 116
MWELEKDVYV VEVDWTPDAP GETVNLTCDT PEEDDITWTS DQRHGVIGSG KTLTITVKAA    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG AFLVEKTSTE VQCKGGNVCV QAQDRYYNSS   300
CSKWACVPCR VRSPRGPTIK PCPPCKCPAP NAAGGPSVFI FPPKIKDVLM ISLSPIVTCV   360
VVDVSEDDPD VQISWFVNNV EVHTAQTQTH REDYNSTLRV VSALPIQHQD WMSGKEFKCK   420
VNNKDLGAPI ERTISKPKGS VRAPQVYVLP PPEEEMTEKQ VTLTCMVTDF MPEDIYVEWT   480
NNGKTELNYK NTEPVLDSDG SYFMYSWLRV EKKNWVERNS YSCSVVHEGL HNHHTTKSFS   540
```

```
-continued

RTPG                                                                    544

SEQ ID NO: 117          moltype = AA  length = 544
FEATURE                 Location/Qualifiers
REGION                  1..544
                        note = Description of sequence: DR1244P mIL12 p40 E81A F82A
                         K106A mIgG2a EW LALA PG
source                  1..544
                        mol_type = protein
                        organism = synthetic construct
SEQUENCE: 117
MWELEKDVYV VEVDWTPDAP GETVNLTCDT PEEDDITWTS DQRHGVIGSG KTLTITVKAA  60
LDAGQYTCHK GGETLSHSHL LLHAKENGIW STEILKNFKN KTFLKCEAPN YSGRFTCSWL  120
VQRNMDLKFN IKSSSSSPDS RAVTCGMASL SAEKVTLDQR DYEKYSVSCQ EDVTCPTAEE  180
TLPIELALEA RQQNKYENYS TSFFIRDIIK PDPPKNLQMK PLKNSQVEVS WEYPDSWSTP  240
HSYFSLKFFV RIQRKKEKMK ETEEGCNQKG AFLVEKTSTE VQCKGGNVCV QAQDRYYNSS  300
CSKWACVPCR VRSPRGPTIK PCPPCKCPAP NAAGGPSVFI FPPKIKDVLM ISLSPIVTCV  360
VVDVSEDDPD VQISWFVNNV EVHTAQTQTH REDYNSTLRV VSALPIQHQD WMSGKEFKCK  420
VNNKDLGAPI ERTISKPKGS VRAPQVYVLP PPEEEMTEKQ VTLTCMVTDF MPEDIYVEWT  480
NNGKTELNYK NTEPVLDSDG SYFMYSWLRV EKKNWVERNS YSCSVVHEGL HNHHTTKSFS  540
RTPG                                                                    544

SEQ ID NO: 118          moltype = DNA  length = 1641
FEATURE                 Location/Qualifiers
misc_feature            1..1641
                        note = Description of sequence: DNA Sequence encoding
                         DR1595P
source                  1..1641
                        mol_type = other DNA
                        organism = synthetic construct
SEQUENCE: 118
atctgggagc tgaagaaaga cgtgtacgtg gtggaactgg actggtatcc cgatgctcct  60
ggcgagatgt tggtgctgac ctgcgatacc cctgaagagg acggcatcac ctggacactg  120
gatcagtcta gcgaggtgct cggcagcggc aagaccctga ccatccaagt gaaagcggct  180
ggcgacgccg gccagtacac ctgtcacaaa ggcggagaag tgctgagcca cagcctgctg  240
ctgctccacg cgaaagagga tggcatttgg agcaccgaca tcctgaagga ccagaaagag  300
cccaagaaca agaccttcct gagatgcgag gccaagaact acagcggccg gttcacatgt  360
tggtggctga ccaccatcag caccgacctg accttcagcg tgaagtccag cagaggcagc  420
agtgatctca ggggcgttac atgtggcgct gccacactgt ctgccgaaag agtgcgggga  480
gacaacaaag aatacgagta cagcgtggaa tgccaagagg acagcgcctg tccagccgcc  540
gaagagtctc tgcctatcga agtgatggtg gacgccgtgc acaagctgaa gtacgagaac  600
tacacctcca gcttttttcat ccgggacatc atcaagcccg atcctccaaa gaacctgcag  660
ctgaagcctc tgaagaacag cagacaggtg gaagtgtcct gggagtaccc cgacacctgg  720
tctacacccc acagctactt cagcctgacc ttttgcgtgc aagtgcaggg caagtccaag  780
cgcgagaaaa aggaccgggt gttcaccgac aagaccagcg ccaccgtgat ctgcagaaag  840
aacgccagca tcagcgtcag agcccaggat cggtactaca gcagctcttg gagcgagtgg  900
gcctcggtac catgtagcgg aggcggagga tccggcggag tggaagtgga accaaaatca  960
tcagacaaga cccacacctg tcctccatgt cctgctccag aagctgaagg gcccccttcc  1020
gtgtttctgt tccctccaaa gcctaaggac accctgatga tctctcggac ccctgaagtg  1080
acctgcgtgg tggtggatgt gtctcacgaa gatccagaag tgaagttcaa ttggtacgtg  1140
gacggcgtgg aagtgcacaa cgccaagacc aagcctagag aggaacagta caactgcacc  1200
tacagagtgg tgtccgtgct gaccgtgctg caccaggatt ggctgaacgg caaagagtac  1260
aagtgcaagg tgtccaacaa ggccctgccc tcttccatcg aaaagaccat ctctaaggcc  1320
aagggccagc ctcgggaacc ccaggtttac acactgcctc catgccggga tgagctgacc  1380
aagaaccagg tgtccctgtg gtgcctggtc aagggcttcc acccttccga tatcgccgtg  1440
gaatgggaga gcaatggcca gcctgagaac aactacaaga caccccctcc tgtgctggac  1500
tccgacggct cattcttcct gtactccaag ctgacagtgg acaagtccag atggcagcag  1560
ggcaacgtgt tctcctgctc cgtgatgcac gaagctttgc acaatcacta cacacagaag  1620
tccctgtctc tgtcccctgg c                                                 1641

SEQ ID NO: 119          moltype = AA  length = 569
FEATURE                 Location/Qualifiers
REGION                  1..569
                        note = Description of sequence: DR1947P (3xAla p40 Fc
                         pre-protein)
source                  1..569
                        mol_type = protein
                        organism = synthetic construct
SEQUENCE: 119
MCHQQLVISW FSLVFLASPL VAIWELKKDV YVVELDWYPD APGEMVVLTC DTPEEDGITW  60
TLDQSSEVLG SGKTLTIQVK AAGDAGQYTC HKGGEVLSHS LLLLHAKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSEP KSSDKTHTCP PCPAPEAAGG  360
PSVFLFPPKP KDTLMISRTP EVTCVVVDVS HEDPEVKFNW YVDGVEVHNA KTKPREEQYN  420
STYRVVSVLT VLHQDWLNGK EYKCKVSNKA LAAPIEKTIS KAKGQPREPQ VYTLPPCRDE  480
LTKNQVSLWC LVKGFYPSDI AVEWESNGQP ENNYKTTPPV LDSDGSFFLY SKLTVDKSRW  540
QQGNVFSCSV LHEALHSHYT QKSLSLSPG                                         569
```

```
SEQ ID NO: 120          moltype = DNA  length = 1707
FEATURE                 Location/Qualifiers
misc_feature            1..1707
                        note = Description of sequence: Nucleic acid sequence
                        encoding DR1947P
source                  1..1707
                        mol_type = other DNA
                        organism = synthetic construct
SEQUENCE: 120
atgtgtcacc agcagctggt catcagctgg ttcagcctgg tgttcctggc ctctcctctg    60
gtggccatct gggagctgaa gaaagacgtg tacgtggtgg aactggactg gtatcccgat   120
gctcctggcg agatggtggt gctgacctgc gatacccctg aagaggacgg catcacctgg   180
acactggatc agtctagcga ggtgctcggc agcggcaaga ccctgaccat ccaagtgaaa   240
gcggctggcg acgccggcca gtacacctgt cacaaaggcg gagaagtgct gagccacagc   300
ctgctgctgc tccacgcgaa agaggatggc atttggagca ccgacatcct gaaggaccag   360
aaagagccca gaacaagac cttcctgaga tgcgaggcca gaactacag cggccggttc      420
acatgttggt ggctgaccac catcagcacc gacctgacct tcagcgtgaa gtccagcaga   480
ggcagcagtg atcctcaggg cgttacatgt ggcgctgcca cactgtctgc cgaaagagtg   540
cggggcgaca caaagaata cgagtacagc gtggaatgcc aagaggacag cgcctgtcca    600
gccgccgaag agtctctgcc tatcgaagtg atggtggacg ccgtgcacaa gctgaagtac   660
gagaactaca cctccagctt ttcatccgg gacatcatca acccgatcc tccaaagaac     720
ctgcagctga gcctctgaa gaacagcaga caggtggaag tgtcctggga gtaccccgac    780
acctggtcta caccccacag ctacttcagc ctgacctttt gcgtgcaagt cagggcaag    840
tccaagcgcg agaaaaagga ccgggtgttc accgacaaga ccagcgccac cgtgatctgc   900
agaaagaacg ccagcatcag cgtgagagcc caggatcggt actacagcag ctcttggag    960
gagtgggcct cggtaccatg tagcggagc ggaggatcg cggaggtgg aagtgaacca     1020
aaatcatcag acaagaccca cacctgtcct ccatgtcctg ctccagaagc tgcaggggc    1080
ccttccgtgt tctgttccc tccaaagcct aaggacaccc tgatgatctc tcggacccct   1140
gaagtgacct gcgtggtggt ggatgtgtct cacgaagatc cagaagtgaa gttcaattgg   1200
tacgtggacg gcgtggaagt gcacaacgcc aagaccaagc ctagagagga acagtacaac   1260
tccacctaca gagtggtgtc cgtgctgacc gtgctgcacc aggattggct gaacggcaaa   1320
gagtacaagt gcaaggtgtc caacaaggcc ctggccgctc ccatcgaaaa gaccatctct   1380
aaggccaagg gccagcctcg ggaacccag gtttacacac tgcctccatg ccgggatgag    1440
ctgaccaaga accaggtgtc cctgtggtgc ctggtcaagg gcttctaccc ttccgatatc   1500
gccgtgaat gggagagcaa tggccagcct gagaacaact acaagacaac ccctcctgtg    1560
ctggactccg acggctcatt cttcctgtac tccaagctga cagtggacaa gtccagatgg   1620
cagcagggca acgtgttctc ctgctccgtg ttgcacgaag ctttgcactc tcactacaca   1680
cagaagtccc tgtctctgtc ccctggc                                      1707

SEQ ID NO: 121          moltype = AA  length = 547
FEATURE                 Location/Qualifiers
REGION                  1..547
                        note = Description of sequence: DR1947M Mature 3xAla p40 Fc
                        protein
source                  1..547
                        mol_type = protein
                        organism = synthetic construct
SEQUENCE: 121
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSEPKS SDKTHTCPPC PAPEAAGPS VFLFPPKPKD TLMISRTPEV    360
TCVVVDVSHE DPEVKFNWYV DGVEVHNAKT KPREEQYNST YRVVSVLTVL HQDWLNGKEY   420
KCKVSNKALA APIEKTISKA KGQPREPQVY TLPPCRDELT KNQVSLWCLV KGFYPSDIAV   480
EWESNGQPEN NYKTTPPVLD SDGSFFLYSK LTVDKSRWQQ GNVFSCSVLH EALHSHYTQK   540
SLSLSPG                                                            547

SEQ ID NO: 122          moltype = AA  length = 460
FEATURE                 Location/Qualifiers
REGION                  1..460
                        note = Description of sequence: DR1948P Wt P35 Fc precursor
                        (signal sequence underlined)
source                  1..460
                        mol_type = protein
                        organism = synthetic construct
SEQUENCE: 122
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSE PKSSDKTHTC   240
PPCPAPEAAG GPSVFLFPPK PKDTLMISRT PEVTCVVVDV SHEDPEVKFN WYVDGVEVHN   300
AKTKPREEQY NSTYRVVSVL TVLHQDWLNG KEYKCKVSNK ALAAPIEKTI SKAKGQPREP   360
QVCTLPPSRD ELTKNQVSLS CAVKGFYPSD IAVEWESNGQ PENNYKTTPP VLDSDGSFFL   420
VSKLTVDKSR WQQGNVFSCS VLHEALHSHY TQKSLSLSPG                        460

SEQ ID NO: 123          moltype = DNA  length = 1380
```

| FEATURE | Location/Qualifiers |
|---|---|
| misc_feature | 1..1380 |
| | note = Description of sequence: Nucleic acid sequence encoding DR1948P |
| source | 1..1380 |
| | mol_type = other DNA |
| | organism = synthetic construct |

SEQUENCE: 123

```
atgtgccctg ccagatctct gctgctggtg gctacactgg tgctgctgga tcatctgagc    60
ctggccagaa acctgccagt gggccacgcct gatcctggca tgtttccttg tctgcaccac   120
agccagaacc tgctgagagc cgtgtccaac atgctgcaga aggccagaca gaccctcgag   180
ttctacccct gcaccagcga ggaaatcgac acgaggaca tcaccaagga caagaccagc    240
accgtggaag cctgcctgcc tctggaactg accaagaacg agagctgcct gaacagcaga   300
gagacagagct tcatcaccaa cggctcttgc ctggcctaca gaaagaccct cttcatgatg   360
gccctgtgcc tgagcagcat ctacgaggac ctgaagatgt accaggtcga gttcaagacc   420
atgaacgcca agctgctgat ggaccccaag cggcagatct tcctggacca gaatatgctg   480
gccgtgatcg acgagctgat gcaggccctg aacttcaaca gcgagacagt gccccagaag   540
tccagcctgg aagaacccga cttctacaag accaagatca agctgtgcat cctgctgcac   600
gccttccgga tcagagccgt gaccatcgac agagtgatga gctacctgaa cgccagcgga   660
ggcggaggat ccggcggagg tggaagtgaa ccaaaatcat cagacaagac ccacacctgt   720
cctccatgtc ctgctccaga agctcagggg ggtccctccg ttttctgtt cccacctaag    780
cctaaggaca ccctgatgat ctctaggacc cctgaagtga cctgcgtggt ggtggatgtg   840
tctcacgaag atcccgaagt gaagttcaat tggtacgtgg acggcgtgga agtgcacaac   900
gccaagacca gcctagaga ggaacagtac aactccaccct acagagtggt gtccgtgctg    960
accgtgctgc accaggattg gctgaacggc aaagagtaca agtgcaaggt gtccaacaag  1020
gccctggccg ctcctatcga aaagaccatc tccaaggcca agggccagcc taggggaaccc  1080
caggtttgca ccctgcctcc aagccgggat gagctgacca gaaaccaggt gtccctgtcc  1140
tgtgccgtga agggcttcta cccttccgat atcgccgtgg aatgggagag caatggccag  1200
cctgagaaca actacaagac aaccccctct gtgctggact ccgacggctc attcttcctg  1260
gtgtccaagc tgacagtgga caagtccaga tggcagcagg gcaacgtgtt ctcctgctcc  1320
gtgctgcacg aagctttgca ctcccactac acccagaagt ccctgtctct gagccctgga  1380
```

| SEQ ID NO: 124 | moltype = AA length = 438 |
|---|---|
| FEATURE | Location/Qualifiers |
| REGION | 1..438 |
| | note = Description of sequence: DR1948M Mature wt hP35 Fc protein without signal peptide |
| source | 1..438 |
| | mol_type = protein |
| | organism = synthetic construct |

SEQUENCE: 124

```
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNASGGG GSGGGGSEPK SSDKTHTCPP CPAPEAAGGP SVFLFPPKPK   240
DTLMISRTPE VTCVVVDVSH EDPEVKFNWY VDGVEVHNAK TKPREEQYNS TYRVVSVLTV   300
LHQDWLNGKE YKCKVSNKAL AAPIEKTISK AKGQPREPQV CTLPPSRDEL TKNQVSLSCA   360
VKGFYPSDIA VEWESNGQPE NNYKTTPPVL DSDGSFFLVS KLTVDKSRWQ QGNVFSCSVL   420
HEALHSHYTQ KSLSLSPG                                                 438
```

| SEQ ID NO: 125 | moltype = AA length = 460 |
|---|---|
| FEATURE | Location/Qualifiers |
| REGION | 1..460 |
| | note = Description of sequence: DR1536P Wt P35 Fc precursor protein |
| source | 1..460 |
| | mol_type = protein |
| | organism = synthetic construct |

SEQUENCE: 125

```
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSE PKSSDKTHTC   240
PPCPAPEAAG GPSVFLFPPK PKDTLMISRT PEVTCVVVDV SHEDPEVKFN WYVDGVEVHN   300
AKTKPREEQY NSTYRVVSVL TVLHQDWLNG KEYKCKVSNK ALAAPIEKTI SKAKGQPREP   360
QVCTLPPSRD ELTKNQVSLS CAVKGFYPSD IAVEWESNGQ PENNYKTTPP VLDSDGSFFL   420
VSKLTVDKSR WQQGNVFSCS VMHEALHNHY TQKSLSLSPG                         460
```

| SEQ ID NO: 126 | moltype = AA length = 569 |
|---|---|
| FEATURE | Location/Qualifiers |
| REGION | 1..569 |
| | note = Description of sequence: DR1537P (3xAla p40 Fc pre-protein) |
| source | 1..569 |
| | mol_type = protein |
| | organism = synthetic construct |

SEQUENCE: 126

```
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
```

```
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCSGG GGSGGGGSEP KSSDKTHTCP PCPAPEAAGG    360
PSVFLFPPKP KDTLMISRTP EVTCVVVDVS HEDPEVKFNW YVDGVEVHNA KTKPREEQYN    420
STYRVVSVLT VLHQDWLNGK EYKCKVSNKA LAAPIEKTIS KAKGQPREPQ VYTLPPCRDE    480
LTKNQVSLWC LVKGFYPSDI AVEWESNGQP ENNYKTTPPV LDSDGSFFLY SKLTVDKSRW    540
QQGNVFSCSV MHEALHNHYT QKSLSLSPG                                     569

SEQ ID NO: 127           moltype = AA  length = 569
FEATURE                  Location/Qualifiers
REGION                   1..569
                         note = Description of sequence: DR2088P 3xAla p40Fc
                          precursor protein
source                   1..569
                         mol_type = protein
                         organism = synthetic construct
SEQUENCE: 127
MCHQQLVISW FSLVFLASPL VAIWELKKDV YVVELDWYPD APGEMVVLTC DTPEEDGITW     60
TLDQSSEVLG SGKTLTIQVK AAGDAGQYTC HKGGEVLSHS LLLLHAKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SGREKKDRVF TDKTSATVIC    300
RKNASISVRA QDRYYSSSWS EWASVPCSGG GGSGGGGSEP KSSDKTHTCP PCPAPEAAGG    360
PSVFLFPPKP KDTLMISRTP EVTCVVVDVS HEDPEVKFNW YVDGVEVHNA KTKPREEQYN    420
STYRVVSVLT VLHQDWLNGK EYKCKVSNKA LAAPIEKTIS KAKGQPREPQ VYTLPPCRDE    480
LTKNQVSLWC LVKGFYPSDI AVEWESNGQP ENNYKTTPPV LDSDGSFFLY SKLTVDKSRW    540
QQGNVFSCSV LHEALHSHYT QKSLSLSPG                                     569

SEQ ID NO: 128           moltype = DNA  length = 1707
FEATURE                  Location/Qualifiers
misc_feature             1..1707
                         note = Description of sequence: Nucleic acid sequence
                          encoding DR2088P
source                   1..1707
                         mol_type = other DNA
                         organism = synthetic construct
SEQUENCE: 128
atgtgtcacc agcagctggt catcagctgg ttcagcctgg tgttcctggc ctctcctctg     60
gtggccatct gggagctgaa gaaagacgtg tacgtggtgg aactggactg gtatcccgat    120
gctcctggcg agatggtggt gctgacctgc gataccccctg aagaggacgg catcacctgg    180
acactggatc agtctagcga ggtgctcggc agcggcaaga ccctgaccat ccaagtgaaa    240
gcggccggcg acgccggcca gtacacctgt cacaaaggcg gagaagtgct gagccacagc    300
ctgctgctgc tccacgcgaa agaggatggc atttggagca ccgacatcct gaaggaccag    360
aaagagccca gaacaagac cttcctgaga tgcgaggcca gaactacag cggccggttc      420
acatgttggt ggctgaccac catcagcacc gacctgacct tcagcgtgaa gtccagcaga    480
ggcagcgatg atcctcaggg cgttacatgt ggcgctgcca cactgtctgc cgaaagagtg    540
cggggcgaca acaaagaata cgagtacagc gtgaatgcc aagaggacag cgcctgtcca      600
gccgccgaag agtctctgcc tatcgaagtg atggtgacg ccgtgcacaa gctgaagtac      660
gagaactaca cctccagctt tttcatccgg gacatcatca gcccgatcc tccaaagaac      720
ctgcagctga agcctgtgaa gaacagcaga caggtggaag tgtcctggga gtacccgaa      780
acctggtcta caccccacag ctacttcagc ctgaccttt gcgtgcaagt gcagggcaag      840
tccgggcgcg agaaaaagga ccgggtgttc accgacaaga ccagcgccac cgtgatctgc    900
agaaagaacg ccagcatcag cgtcagagcc caggatcggt actacagcag ctcttggagc    960
gagtggcct cggtaccatg tagcggaggc ggaggatccg gcggaggtgg aagtgaacca   1020
aaatcatcag acaagaccca cacctgtcct ccatgtcctg ctccagaagc tgcagggggc   1080
ccttccgtgt ttctgttccc tccaaagcct aaggacaccc tgatgatctc tcggaccct   1140
gaagtgacct gcgtggtggt ggatgtgtct cacgaagatc cagaagtgaa gttcaattgg   1200
tacgtggacg gcgtggaagt gcacaacgcc aagaccaag ctagagagga acagtacaac    1260
tccacctaca gagtggtgtc cgtgctgacc gtgctgcacc aggattggct gaacggcaaa   1320
gagtacaagt gcaaggtgtc caacaaggcc ctggccgctc ccatcgaaaa gaccatctct   1380
aaggccaagg gccagcctcg gaacccccag gtttacacac tgcctccatg ccgggatgag   1440
ctgaccaaga accaggtgtc cctgtggtgc ctggtcaagg gcttctaccc ttccgatatc   1500
gccgtggaat gggagagcaa tggccagcct gagaacaact acaagacaac ccctcctgtg   1560
ctggactccg acggctcatt cttcctgtac tccaagctga cagtggacaa gtccagatgg   1620
cagcagggca acgtgttctc ctgctccgtg ttgcacgaag cttttgcactc tcactacaca   1680
cagaagtccc tgtctctgtc ccctggc                                       1707

SEQ ID NO: 129           moltype = AA  length = 547
FEATURE                  Location/Qualifiers
REGION                   1..547
                         note = Description of sequence: DR2088M Mature 3xAla p40 Fc
                          protein
source                   1..547
                         mol_type = protein
                         organism = synthetic construct
SEQUENCE: 129
IWELKKDVYV VELDWYPDAP GEMVVLTCDT PEEDGITWTL DQSSEVLGSG KTLTIQVKAA     60
GDAGQYTCHK GGEVLSHSLL LLHAKEDGIW STDILKDQKE PKNKTFLRCE AKNYSGRFTC    120
```

```
WWLTTISTDL  TFSVKSSRGS  SDPQGVTCGA  ATLSAERVRG  DNKEYEYSVE  CQEDSACPAA  180
EESLPIEVMV  DAVHKLKYEN  YTSSFFIRDI  IKPDPPKNLQ  LKPLKNSRQV  EVSWEYPDTW  240
STPHSYFSLT  FCVQVQGKSG  REKKDRVFTD  KTSATVICRK  NASISVRAQD  RYYSSSWSEW  300
ASVPCSGGGG  SGGGGSEPKS  SDKTHTCPPC  PAPEAAGGPS  VFLFPPKPKD  TLMISRTPEV  360
TCVVVDVSHE  DPEVKFNWYV  DGVEVHNAKT  KPREEQYNST  YRVVSVLTVL  HQDWLNGKEY  420
KCKVSNKALA  APIEKTISKA  KGQPREPQVY  TLPPCRDELT  KNQVSLWCLV  KGFYPSDIAV  480
EWESNGQPEN  NYKTTPPVLD  SDGSFFLYSK  LTVDKSRWQQ  GNVFSCSVLH  EALHSHYTQK  540
SLSLSPG                                                                 547

SEQ ID NO: 130             moltype = AA  length = 569
FEATURE                    Location/Qualifiers
REGION                     1..569
                           note = Description of sequence: DR2092P 3xAla p40Fc
                            precursor protein
source                     1..569
                           mol_type = protein
                           organism = synthetic construct
SEQUENCE: 130
MCHQQLVISW  FSLVFLASPL  VAIWELKKDV  YVVELDWYPD  APGEMVVLTC  DTPEEDGITW   60
TLDQSSEVLG  SGKTLTIQVK  AAGDAGQYTC  HKGGEVLSHS  LLLLHAKEDG  IWSTDILKDQ  120
KEPKNKTFLR  CEAKNYSGRF  TCWWLTTIST  DLTFSVKSSR  GSSDPQGVTC  GAATLSAERV  180
RGDNKEYEYS  VECQEDSACP  AAEESLPIEV  MVDAVHKLKY  ENYTSSFFIR  DIIKPDPPKN  240
LQLKPLKNSR  QVEVSWEYPD  TWSTPHSYFS  LTFCVQVQGK  SGREKKDRVF  TDKTSATVIC  300
RKNASISVRA  QDRYYSSSWS  EWASVPCSGG  GGSGGGGSEP  KSSDKTHTCP  PCPAPEAAGG  360
PSVFLFPPKP  KDTLMISRTP  EVTCVVVDVS  HEDPEVKFNW  YVDGVEVHNA  KTKPREEQYN  420
STYRVVSVLT  VLHQDWLNGK  EYKCKVSNKA  LAAPIEKTIS  KAKGQPREPQ  VYTLPPCRDE  480
LTKNQVSLWC  LVKGFYPSDI  AVEWESNGQP  ENNYKTTPPV  LDSDGSFFLY  SKLTVDKSRW  540
QQGNVFSCSV  MHEALHNHYT  QKSLSLSPG                                       569

SEQ ID NO: 131             moltype = DNA  length = 1707
FEATURE                    Location/Qualifiers
misc_feature               1..1707
                           note = Description of sequence: Nucleic acid sequence
                            encoding DR2092P
source                     1..1707
                           mol_type = other DNA
                           organism = synthetic construct
SEQUENCE: 131
atgtgtcacc  agcagctggt  catcagctgg  ttcagcctgg  tgttcctggc  ctctcctctg    60
gtggccatct  gggagctgaa  gaaagacgtg  tacgtggtgg  aactggactg  gtatcccgat   120
gctcctggcg  agatggtggt  gctgacctgc  gataccctg   aagaggacgg  catcacctgg   180
acactggatc  agtctagcga  ggtgctcggc  agcggcaaga  ccctgaccat  ccaagtgaaa   240
gcggccggca  acgccggcca  gtacacctgt  cacaaaggcg  gagaagtgct  gagccacagc   300
ctgctgctgc  tccacgcgaa  agaggatggc  atttggagca  ccgacatcct  gaaggaccag   360
aaagagccca  gaacaagac   cttcctgaga  tgcgaggcca  agaactacag  cggccggttc   420
acatgttggt  ggctgaccac  catcagcacc  gacctgacct  tcagcgtgaa  gtccagcaga   480
ggcagcagtg  atcctcaggg  cgttacatgt  ggcgctgcca  cactgtctgc  cgaaagagtg   540
cggggcgaca  acaaagaata  cgagtacagc  gtgaatgcc   aagaggacag  cgcctgtcca   600
gccgccgaag  agtctctgcc  tatcgaagtg  atggtggacg  ccgtgcacaa  gctgaagtac   660
gagaactaca  cctccagctt  tttcatccgg  gacatcatca  gcccgatcc   tccaaagaac   720
ctgcagctga  agcctctgaa  gaacagcaga  caggtggaag  tgtcctggga  gtaccccgac   780
acctggtcta  caccccacag  ctacttcagc  ctgaccttt   gcgtgcaagt  gcagggcaag   840
tccgggcgcg  agaaaaagga  ccgggtgttc  accgacaaga  ccagcgccac  cgtgatctgc   900
agaaagaacg  ccagcatcag  cgtcagagcc  caggatcggt  actacagcag  ctcttggagc   960
gagtggcct   cggtaccatg  tagcggaggc  ggaggatccg  gcggaggcgg  atctgaacca  1020
aaatcatcag  acaagaccca  cacctgtcct  ccatgtcctg  ctccaagagc  tgctggggc   1080
ccttccgtgt  ttctgttccc  tccaaagcct  aaggacaccc  tgatgatctc  tcggacccct  1140
gaagtgacct  gcgtggtggt  ggatgtgtct  cacgaagatc  cagaagtgaa  gttcaattgg  1200
tacgtggacg  gcgtggaagt  gcacaacgcc  aagaccctag  agagagga    acagtacaac  1260
tccacctaca  gagtggtgtc  cgtgctgacc  gtgctgcaca  aggattggct  gaacggcaaa  1320
gagtacaagt  gcaaggtgtc  caacaaggcc  ctggccgctc  ccatcgaaaa  gaccatctct  1380
aaggccaagg  gccagcctcg  gaacccag    gtttacacac  tgcctccatg  ccgggatgag  1440
ctgaccaaga  accaggtgtc  cctgtggtgc  ctggtcaagg  gcttctaccc  ttccgatatc  1500
gccgtggaat  gggagagcaa  tggccagcct  gagaacaact  acaagacaac  ccctccgtg   1560
ctggactccg  acggctcatt  cttcctgtac  tccaagctga  cagtggacaa  gtccagatgg  1620
cagcagggca  acgtgttctc  ctgctccgtg  atgcacgaag  ctttgcacaa  tcactacaca  1680
cagaagtccc  tgtctctgtc  ccctggc                                         1707

SEQ ID NO: 132             moltype = AA  length = 547
FEATURE                    Location/Qualifiers
REGION                     1..547
                           note = Description of sequence: DR2092M Mature 3xAla p40Fc
                            protein
source                     1..547
                           mol_type = protein
                           organism = synthetic construct
SEQUENCE: 132
IWELKKDVYV  VELDWYPDAP  GEMVVLTCDT  PEEDGITWTL  DQSSEVLGSG  KTLTIQVKAA   60
GDAGQYTCHK  GGEVLSHSLL  LLHAKEDGIW  STDILKDQKE  PKNKTFLRCE  AKNYSGRFTC  120
```

```
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSG REKKDRVFTD KTSATVICRK NASISVRAQD RYYSSSWSEW   300
ASVPCSGGGG SGGGGSEPKS SDKTHTCPPC PAPEAAGGPS VFLFPPKPKD TLMISRTPEV   360
TCVVVDVSHE DPEVKFNWYV DGVEVHNAKT KPREEQYNST YRVVSVLTVL HQDWLNGKEY   420
KCKVSNKALA APIEKTISKA KGQPREPQVY TLPPCRDELT KNQVSLWCLV KGFYPSDIAV   480
EWESNGQPEN NYKTTPPVLD SDGSFFLYSK LTVDKSRWQQ GNVFSCSVMH EALHNHYTQK   540
SLSLSPG                                                            547

SEQ ID NO: 133          moltype = AA  length = 569
FEATURE                 Location/Qualifiers
REGION                  1..569
                        note = Description of sequence: DR2455P 3xAla p40Fc
                         precursor protein
source                  1..569
                        mol_type = protein
                        organism = synthetic construct
SEQUENCE: 133
MCHQQLVISW FSLVFLASPL VAIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV LHEALHSHYT QKSLSLSPG                                    569

SEQ ID NO: 134          moltype = DNA  length = 1707
FEATURE                 Location/Qualifiers
misc_feature            1..1707
                        note = Description of sequence: Nucleic acid sequence
                         encoding DR2455P
source                  1..1707
                        mol_type = other DNA
                        organism = synthetic construct
SEQUENCE: 134
atgtgccatc aacagcttgt tatcagctgg ttctcattgg tcttcctggc aagcccactg    60
gtggcaatct gggaactgaa gaaagacgtg tacgtagtgg aactggactg gtatcctgac   120
gctcctgggg agatggtcgt tctgacctgc gataccccgg aagaggatgg aattacctgg   180
accctcgacc agtcttcaga agtgctgggc agcggaaaaa cactgaccat tcaggtgaag   240
gagttcggcg atgccggaca gtacacctgc cataagggtg gcgaagtgtt gtcccatage   300
ttgctgctcc tgcataaaaa ggaggacgga atctggagca ccgacattct gaaggaccag   360
aaggaaccaa agaacaaaac attttctgcg tgcgaggcga aaaactactc tggccgcttc   420
acctgttggt ggctgacaac catcagcacc gatctgacct tctccgtgaa gtcctcacgc   480
ggctccagcg atcctcaggg tgttacttgc ggagctgcaa cgcttagtgc ggaaagagtg   540
aggggtgata acaaggaata cgaatactcc gtgaatgtc aggaagatag cgcctgccct   600
gctgccgagg aatcattgcc aatcgaggtg atggtgacg ccgtgcataa gctgaagtac   660
gaaaattaca cgagcagttt tttcattcgc gatatcatta gccagacccc tcccaaaaac   720
ttgcagctga gcctctgaa gaacctagg caggtcgagg tttcttggga ataccccagt   780
acttggtcca cccctcacag ctatttttcc ttgacgttct gcgtccaggt gcaaggcaag   840
tccaagcggg aaaaaaagga cagggtgttt accgataaga ctagcgccac tgtgatttgc   900
cgtaaaaacg ctagtatttc cgtgcgtgcc caagaccgct actatagctc cagctggtcc   960
gagtgggcca gcgttccctg ttccggcggt ggggggtccg gcggtggcgg ttccgagcct  1020
aagagtagcg acaagactca cacctgtccc ccttgtcccg cgccggaggc cgctggaggt  1080
ccttcagtat tcctgtttcc tccaaagcct aaagataccc tgatgatctc tcgcacgcca  1140
gaggttactt gcgtggtagt ggacgtatcc cacgaagatc ctgaagtcaa gttcaactgg  1200
tacgtcgatg gagtggaggt gcataacgct aagacaaaac caagagagga acagtacaac  1260
tctacatacc gggttgtgtc cgtgctgaca gtgctgcacc aagactggct taatggcaaa  1320
gagtataagt gcaaagtctc taacaaagcc ctggcggccc ccattgaaaa gactattagc  1380
aaaagctaag gccaaccgag ggagccacag gtttacacgc tgcctccatg ccgtgacgaa  1440
ctcaccaaga atcaggtgtc cctgtggtgt ttggtgaaag cttttaccc cagcgatatc  1500
gccgtggagt gggagagcaa tggccagcct gaaaataact ataaaacaac cccacccgtg  1560
ctggacagtg acggttcctt cttttttgtat tctaagctga ccgtggacaa aagcaggtgg  1620
caacagggaa acgtctttc ttgctcagtg ctgcacgagg ccctccactc tcactatacg  1680
cagaagtctc tgtctctgtc cccaggc                                     1707

SEQ ID NO: 135          moltype = AA  length = 547
FEATURE                 Location/Qualifiers
REGION                  1..547
                        note = Description of sequence: DR2455M 3xAla p40Fc mature
                         protein
source                  1..547
                        mol_type = protein
                        organism = synthetic construct
SEQUENCE: 135
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
```

```
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSEPKS SDKTHTCPPC PAPEAAGGPS VFLFPPKPKD TLMISRTPEV    360
TCVVVDVSHE DPEVKFNWYV DGVEVHNAKT KPREEQYNST YRVVSVLTVL HQDWLNGKEY    420
KCKVSNKALA APIEKTISKA KGQPREPQVY TLPPCRDELT KNQVSLWCLV KGFYPSDIAV    480
EWESNGQPEN NYKTTPPVLD SDGSFFLYSK LTVDKSRWQQ GNVFSCSVLH EALHSHYTQK    540
SLSLSPG                                                              547

SEQ ID NO: 136           moltype = AA  length = 569
FEATURE                  Location/Qualifiers
REGION                   1..569
                         note = Description of sequence: DR2456P p40 LALA PA K282G
source                   1..569
                         mol_type = protein
                         organism = synthetic construct
SEQUENCE: 136
MCHQQLVISW FSLVFLASPL VAIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SGREKKDRVF TDKTSATVIC    300
RKNASISVRA QDRYYSSSWS EWASVPCSGG GGSGGGGSEP KSSDKTHTCP PCPAPEAAGG    360
PSVFLFPPKP KDTLMISRTP EVTCVVVDVS HEDPEVKFNW YVDGVEVHNA KTKPREEQYN    420
STYRVVSVLT VLHQDWLNGK EYKCKVSNKA LAAPIEKTIS KAKGQPREPQ VYTLPPCRDE    480
LTKNQVSLWC LVKGFYPSDI AVEWESNGQP ENNYKTTPPV LDSDGSFFLY SKLTVDKSRW    540
QQGNVFSCSV LHEALHSHYT QKSLSLSPG                                      569

SEQ ID NO: 137           moltype = DNA  length = 1707
FEATURE                  Location/Qualifiers
misc_feature             1..1707
                         note = Description of sequence: Nucleic acid sequence
                           encoding DR2456P
source                   1..1707
                         mol_type = other DNA
                         organism = synthetic construct
SEQUENCE: 137
atgtgccatc aacagctcgt tatcagctgg ttctctcttg tgttccttgc ttccccctct     60
gtggcaattt gggagcttaa aaaggacgtt tacgtagtgg agctggactg gtatccagac    120
gcgccgggtg agatggtagt gttgacctgt gacaccccag aagaggacgg aatcacctgg    180
acattggatc agagttccga ggtgctcggc agcggcaaga cactgaccat ccaggtgaaa    240
gaatttggtg acgccggtca atacacttgt cacaaggggtg gcgaggtgtt gtctcactcc    300
cttctgctcc ttcataaaaa ggaagacggc atctggagta cggacatcct gaaggaccag    360
aaggagccta gaataagac cttcctgcgt tgcgaggcca agaactactc tggccgcttt    420
acttgttggt ggctcacaac tatctcaacc gacctgacct tttctgtaaa aagctctcgg    480
ggcagctccg atcctcaggg tgttacttgc ggggcagcca ccctgagcgc cgagcgtgtg    540
cgcggcgaca ataaagagta cgaatactct gttgagtgtc aggaggactc agcttgcccc    600
gcagcggaag agtctttgcc tatcgaggtc atggtggacg ccgtgcataa gctgaaatac    660
gagaattata caagctcatt ctttatccgt gatattatca gcccgatcc cccgaagaat    720
ctccagctga aaccctgaa gaactcccgc caggtcgagg tgagctggga gtaccccgat    780
acctggagta ctcccacag ctatttcagt ctcaccttt gcgtgcaggt gcagggaaag    840
tctggtcgcg agaagaaaga tcgcgtattt accgataaga ccagtgctac tgtcatttgc    900
cgcaaaaacg cgagcatctc cgttcgcgct caggaccgct actattctag ctcatggtca    960
gagtgggcca gtgtaccttg tagcggcgga ggggtagcg gtggcggtgg ctccgagccc   1020
aaaagtagcg acaagacaca cacctgtccc ccttgcccag ctcccgaggc cgctggaggc   1080
ccctccgtat tccttttcc cccgaagcct aaggacaccc ttatgatctc tcgtaccct    1140
gaggtgactt gcgttgtcgt tgatgtcagc cacgaagatc cagaggtgaa gttcaactgg   1200
tatgtcgatg gcgttgaggt ccataacgct aaaacaaagc caggagga acagtataac    1260
tccacttacc gcgtcgtgtc cgttctgaca gtattgcatc aagattggct gaacggcaag   1320
gagtacaagt gcaaggtctc aaacaaggcc ttggcagctc ctattgagaa gaccatcagc   1380
aaggcgaagg gacagcctcg ggaacccag gtctacacgc tgccccttg ccgcgatgaa    1440
ctcactaaaa atcaggtgtc cctgtggtgc ctcgtgaagg gattctaccc tagcgatatt    1500
gctgtggaat gggaaagcaa cggtcagcct gaaaacaatt acaagacaac tccacctgtc   1560
ttggattcag atggcagctt ttttctgtac tccaagctca ccgtggacaa gtcccgttgg   1620
caacagggta acgtgttttc ttgcagcgtt cttcacgaag ccctgcactc ccattatact   1680
cagaagtcct tgtcactttc acctggg                                      1707

SEQ ID NO: 138           moltype = AA  length = 547
FEATURE                  Location/Qualifiers
REGION                   1..547
                         note = Description of sequence: DR2456M 3xAla p40Fc mature
                           protein
source                   1..547
                         mol_type = protein
                         organism = synthetic construct
SEQUENCE: 138
IWELKKDVYV VELDWYPDAP GEMVVLTCDT PEEDGITWTL DQSSEVLGSG KTLTIQVKEF     60
GDAGQYTCHG GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
```

```
EESLPIEVMV DAVHKLKYEN YTSSFFIRDI IKPDPPKNLQ LKPLKNSRQV EVSWEYPDTW  240
STPHSYFSLT FCVQVQGKSG REKKDRVFTD KTSATVICRK NASISVRAQD RYYSSSWSEW  300
ASVPCSGGGG SGGGGSEPKS SDKTHTCPPC PAPEAAGGPS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALA APIEKTISKA KGQPREPQVY TLPPCRDELT KNQVSLWCLV KGFYPSDIAV  480
EWESNGQPEN NYKTTPPVLD SDGSFFLYSK LTVDKSRWQQ GNVFSCSVLH EALHSHYTQK  540
SLSLSPG                                                           547

SEQ ID NO: 139          moltype = AA  length = 569
FEATURE                 Location/Qualifiers
REGION                  1..569
                        note = Description of sequence: DR2086P precursor with
                          signal human p40 E81A F82A K106A K260Q hIgG1 KiH knob
                          C220S LALAPA S354C M428L N434S DelK447
source                  1..569
                        mol_type = protein
                        organism = synthetic construct
SEQUENCE: 139
MCHQQLVISW FSLVFLASPL VAIWELKKDV YVVELDWYPD APGEMVVLTC DTPEEDGITW  60
TLDQSSEVLG SGKTLTIQVK AAGDAGQYTC HKGGEVLSHS LLLLHAKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SQREKKDRVF TDKTSATVIC  300
RKNASISVRA QDRYYSSSWS EWASVPCSGG GGSGGGGSEP KSSDKTHTCP PCPAPEAAGG  360
PSVFLFPPKP KDTLMISRTP EVTCVVVDVS HEDPEVKFNW YVDGVEVHNA KTKPREEQYN  420
STYRVVSVLT VLHQDWLNGK EYKCKVSNKA LAAPIEKTIS KAKGQPREPQ VYTLPPCRDE  480
LTKNQVSLWC LVKGFYPSDI AVEWESNGQP ENNYKTTPPV LDSDGSFFLY SKLTVDKSRW  540
QQGNVFSCSV LHEALHSHYT QKSLSLSPG                                   569

SEQ ID NO: 140          moltype = AA  length = 569
FEATURE                 Location/Qualifiers
REGION                  1..569
                        note = Description of sequence: Nucleic Acid Sequence
                          encoding DR2086P
source                  1..569
                        mol_type = protein
                        organism = synthetic construct
SEQUENCE: 140
MCHQQLVISW FSLVFLASPL VAIWELKKDV YVVELDWYPD APGEMVVLTC DTPEEDGITW  60
TLDQSSEVLG SGKTLTIQVK AAGDAGQYTC HKGGEVLSHS LLLLHAKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SQREKKDRVF TDKTSATVIC  300
RKNASISVRA QDRYYSSSWS EWASVPCSGG GGSGGGGSEP KSSDKTHTCP PCPAPEAAGG  360
PSVFLFPPKP KDTLMISRTP EVTCVVVDVS HEDPEVKFNW YVDGVEVHNA KTKPREEQYN  420
STYRVVSVLT VLHQDWLNGK EYKCKVSNKA LAAPIEKTIS KAKGQPREPQ VYTLPPCRDE  480
LTKNQVSLWC LVKGFYPSDI AVEWESNGQP ENNYKTTPPV LDSDGSFFLY SKLTVDKSRW  540
QQGNVFSCSV LHEALHSHYT QKSLSLSPG                                   569

SEQ ID NO: 141          moltype = AA  length = 547
FEATURE                 Location/Qualifiers
REGION                  1..547
                        note = Description of sequence: DR2086M human p40 E81A F82A
                          K106A K260Q hIgG1 KiH knob C220S LALAPA S354C M428L N434S
                          DelK447
source                  1..547
                        mol_type = protein
                        organism = synthetic construct
SEQUENCE: 141
IWELKKDVYV VELDWYPDAP GEMVVLTCDT PEEDGITWTL DQSSEVLGSG KTLTIQVKAA  60
GDAGQYTCHK GGEVLSHSLL LLHAKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSQ REKKDRVFTD KTSATVICRK NASISVRAQD RYYSSSWSEW  300
ASVPCSGGGG SGGGGSEPKS SDKTHTCPPC PAPEAAGGPS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALA APIEKTISKA KGQPREPQVY TLPPCRDELT KNQVSLWCLV KGFYPSDIAV  480
EWESNGQPEN NYKTTPPVLD SDGSFFLYSK LTVDKSRWQQ GNVFSCSVLH EALHSHYTQK  540
SLSLSPG                                                           547

SEQ ID NO: 142          moltype = AA  length = 569
FEATURE                 Location/Qualifiers
REGION                  1..569
                        note = Description of sequence: DR2087P precursor with
                          signal human p40 E81A F82A K106A K260N hIgG1 KiH knob
                          C220S LALAPA S354C M428L N434S DelK447
source                  1..569
                        mol_type = protein
                        organism = synthetic construct
```

```
SEQUENCE: 142
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SNREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV LHEALHSHYT QKSLSLSPG                                    569

SEQ ID NO: 143          moltype = AA  length = 569
FEATURE                 Location/Qualifiers
REGION                  1..569
                        note = Description of sequence: Nucleic Acid Sequence
                          encoding DR2087P
source                  1..569
                        mol_type = protein
                        organism = synthetic construct
SEQUENCE: 143
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SNREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV LHEALHSHYT QKSLSLSPG                                    569

SEQ ID NO: 144          moltype = AA  length = 547
FEATURE                 Location/Qualifiers
REGION                  1..547
                        note = Description of sequence: DR2087M Mature human p40
                          E81A F82A K106A K260N hIgG1 KiH knob C220S LALAPA S354C
                          M428L N434S DelK447
source                  1..547
                        mol_type = protein
                        organism = synthetic construct
SEQUENCE: 144
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSN REKKDRVFTD KTSATVICRK NASISVRAQD RYYSSSWSEW   300
ASVPCSGGGG SGGGGSEPKS SDKTHTCPPC PAPEAAGGPS VFLFPPKPKD TLMISRTPEV   360
TCVVVDVSHE DPEVKFNWYV DGVEVHNAKT KPREEQYNST YRVVSVLTVL HQDWLNGKEY   420
KCKVSNKALA APIEKTISKA KGQPREPQVY TLPPCRDELT KNQVSLWCLV KGFYPSDIAV   480
EWESNGQPEN NYKTTPPVLD SDGSFFLYSK LTVDKSRWQQ GNVFSCSVLH EALHSHYTQK   540
SLSLSPG                                                            547

SEQ ID NO: 145          moltype = AA  length = 569
FEATURE                 Location/Qualifiers
REGION                  1..569
                        note = Description of sequence: DR2090P precursor with
                          signal human p40 E81A F82A K106A K260Q hIgG1 KiH knob
                          C220S LALAPA S354C DelK447
source                  1..569
                        mol_type = protein
                        organism = synthetic construct
SEQUENCE: 145
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SQREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                    569

SEQ ID NO: 146          moltype = AA  length = 569
FEATURE                 Location/Qualifiers
REGION                  1..569
                        note = Description of sequence: Nucleic Acid Sequence
                          encoding DR2090P
```

```
                                             -continued source                  1..569
                        mol_type = protein
                        organism = synthetic construct
SEQUENCE: 146
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SQREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                    569

SEQ ID NO: 147          moltype = AA   length = 569
FEATURE                 Location/Qualifiers
REGION                  1..569
                        note = Description of sequence: DR2090M mature human p40
                         E81A F82A K106A K260Q hIgG1 KiH knob C220S LALAPA S354C
                         DelK447
source                  1..569
                        mol_type = protein
                        organism = synthetic construct
SEQUENCE: 147
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SQREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                    569

SEQ ID NO: 148          moltype = AA   length = 569
FEATURE                 Location/Qualifiers
REGION                  1..569
                        note = Description of sequence: DR2091P precursor with
                         signal human p40 E81A F82A K106A K260N hIgG1 KiH knob
                         C220S LALAPA S354C DelK447
source                  1..569
                        mol_type = protein
                        organism = synthetic construct
SEQUENCE: 148
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SNREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                    569

SEQ ID NO: 149          moltype = AA   length = 569
FEATURE                 Location/Qualifiers
REGION                  1..569
                        note = Description of sequence: Nucleic Acid Sequence
                         encoding DR2091P
source                  1..569
                        mol_type = protein
                        organism = synthetic construct
SEQUENCE: 149
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SNREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                    569

SEQ ID NO: 150          moltype = AA   length = 547
FEATURE                 Location/Qualifiers
```

|  |  |  |
|---|---|---|
| REGION | 1..547 | |
| | note = Description of sequence: DR2091M mature human p40 E81A F82A K106A K260N hIgG1 KiH knob C220S LALAPA S354C DelK447 | |
| source | 1..547 | |
| | mol_type = protein | |
| | organism = synthetic construct | |

SEQUENCE: 150

```
IWELKKDVYV VELDWYPDAP GEMVVLTCDT PEEDGITWTL DQSSEVLGSG KTLTIQVKAA   60
GDAGQYTCHK GGEVLSHSLL LLLHAKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSN REKKDRVFTD KTSATVICRK NASISVRAQD RYYSSSWSEW  300
ASVPCSGGGG SGGGGSEPKS SDKTHTCPPC PAPEAAGGPS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALA APIEKTISKA KGQPREPQVY TLPPCRDELT KNQVSLWCLV KGFYPSDIAV  480
EWESNGQPEN NYKTTPPVLD SDGSFFLYSK LTVDKSRWQQ GNVFSCSVMH EALHNHYTQK  540
SLSLSPG                                                           547
```

|  |  |  |
|---|---|---|
| SEQ ID NO: 151 | moltype = AA length = 569 | |
| FEATURE | Location/Qualifiers | |
| REGION | 1..569 | |
| | note = Description of sequence: DR2092P precursor with signal human p40 E81A F82A K106A K260G hIgG1 KiH knob C220S LALAPA S354C DelK447 | |
| source | 1..569 | |
| | mol_type = protein | |
| | organism = synthetic construct | |

SEQUENCE: 151

```
MCHQQLVISW FSLVFLASPL VAIWELKKDV YVVELDWYPD APGEMVVLTC DTPEEDGITW   60
TLDQSSEVLG SGKTLTIQVK AAGDAGQYTC HKGGEVLSHS LLLLHAKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SGREKKDRVF TDKTSATVIC  300
RKNASISVRA QDRYYSSSWS EWASVPCSGG GGSGGGGSEP KSSDKTHTCP PCPAPEAAGG  360
PSVFLFPPKP KDTLMISRTP EVTCVVVDVS HEDPEVKFNW YVDGVEVHNA KTKPREEQYN  420
STYRVVSVLT VLHQDWLNGK EYKCKVSNKA LAAPIEKTIS KAKGQPREPQ VYTLPPCRDE  480
LTKNQVSLWC LVKGFYPSDI AVEWESNGQP ENNYKTTPPV LDSDGSFFLY SKLTVDKSRW  540
QQGNVFSCSV MHEALHNHYT QKSLSLSPG                                    569
```

|  |  |  |
|---|---|---|
| SEQ ID NO: 152 | moltype = AA length = 569 | |
| FEATURE | Location/Qualifiers | |
| REGION | 1..569 | |
| | note = Description of sequence: Nucleic Acid Sequence encoding DR2092P | |
| source | 1..569 | |
| | mol_type = protein | |
| | organism = synthetic construct | |

SEQUENCE: 152

```
MCHQQLVISW FSLVFLASPL VAIWELKKDV YVVELDWYPD APGEMVVLTC DTPEEDGITW   60
TLDQSSEVLG SGKTLTIQVK AAGDAGQYTC HKGGEVLSHS LLLLHAKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SGREKKDRVF TDKTSATVIC  300
RKNASISVRA QDRYYSSSWS EWASVPCSGG GGSGGGGSEP KSSDKTHTCP PCPAPEAAGG  360
PSVFLFPPKP KDTLMISRTP EVTCVVVDVS HEDPEVKFNW YVDGVEVHNA KTKPREEQYN  420
STYRVVSVLT VLHQDWLNGK EYKCKVSNKA LAAPIEKTIS KAKGQPREPQ VYTLPPCRDE  480
LTKNQVSLWC LVKGFYPSDI AVEWESNGQP ENNYKTTPPV LDSDGSFFLY SKLTVDKSRW  540
QQGNVFSCSV MHEALHNHYT QKSLSLSPG                                    569
```

|  |  |  |
|---|---|---|
| SEQ ID NO: 153 | moltype = AA length = 547 | |
| FEATURE | Location/Qualifiers | |
| REGION | 1..547 | |
| | note = Description of sequence: DR2092M human p40 E81A F82A K106A K260G hIgG1 KiH knob C220S LALAPA S354C DelK447 | |
| source | 1..547 | |
| | mol_type = protein | |
| | organism = synthetic construct | |

SEQUENCE: 153

```
IWELKKDVYV VELDWYPDAP GEMVVLTCDT PEEDGITWTL DQSSEVLGSG KTLTIQVKAA   60
GDAGQYTCHK GGEVLSHSLL LLHAKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSG REKKDRVFTD KTSATVICRK NASISVRAQD RYYSSSWSEW  300
ASVPCSGGGG SGGGGSEPKS SDKTHTCPPC PAPEAAGGPS VFLFPPKPKD TLMISRTPEV  360
TCVVVDVSHE DPEVKFNWYV DGVEVHNAKT KPREEQYNST YRVVSVLTVL HQDWLNGKEY  420
KCKVSNKALA APIEKTISKA KGQPREPQVY TLPPCRDELT KNQVSLWCLV KGFYPSDIAV  480
EWESNGQPEN NYKTTPPVLD SDGSFFLYSK LTVDKSRWQQ GNVFSCSVMH EALHNHYTQK  540
SLSLSPG                                                           547
```

```
SEQ ID NO: 154          moltype = AA  length = 465
FEATURE                 Location/Qualifiers
REGION                  1..465
                        note = Description of sequence: DR1535P Precursor
source                  1..465
                        mol_type = protein
                        organism = synthetic construct
SEQUENCE: 154
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSG GGGSEPKSSD   240
KTHTCPPCPA PEAAGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALAAP IEKTISKAKG   360
QPREPQVCTL PPSRDELTKN QVSLSCAVKG FYPSDIAVEW ESNGQPENNY KTTPPVLDSD   420
GSFFLVSKLT VDKSRWQQGN VFSCSVMHEA LHNHYTQKSL SLSPG                   465

SEQ ID NO: 155          moltype = AA  length = 306
FEATURE                 Location/Qualifiers
REGION                  1..306
                        note = Description of sequence: hP40 E81A/F82A/K106A/K282G
source                  1..306
                        mol_type = protein
                        organism = synthetic construct
SEQUENCE: 155
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSG REKKDRVFTD KTSATVICRK NASISVRAQD RYYSSSWSEW   300
ASVPCS                                                              306

SEQ ID NO: 156          moltype = AA  length = 306
FEATURE                 Location/Qualifiers
REGION                  1..306
                        note = Description of sequence: "hP40 E81A/F82A/K106A/K282A
                        "
source                  1..306
                        mol_type = protein
                        organism = synthetic construct
SEQUENCE: 156
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRA DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSG REKKDRVFTD KTSATVICRK NASISVRAQD RYYSSSWSEW   300
ASVPCS                                                              306

SEQ ID NO: 157          moltype = AA  length = 306
FEATURE                 Location/Qualifiers
REGION                  1..306
                        note = Description of sequence: hP40 E81A/F82A/K106A/K282N
source                  1..306
                        mol_type = protein
                        organism = synthetic construct
SEQUENCE: 157
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRN DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSG REKKDRVFTD KTSATVICRK NASISVRAQD RYYSSSWSEW   300
ASVPCS                                                              306

SEQ ID NO: 158          moltype = AA  length = 306
FEATURE                 Location/Qualifiers
REGION                  1..306
                        note = Description of sequence: hP40 E81A/F82A/K106A/K282Q
source                  1..306
                        mol_type = protein
                        organism = synthetic construct
SEQUENCE: 158
IWELKKDVYV VELDWYPDAP GEMVVLTCDT PEEDGITWTL DQSSEVLGSG KTLTIQVKAA    60
GDAGQYTCHK GGEVLSHSLL LLHAKEDGIW STDILKDQKE PKNKTFLRCE AKNYSGRFTC   120
WWLTTISTDL TFSVKSSRGS SDPQGVTCGA ATLSAERVRQ DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSG REKKDRVFTD KTSATVICRK NASISVRAQD RYYSSSWSEW   300
ASVPCS                                                              306
```

-continued

```
SEQ ID NO: 159            moltype = AA   length = 306
FEATURE                   Location/Qualifiers
REGION                    1..306
                          note = Description of sequence: hP40 E81A/F82A/K282G
source                    1..306
                          mol_type = protein
                          organism = synthetic construct
SEQUENCE: 159
IWELKKDVYV VELDWYPDAP GEMVVLTCDT PEEDGITWTL DQSSEVLGSG KTLTIQVKAA   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSG REKKDRVFTD KTSATVICRK NASISVRAQD RYYSSSWSEW  300
ASVPCS                                                             306

SEQ ID NO: 160            moltype = AA   length = 306
FEATURE                   Location/Qualifiers
REGION                    1..306
                          note = Description of sequence: hP40 E81A/F82A/K282A
source                    1..306
                          mol_type = protein
                          organism = synthetic construct
SEQUENCE: 160
IWELKKDVYV VELDWYPDAP GEMVVLTCDT PEEDGITWTL DQSSEVLGSG KTLTIQVKAA   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRA DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSG REKKDRVFTD KTSATVICRK NASISVRAQD RYYSSSWSEW  300
ASVPCS                                                             306

SEQ ID NO: 161            moltype = AA   length = 306
FEATURE                   Location/Qualifiers
REGION                    1..306
                          note = Description of sequence: hP40 E81A/F82A/K282N
source                    1..306
                          mol_type = protein
                          organism = synthetic construct
SEQUENCE: 161
IWELKKDVYV VELDWYPDAP GEMVVLTCDT PEEDGITWTL DQSSEVLGSG KTLTIQVKAA   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRN DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSG REKKDRVFTD KTSATVICRK NASISVRAQD RYYSSSWSEW  300
ASVPCS                                                             306

SEQ ID NO: 162            moltype = AA   length = 306
FEATURE                   Location/Qualifiers
REGION                    1..306
                          note = Description of sequence: E81A/F82A/K282Q
source                    1..306
                          mol_type = protein
                          organism = synthetic construct
SEQUENCE: 162
IWELKKDVYV VELDWYPDAP GEMVVLTCDT PEEDGITWTL DQSSEVLGSG KTLTIQVKAA   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRQ DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSG REKKDRVFTD KTSATVICRK NASISVRAQD RYYSSSWSEW  300
ASVPCS                                                             306

SEQ ID NO: 163            moltype = AA   length = 559
FEATURE                   Location/Qualifiers
REGION                    1..559
                          note = Description of sequence: DR1442P
source                    1..559
                          mol_type = protein
                          organism = synthetic construct
SEQUENCE: 163
MCHQQLVISW FSLVFLASPL VAIWELKKDV YVVELDWYPD APGEMVVLTC DTPEEDGITW   60
TLDQSSEVLG SGKTLTIQVK AAGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSEP KSSDKTHTCP PCPAPEAAGG PSVFLFPPKP  360
KDTLMISRTP EVTCVVVDVS HEDPEVKFNW YVDGVEVHNA KTKPREEQYN STYRVVSVLT  420
VLHQDWLNGK EYKCKVSNKA LAAPIEKTIS KAKGQPREPQ VYTLPPCRDE LTKNQVSLWC  480
LVKGFYPSDI AVEWESNGQP ENNYKTTPPV LDSDGSFFLY SKLTVDKSRW QQGNVFSCSV  540
MHEALHNHYT QKSLSLSPG                                               559
```

```
SEQ ID NO: 164          moltype = AA   length = 465
FEATURE                 Location/Qualifiers
REGION                  1..465
                        note = Description of sequence: DR1535P
source                  1..465
                        mol_type = protein
                        organism = synthetic construct
SEQUENCE: 164
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSG GGGSEPKSSD   240
KTHTCPPCPA PEAAGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALAAP IEKTISKAKG   360
QPREPQVCTL PPSRDELTKN QVSLSCAVKG FYPSDIAVEW ESNGQPENNY KTTPPVLDSD   420
GSFFLVSKLT VDKSRWQQGN VFSCSVMHEA LHNHYTQKSL SLSPG                   465

SEQ ID NO: 165          moltype = AA   length = 460
FEATURE                 Location/Qualifiers
REGION                  1..460
                        note = Description of sequence: DR1536P
source                  1..460
                        mol_type = protein
                        organism = synthetic construct
SEQUENCE: 165
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSE PKSSDKTHTC   240
PPCPAPEAAG GPSVFLFPPK PKDTLMISRT PEVTCVVVDV SHEDPEVKFN WYVDGVEVHN   300
AKTKPREEQY NSTYRVVSVL TVLHQDWLNG KEYKCKVSNK ALAAPIEKTI SKAKGQPREP   360
QVCTLPPSRD ELTKNQVSLS CAVKGFYPSD IAVEWESNGQ PENNYKTTPP VLDSDGSFFL   420
VSKLTVDKSR WQQGNVFSCS VMHEALHNHY TQKSLSLSPG                         460

SEQ ID NO: 166          moltype = AA   length = 569
FEATURE                 Location/Qualifiers
REGION                  1..569
                        note = Description of sequence: DR1537P
source                  1..569
                        mol_type = protein
                        organism = synthetic construct
SEQUENCE: 166
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDDPKN   240
LQLKPLKNSR QVEVSWEYPD TWSTPHSYFS LTFCVQVQSK SKREKKDRVF TDKTSATVIC   300
RKNASISVRA QDRYYSSSWS EWASVPCSGG GGSGGGGSEP KSSDKTHTCP PCPAPEAAGG   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LAAPIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                     569

SEQ ID NO: 167          moltype = AA   length = 460
FEATURE                 Location/Qualifiers
REGION                  1..460
                        note = Description of sequence: DR1572P
source                  1..460
                        mol_type = protein
                        organism = synthetic construct
SEQUENCE: 167
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSE PKSCDKTHTC   240
PPCPAPEAAG GPSVFLFPPK PKDTLMISRT PEVTCVVVDV SHEDPEVKFN WYVDGVEVHN   300
AKTKPREEQY NSTYRVVSVL TVLHQDWLNG KEYKCKVSNK ALAAPIEKTI SKAKGQPREP   360
QVCTLPPSRD ELTKNQVSLS CAVKGFYPSD IAVEWESNGQ PENNYKTTPP VLDSDGSFFL   420
VSKLTVDKSR WQQGNVFSCS VMHEALHNHY TQKSLSLSPG                         460

SEQ ID NO: 168          moltype = AA   length = 569
FEATURE                 Location/Qualifiers
REGION                  1..569
                        note = Description of sequence: DR1573P
source                  1..569
                        mol_type = protein
                        organism = synthetic construct
SEQUENCE: 168
MCHQQLVISW FSLVFLASPL VAIWELKKDV YVVELDWYPD APGEMVVLTC DTPEEDGITW    60
```

```
TLDQSSEVLG SGKTLTIQVK AAGDAGQYTC HKGGEVLSHS LLLLHAKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYSSSWS  EWASVPCSGG GGSGGGGSEP KSCDKTHTCP PCPAPEAAGG    360
PSVFLFPPKP KDTLMISRTP EVTCVVVDVS HEDPEVKFNW YVDGVEVHNA KTKPREEQYN    420
STYRVVSVLT VLHQDWLNGK EYKCKVSNKA LAAPIEKTIS KAKGQPREPQ VYTLPPCRDE    480
LTKNQVSLWC LVKGFYPSDI AVEWESNGQP ENNYKTTPPV LDSDGSFFLY SKLTVDKSRW    540
QQGNVFSCSV MHEALHNHYT QKSLSLSPG                                     569

SEQ ID NO: 169         moltype = AA  length = 559
FEATURE                Location/Qualifiers
REGION                 1..559
                       note = Description of sequence: DR1588P
source                 1..559
                       mol_type = protein
                       organism = synthetic construct
SEQUENCE: 169
MCHQQLVISW FSLVFLASPL VAIWELKKDV YVVELDWYPD APGEMVVLTC DTPEEDGITW     60
TLDQSSEVLG SGKTLTIQVK AAGDAGQYTC HKGGEVLSHS LLLLHAKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYSSSWS  EWASVPCSEP KSSDKTHTCP PCPAPEFEGG PSVFLFPPKP    360
KDTLMISRTP EVTCVVVDVS HEDPEVKFNW YVDGVEVHNA KTKPREEQYN STYRVVSVLT    420
VLHQDWLNGK EYKCKVSNKA LPASIEKTIS KAKGQPREPQ VYTLPPCRDE LTKNQVSLWC    480
LVKGFYPSDI AVEWESNGQP ENNYKTTPPV LDSDGSFFLY SKLTVDKSRW QQGNVFSCSV    540
MHEALHNHYT QKSLSLSPG                                                559

SEQ ID NO: 170         moltype = AA  length = 465
FEATURE                Location/Qualifiers
REGION                 1..465
                       note = Description of sequence: DR1589P
source                 1..465
                       mol_type = protein
                       organism = synthetic construct
SEQUENCE: 170
MCPARSLLLV ATLVLLDHLS LARNLPVATP DPGMFPCLHH SQNLLRAVSN MLQKARQTLE     60
FYPCTSEEID HEDITKDKTS TVEACLPLEL TKNESCLNSR ETSFITNGSC LASRKTSFMM    120
ALCLSSIYED LKMYQVEFKT MNAKLLMDPK RQIFLDQNML AVIDELMQAL NFNSETVPQK    180
SSSLEEPDFYK TKIKLCILLH AFRIRAVTID RVMSYLNASG GGGSGGGGSG GGGSEPKSSD   240
KTHTCPPCPA PEFEGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAS IEKTISKAKG    360
QPREPQVCTL PPSRDELTKN QVSLSCAVKG FYPSDIAVEW ESNGQPENNY KTTPPVLDSD    420
GSFFLVSKLT VDKSRWQQGN VFSCSVMHEA LHNHYTQKSL SLSPG                   465

SEQ ID NO: 171         moltype = AA  length = 553
FEATURE                Location/Qualifiers
REGION                 1..553
                       note = Description of sequence: DR1590P
source                 1..553
                       mol_type = protein
                       organism = synthetic construct
SEQUENCE: 171
MCHQQLVISW FSLVFLASPL VAIWELKKDV YVVELDWYPD APGEMVVLTC DTPEEDGITW     60
TLDQSSEVLG SGKTLTIQVK AAGDAGQYTC HKGGEVLSHS LLLLHAKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYSSSWS  EWASVPCSEP KSSDKTHTCP PCPAPEAEGA PSVFLFPPKP    360
KDTLMISRTP EVTCVVVDVS HEDPEVKFNW YVDGVEVHNA KTKPREEQYN STYRVVSVLT    420
VLHQDWLNGK EYKCKVSNKA LPAPIEKTIS KAKGQPREPQ VYTLLTKNQV SLWCLVKGFY    480
PSDIAVEWES NGQPENNYKT TPPVLDSDGS FFLYSKLTVD KSRWQQGNVF SCSVMHEALH    540
NHYTQKSLSL SPG                                                      553

SEQ ID NO: 172         moltype = AA  length = 465
FEATURE                Location/Qualifiers
REGION                 1..465
                       note = Description of sequence: DR1591P
source                 1..465
                       mol_type = protein
                       organism = synthetic construct
SEQUENCE: 172
MCPARSLLLV ATLVLLDHLS LARNLPVATP DPGMFPCLHH SQNLLRAVSN MLQKARQTLE     60
FYPCTSEEID HEDITKDKTS TVEACLPLEL TKNESCLNSR ETSFITNGSC LASRKTSFMM    120
ALCLSSIYED LKMYQVEFKT MNAKLLMDPK RQIFLDQNML AVIDELMQAL NFNSETVPQK    180
SSSLEEPDFYK TKIKLCILLH AFRIRAVTID RVMSYLNASG GGGSGGGGSG GGGSEPKSSD   240
KTHTCPPCPA PEAEGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
```

```
QPREPQVCTL PPSRDELTKN QVSLSCAVKG FYPSDIAVEW ESNGQPENNY KTTPPVLDSD    420
GSFFLVSKLT VDKSRWQQGN VFSCSVMHEA LHNHYTQKSL SLSPG                   465

SEQ ID NO: 173              moltype = AA  length = 569
FEATURE                     Location/Qualifiers
REGION                      1..569
                            note = Description of sequence: DR1595P
source                      1..569
                            mol_type = protein
                            organism = synthetic construct
SEQUENCE: 173
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCSGG GGSGGGGSEP KSSDKTHTCP PCPAPEAEGA   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LPSSIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV MHEALHNHYT QKSLSLSPG                                    569

SEQ ID NO: 174              moltype = AA  length = 460
FEATURE                     Location/Qualifiers
REGION                      1..460
                            note = Description of sequence: DR1596P
source                      1..460
                            mol_type = protein
                            organism = synthetic construct
SEQUENCE: 174
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSE PKSSDKTHTC   240
PPCPAPEAEG APSVFLFPPK PKDTLMISRT PEVTCVVVDV SHEDPEVKFN WYVDGVEVHN   300
AKTKPREEQY NSTYRVVSVL TVLHQDWLNG KEYKCKVSNK ALPSSIEKTI SKAKGQPREP   360
QVCTLPPSRD ELTKNQVSLS CAVKGFYPSD IAVEWESNGQ PENNYKTTPP VLDSDGSFFL   420
VSKLTVDKSR WQQGNVFSCS VMHEALHNHY TQKSLSLSPG                         460

SEQ ID NO: 175              moltype = AA  length = 569
FEATURE                     Location/Qualifiers
REGION                      1..569
                            note = Description of sequence: DR1597P
source                      1..569
                            mol_type = protein
                            organism = synthetic construct
SEQUENCE: 175
MCHQQLVISW FSLVFLASPL VAIWELKKDV YVVELDWYPD APGEMVVLTC DTPEEDGITW    60
TLDQSSEVLG SGKTLTIQVK AAGDAGQYTC HKGGEVLSHS LLLLHAKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCSGG GGSGGGGSEP KSSDKTHTCP PCPAPEAEGA   360
PSVFLFPPKP KDTLMISRTP EVTCVVVDVS HEDPEVKFNW YVDGVEVHNA KTKPREEQYN   420
STYRVVSVLT VLHQDWLNGK EYKCKVSNKA LPSSIEKTIS KAKGQPREPQ VYTLPPCRDE   480
LTKNQVSLWC LVKGFYPSDI AVEWESNGQP ENNYKTTPPV LDSDGSFFLY SKLTVDKSRW   540
QQGNVFSCSV LHEALHSHYT QKSLSLSPG                                    569

SEQ ID NO: 176              moltype = AA  length = 460
FEATURE                     Location/Qualifiers
REGION                      1..460
                            note = Description of sequence: DR1598P
source                      1..460
                            mol_type = protein
                            organism = synthetic construct
SEQUENCE: 176
MCPARSLLLV ATLVLLDHLS LARNLPVATP DPGMFPCLHH SQNLLRAVSN MLQKARQTLE    60
FYPCTSEEID HEDITKDKTS TVEACLPLEL TKNESCLNSR ETSFITNGSC LASRKTSFMM   120
ALCLSSIYED LKMYQVEFKT MNAKLLMDPK RQIFLDQNML AVIDELMQAL NFNSETVPQK   180
SSLEEPDFYK TKIKLCILLH AFRIRAVTID RVMSYLNASG GGGSGGGGSE PKSSDKTHTC   240
PPCPAPEAEG APSVFLFPPK PKDTLMISRT PEVTCVVVDV SHEDPEVKFN WYVDGVEVHN   300
AKTKPREEQY NSTYRVVSVL TVLHQDWLNG KEYKCKVSNK ALPSSIEKTI SKAKGQPREP   360
QVCTLPPSRD ELTKNQVSLS CAVKGFYPSD IAVEWESNGQ PENNYKTTPP VLDSDGSFFL   420
VSKLTVDKSR WQQGNVFSCS VLHEALHSHY TQKSLSLSPG                         460

SEQ ID NO: 177              moltype = AA  length = 189
FEATURE                     Location/Qualifiers
REGION                      1..189
                            note = Description of sequence: Human p19P Precursor Wild
```

```
                            type UniProt Ref: Q9NPF7
source                  1..189
                        mol_type = protein
                        organism = synthetic construct
SEQUENCE: 177
MLGSRAVMLL LLLPWTAQGR AVPGGSSPAW TQCQQLSQKL CTLAWSAHPL VGHMDLREEG    60
DEETTNDVPH IQCGDGCDPQ GLRDNSQFCL QRIHQGLIFY EKLLGSDIFT GEPSLLPDSP   120
VGQLHASLLG LSQLLQPEGH HWETQQIPSL SPSQPWQRLL LRFKILRSLQ AFVAVAARVF   180
AHGAATLSP                                                          189

SEQ ID NO: 178          moltype = AA  length = 170
FEATURE                 Location/Qualifiers
REGION                  1..170
                        note = Description of sequence: Human P19M Mature Wild type
                        p19 UniProt Ref: Q9NPF7
source                  1..170
                        mol_type = protein
                        organism = synthetic construct
SEQUENCE: 178
RAVPGGSSPA WTQCQQLSQK LCTLAWSAHP LVGHMDLREE GDEETTNDVP HIQCGDGCDP    60
QGLRDNSQFC LQRIHQGLIF YEKLLGSDIF TGEPSLLPDS PVGQLHASLL GLSQLLQPEG   120
HHWETQQIPS LSPSQPWQRL LLRFKILRSL QAFVAVAARV FAHGAATLSP              170

SEQ ID NO: 179          moltype = AA  length = 22
FEATURE                 Location/Qualifiers
REGION                  1..22
                        note = Description of sequence: Wild type human p35 signal
                        peptide
source                  1..22
                        mol_type = protein
                        organism = synthetic construct
SEQUENCE: 179
MCPARSLLLV ATLVLLDHLS LA                                             22

SEQ ID NO: 180          moltype = AA  length = 22
FEATURE                 Location/Qualifiers
REGION                  1..22
                        note = Description of sequence: Wild type human p40 signal
                        peptide
source                  1..22
                        mol_type = protein
                        organism = synthetic construct
SEQUENCE: 180
MCHQQLVISW FSLVFLASPL VA                                             22

SEQ ID NO: 181          moltype = AA  length = 142
FEATURE                 Location/Qualifiers
REGION                  1..142
                        note = Description of sequence: mREH
source                  1..142
                        mol_type = protein
                        organism = synthetic construct
SEQUENCE: 181
APTSSSTSSS TAEAQQQQQH LEQLRMDLEE LLSRMENYRN LKLPRMLTFK FYLPKQATEL    60
KDLQCLEDEL GPLRHVLDLT QSKSFQLEDA ENFISNIRVT VVKLKGSDNT FECQFDDESA   120
TVVDFLRRWI AFCHSIISTS PQ                                            142
```